United States Patent
Henderson et al.

(10) Patent No.: US 12,369,960 B2
(45) Date of Patent: Jul. 29, 2025

(54) METHOD FOR ENERGY DISTRIBUTION IN A SURGICAL MODULAR ENERGY SYSTEM

(71) Applicant: Cilag GmbH International, Zug (CH)

(72) Inventors: Joshua M. Henderson, Cincinnati, OH (US); Joshua P. Morgan, Loveland, OH (US); Andrew W. Carroll, Cincinnati, OH (US); Jeffrey L Aldridge, Lebanon, OH (US); Eitan T. Wiener, Cincinnati, OH (US); Ryan M. Asher, Cincinnati, OH (US); John B. Schulte, West Chester, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 463 days.

(21) Appl. No.: 17/847,943

(22) Filed: Jun. 23, 2022

(65) Prior Publication Data
US 2023/0039037 A1    Feb. 9, 2023

Related U.S. Application Data

(63) Continuation of application No. 16/562,142, filed on Sep. 5, 2019, now Pat. No. 11,628,006.
(Continued)

(51) Int. Cl.
*A61B 18/00* (2006.01)
*A61B 17/072* (2006.01)
(Continued)

(52) U.S. Cl.
CPC ............ *A61B 18/00* (2013.01); *A61B 17/072* (2013.01); *A61B 17/320068* (2013.01);
(Continued)

(58) Field of Classification Search
CPC ......... A61B 18/00; A61B 34/20; A61B 34/25; A61B 34/35; A61B 34/74; A61B 90/361;
(Continued)

(56) References Cited

U.S. PATENT DOCUMENTS

| 4,171,700 A | 10/1979 | Farin |
| 4,849,752 A | 7/1989 | Bryant |

(Continued)

FOREIGN PATENT DOCUMENTS

| CA | 2986408 A1 * 11/2013 | ........... A61B 5/0022 |
| EP | 0408160 A1    1/1991 | |

(Continued)

OTHER PUBLICATIONS

Sorrells, P., "Application Note AN680. Passive RFID Basics," retrieved from http://ww1.microchip.com/downloads/en/AppNotes/00680b.pdf on Feb. 26/2020, Dec. 31, 1998, pp. 1-7.
(Continued)

*Primary Examiner* — Aaron F Roane

(57) ABSTRACT

A method of operating a modular surgical system including a control module, a first surgical module, and a second surgical module is disclosed. The method includes detachably connecting the first surgical module to the control module by stacking the first surgical module with the control module in a stack configuration, detachably connecting the second surgical module to the first surgical module by stacking the second surgical module with the control module and the first surgical module in the stack configuration, powering up the modular surgical system, and monitoring distribution of power from a power supply of the control module to the first surgical module and the second surgical module.

20 Claims, 59 Drawing Sheets

Related U.S. Application Data

(60) Provisional application No. 62/826,588, filed on Mar. 29, 2019, provisional application No. 62/826,592, filed on Mar. 29, 2019, provisional application No. 62/826,587, filed on Mar. 29, 2019, provisional application No. 62/826,584, filed on Mar. 29, 2019, provisional application No. 62/728,480, filed on Sep. 7, 2018.

(51) Int. Cl.
| | | |
|---|---|---|
| *A61B 17/32* | (2006.01) | |
| *A61B 18/12* | (2006.01) | |
| *A61B 18/14* | (2006.01) | |
| *A61B 18/16* | (2006.01) | |
| *A61B 34/00* | (2016.01) | |
| *A61B 34/20* | (2016.01) | |
| *A61B 34/35* | (2016.01) | |
| *A61B 90/00* | (2016.01) | |
| *A61B 90/90* | (2016.01) | |
| *G06F 8/65* | (2018.01) | |
| *G16H 20/40* | (2018.01) | |
| *H01R 43/26* | (2006.01) | |
| *H04B 5/72* | (2024.01) | |
| *H04L 9/40* | (2022.01) | |
| *H04L 49/25* | (2022.01) | |
| *H04L 67/10* | (2022.01) | |
| *H04L 67/12* | (2022.01) | |
| *H04M 1/72406* | (2021.01) | |
| *H05K 5/30* | (2025.01) | |
| *A61B 17/00* | (2006.01) | |
| *A61B 34/30* | (2016.01) | |
| *A61B 34/37* | (2016.01) | |
| *A61B 90/30* | (2016.01) | |
| *H04L 27/04* | (2006.01) | |
| *H05K 5/00* | (2006.01) | |
| *H05K 7/02* | (2006.01) | |

(52) U.S. Cl.
CPC .. *A61B 17/320092* (2013.01); *A61B 18/1206* (2013.01); *A61B 18/1233* (2013.01); *A61B 18/1445* (2013.01); *A61B 18/16* (2013.01); *A61B 34/20* (2016.02); *A61B 34/25* (2016.02); *A61B 34/35* (2016.02); *A61B 34/74* (2016.02); *A61B 90/361* (2016.02); *A61B 90/90* (2016.02); *G06F 8/65* (2013.01); *G16H 20/40* (2018.01); *H01R 43/26* (2013.01); *H04B 5/72* (2024.01); *H04L 49/25* (2013.01); *H04L 63/0245* (2013.01); *H04L 67/10* (2013.01); *H04L 67/12* (2013.01); *H04M 1/72406* (2021.01); *H05K 5/30* (2025.01); *A61B 2017/00026* (2013.01); *A61B 2017/00199* (2013.01); *A61B 2017/00221* (2013.01); *A61B 2017/00225* (2013.01); *A61B 2017/00398* (2013.01); *A61B 2017/00477* (2013.01); *A61B 2017/00526* (2013.01); *A61B 2017/00973* (2013.01); *A61B 2017/07257* (2013.01); *A61B 2017/07271* (2013.01); *A61B 2017/07285* (2013.01); *A61B 2017/320074* (2017.08); *A61B 2018/00178* (2013.01); *A61B 2018/00208* (2013.01); *A61B 2018/00601* (2013.01); *A61B 2018/0063* (2013.01); *A61B 2018/00642* (2013.01); *A61B 2018/00702* (2013.01); *A61B 2018/00708* (2013.01); *A61B 2018/0072* (2013.01); *A61B 2018/00732* (2013.01); *A61B 2018/00767* (2013.01); *A61B 2018/00845* (2013.01); *A61B 2018/00875* (2013.01); *A61B 2018/00916* (2013.01); *A61B 2018/0094* (2013.01); *A61B 2018/00958* (2013.01); *A61B 2018/00994* (2013.01); *A61B 2018/1253* (2013.01); *A61B 2018/126* (2013.01); *A61B 2018/1273* (2013.01); *A61B 2018/128* (2013.01); *A61B 2018/1286* (2013.01); *A61B 2018/165* (2013.01); *A61B 2034/2048* (2016.02); *A61B 2034/2055* (2016.02); *A61B 2034/305* (2016.02); *A61B 34/37* (2016.02); *A61B 90/30* (2016.02); *A61B 90/37* (2016.02); *A61B 2090/371* (2016.02); *A61B 2090/378* (2016.02); *A61B 2218/002* (2013.01); *A61B 2218/007* (2013.01); *A61B 2218/008* (2013.01); *A61B 2560/0443* (2013.01); *A61B 2560/0456* (2013.01); *H01R 2201/12* (2013.01); *H04L 27/04* (2013.01); *H05K 5/0026* (2013.01); *H05K 5/0065* (2013.01); *H05K 7/023* (2013.01)

(58) Field of Classification Search
CPC .................. A61B 90/90; A61B 17/072; A61B 17/320068; A61B 17/320092; A61B 18/1206; A61B 18/1233; A61B 18/1445; A61B 18/16; A61B 2034/2048; A61B 2034/2055; A61B 2034/305; A61B 34/37; A61B 90/30; A61B 90/37; A61B 2090/371; A61B 2090/378; A61B 2017/320074; A61B 2017/00026; A61B 2017/00199; A61B 2017/00221; A61B 2017/00225; A61B 2017/00398; A61B 2017/00477; A61B 2017/00526; A61B 2017/00973; A61B 2017/07257; A61B 2017/07271; A61B 2017/07285; A61B 2018/00178; A61B 2018/00208; A61B 2018/00601; A61B 2018/0063; A61B 2018/00642; A61B 2018/00702; A61B 2018/00708; A61B 2018/0072; A61B 2018/00732; A61B 2018/00767; A61B 2018/00845; A61B 2018/00875; A61B 2018/00916; A61B 2018/0094; A61B 2018/00958; A61B 2018/00994; A61B 2018/1253; A61B 2018/126; A61B 2018/1273; A61B 2018/128; A61B 2018/1286; A61B 2018/165; A61B 2218/002; A61B 2218/007; A61B 2218/008; A61B 2560/0443; A61B 2560/0456; G16H 20/40; H04M 1/72406; H04B 5/72; H05K 5/30; H05K 5/0026; H05K 5/0065; H05K 7/023; G06F 8/65; H01R 43/26; H01R 2201/12; H04L 49/25; H04L 63/0245; H04L 67/10; H04L 67/12; H04L 27/04
USPC .......................................................... 606/1
See application file for complete search history.

(56) References Cited

U.S. PATENT DOCUMENTS

| | | |
|---|---|---|
| D303,787 S | 10/1989 | Messenger et al. |
| D327,061 S | 6/1992 | Soren et al. |
| 5,189,277 A | 2/1993 | Boisvert et al. |
| 5,204,669 A | 4/1993 | Dorfe et al. |
| 5,318,563 A | 6/1994 | Malis et al. |
| 5,325,270 A | 6/1994 | Wenger et al. |
| 5,425,375 A | 6/1995 | Chin et al. |
| D379,346 S | 5/1997 | Mieki |
| 5,690,504 A | 11/1997 | Scanlan et al. |

(56) References Cited

U.S. PATENT DOCUMENTS

| | | |
|---|---|---|
| 5,693,042 A | 12/1997 | Boiarski et al. |
| 5,724,468 A | 3/1998 | Leone et al. |
| 6,049,467 A | 4/2000 | Tamarkin et al. |
| 6,055,458 A | 4/2000 | Cochran et al. |
| D431,811 S | 10/2000 | Nishio et al. |
| 6,179,136 B1 | 1/2001 | Kluge et al. |
| 6,269,411 B1 | 7/2001 | Reasoner |
| 6,288,606 B1 | 9/2001 | Ekman et al. |
| 6,416,471 B1 | 7/2002 | Kumar et al. |
| 6,546,270 B1 | 4/2003 | Goldin et al. |
| 6,584,358 B2 | 6/2003 | Carter et al. |
| 6,611,793 B1 | 8/2003 | Burnside et al. |
| 6,731,514 B2 | 5/2004 | Evans |
| 6,760,218 B2 | 7/2004 | Fan |
| 6,839,238 B2 | 1/2005 | Derr et al. |
| 6,843,657 B2 | 1/2005 | Driscoll et al. |
| 6,913,471 B2 | 7/2005 | Smith |
| 7,009,511 B2 | 3/2006 | Mazar et al. |
| 7,044,949 B2 | 5/2006 | Orszulak et al. |
| 7,074,205 B1 | 7/2006 | Duffy et al. |
| 7,134,994 B2 | 11/2006 | Alpert et al. |
| 7,171,784 B2 | 2/2007 | Eenigenburg |
| 7,217,269 B2 | 5/2007 | El-Galley et al. |
| 7,252,664 B2 | 8/2007 | Nasab et al. |
| 7,331,699 B2 | 2/2008 | Gawalkiewicz et al. |
| 7,344,532 B2 | 3/2008 | Goble et al. |
| 7,353,068 B2 | 4/2008 | Tanaka et al. |
| 7,408,439 B2 | 8/2008 | Wang et al. |
| D579,876 S | 11/2008 | Novotney et al. |
| D583,328 S | 12/2008 | Chiang |
| 7,496,418 B2 | 2/2009 | Kim et al. |
| D589,447 S | 3/2009 | Sasada et al. |
| 7,500,747 B2 | 3/2009 | Howell et al. |
| 7,518,502 B2 | 4/2009 | Austin et al. |
| 7,563,259 B2 | 7/2009 | Takahashi |
| 7,601,149 B2 | 10/2009 | DiCarlo et al. |
| 7,637,907 B2 | 12/2009 | Blaha |
| 7,656,671 B2 | 2/2010 | Liu et al. |
| 7,757,028 B2 | 7/2010 | Druke et al. |
| D631,252 S | 1/2011 | Leslie |
| 7,932,826 B2 | 4/2011 | Fritchie et al. |
| 7,945,065 B2 | 5/2011 | Menzl et al. |
| 7,945,342 B2 | 5/2011 | Tsai et al. |
| 7,982,776 B2 | 7/2011 | Dunki-Jacobs et al. |
| 7,995,045 B2 | 8/2011 | Dunki-Jacobs |
| 8,019,094 B2 | 9/2011 | Hsieh et al. |
| D655,678 S | 3/2012 | Kobayashi et al. |
| D657,368 S | 4/2012 | Magee et al. |
| 8,218,279 B2 | 7/2012 | Liao et al. |
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,504,136 B1 | 8/2013 | Sun et al. |
| 8,540,709 B2 | 9/2013 | Allen |
| 8,567,393 B2 | 10/2013 | Hickle et al. |
| D704,839 S | 5/2014 | Juzkiw et al. |
| 8,795,001 B1 | 8/2014 | Lam et al. |
| 8,819,581 B2 | 8/2014 | Nakamura et al. |
| D716,333 S | 10/2014 | Chotin et al. |
| 8,917,513 B1 | 12/2014 | Hazzard |
| 8,920,186 B2 | 12/2014 | Shishikura |
| 8,923,012 B2 | 12/2014 | Kaufman et al. |
| 8,968,296 B2 | 3/2015 | McPherson |
| 8,986,288 B2 | 3/2015 | Konishi |
| 9,017,326 B2 | 4/2015 | DiNardo et al. |
| D729,267 S | 5/2015 | Yoo et al. |
| 9,055,870 B2 | 6/2015 | Meador et al. |
| 9,065,394 B2 | 6/2015 | Lim et al. |
| 9,129,054 B2 | 9/2015 | Nawana et al. |
| 9,160,853 B1 | 10/2015 | Daddi et al. |
| 9,168,054 B2 | 10/2015 | Turner et al. |
| 9,168,091 B2 | 10/2015 | Janssen et al. |
| 9,198,711 B2 | 12/2015 | Joseph |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,281,615 B1 | 3/2016 | Plaza et al. |
| 9,320,646 B2 | 4/2016 | Todd et al. |
| 9,345,481 B2 | 5/2016 | Hall et al. |
| 9,345,900 B2 | 5/2016 | Wu et al. |
| 9,351,653 B1 | 5/2016 | Harrison |
| 9,427,255 B2 | 8/2016 | Griffith et al. |
| 9,430,438 B2 | 8/2016 | Biskup |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,491,895 B2 | 11/2016 | Steeves et al. |
| 9,532,827 B2 | 1/2017 | Morgan et al. |
| 9,589,720 B2 | 3/2017 | Akahane |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,666,974 B2 | 5/2017 | Bopp |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| 9,867,670 B2 | 1/2018 | Brannan et al. |
| 9,907,196 B2 | 2/2018 | Susini et al. |
| 9,971,395 B2 | 4/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |

(56) References Cited

U.S. PATENT DOCUMENTS

| | | |
|---|---|---|
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| D924,139 S | 7/2021 | Jayme |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,083,489 B2 | 8/2021 | Fujii et al. |
| 11,116,587 B2 | 9/2021 | Wolf et al. |
| D939,545 S | 12/2021 | Oberkircher et al. |
| 11,218,822 B2 | 1/2022 | Morgan et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |
| 11,298,128 B2 | 4/2022 | Messerly et al. |
| 11,304,763 B2 | 4/2022 | Shelton, IV et al. |
| 11,314,846 B1 | 4/2022 | Colin et al. |
| 11,350,978 B2 | 6/2022 | Henderson et al. |
| 11,369,366 B2 | 6/2022 | Scheib et al. |
| 11,419,604 B2 | 8/2022 | Scheib et al. |
| 11,424,027 B2 | 8/2022 | Shelton, IV |
| 11,471,206 B2 | 10/2022 | Henderson et al. |
| 11,478,820 B2 | 10/2022 | Bales, Jr. et al. |
| 11,504,192 B2 | 11/2022 | Shelton, IV et al. |
| 11,510,720 B2 | 11/2022 | Morgan et al. |
| 11,559,307 B2 | 1/2023 | Shelton, IV et al. |
| 11,564,678 B2 | 1/2023 | Scheib et al. |
| 2001/0029315 A1 | 10/2001 | Sakurai et al. |
| 2003/0078631 A1 | 4/2003 | Nelson et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0111045 A1 | 6/2004 | Sullivan et al. |
| 2005/0010209 A1 | 1/2005 | Lee et al. |
| 2005/0013459 A1 | 1/2005 | Maekawa |
| 2005/0113823 A1 | 5/2005 | Reschke et al. |
| 2005/0165390 A1 | 7/2005 | Mauti et al. |
| 2005/0229110 A1 | 10/2005 | Gegner et al. |
| 2005/0251233 A1 | 11/2005 | Kanzius |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0256516 A1 | 11/2006 | Cho |
| 2007/0076363 A1 | 4/2007 | Liang et al. |
| 2007/0282321 A1 | 12/2007 | Shah et al. |
| 2008/0072896 A1 | 3/2008 | Setzer et al. |
| 2008/0129465 A1 | 6/2008 | Rao |
| 2008/0249377 A1 | 10/2008 | Molducci et al. |
| 2009/0036884 A1 | 2/2009 | Gregg et al. |
| 2009/0131929 A1 | 5/2009 | Shimizu |
| 2009/0216091 A1 | 8/2009 | Arndt |
| 2009/0234352 A1 | 9/2009 | Behnke et al. |
| 2010/0036405 A1 | 2/2010 | Giordano et al. |
| 2010/0069939 A1 | 3/2010 | Konishi |
| 2010/0076453 A1 | 3/2010 | Morris et al. |
| 2010/0092006 A1 | 4/2010 | Rosen |
| 2010/0120266 A1 | 5/2010 | Rimborg |
| 2010/0198200 A1 | 8/2010 | Horvath |
| 2010/0312239 A1 | 12/2010 | Sclig |
| 2011/0125149 A1 | 5/2011 | El-Galley et al. |
| 2011/0130689 A1 | 6/2011 | Cohen et al. |
| 2011/0245630 A1 | 10/2011 | St. Pierre et al. |
| 2011/0273465 A1 | 11/2011 | Konishi et al. |
| 2011/0306840 A1 | 12/2011 | Allen et al. |
| 2012/0029304 A1 | 2/2012 | Medina et al. |
| 2012/0116380 A1 | 5/2012 | Madan et al. |
| 2012/0132661 A1 | 5/2012 | Gu et al. |
| 2012/0319890 A1 | 12/2012 | McCormack et al. |
| 2013/0031201 A1 | 1/2013 | Kagan et al. |
| 2013/0176220 A1 | 7/2013 | Merschon et al. |
| 2013/0197503 A1 | 8/2013 | Orszulak |
| 2013/0267975 A1 | 10/2013 | Timm et al. |
| 2013/0268283 A1 | 10/2013 | Vann et al. |
| 2014/0009894 A1 | 1/2014 | Yu |
| 2014/0058714 A1 | 2/2014 | Boyer |
| 2014/0087573 A1 | 3/2014 | Kroeckel |
| 2014/0155721 A1 | 6/2014 | Hauck et al. |
| 2014/0194683 A1 | 7/2014 | Nakaguchi |
| 2014/0226572 A1 | 8/2014 | Thota et al. |
| 2014/0262598 A1 | 9/2014 | Miki et al. |
| 2014/0263552 A1 | 9/2014 | Hall et al. |
| 2015/0190189 A1 | 7/2015 | Yates et al. |
| 2015/0272575 A1 | 10/2015 | Leimbach et al. |
| 2015/0289929 A1 | 10/2015 | Toth et al. |
| 2016/0045247 A1 | 2/2016 | Heim et al. |
| 2016/0058286 A1 | 3/2016 | Joshua et al. |
| 2016/0062954 A1 | 3/2016 | Ruff et al. |
| 2016/0074096 A1 | 3/2016 | Lieu |
| 2016/0120591 A1 | 5/2016 | Smith et al. |
| 2016/0287312 A1 | 10/2016 | Tegg et al. |
| 2017/0000553 A1 | 1/2017 | Wiener et al. |
| 2017/0078455 A1 | 3/2017 | Fisher et al. |
| 2017/0090507 A1 | 3/2017 | Wiener et al. |
| 2017/0189096 A1 | 7/2017 | Danziger et al. |
| 2017/0202595 A1 | 7/2017 | Shelton, IV |
| 2017/0251305 A1 | 8/2017 | Fathollahi |
| 2017/0252091 A1 | 9/2017 | Honda |
| 2017/0296213 A1 | 10/2017 | Swensgard et al. |
| 2017/0319259 A1 | 11/2017 | Dunning |
| 2017/0360466 A1 | 12/2017 | Brown et al. |
| 2018/0014872 A1 | 1/2018 | Dickerson |
| 2018/0042659 A1 | 2/2018 | Rupp et al. |
| 2018/0049795 A1 | 2/2018 | Swayze et al. |
| 2018/0065248 A1 | 3/2018 | Barral et al. |
| 2018/0078216 A1 | 3/2018 | Baker et al. |
| 2018/0082480 A1 | 3/2018 | White et al. |
| 2018/0099161 A1 | 4/2018 | Honda |
| 2018/0221005 A1 | 8/2018 | Hamel et al. |
| 2018/0228528 A1 | 8/2018 | Fraasch et al. |
| 2018/0262916 A1 | 9/2018 | Polley et al. |
| 2018/0263557 A1 | 9/2018 | Kahlman |
| 2018/0296283 A1 | 10/2018 | Crawford et al. |
| 2018/0333207 A1 | 11/2018 | Moctezuma De La Barrera |
| 2019/0069957 A1 | 3/2019 | Barral et al. |
| 2019/0200906 A1 | 7/2019 | Shelton, IV et al. |
| 2019/0200981 A1 | 7/2019 | Harris et al. |
| 2019/0201046 A1 | 7/2019 | Shelton, IV et al. |
| 2019/0201102 A1 | 7/2019 | Shelton, IV et al. |
| 2019/0201140 A1 | 7/2019 | Yates et al. |
| 2019/0201158 A1 | 7/2019 | Shelton, IV et al. |
| 2019/0206562 A1 | 7/2019 | Shelton, IV et al. |
| 2019/0224434 A1 | 7/2019 | Silver et al. |
| 2019/0247141 A1 | 8/2019 | Batchelor et al. |
| 2019/0278262 A1 | 9/2019 | Taylor et al. |
| 2019/0279524 A1 | 9/2019 | Stoyanov et al. |
| 2020/0004487 A1 | 1/2020 | Hanajima et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015907 A1 | 1/2020 | Scheib |
| 2020/0015924 A1 | 1/2020 | Scheib et al. |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078078 A1 | 3/2020 | Henderson et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078083 A1 | 3/2020 | Sprinkle et al. |
| 2020/0078089 A1 | 3/2020 | Henderson et al. |
| 2020/0078110 A1 | 3/2020 | Henderson et al. |

(56) References Cited

U.S. PATENT DOCUMENTS

| | | |
|---|---|---|
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0265398 A1 | 8/2020 | Lembo |
| 2020/0268472 A1 | 8/2020 | Wolf et al. |
| 2020/0305924 A1 | 10/2020 | Carroll |
| 2020/0305945 A1 | 10/2020 | Morgan et al. |
| 2021/0196383 A1 | 7/2021 | Shelton, IV et al. |
| 2021/0203889 A1 | 7/2021 | Fung et al. |
| 2021/0212717 A1 | 7/2021 | Yates et al. |
| 2021/0236755 A1 | 8/2021 | King et al. |
| 2021/0385889 A1 | 12/2021 | Patel |
| 2022/0032442 A1 | 2/2022 | Sheffield et al. |
| 2022/0151704 A1 | 5/2022 | Nikou |
| 2022/0261056 A1 | 8/2022 | Motoi et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0338049 A1 | 10/2022 | Ross et al. |

FOREIGN PATENT DOCUMENTS

| | | |
|---|---|---|
| EP | 0473987 A1 | 3/1992 |
| EP | 0929263 B1 | 7/1999 |
| EP | 1006892 B1 | 6/2009 |
| EP | 2942023 A2 | 11/2015 |
| JP | 2001029353 A | 2/2001 |
| WO | WO-0112089 A1 | 2/2001 |
| WO | WO-2008053485 A1 | 5/2008 |
| WO | WO-2014031800 A1 | 2/2014 |
| WO | WO-2014071184 A1 | 5/2014 |
| WO | WO-2015047693 A1 | 4/2015 |
| WO | WO-2017058617 A2 | 4/2017 |
| WO | WO-2018116247 A1 | 6/2018 |
| WO | WO-2019215354 A1 | 11/2019 |
| WO | WO-2021044136 A1 | 3/2021 |

OTHER PUBLICATIONS

IEEE Std 802.3-2012 (Revision of IEEE Std 802.3-2008, published Dec. 28, 2012.

"ATM-MPLS Network Interworking Version 2.0, af-aic-0178.001" ATM Standard, The ATM Forum Technical Committee, published Aug. 2003.

Zhu et al. "Haptic-feedback smart glove as a creative human-machine interface (HMI) for virtual/augmented reality applications," SCI. ADV, vol. 6, No. 19, May 8, 2020.

Qian, et al., "A Review of Augmented Reality in Robotic-Assisted Surgery", IEEE Transactions On Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Li et al., "Wearable Energy Harvesters Generating Electricity From Low-Frequency Human Limb Movement," Microsystems & Nanoengineering (2018), vol. 4(24), 13 pages.

* cited by examiner

METHOD FOR ENERGY DISTRIBUTION IN A SURGICAL MODULAR ENERGY SYSTEM

CROSS-REFERENCE TO RELATED APPLICATIONS

This application is a continuation application claiming priority under 35 U.S.C. § 120 to U.S. patent application Ser. No. 16/562,142, titled METHOD FOR ENERGY DISTRIBUTION IN A SURGICAL MODULAR ENERGY SYSTEM, filed Sep. 5, 2019, now U.S. Patent application Publication No. 2020/0078070, which claims priority under 35 U.S.C. § 119(e) to U.S. Provisional Patent Application Ser. No. 62/826,584, titled MODULAR SURGICAL PLATFORM ELECTRICAL ARCHITECTURE, filed Mar. 29, 2019, the disclosures of which are herein incorporated by reference in their entireties.

This application is a continuation application claiming priority under 35 U.S.C. § 120 to U.S. patent application Ser. No. 16/562,142, titled METHOD FOR ENERGY DISTRIBUTION IN A SURGICAL MODULAR ENERGY SYSTEM, filed Sep. 5, 2019, now U.S. Patent application Publication No. 2020/0078070, which claims priority under 35 U.S.C. § 119(e) to U.S. Provisional Patent Application Ser. No. 62/826,587, titled MODULAR ENERGY SYSTEM CONNECTIVITY, filed Mar. 29, 2019, the disclosures of which are herein incorporated by reference in their entireties.

This application is a continuation application claiming priority under 35 U.S.C. § 120 to U.S. patent application Ser. No. 16/562,142, titled METHOD FOR ENERGY DISTRIBUTION IN A SURGICAL MODULAR ENERGY SYSTEM, filed Sep. 5, 2019, now U.S. Patent application Publication No. 2020/0078070, which claims priority under 35 U.S.C. § 119(e) to U.S. Provisional Patent Application Ser. No. 62/826,588, titled MODULAR ENERGY SYSTEM INSTRUMENT COMMUNICATION TECHNIQUES, filed Mar. 29, 2019, the disclosures of which are herein incorporated by reference in their entireties.

This application is a continuation application claiming priority under 35 U.S.C. § 120 to U.S. patent application Ser. No. 16/562,142, titled METHOD FOR ENERGY DISTRIBUTION IN A SURGICAL MODULAR ENERGY SYSTEM, filed Sep. 5, 2019, now U.S. Patent application Publication No. 2020/0078070, which claims priority under 35 U.S.C. § 119(e) to U.S. Provisional Patent Application Ser. No. 62/826,592, titled MODULAR ENERGY DELIVERY SYSTEM, filed Mar. 29, 2019, the disclosures of which are herein incorporated by reference in their entireties.

This application is a continuation application claiming priority under 35 U.S.C. § 120 to U.S. patent application Ser. No. 16/562,142, titled METHOD FOR ENERGY DISTRIBUTION IN A SURGICAL MODULAR ENERGY SYSTEM, filed Sep. 5, 2019, now U.S. Patent application Publication No. 2020/0078070, which claims priority under 35 U.S.C. § 119(e) to U.S. Provisional Patent Application Ser. No. 62/728,480, titled MODULAR ENERGY SYSTEM AND USER INTERFACE, filed Sep. 7, 2018, the disclosures of which are herein incorporated by reference in their entireties.

BACKGROUND

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, there are unmet consumer needs for capital equipment and other surgical technology to be consolidated in order to decrease the equipment footprint within the OR, streamline the equipment's interfaces, and improve surgical staff efficiency during a surgical procedure by reducing the number of devices that surgical staff members need to interact with.

SUMMARY

In various embodiments, a method of operating a modular surgical system including a control module, a first surgical module, and a second surgical module is disclosed. The method includes detachably connecting the first surgical module to the control module by stacking the first surgical module with the control module in a stack configuration, detachably connecting the second surgical module to the first surgical module by stacking the second surgical module with the control module and the first surgical module in the stack configuration, powering up the modular surgical system, and monitoring distribution of power from a power supply of the control module to the first surgical module and the second surgical module.

In various embodiments, a method of operating a modular surgical system including a control module, a first surgical module, and a second surgical module is disclosed. The method includes detachably connecting the first surgical module to the control module by stacking the first surgical module with the control module in a stack configuration, detachably connecting the second surgical module to the first surgical module by stacking the second surgical module with the control module and the first surgical module in the stack configuration, attaching a first surgical instrument to an energy port of the first surgical module, attaching a second surgical instrument to an energy port of the second surgical module, activating the first surgical instrument, activating the second surgical instrument, and allocating power from a power supply of the control module to the first surgical module and the second surgical module.

In various embodiments, a method of operating a modular surgical system including a control module, a first surgical module, and a second surgical module is disclosed. The method includes detachably connecting the first surgical module to the control module by stacking the first surgical module with the control module in a stack configuration, detachably connecting the second surgical module to the first surgical module by stacking the second surgical module with the control module and the first surgical module in the stack configuration, and simultaneously supplying power from a power supply in the control module to the first surgical module to generate a first therapeutic energy and to the second surgical module through the first surgical module to generate a second therapeutic energy.

FIGURES

The various aspects described herein, both as to organization and methods of operation, together with further objects and advantages thereof, may best be understood by reference to the following description, taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DESCRIPTION

Figure 1:
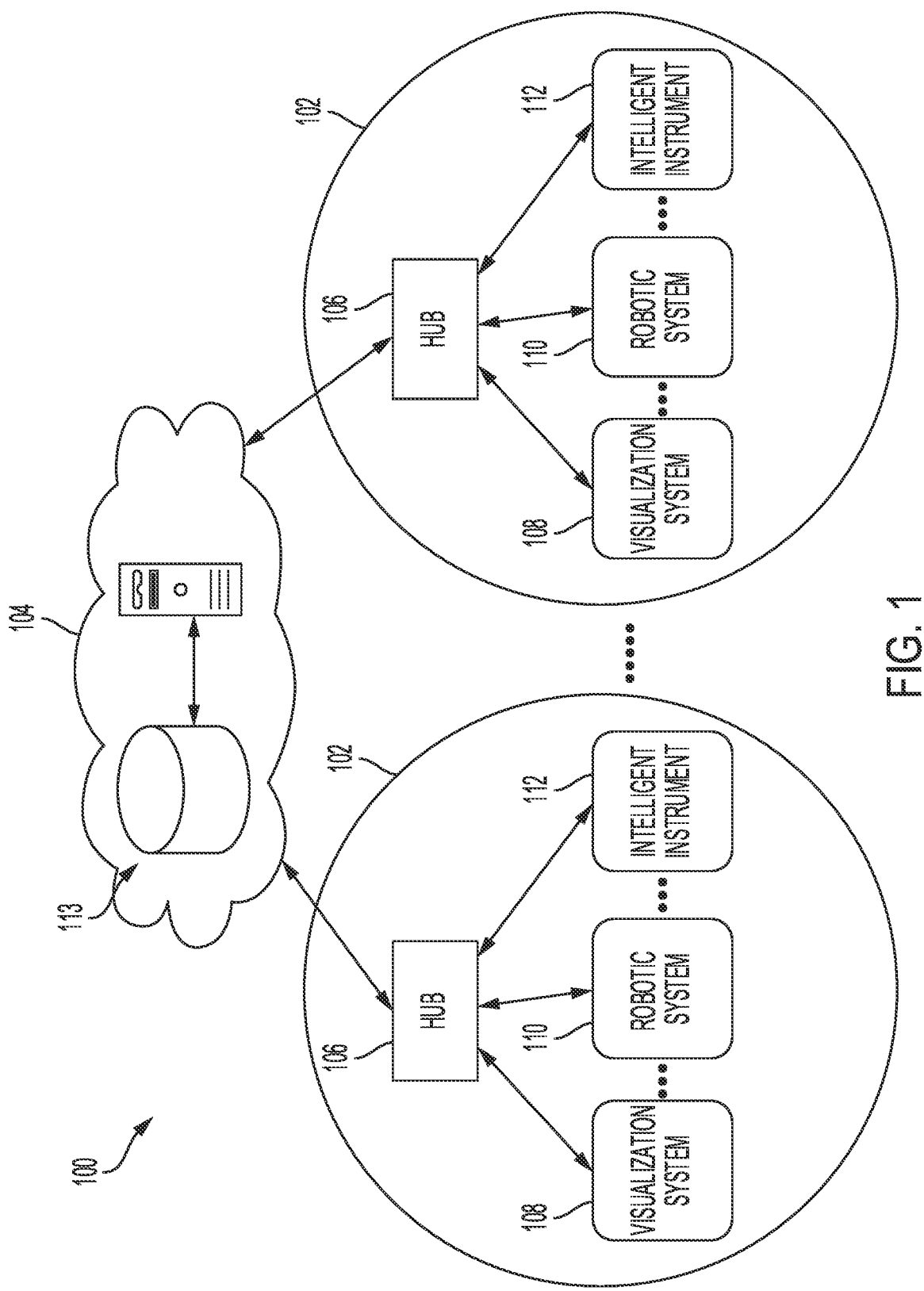
FIG. 1 is a block diagram of a computer-implemented interactive surgical system, in accordance with at least one aspect of the present disclosure.

Applicant of the present application owns the following U.S. patent applications filed on Sep. 5, 2019, the disclosures of each of which are herein incorporated by reference in their entireties:

U.S. patent application Ser. No. 16/562,123, titled METHOD FOR CONSTRUCTING AND USING A MODULAR SURGICAL ENERGY SYSTEM WITH MULTIPLE DEVICES, now U.S. Patent Application Publication No. 2020/0100830;

U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;

U.S. patent application Ser. No. 16/562,169, titled SURGICAL MODULAR ENERGY SYSTEM WITH A SEGMENTED BACKPLANE, now U.S. Patent Application Publication No. 2020/0078112;

U.S. patent application Ser. No. 16/562,185, titled SURGICAL MODULAR ENERGY SYSTEM WITH FOOTER MODULE, now U.S. Patent Application Publication No. 2020/0078115;

U.S. patent application Ser. No. 16/562,203, titled POWER AND COMMUNICATION MITIGATION ARRANGEMENT FOR MODULAR SURGICAL ENERGY SYSTEM, now U.S. Patent Application Publication No. 2020/0078118;

U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;

U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;

U.S. patent application Ser. No. 16/562,243, titled MODULAR SURGICAL ENERGY SYSTEM WITH MODULE POSITIONAL AWARENESS WITH DIGITAL LOGIC, now U.S. Patent Application Publication No. 2020/0078120;

U.S. patent application Ser. No. 16/562,135, titled METHOD FOR CONTROLLING AN ENERGY MODULE OUTPUT, now U.S. Patent Application Publication No. 2020/0078076;

U.S. patent application Ser. No. 16/562,180, titled ENERGY MODULE FOR DRIVING MULTIPLE ENERGY MODALITIES, now U.S. Patent Application Publication No. 2020/0078080;

U.S. patent application Ser. No. 16/562,184, titled GROUNDING ARRANGEMENT OF ENERGY MODULES, now U.S. Patent Application Publication No. 2020/0078081;

U.S. patent application Ser. No. 16/562,188, titled BACKPLANE CONNECTOR DESIGN TO CONNECT STACKED ENERGY MODULES, now U.S. Patent Application Publication No. 2020/0078116;

U.S. patent application Ser. No. 16/562,195, titled ENERGY MODULE FOR DRIVING MULTIPLE ENERGY MODALITIES THROUGH A PORT, now U.S. Patent Application Publication No. 2020/0078117;

U.S. patent application Ser. No. 16/562,202, titled SURGICAL INSTRUMENT UTILIZING DRIVE SIGNAL TO POWER SECONDARY FUNCTION, now U.S. Patent Application Publication No. 2020/0078082;

U.S. patent application Ser. No. 16/562,144, titled METHOD FOR CONTROLLING A MODULAR ENERGY SYSTEM USER INTERFACE, now U.S. Patent Application Publication No. 2020/0078106;

U.S. patent application Ser. No. 16/562,151, titled PASSIVE HEADER MODULE FOR A MODULAR ENERGY SYSTEM, now U.S. Patent Application Publication No. 2020/0078110;

U.S. patent application Ser. No. 16/562,157, titled CONSOLIDATED USER INTERFACE FOR MODULAR ENERGY SYSTEM, now U.S. Patent Application Publication No. 2020/0081585;

U.S. patent application Ser. No. 16/562,159, titled AUDIO TONE CONSTRUCTION FOR AN ENERGY MODULE OF A MODULAR ENERGY SYSTEM, now U.S. Pat. No. 11,218,822;

U.S. patent application Ser. No. 16/562,163, titled ADAPTABLY CONNECTABLE AND REASSIGNABLE SYSTEM ACCESSORIES FOR MODULAR ENERGY SYSTEM, now U.S. Patent Application Publication No. 2020/0078111;

U.S. patent application Ser. No. 16/562,125, titled METHOD FOR COMMUNICATING BETWEEN MODULES AND DEVICES IN A MODULAR SURGICAL SYSTEM, now U.S. Patent Application Publication No. 2020/0100825;

U.S. patent application Ser. No. 16/562,137, titled FLEXIBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEXIBLE NEUTRAL ELECTRODE, now U.S. Patent Application Publication No. 2020/0078077;

U.S. patent application Ser. No. 16/562,154, titled SMART RETURN PAD SENSING THROUGH MODULATION OF NEAR FIELD COMMUNICATION AND CONTACT QUALITY MONITORING SIGNALS, now U.S. Patent Application Publication No. 2020/0078089;

U.S. patent application Ser. No. 16/562,162, titled AUTOMATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPARATE BUT CONNECTED MODULES, now U.S. Patent Application Publication No. 2020/0078078;

U.S. patent application Ser. No. 16/562,170, titled MANAGING SIMULTANEOUS MONOPOLAR OUTPUTS USING DUTY CYCLE AND SYNCHRONIZATION, now U.S. Patent Application Publication No. 2020/0078079;

U.S. patent application Ser. No. 16/562,172, titled PORT PRESENCE DETECTION SYSTEM FOR MODULAR ENERGY SYSTEM, now U.S. Patent Application Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPONENTS OF A MODULAR ENERGY SYSTEM, now U.S. Patent Application Publication No. 2020/0078114;

U.S. Design patent application Ser. No. 29/704,610, titled ENERGY MODULE, now U.S. Pat. No. D928,725;

U.S. Design patent application Ser. No. 29/704,614, titled ENERGY MODULE MONOPOLAR PORT WITH FOURTH SOCKET AMONG THREE OTHER SOCKETS, now U.S. Pat. No. D928,726;

U.S. Design patent application Ser. No. D/704,616, titled BACKPLANE CONNECTOR FOR ENERGY MODULE, now U.S. Pat. No. D924,139; and U.S. Design patent application Ser. No. 29/704,617, titled ALERT SCREEN FOR ENERGY MODULE, now U.S. Pat. No. D939,545.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
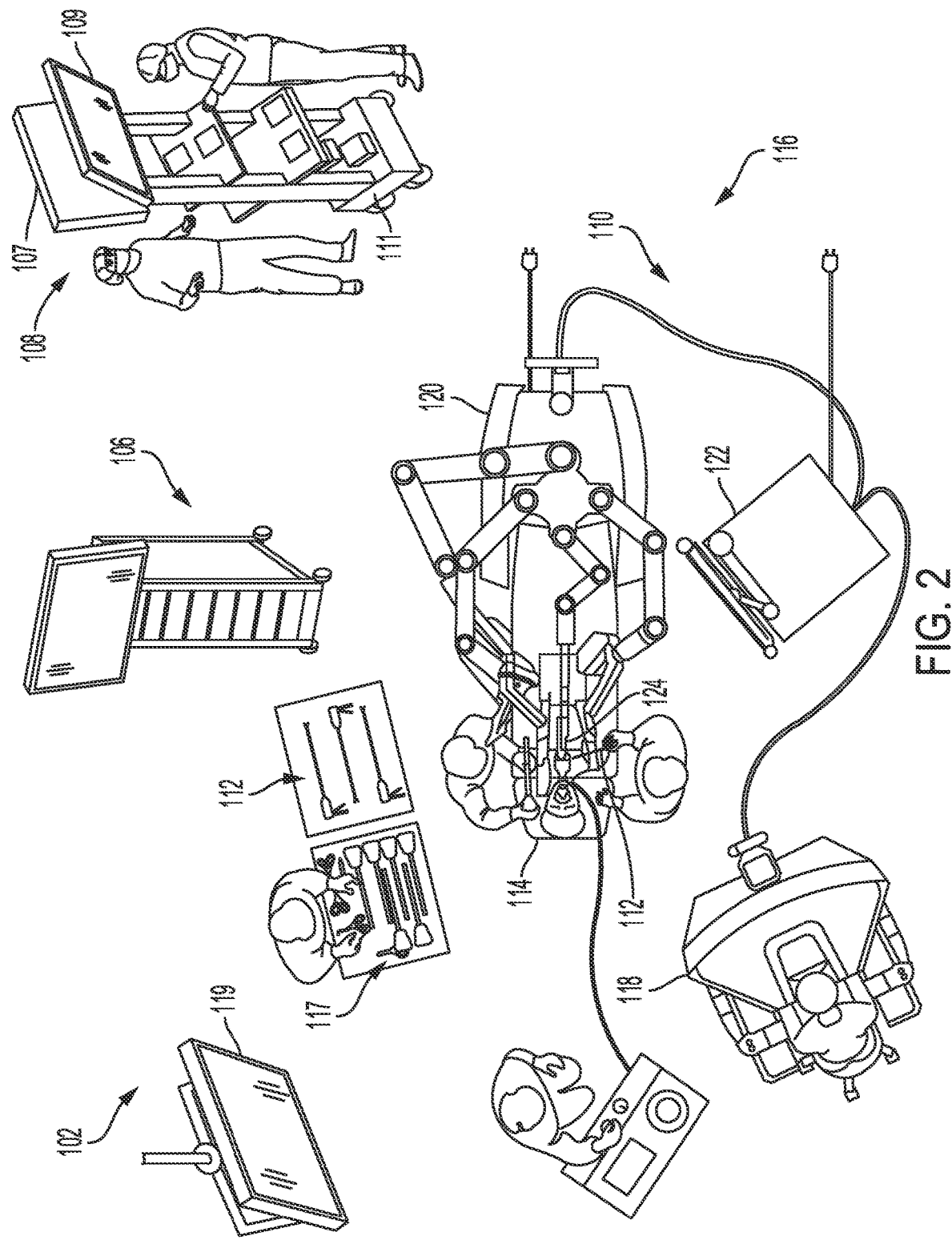
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area. In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
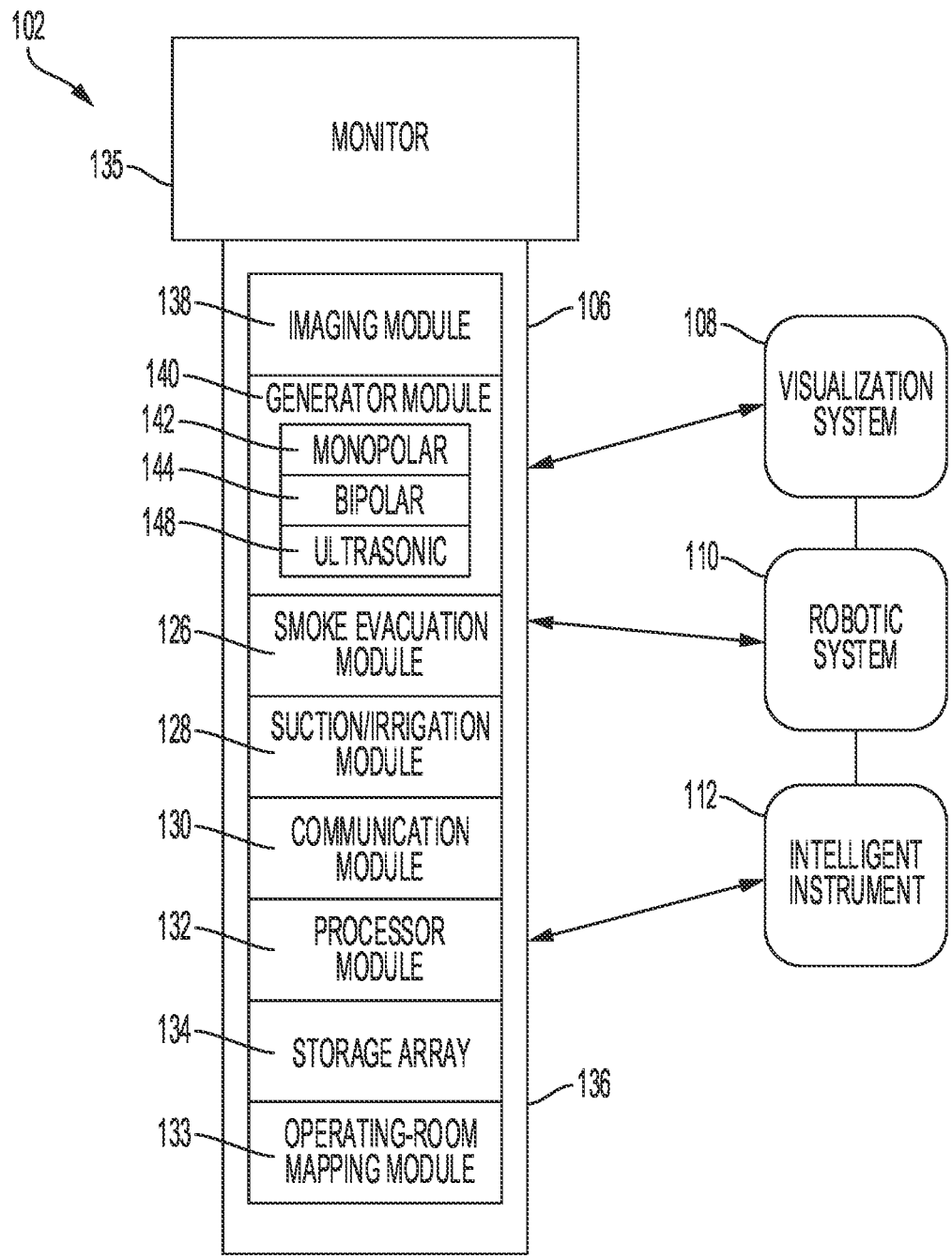
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 4:
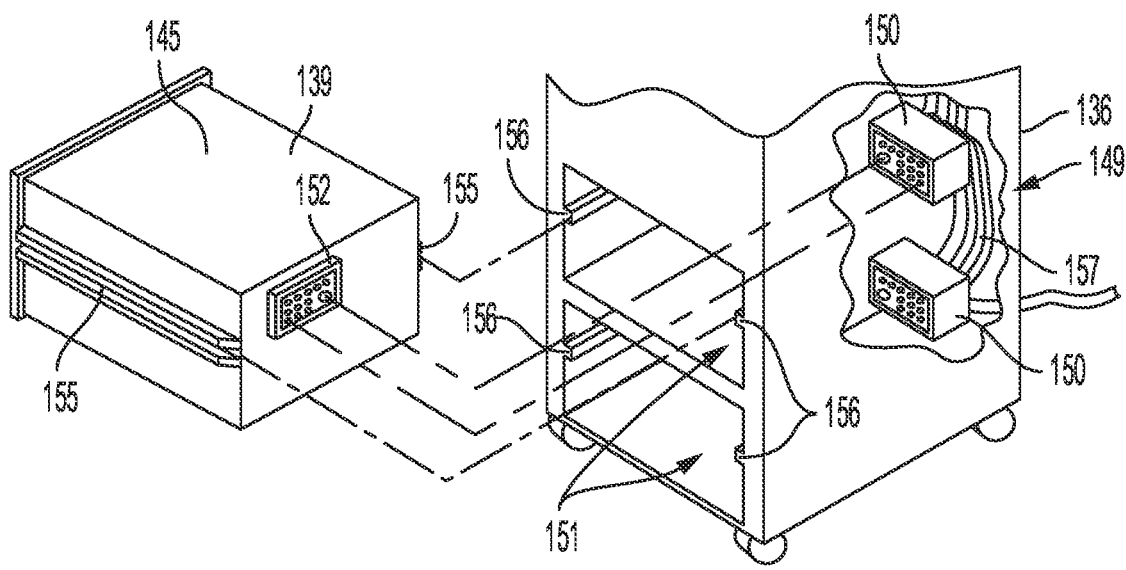
FIG. 4 is a partial perspective view of a surgical hub enclosure, and of a combo generator module slidably receivable in a drawer of the surgical hub enclosure, in accordance with at least one aspect of the present disclosure.
Figure 5:
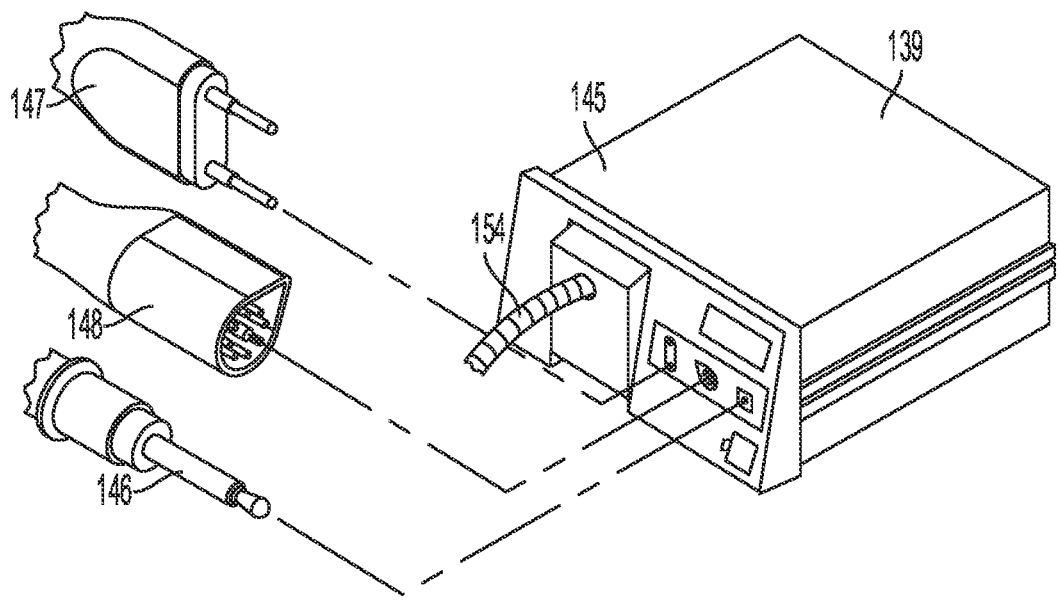
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
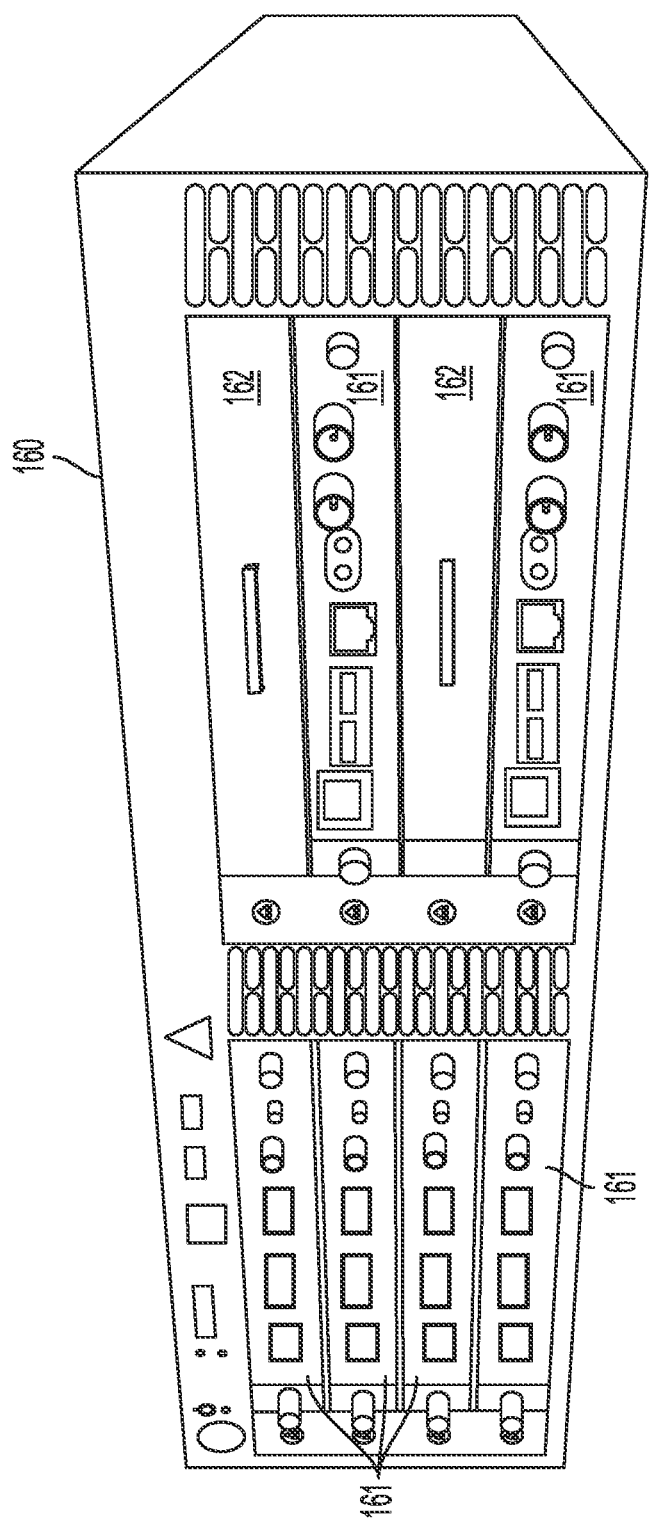
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
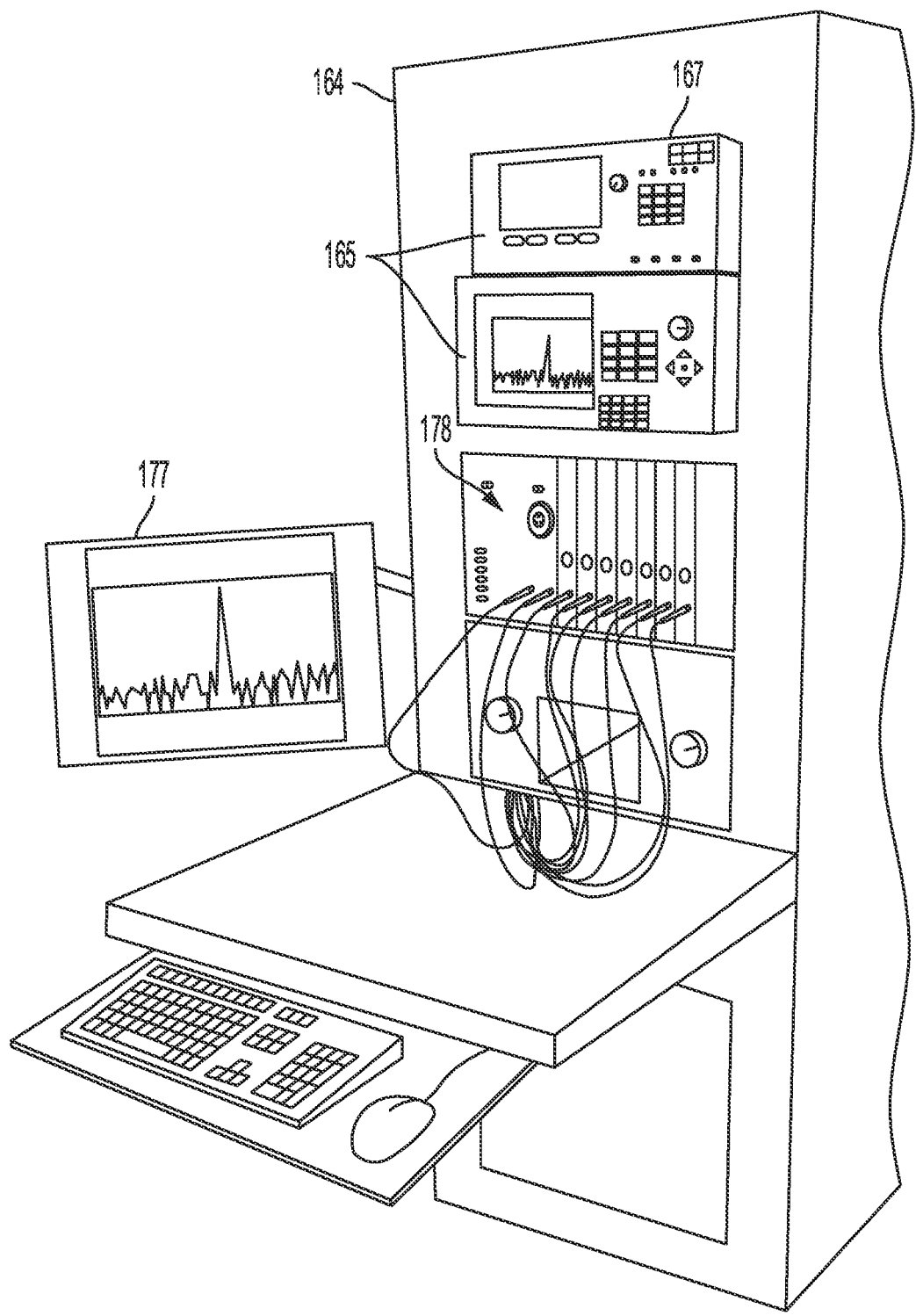
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
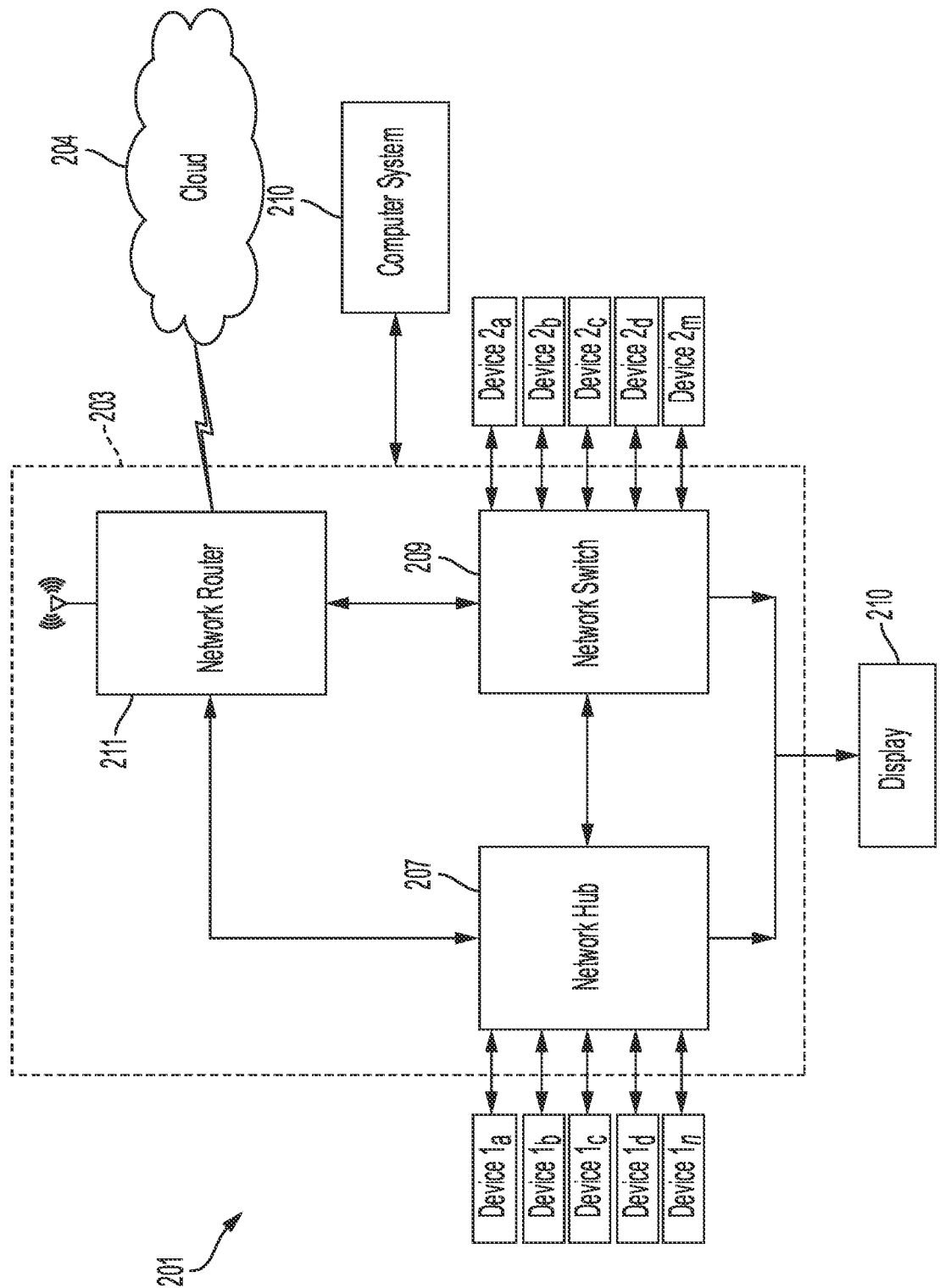
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/ 2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
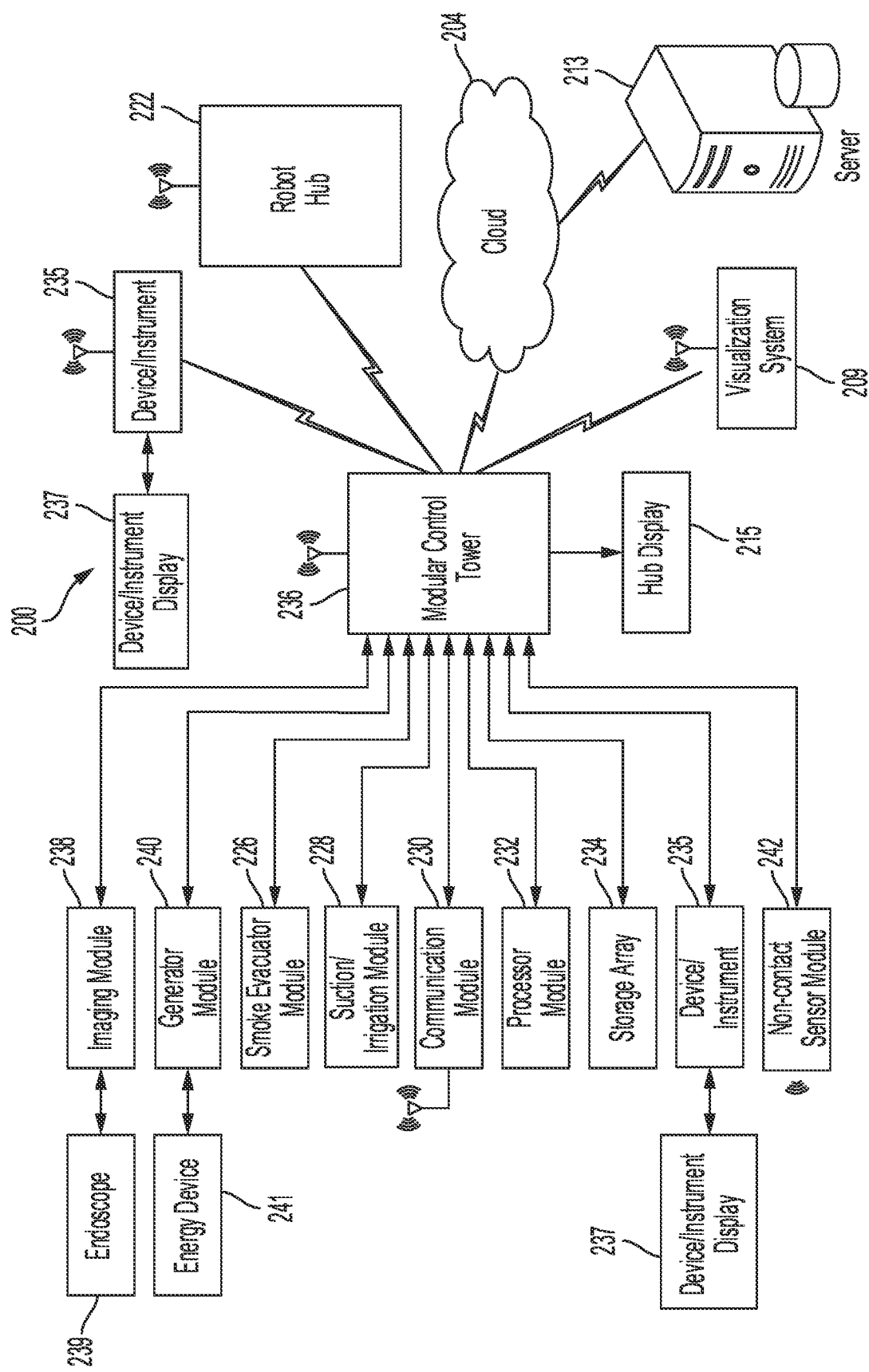
FIG. 9 illustrates a computer-implemented interactive surgical system, in accordance with at least one aspect of the present disclosure.
Figure 10:
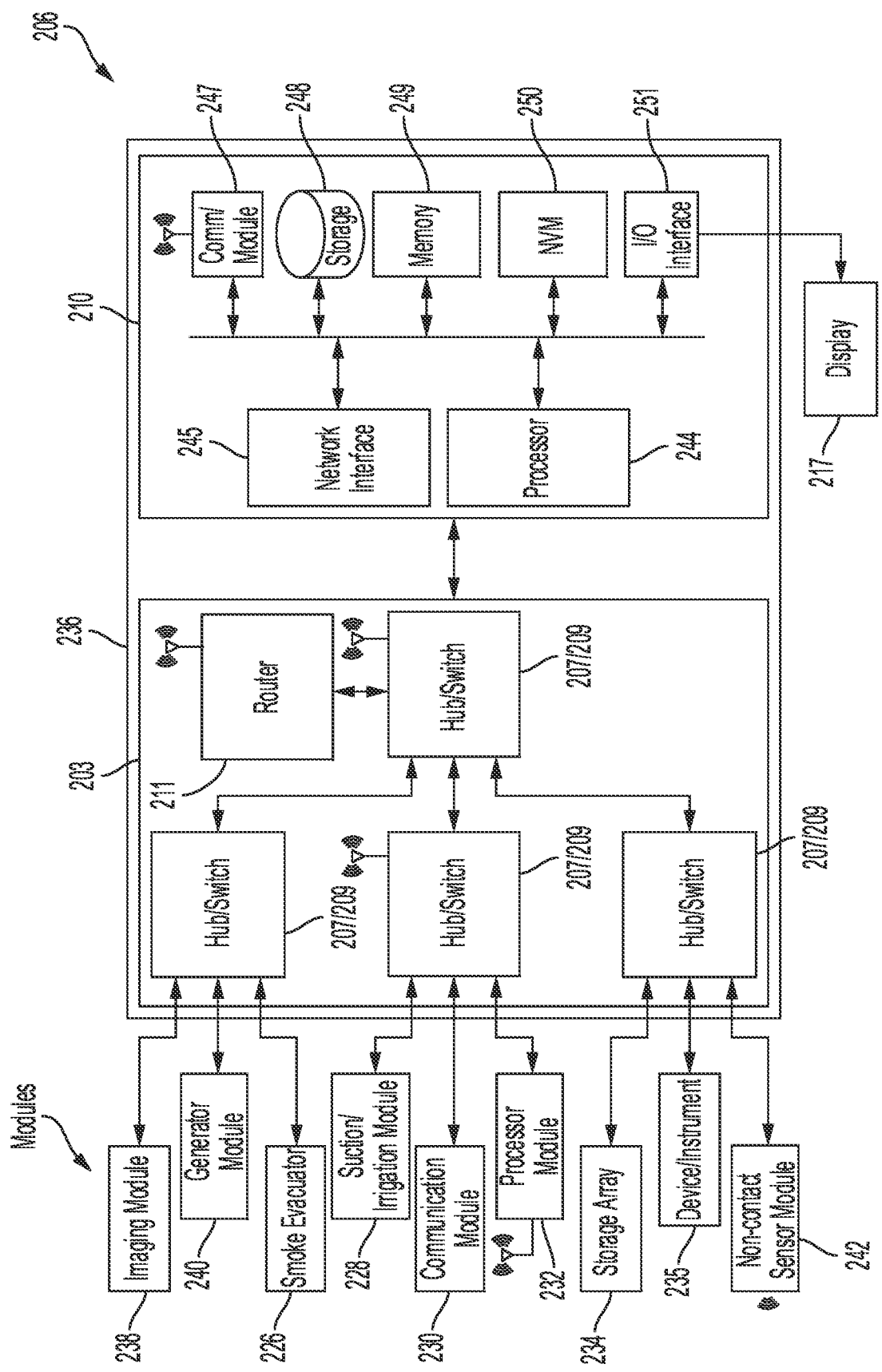
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
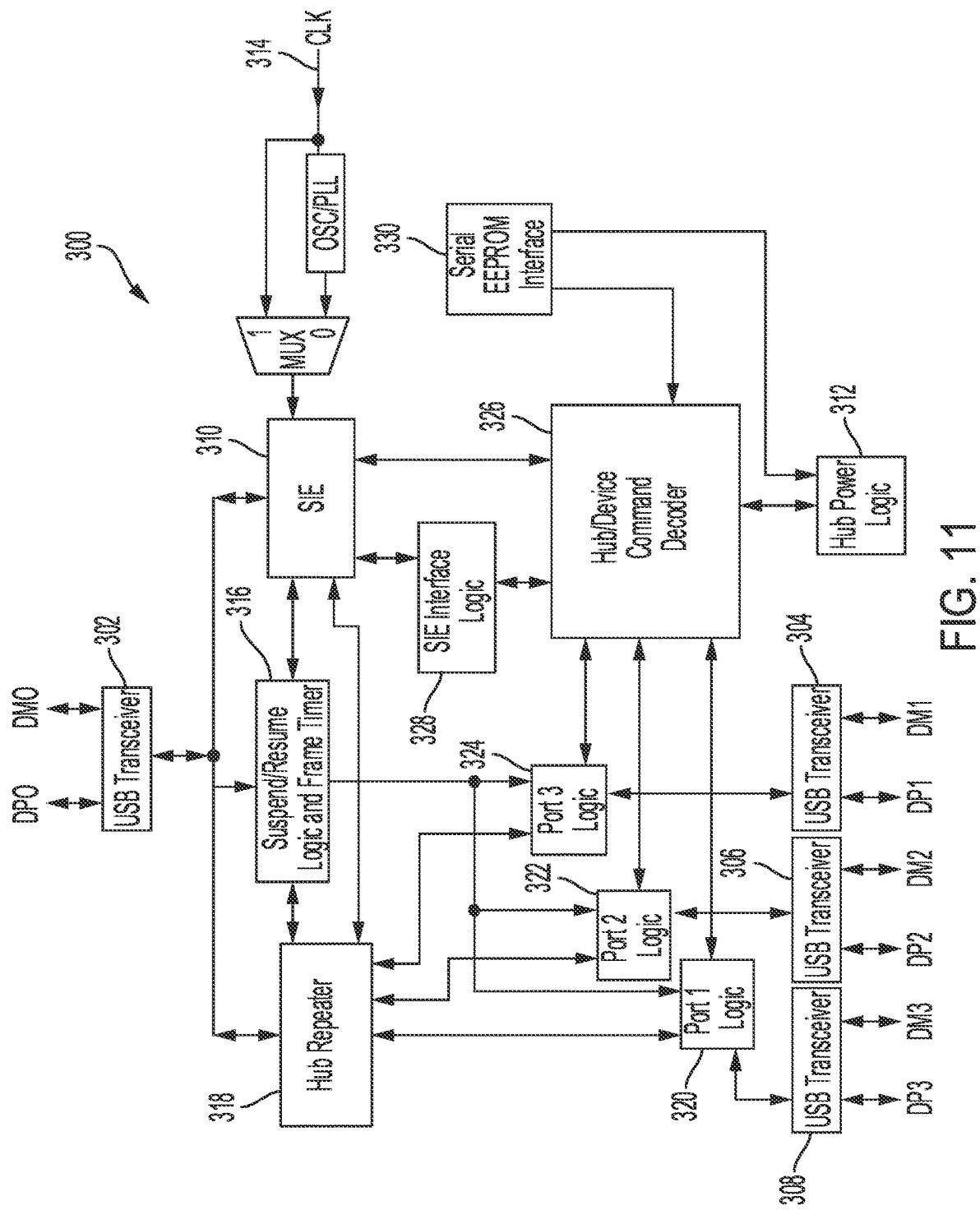
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
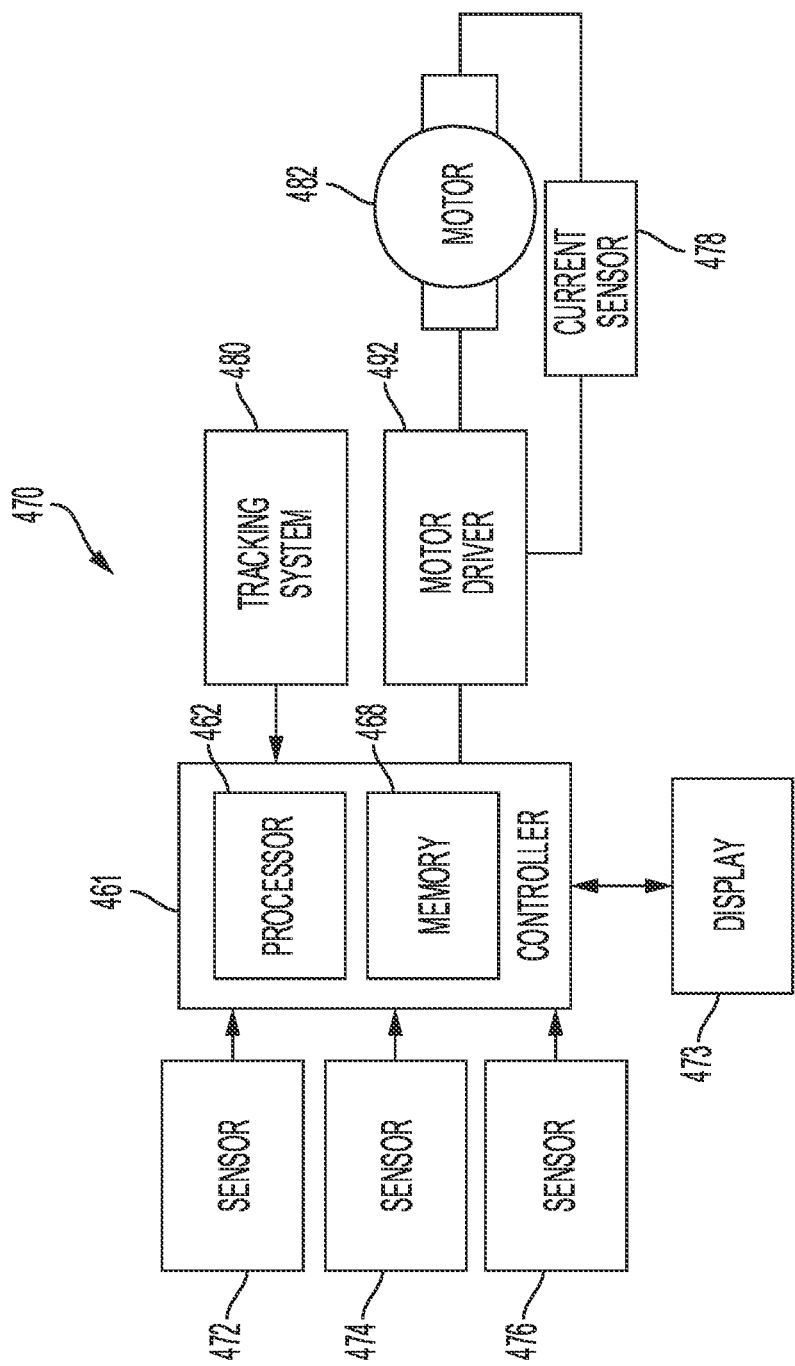
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive a clamp arm closure member. A tracking system 480 is configured to determine the position of the longitudinally movable displacement member. The position information is provided to the processor 462, which can be programmed or configured to determine the position of the longitudinally movable drive member as well as the position of the closure member. Additional motors may be provided at the tool driver interface to control closure tube travel, shaft rotation, articulation, or clamp arm closure, or a combination of the above. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife, articulation systems, clamp arm, or a combination of the above. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable battery cells. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a longitudinal displacement member to open and close a clamp arm, which can be adapted and configured to include a rack of drive teeth. In other aspects, the displacement member represents a clamp arm closure member configured to close and to open a clamp arm of a stapler, ultrasonic, or electrosurgical device, or combinations of the above. Accordingly, as used herein, the term displacement member is used generically to refer to any movable member of the surgical instrument or tool such as the drive member, the clamp arm, or any element that can be displaced. Accordingly, the absolute positioning system can, in effect, track the displacement of the clamp arm by tracking the linear displacement of the longitudinally movable drive member. In other aspects, the absolute positioning system can be configured to track the position of a clamp arm in the process of closing or opening. In various other aspects, the displacement member may be coupled to any position sensor 472 suitable for measuring linear displacement. Thus, the longitudinally movable drive member, or clamp arm, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member to open and close a clamp arm.

A single revolution of the sensor element associated with the position sensor 472 is equivalent to a longitudinal linear displacement $d_1$ of the displacement member, where $d_1$ is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement $d_1+d_2+ \ldots d_n$ of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertia, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil in a stapler or a clamp arm in an ultrasonic or electrosurgical instrument. The sensor 476, such as, for example, a load sensor, can measure the firing force applied to a closure member coupled to a clamp arm of the surgical instrument or tool or the force applied by a clamp arm to tissue located in the jaws of an ultrasonic or electrosurgical instrument. Alternatively, a current sensor 478 can be employed to measure the current drawn by the motor 482. The displacement member also may be configured to engage a clamp arm to open or close the clamp arm. The force sensor may be configured to measure the clamping force on tissue. The force required to advance the displacement member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A load sensor 476 can measure the force used to operate the clamp arm element, for example, to capture tissue between the clamp arm and an ultrasonic blade or to capture tissue between the clamp arm and a jaw of an electrosurgical instrument. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
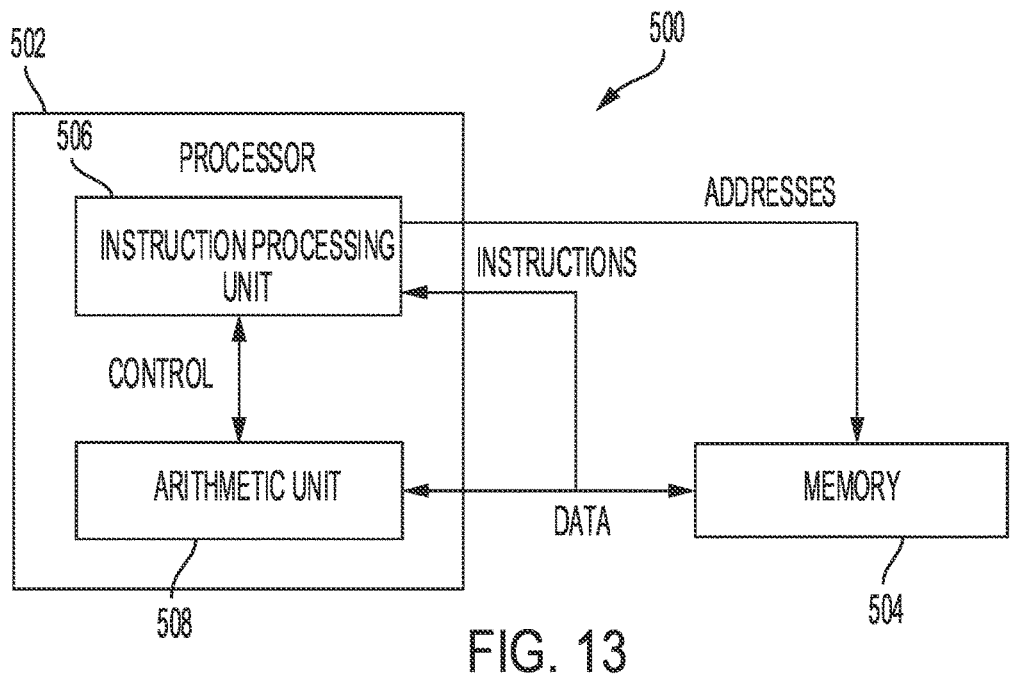
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
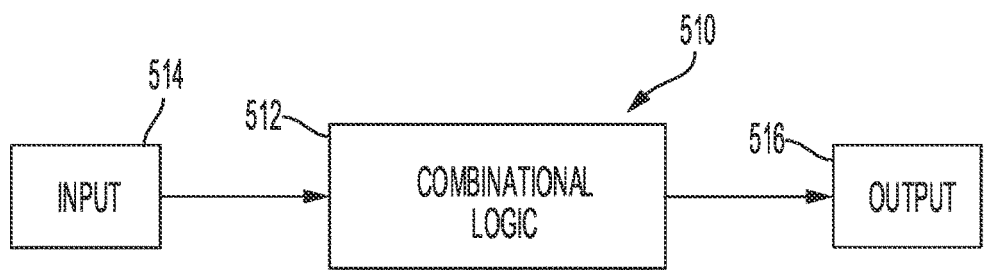
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
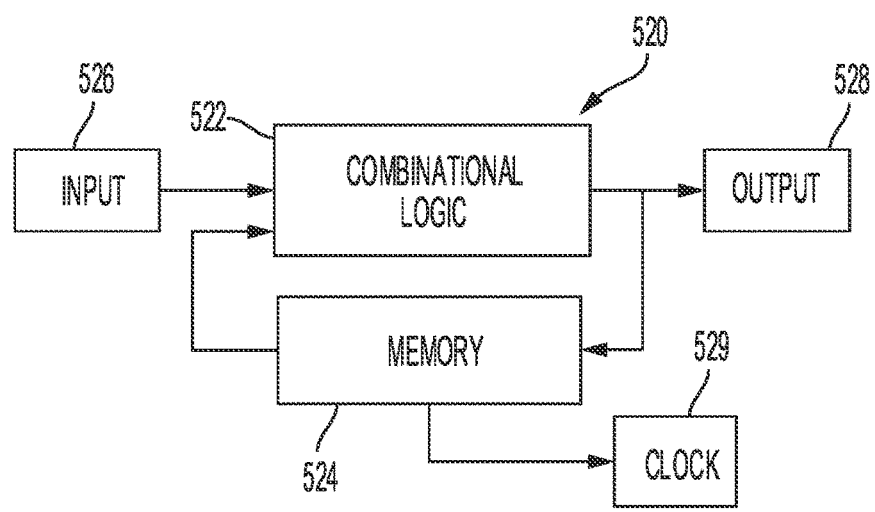
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
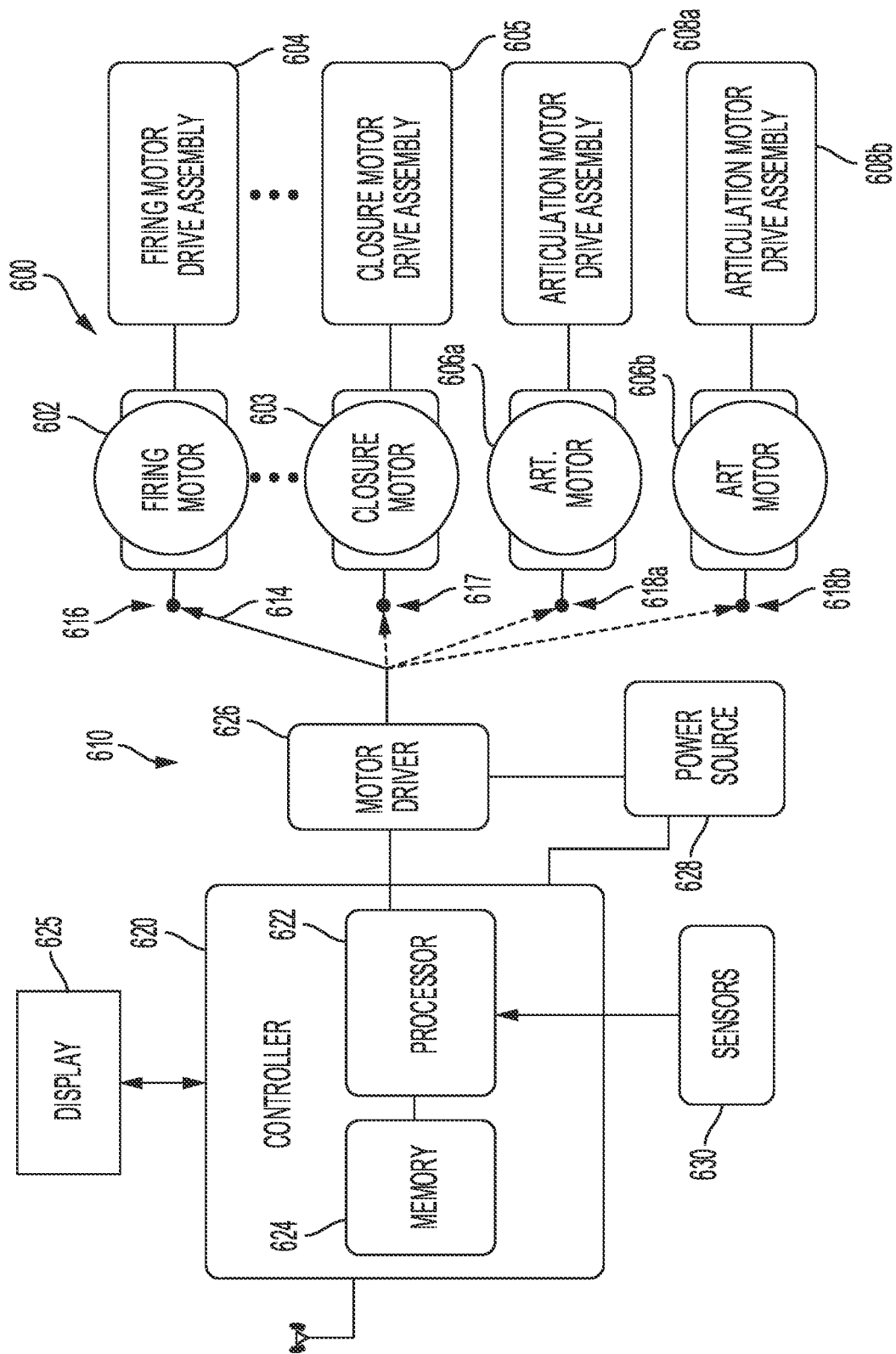
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the clamp arm closure member. The closure member may be retracted by reversing the direction of the motor 602, which also causes the clamp arm to open.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motor 603 may be operably coupled to a closure motor drive assembly 605 which can be configured to transmit closure motions, generated by the motor 603 to the end effector, in particular to displace a closure tube to close the clamp arm and compress tissue between the clamp arm and either an ultrasonic blade or jaw member of an electrosurgical device. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube or closure member to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example. In various aspects, the microcontroller 620 may communicate over a wired or wireless channel, or combinations thereof.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor 622 is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the closure member coupled to the clamp arm of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618*a*, 618*b*.

Figure 17:
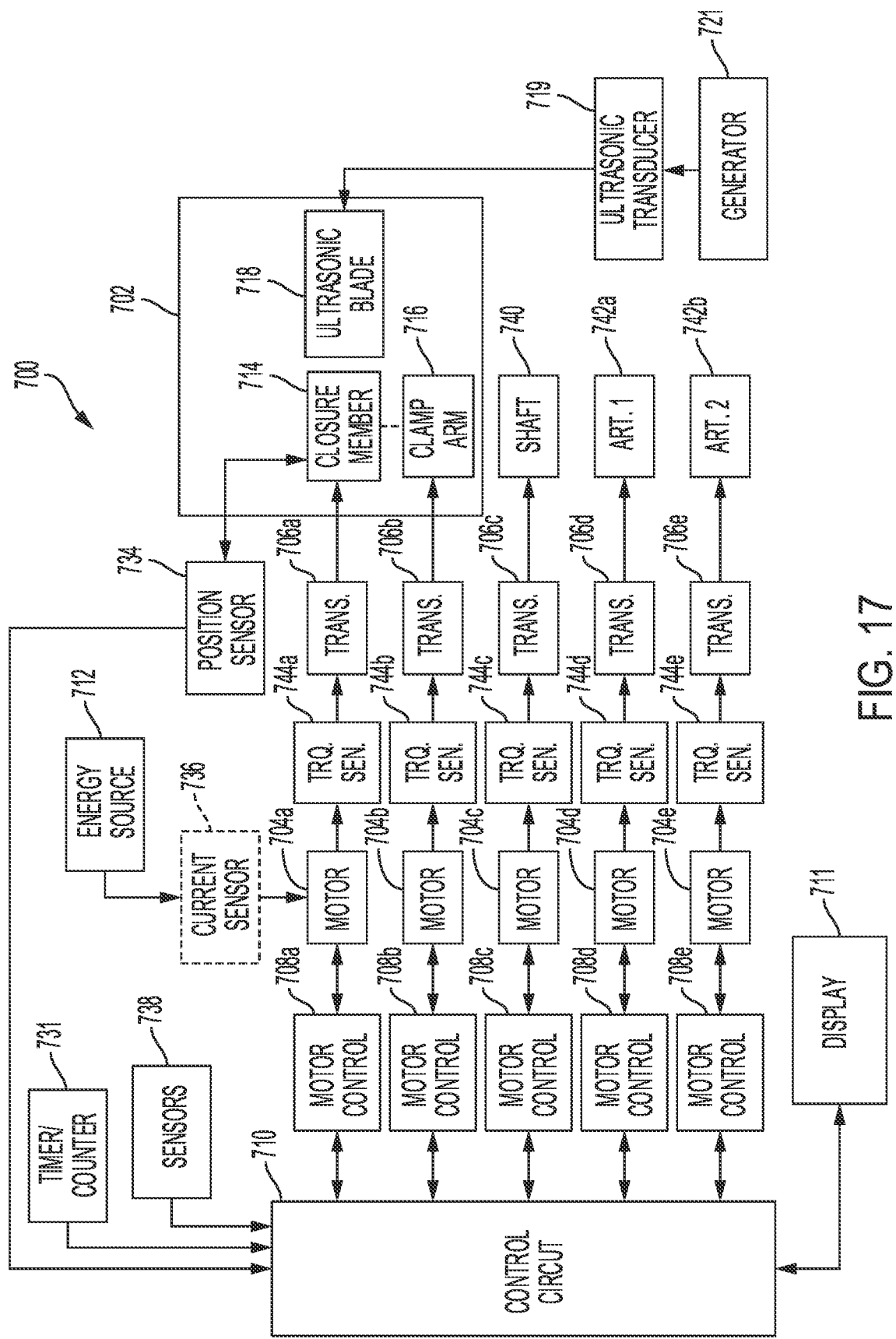
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, or one or more articulation members, or combinations thereof. The surgical instrument 700 comprises a control circuit 710 configured to control motor-driven firing members, closure members, shaft members, or one or more articulation members, or combinations thereof.

In one aspect, the robotic surgical instrument 700 comprises a control circuit 710 configured to control a clamp arm 716 and a closure member 714 portion of an end effector 702, an ultrasonic blade 718 coupled to an ultrasonic transducer 719 excited by an ultrasonic generator 721, a shaft 740, and one or more articulation members 742*a*, 742*b* via a plurality of motors 704*a*-704*e*. A position sensor 734 may be configured to provide position feedback of the closure member 714 to the control circuit 710. Other sensors 738 may be configured to provide feedback to the control circuit 710. A timer/counter 731 provides timing and counting information to the control circuit 710. An energy source 712 may be provided to operate the motors 704*a*-704*e*, and a current sensor 736 provides motor current feedback to the control circuit 710. The motors 704*a*-704*e* can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the closure member 714 as determined by the position sensor 734 with the output of the timer/counter 731 such that the control circuit 710 can determine the position of the closure member 714 at a specific time (t) relative to a starting position or the time (t) when the closure member 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the clamp arm 716. Other control programs control the rotation of the shaft 740 and the articulation members 742*a*, 742*b*.

In one aspect, the control circuit 710 may generate motor set point signals. The motor set point signals may be provided to various motor controllers 708*a*-708*e*. The motor controllers 708*a*-708*e* may comprise one or more circuits configured to provide motor drive signals to the motors 704*a*-704*e* to drive the motors 704*a*-704*e* as described herein. In some examples, the motors 704*a*-704*e* may be brushed DC electric motors. For example, the velocity of the motors 704*a*-704*e* may be proportional to the respective motor drive signals. In some examples, the motors 704*a*-704*e* may be brushless DC electric motors, and the respective motor drive signals may comprise a PWM signal provided to one or more stator windings of the motors 704*a*-704*e*. Also, in some examples, the motor controllers 708*a*-708*e* may be omitted and the control circuit 710 may generate the motor drive signals directly.

In one aspect, the control circuit 710 may initially operate each of the motors 704*a*-704*e* in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704*a*-704*e* during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704*a*-704*e* based on translation data describing a position of the displacement member in a closed-loop manner to translate the displacement member at a constant velocity.

In one aspect, the motors 704*a*-704*e* may receive power from an energy source 712. The energy source 712 may be a DC power supply driven by a main alternating current power source, a battery, a super capacitor, or any other suitable energy source. The motors 704*a*-704*e* may be mechanically coupled to individual movable mechanical elements such as the closure member 714, clamp arm 716, shaft 740, articulation 742*a*, and articulation 742*b* via respective transmissions 706*a*-706*e*. The transmissions 706*a*-706*e* may include one or more gears or other linkage components to couple the motors 704*a*-704*e* to movable mechanical elements. A position sensor 734 may sense a position of the closure member 714. The position sensor 734 may be or include any type of sensor that is capable of generating position data that indicate a position of the closure member 714. In some examples, the position sensor 734 may include an encoder configured to provide a series of pulses to the control circuit 710 as the closure member 714 translates distally and proximally. The control circuit 710 may track the pulses to determine the position of the closure member 714. Other suitable position sensors may be used, including, for example, a proximity sensor. Other types of position sensors may provide other signals indicating motion of the closure member 714. Also, in some examples, the position sensor 734 may be omitted. Where any of the motors 704a-704e is a stepper motor, the control circuit 710 may track the position of the closure member 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the closure member 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the closure member 714. The transmission 706a comprises movable mechanical elements such as rotating elements and a firing member to control the movement of the closure member 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the closure member 714. A position sensor 734 may be configured to provide the position of the closure member 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the closure member 714 translates distally, the clamp arm 716 closes towards the ultrasonic blade 718.

In one aspect, the control circuit 710 is configured to drive a closure member such as the clamp arm 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the clamp arm 716. The transmission 706b comprises movable mechanical elements such as rotating elements and a closure member to control the movement of the clamp arm 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the clamp arm 716. The position sensor 734 may be configured to provide the position of the closure member as a feedback signal to the control circuit 710. Additional sensors 738 in the end effector 702 may provide the closure force feedback signal to the control circuit 710. The pivotable clamp arm 716 is positioned opposite the ultrasonic blade 718. When ready to use, the control circuit 710 may provide a closure signal to the motor control 708b. In response to the closure signal, the motor 704b advances a closure member to grasp tissue between the clamp arm 716 and the ultrasonic blade 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702 ±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-

704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the clamp arm 716 to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the ultrasonic blade 718 has tissue on it, and (4) the load and position on both articulation rods.

In one aspect, the one or more sensors 738 may comprise a strain gauge, such as a micro-strain gauge, configured to measure the magnitude of the strain in the clamp arm 716 during a clamped condition. The strain gauge provides an electrical signal whose amplitude varies with the magnitude of the strain. The sensors 738 may comprise a pressure sensor configured to detect a pressure generated by the presence of compressed tissue between the clamp arm 716 and the ultrasonic blade 718. The sensors 738 may be configured to detect impedance of a tissue section located between the clamp arm 716 and the ultrasonic blade 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the clamp arm 716 by the closure drive system. For example, one or more sensors 738 can be at an interaction point between the closure tube and the clamp arm 716 to detect the closure forces applied by the closure tube to the clamp arm 716. The forces exerted on the clamp arm 716 can be representative of the tissue compression experienced by the tissue section captured between the clamp arm 716 and the ultrasonic blade 718. The one or more sensors 738 can be positioned at various interaction points along the closure drive system to detect the closure forces applied to the clamp arm 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the clamp arm 716.

In one aspect, a current sensor 736 can be employed to measure the current drawn by each of the motors 704a-704e. The force required to advance any of the movable mechanical elements such as the closure member 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move the closure member 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECHNIQUES FOR ROBOTIC SURGICAL INSTRUMENT, filed Jun. 29, 2017, which is herein incorporated by reference in its entirety.

Figure 18:
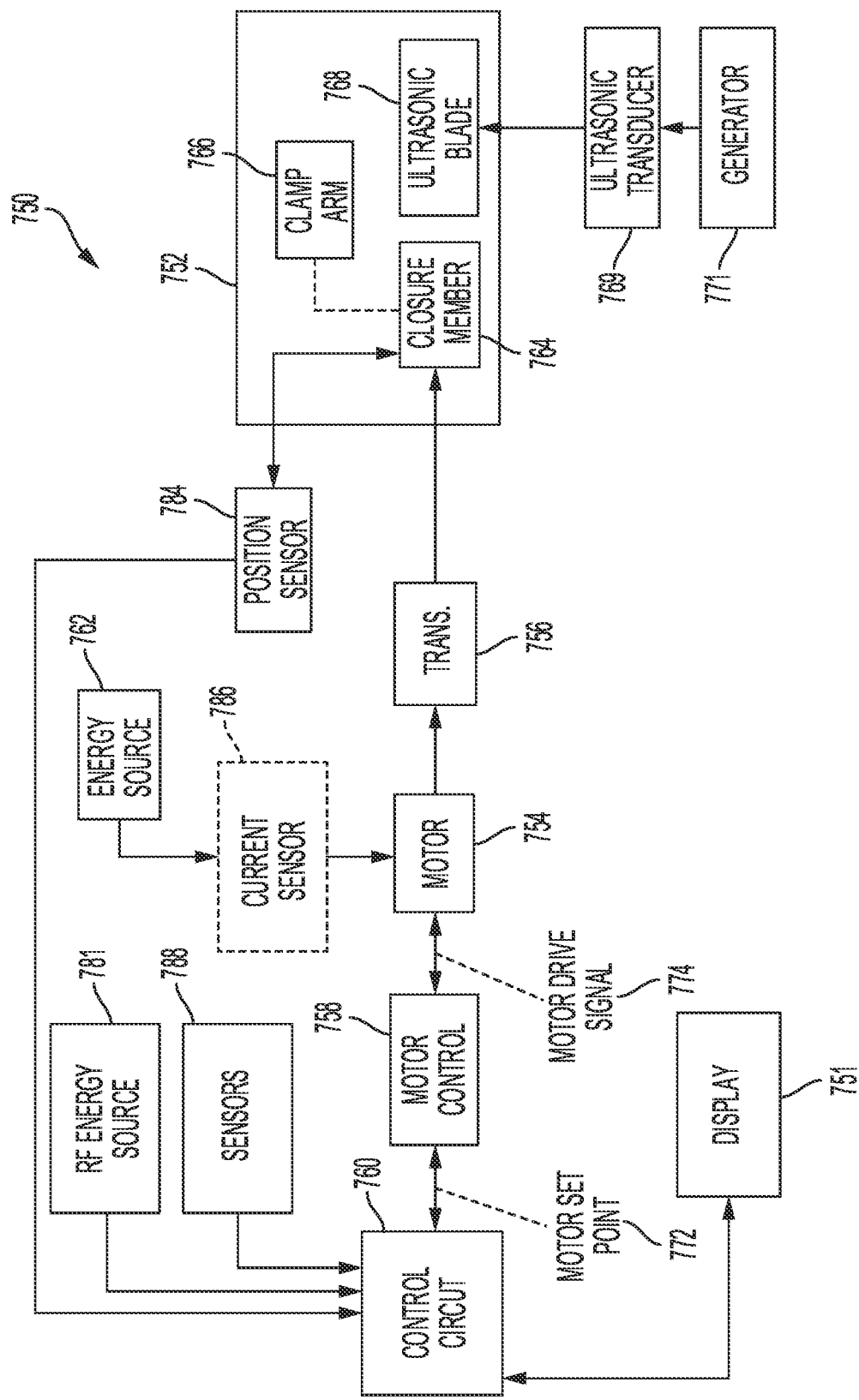
FIG. 18 illustrates a block diagram of a surgical instrument programmed to control the distal translation of a displacement member, in accordance with at least one aspect of the present disclosure.

FIG. 18 illustrates a schematic diagram of a surgical instrument 750 configured to control the distal translation of a displacement member according to one aspect of this disclosure. In one aspect, the surgical instrument 750 is programmed to control the distal translation of a displacement member such as the closure member 764. The surgical instrument 750 comprises an end effector 752 that may comprise a clamp arm 766, a closure member 764, and an ultrasonic blade 768 coupled to an ultrasonic transducer 769 driven by an ultrasonic generator 771.

The position, movement, displacement, and/or translation of a linear displacement member, such as the closure member 764, can be measured by an absolute positioning system, sensor arrangement, and position sensor 784. Because the closure member 764 is coupled to a longitudinally movable drive member, the position of the closure member 764 can be determined by measuring the position of the longitudinally movable drive member employing the position sensor 784. Accordingly, in the following description, the position, displacement, and/or translation of the closure member 764 can be achieved by the position sensor 784 as described herein. A control circuit 760 may be programmed to control the translation of the displacement member, such as the closure member 764. The control circuit 760, in some examples, may comprise one or more microcontrollers, microprocessors, or other suitable processors for executing instructions that cause the processor or processors to control the displacement member, e.g., the closure member 764, in the manner described. In one aspect, a timer/counter 781 provides an output signal, such as the elapsed time or a digital count, to the control circuit 760 to correlate the position of the closure member 764 as determined by the position sensor 784 with the output of the timer/counter 781 such that the control circuit 760 can determine the position of the closure member 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the closure member 764 via a transmission 756. The transmission 756 may include one or more gears or other linkage components to couple the motor 754 to the closure member 764. A position sensor 784 may sense a position of the closure member 764. The position sensor 784 may be or include any type of sensor that is capable of generating position data that indicate a position of the closure member 764. In some examples, the position sensor 784 may include an encoder configured to provide a series of pulses to the control circuit 760 as the closure member 764 translates distally and proximally. The control circuit 760 may track the pulses to determine the position of the closure member 764. Other suitable position sensors may be used, including, for example, a proximity sensor. Other types of position sensors may provide other signals indicating motion of the closure member 764. Also, in some examples, the position sensor 784 may be omitted. Where the motor 754 is a stepper motor, the control circuit 760 may track the position of the closure member 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the clamp arm 766 during a clamped condition. The strain gauge provides an electrical signal whose amplitude varies with the magnitude of the strain. The sensors 788 may comprise a pressure sensor configured to detect a pressure generated by the presence of compressed tissue between the clamp arm 766 and the ultrasonic blade 768. The sensors 788 may be configured to detect impedance of a tissue section located between the clamp arm 766 and the ultrasonic blade 768 that is indicative of the thickness and/or fullness of tissue located therebetween.

The sensors 788 may be is configured to measure forces exerted on the clamp arm 766 by a closure drive system. For example, one or more sensors 788 can be at an interaction point between a closure tube and the clamp arm 766 to detect the closure forces applied by a closure tube to the clamp arm 766. The forces exerted on the clamp arm 766 can be representative of the tissue compression experienced by the tissue section captured between the clamp arm 766 and the ultrasonic blade 768. The one or more sensors 788 can be positioned at various interaction points along the closure drive system to detect the closure forces applied to the clamp arm 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the clamp arm 766.

A current sensor 786 can be employed to measure the current drawn by the motor 754. The force required to advance the closure member 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move a closure member 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or closure member 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical sealing and cutting implements. For example, a motor 754 may drive a displacement member distally and proximally along a longitudinal axis of the end effector 752. The end effector 752 may comprise a pivotable clamp arm 766 and, when configured for use, an ultrasonic blade 768 positioned opposite the clamp arm 766. A clinician may grasp tissue between the clamp arm 766 and the ultrasonic blade 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, the closure member 764 with a cutting element positioned at a distal end, may cut the tissue between the ultrasonic blade 768 and the clamp arm 766.

In various examples, the surgical instrument 750 may comprise a control circuit 760 programmed to control the distal translation of the displacement member, such as the closure member 764, for example, based on one or more tissue conditions. The control circuit 760 may be programmed to sense tissue conditions, such as thickness, either directly or indirectly, as described herein. The control circuit 760 may be programmed to select a control program based on tissue conditions. A control program may describe the distal motion of the displacement member. Different control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
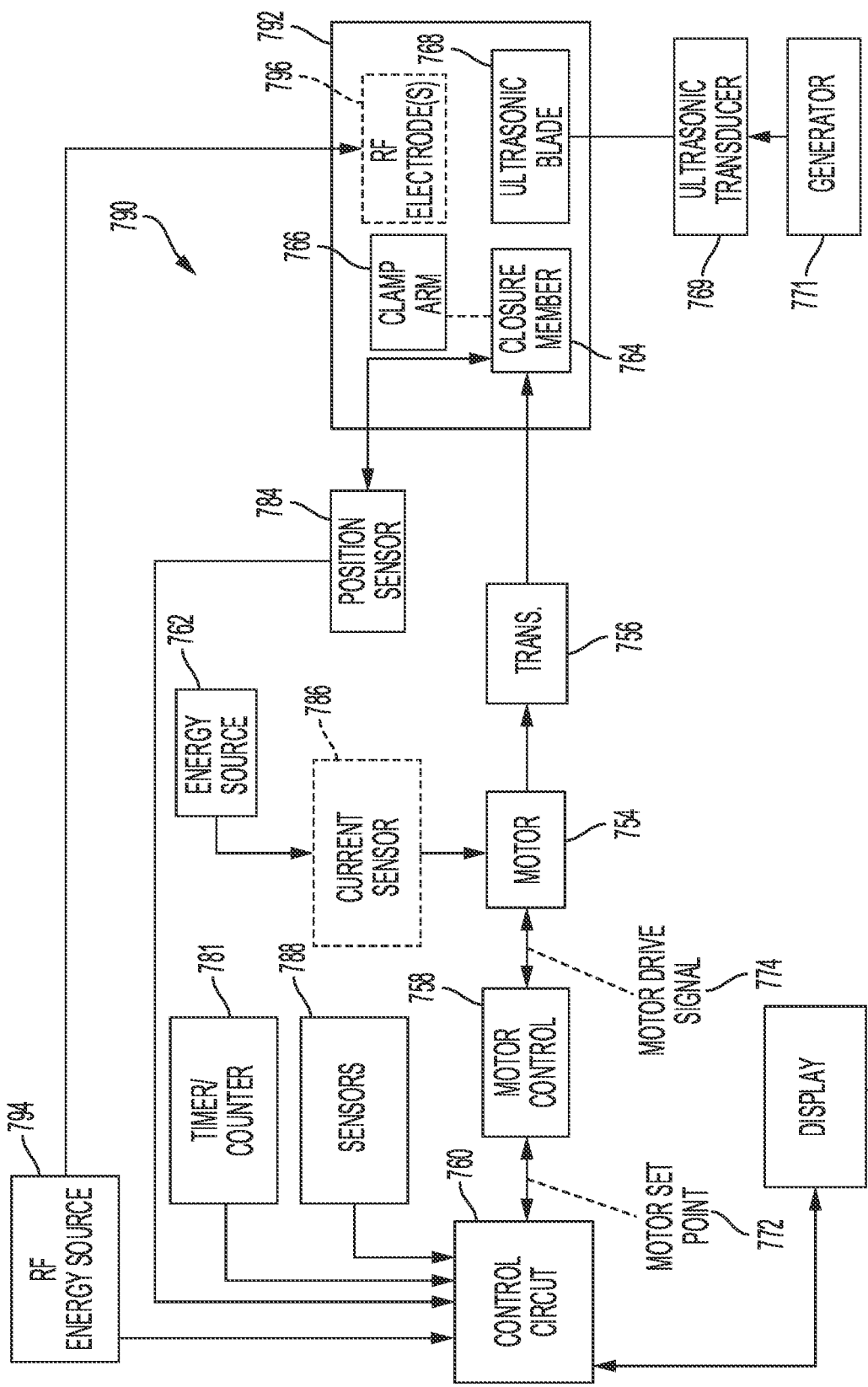
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the closure member 764. The surgical instrument 790 comprises an end effector 792 that may comprise a clamp arm 766, a closure member 764, and an ultrasonic blade 768 which may be interchanged with or work in conjunction with one or more RF electrodes 796 (shown in dashed line). The ultrasonic blade 768 is coupled to an ultrasonic transducer 769 driven by an ultrasonic generator 771.

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In some examples, the position sensor 784 may be omitted. Where the motor 754 is a stepper motor, the control circuit 760 may track the position of the closure member 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

An RF energy source 794 is coupled to the end effector 792 and is applied to the RF electrode 796 when the RF electrode 796 is provided in the end effector 792 in place of the ultrasonic blade 768 or to work in conjunction with the ultrasonic blade 768. For example, the ultrasonic blade is made of electrically conductive metal and may be employed as the return path for electrosurgical RF current. The control circuit 760 controls the delivery of the RF energy to the RF electrode 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Generator Hardware

In various aspects smart ultrasonic energy devices may comprise adaptive algorithms to control the operation of the ultrasonic blade. In one aspect, the ultrasonic blade adaptive control algorithms are configured to identify tissue type and adjust device parameters. In one aspect, the ultrasonic blade control algorithms are configured to parameterize tissue type. An algorithm to detect the collagen/elastic ratio of tissue to tune the amplitude of the distal tip of the ultrasonic blade is described in the following section of the present disclosure. Various aspects of smart ultrasonic energy devices are described herein in connection with FIGS. 12-19, for example. Accordingly, the following description of adaptive ultrasonic blade control algorithms should be read in conjunction with FIGS. 12-19 and the description associated therewith.

In certain surgical procedures it would be desirable to employ adaptive ultrasonic blade control algorithms. In one aspect, adaptive ultrasonic blade control algorithms may be employed to adjust the parameters of the ultrasonic device based on the type of tissue in contact with the ultrasonic blade. In one aspect, the parameters of the ultrasonic device may be adjusted based on the location of the tissue within the jaws of the ultrasonic end effector, for example, the location of the tissue between the clamp arm and the ultrasonic blade. The impedance of the ultrasonic transducer may be employed to differentiate what percentage of the tissue is located in the distal or proximal end of the end effector. The reactions of the ultrasonic device may be based on the tissue type or compressibility of the tissue. In another aspect, the parameters of the ultrasonic device may be adjusted based on the identified tissue type or parameterization. For example, the mechanical displacement amplitude of the distal tip of the ultrasonic blade may be tuned based on the ration of collagen to elastin tissue detected during the tissue identification procedure. The ratio of collagen to elastin tissue may be detected used a variety of techniques including infrared (IR) surface reflectance and emissivity. The force applied to the tissue by the clamp arm and/or the stroke of the clamp arm to produce gap and compression. Electrical continuity across a jaw equipped with electrodes may be employed to determine what percentage of the jaw is covered with tissue.

Figure 20:
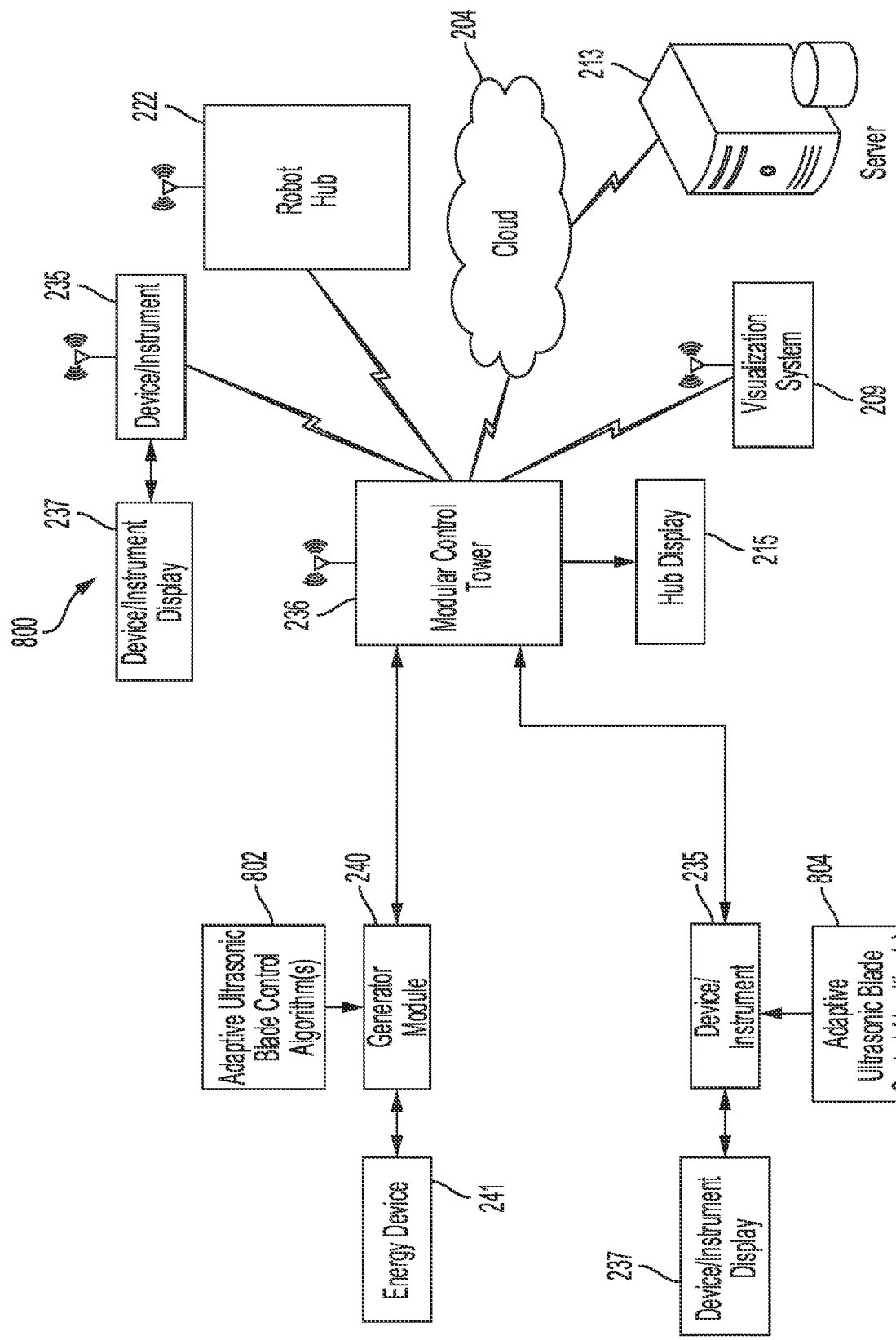
FIG. 20 is a system configured to execute adaptive ultrasonic blade control algorithms in a surgical data network comprising a modular communication hub, in accordance with at least one aspect of the present disclosure.

FIG. 20 is a system 800 configured to execute adaptive ultrasonic blade control algorithms in a surgical data network comprising a modular communication hub, in accordance with at least one aspect of the present disclosure. In one aspect, the generator module 240 is configured to execute the adaptive ultrasonic blade control algorithm(s) 802. In another aspect, the device/instrument 235 is configured to execute the adaptive ultrasonic blade control algorithm(s) 804. In another aspect, both the generator module 240 and the device/instrument 235 are configured to execute the adaptive ultrasonic blade control algorithms 802, 804.

The generator module 240 may comprise a patient isolated stage in communication with a non-isolated stage via a power transformer. A secondary winding of the power transformer is contained in the isolated stage and may comprise a tapped configuration (e.g., a center-tapped or a non-center-tapped configuration) to define drive signal outputs for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, the drive signal outputs may output an ultrasonic drive signal (e.g., a 420V root-mean-square (RMS) drive signal) to an ultrasonic surgical instrument 241, and the drive signal outputs may output an RF electrosurgical drive signal (e.g., a 100V RMS drive signal) to an RF electrosurgical instrument 241. Aspects of the generator module 240 are described herein with reference to FIGS. 21-22.

The generator module 240 or the device/instrument 235 or both are coupled the modular control tower 236 connected to multiple operating theater devices such as, for example, intelligent surgical instruments, robots, and other computerized devices located in the operating theater, as described with reference to FIGS. 8-11, for example.

Figure 21:
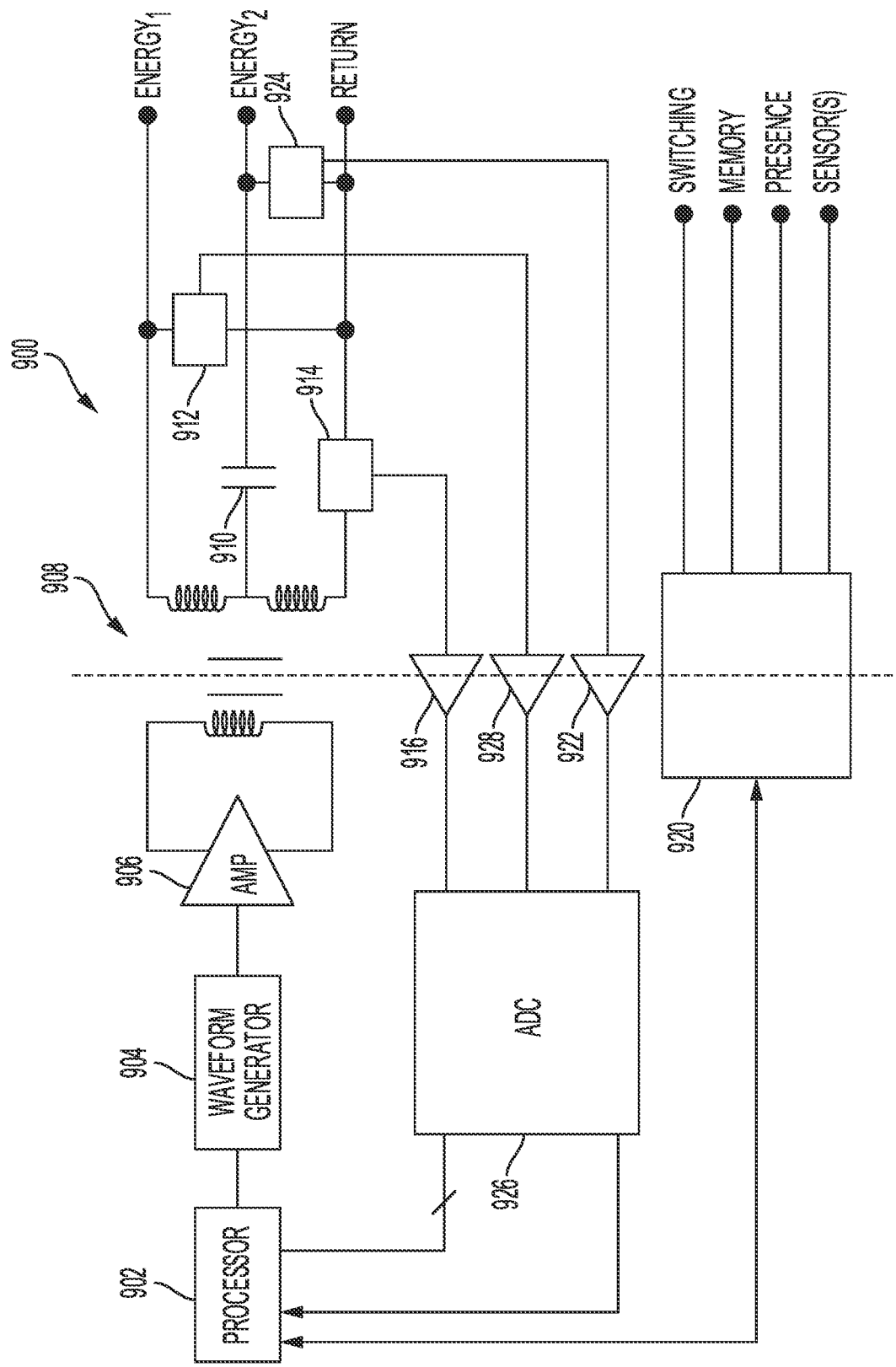
FIG. 21 illustrates an example of a generator, in accordance with at least one aspect of the present disclosure.

FIG. 21 illustrates an example of a generator 900, which is one form of a generator configured to couple to an ultrasonic instrument and further configured to execute adaptive ultrasonic blade control algorithms in a surgical data network comprising a modular communication hub as shown in FIG. 20. The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled $ENERGY_1$ and RETURN. A second signal of a second energy modality is coupled across a capacitor 910 and is provided to the surgical instrument between the terminals labeled $ENERGY_2$ and RETURN. It will be appreciated that more than two energy modalities may be output and thus the subscript "n" may be used to designate that up to n $ENERGY_n$ terminals may be provided, where n is a positive integer greater than 1. It also will be appreciated that up to "n" return paths $RETURN_n$ may be provided without departing from the scope of the present disclosure.

A first voltage sensing circuit 912 is coupled across the terminals labeled $ENERGY_1$ and the RETURN path to measure the output voltage therebetween. A second voltage sensing circuit 924 is coupled across the terminals labeled $ENERGY_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled $ENERGY_1$/RETURN or the second voltage sensing circuit 924 coupled across the terminals labeled $ENERGY_2$/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality $ENERGY_1$ may be ultrasonic energy and the second energy modality $ENERGY_2$ may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths $RETURN_n$ may be provided for each energy modality $ENERGY_n$. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled $ENERGY_1$ and RETURN as shown in FIG. 21. In one example, a connection of RF bipolar electrodes to the generator 900 output would be preferably located between the output labeled $ENERGY_2$ and RETURN. In the case of monopolar output, the preferred connections would be active electrode (e.g., pencil or other probe) to the $ENERGY_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 22:
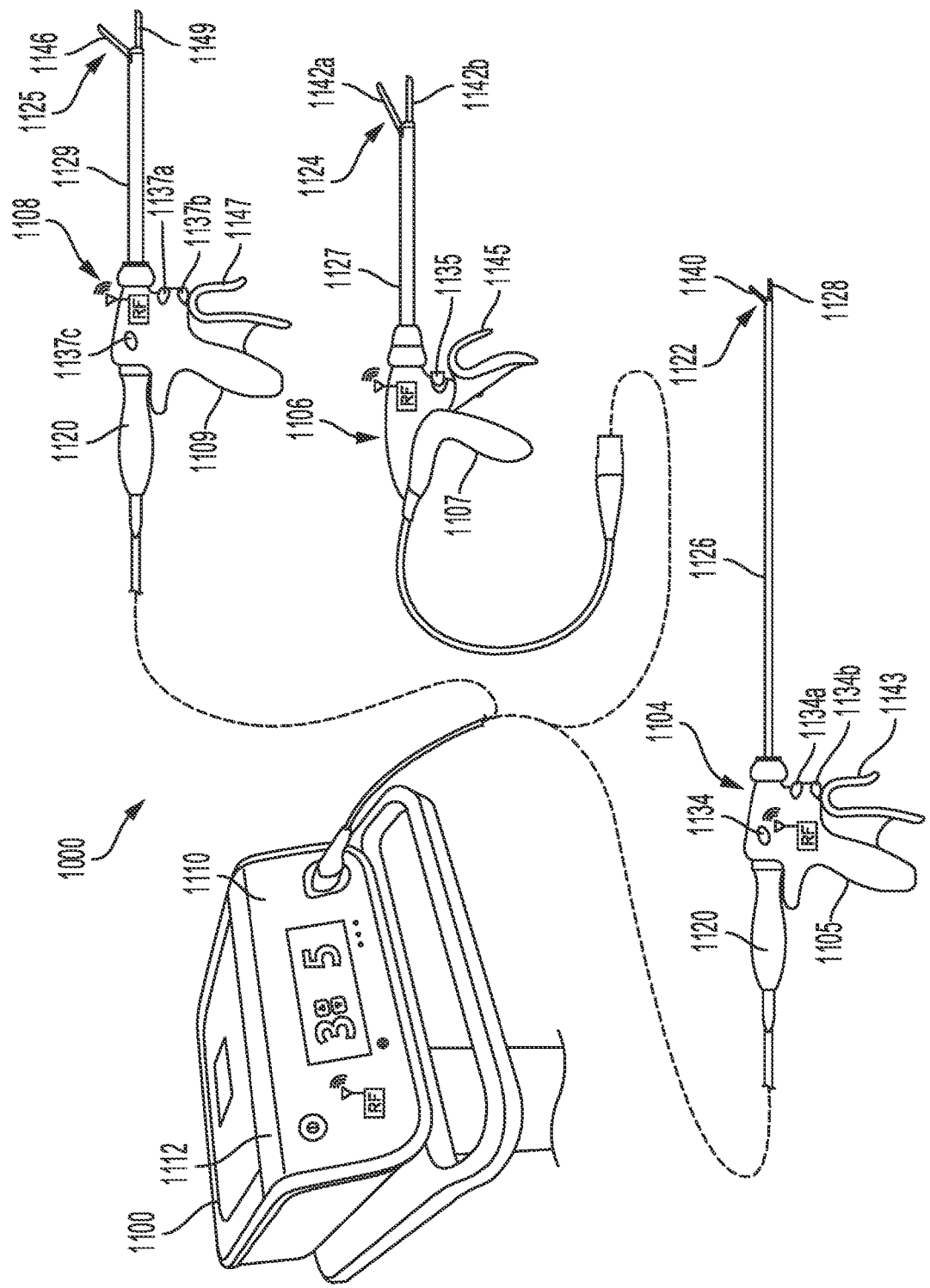
FIG. 22 is a surgical system comprising a generator and various surgical instruments usable therewith, in accordance with at least one aspect of the present disclosure.

FIG. 22 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 22 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1134a, 1134b, 1134c to energize and drive the ultrasonic blade 1128 or other function. The toggle buttons 1134a, 1134b, 1134c can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124. The end effector 1124 comprises electrodes in clamp arms 1142a, 1142b and return through an electrical conductor portion of the shaft 1127. The electrodes are coupled to and energized by a bipolar energy source within the generator 1100. The handpiece 1107 comprises a trigger 1145 to operate the clamp arms 1142a, 1142b and an energy button 1135 to actuate an energy switch to energize the electrodes in the end effector 1124.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 1137a, 1137b, 1137c to energize and drive the ultrasonic blade 1149 or other function. The toggle buttons 1137a, 1137b, 1137c can be configured to energize the ultrasonic transducer 1120 with the generator 1100 and energize the ultrasonic blade 1149 with a bipolar energy source also contained within the generator 1100.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 22 the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator

1100. The generator 1100 also may comprise one or more output devices 1112. Further aspects of generators for digitally generating electrical signal waveforms and surgical instruments are described in US patent publication US-2017-0086914-A1, which is herein incorporated by reference in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 23:
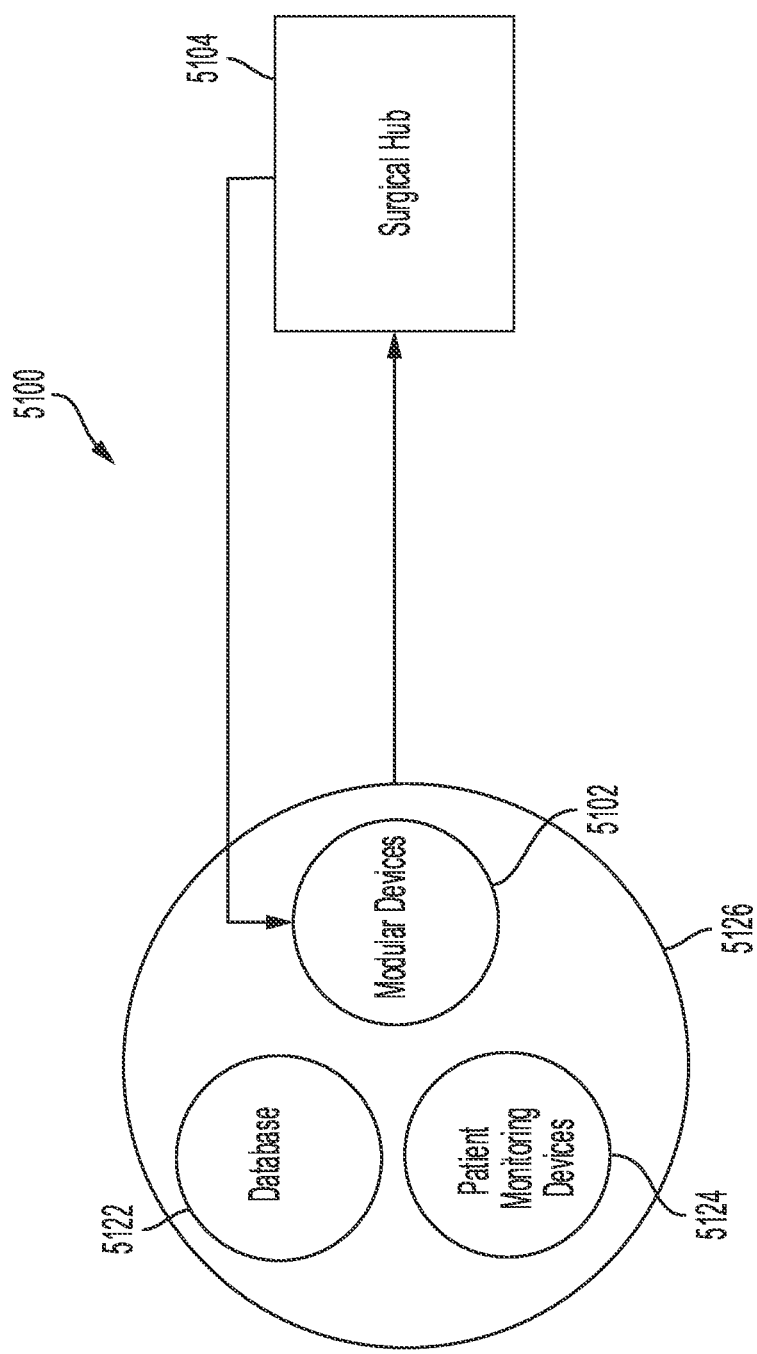
FIG. 23 is a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 23 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure (scanned by a scanner, for example) and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-11, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 24-30. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIGS. 3 and 4. The modular energy system 2000 can also include a variety of different components or accessories that are also connectable to or otherwise associatable with the modules 2001. In another aspect, the modular energy system 2000 can be embodied as a generator module 140, 240 (FIGS. 3 and 10) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 24:
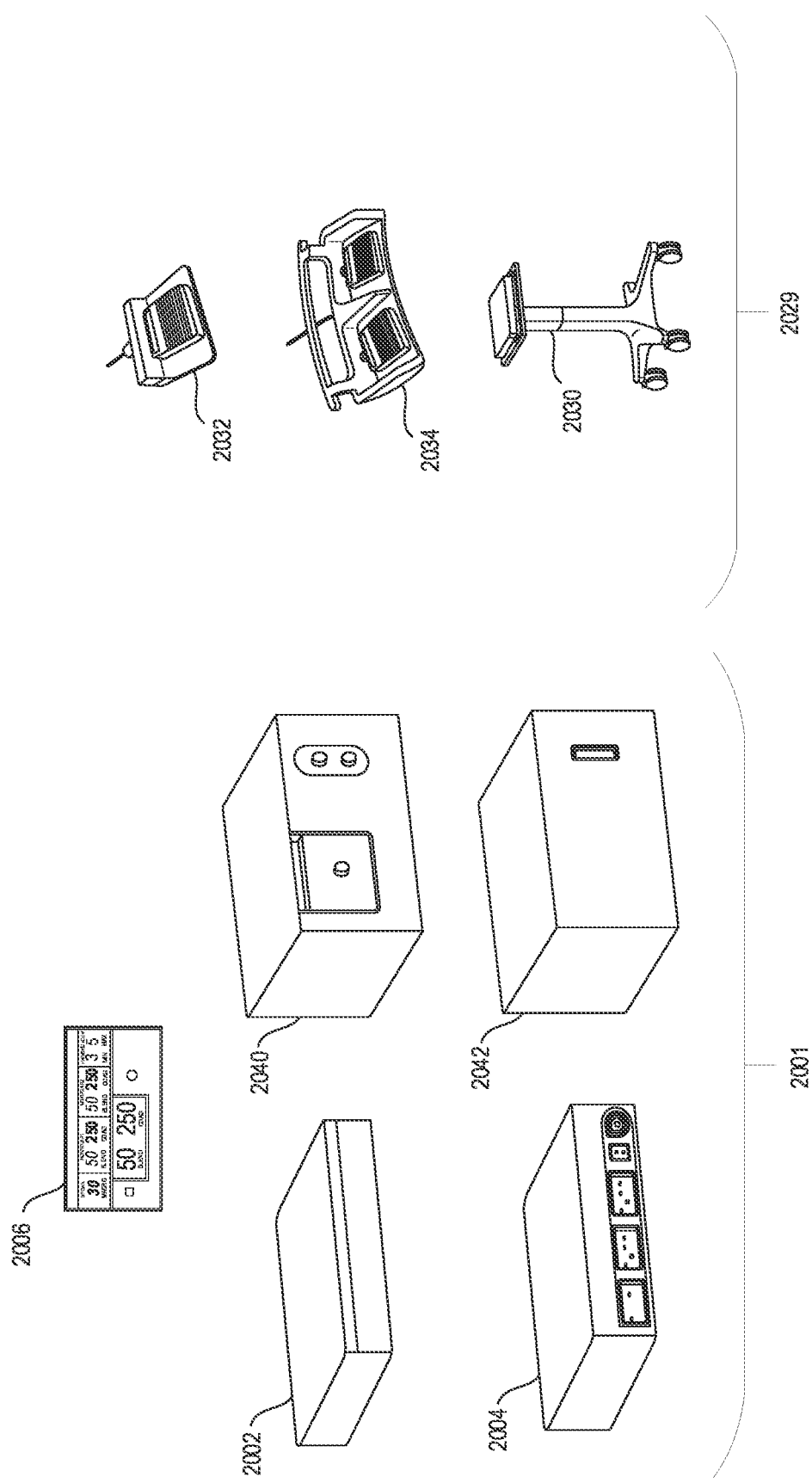
FIG. 24 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 24. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140, 240 (FIGS. 3 and 10), can be configured to generate one or multiple energy modalities for driving electrosurgical and/or ultrasonic surgical instruments connected thereto, such as is described above in connection with the generator 900 illustrated in FIG. 21. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-11.

Figure 25B:
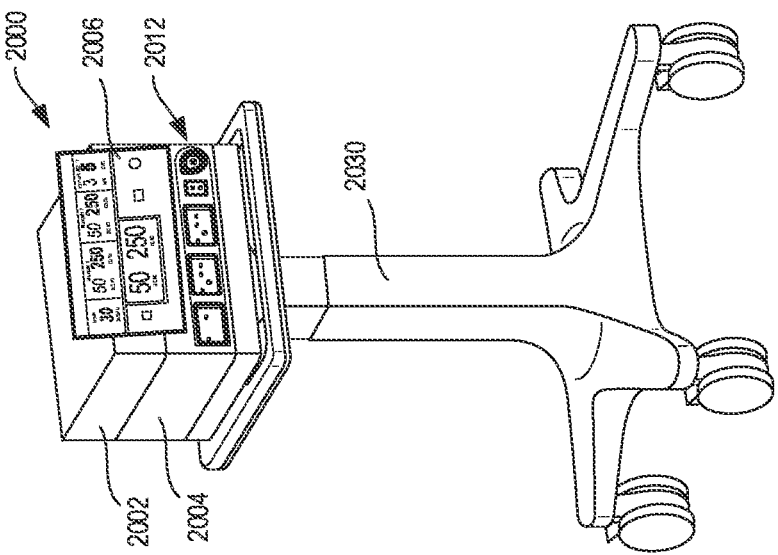
FIG. 25B is the modular energy system shown in FIG. 25A mounted to a cart, in accordance with at least one aspect of the present disclosure.
Figure 25A:
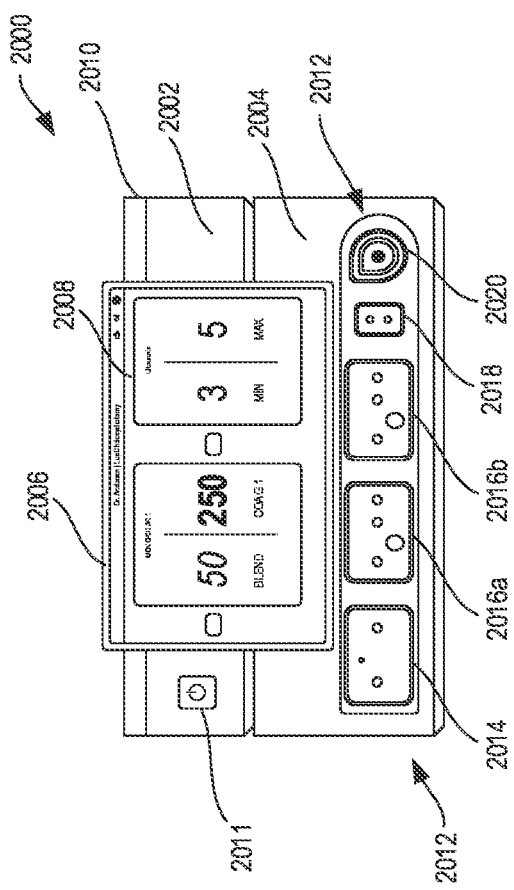
FIG. 25A is a first illustrative modular energy system configuration including a header module and a display screen that renders a graphical user interface (GUI) for relaying information regarding modules connected to the header module, in accordance with at least one aspect of the present disclosure.
Figure 29:
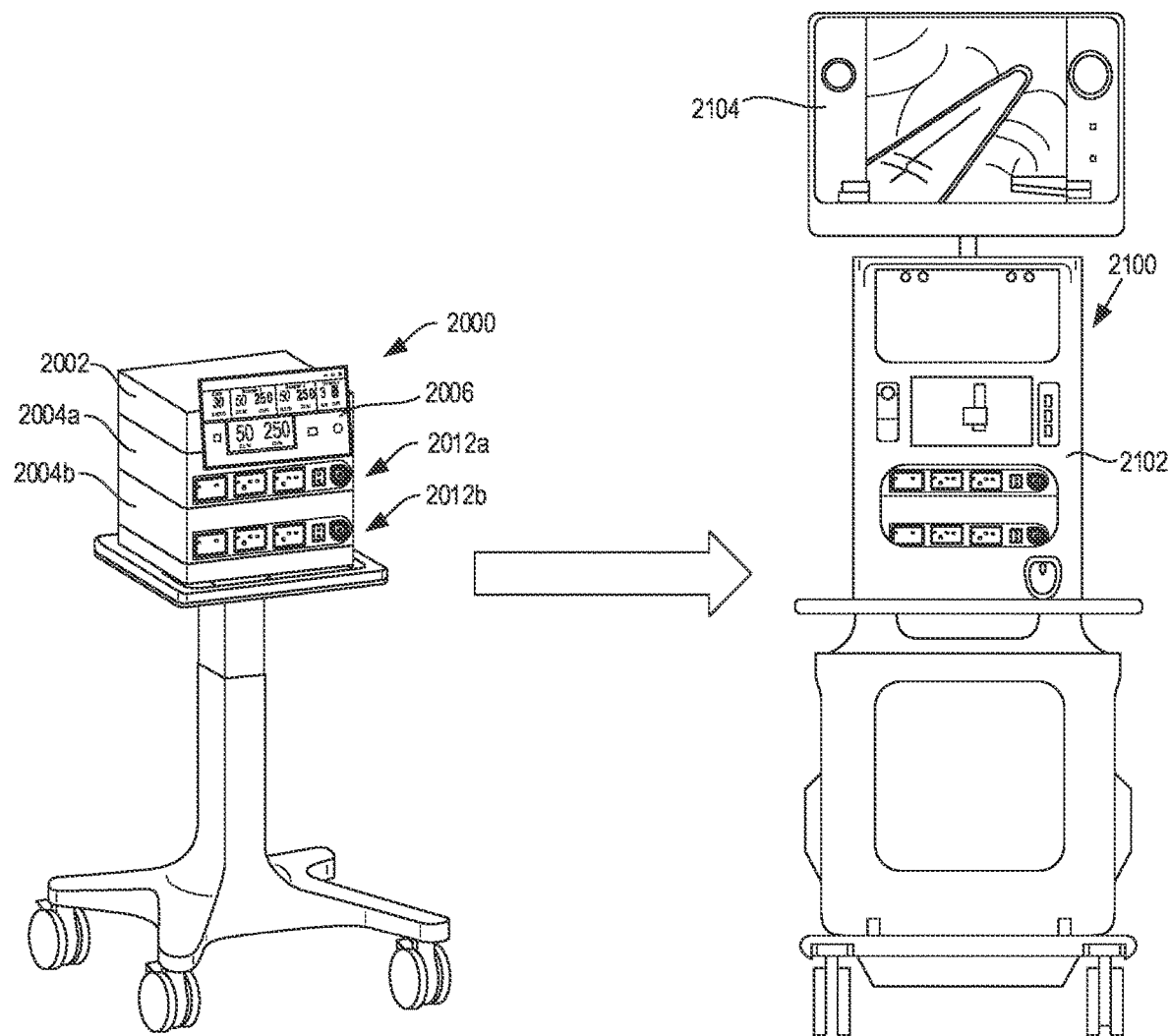
FIG. 29 is a diagram of a modular energy system including communicably connectable surgical platforms, in accordance with at least one aspect of the present disclosure.

Referring now to FIG. 25A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 30. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 29. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 25A, the energy module 2004 can include a port assembly 2012 including a number of different ports configured to deliver different energy modalities to corresponding surgical instruments that are connectable thereto. In the particular aspect illustrated in FIGS. 24-30, the port assembly 2012 includes a bipolar port 2014, a first monopolar port 2016a, a second monopolar port 2018b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 25A and 25B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 26A:
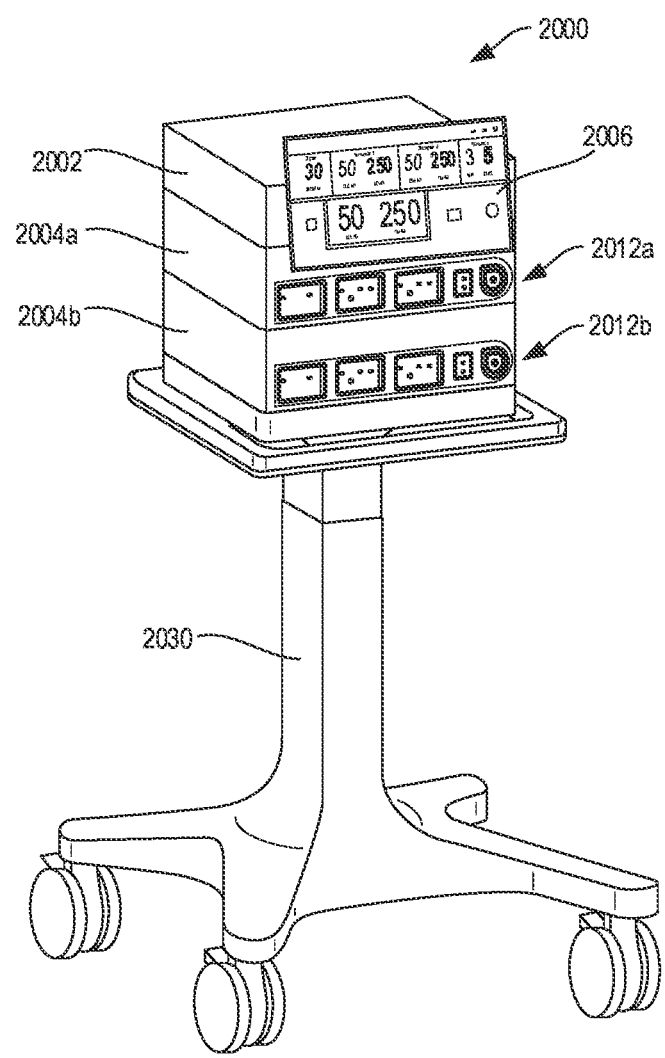
FIG. 26A is a second illustrative modular energy system configuration including a header module, a display screen, an energy module, and an expanded energy module connected together and mounted to a cart, in accordance with at least one aspect of the present disclosure.
Figure 26B:
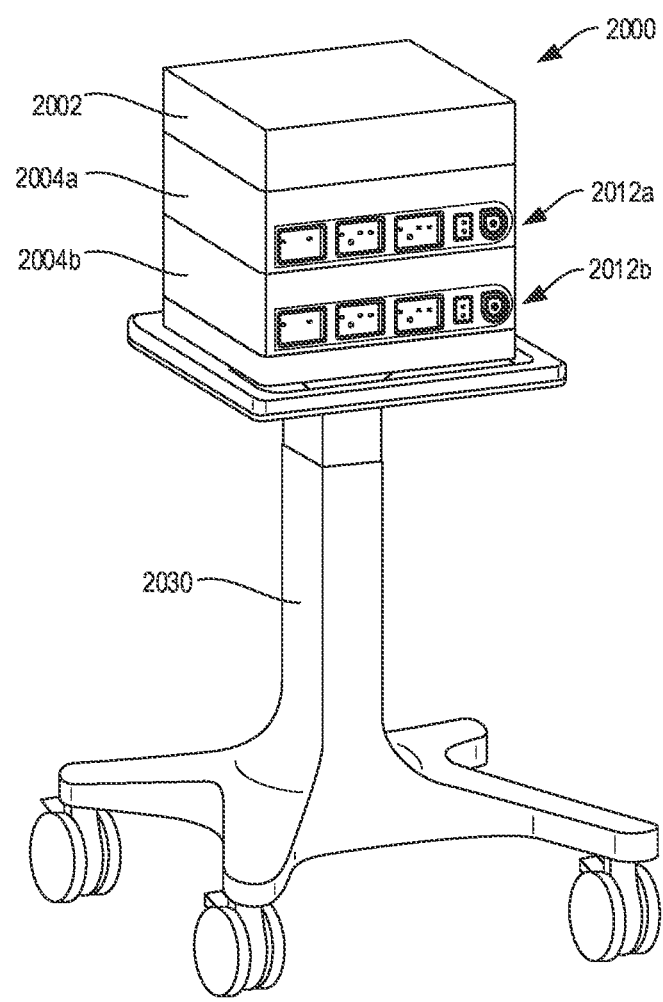
FIG. 26B is a third illustrative modular energy system configuration that is similar to the second configuration shown in FIG. 25A, except that the header module lacks a display screen, in accordance with at least one aspect of the present disclosure.

FIG. 26A illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 26B illustrates a third illustrative configuration that is similar to the second configuration, except that the header module 2002 lacks a display screen 2006. This configuration can be suitable for robotic surgical applications or mobile display applications, as noted above.

Figure 27:
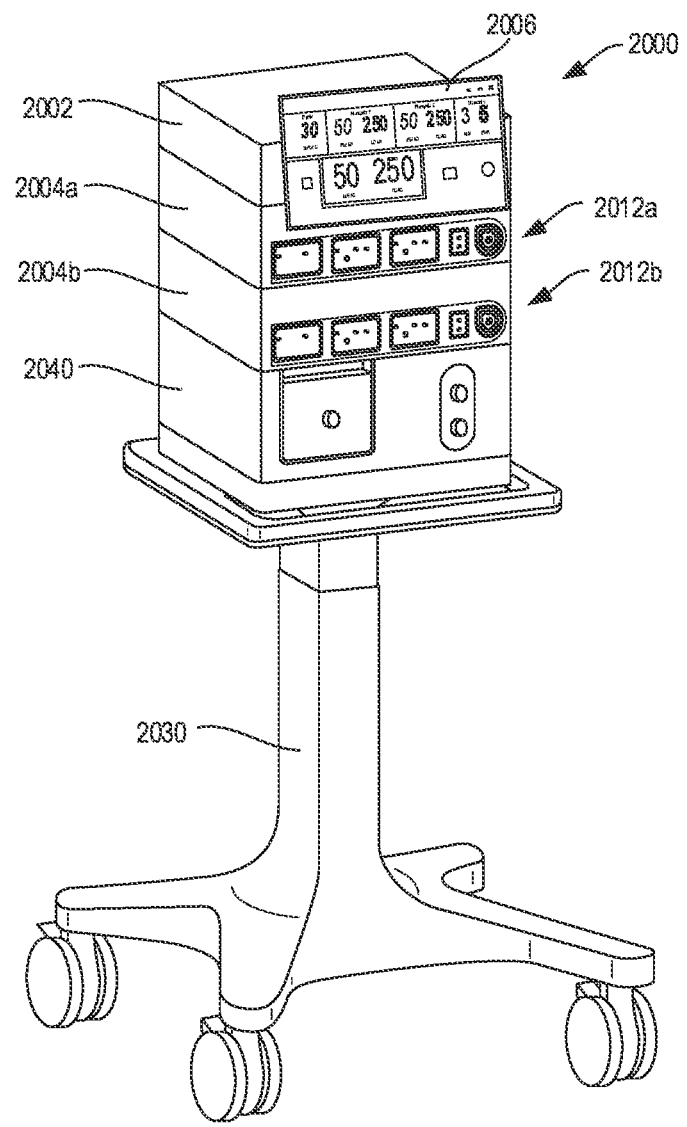
FIG. 27 is a fourth illustrative modular energy system configuration including a header module, a display screen, an energy module, an expanded energy module, and a technology module connected together and mounted to a cart, in accordance with at least one aspect of the present disclosure.

FIG. 27 illustrates a fourth illustrative configuration of the modular energy system 2000 including a header module 2002 (including a display screen 2006), a first energy module 2004a, a second energy module 2004b, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

Figure 28:
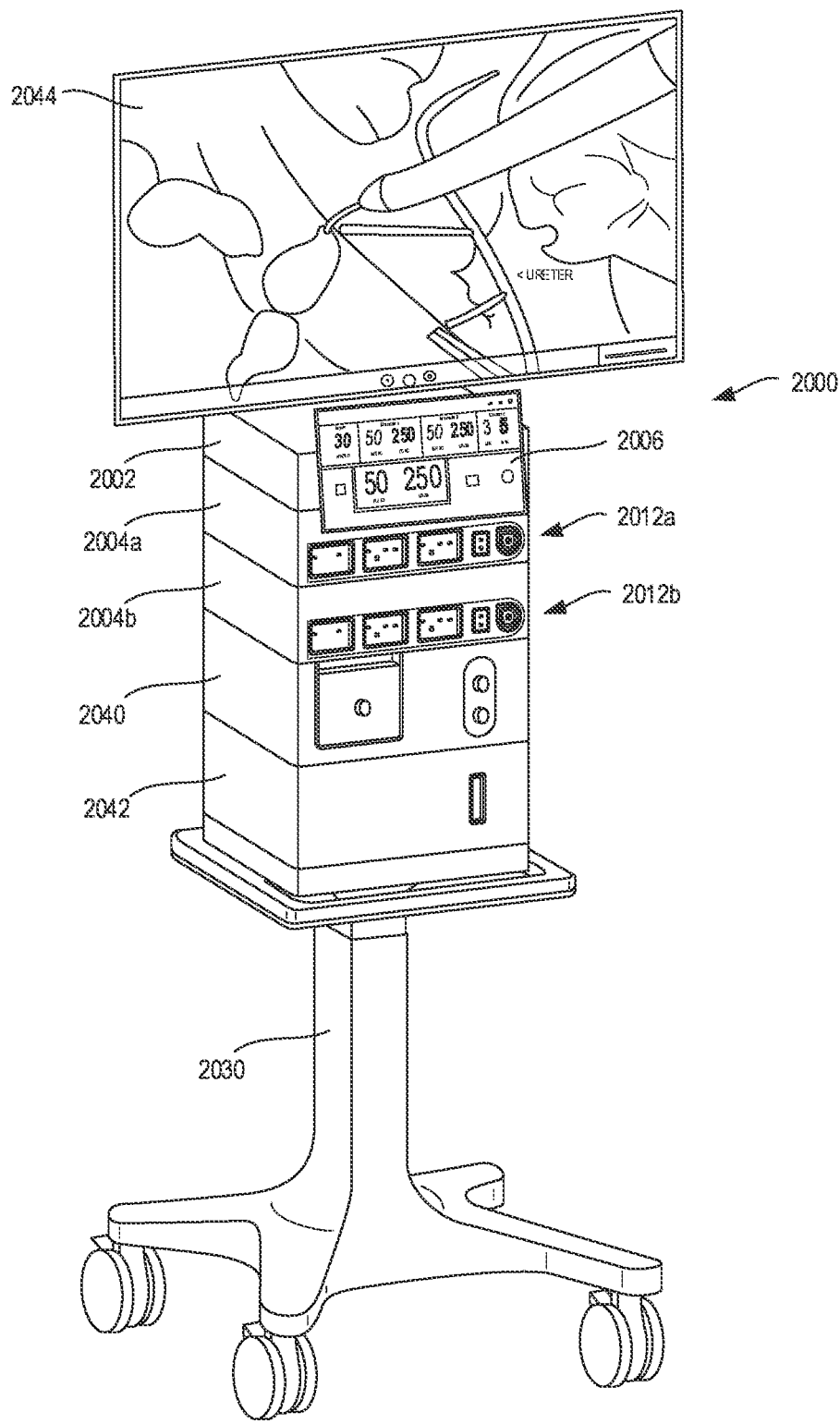
FIG. 28 is a fifth illustrative modular energy system configuration including a header module, a display screen, an energy module, an expanded energy module, a technology module, and a visualization module connected together and mounted to a cart, in accordance with at least one aspect of the present disclosure.

FIG. 28 illustrates a fifth illustrative configuration of the modular energy system 2000 including a header module 2002 (including a display screen 2006), a first energy module 2004a, a second energy module 2004b, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 25A-29 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 29. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems (e.g., a visualization system 108 and/or a robotic system 110 as described in connection with FIGS. 1 and 2).

Figure 30:
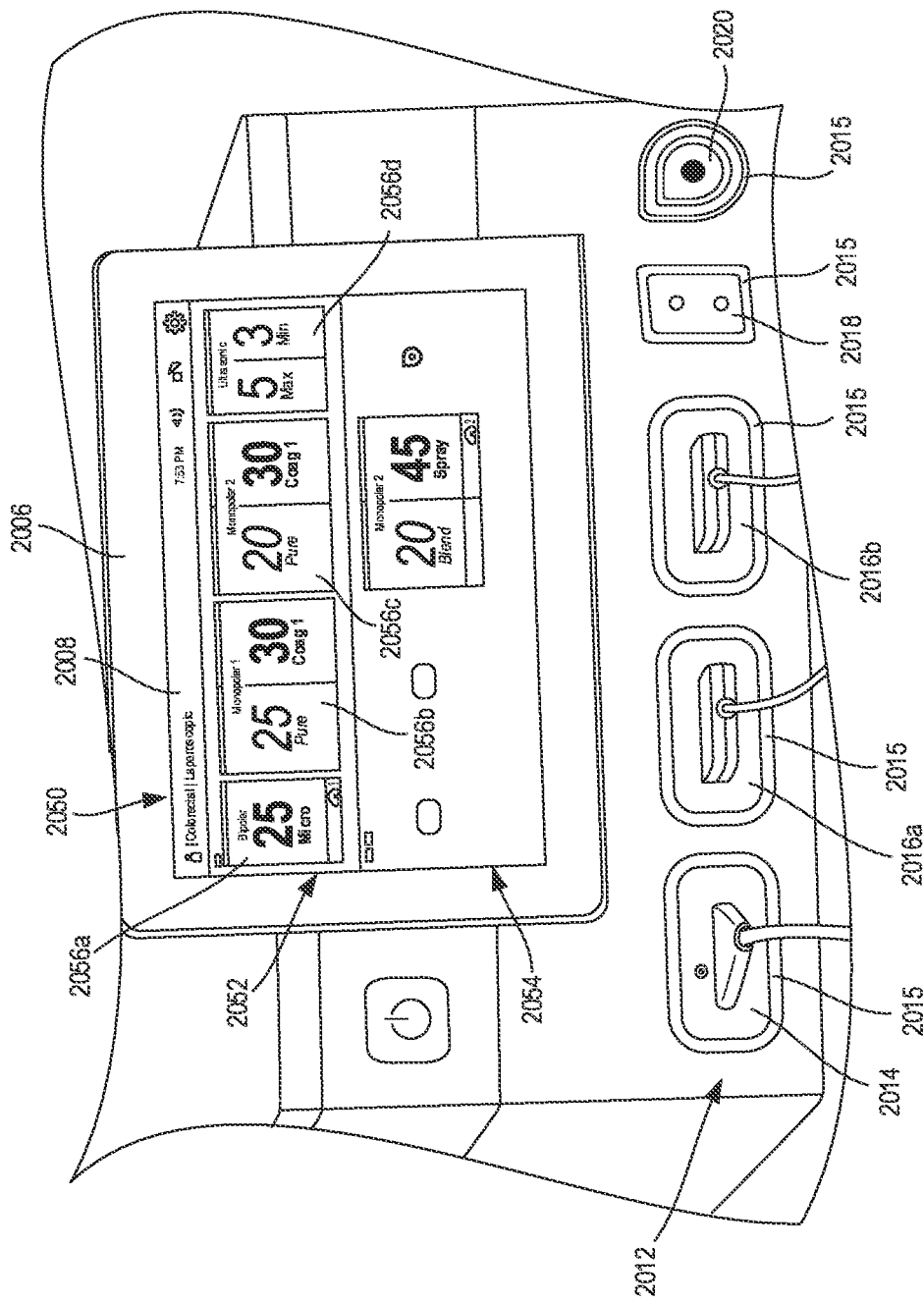
FIG. 30 is a perspective view of a header module of a modular energy system including a user interface, in accordance with at least one aspect of the present disclosure.

Referring now to FIG. 30, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 30, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056a corresponding to the bipolar port 2014, a second widget 2056b corresponding to the first monopolar port 2016a, a third widget 2056c corresponding to the second monopolar port 2016b, and a fourth widget 2056d corresponding to the combination energy port 2020. Each of these widgets 2056a-d provides data related to its corresponding port of the port assembly 2012 and controls for controlling the modes and other features of the energy modality delivered by the energy module 2004 through the respective port of the port assembly 2012. For example, the widgets 2056a-d can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the activation of each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 31:
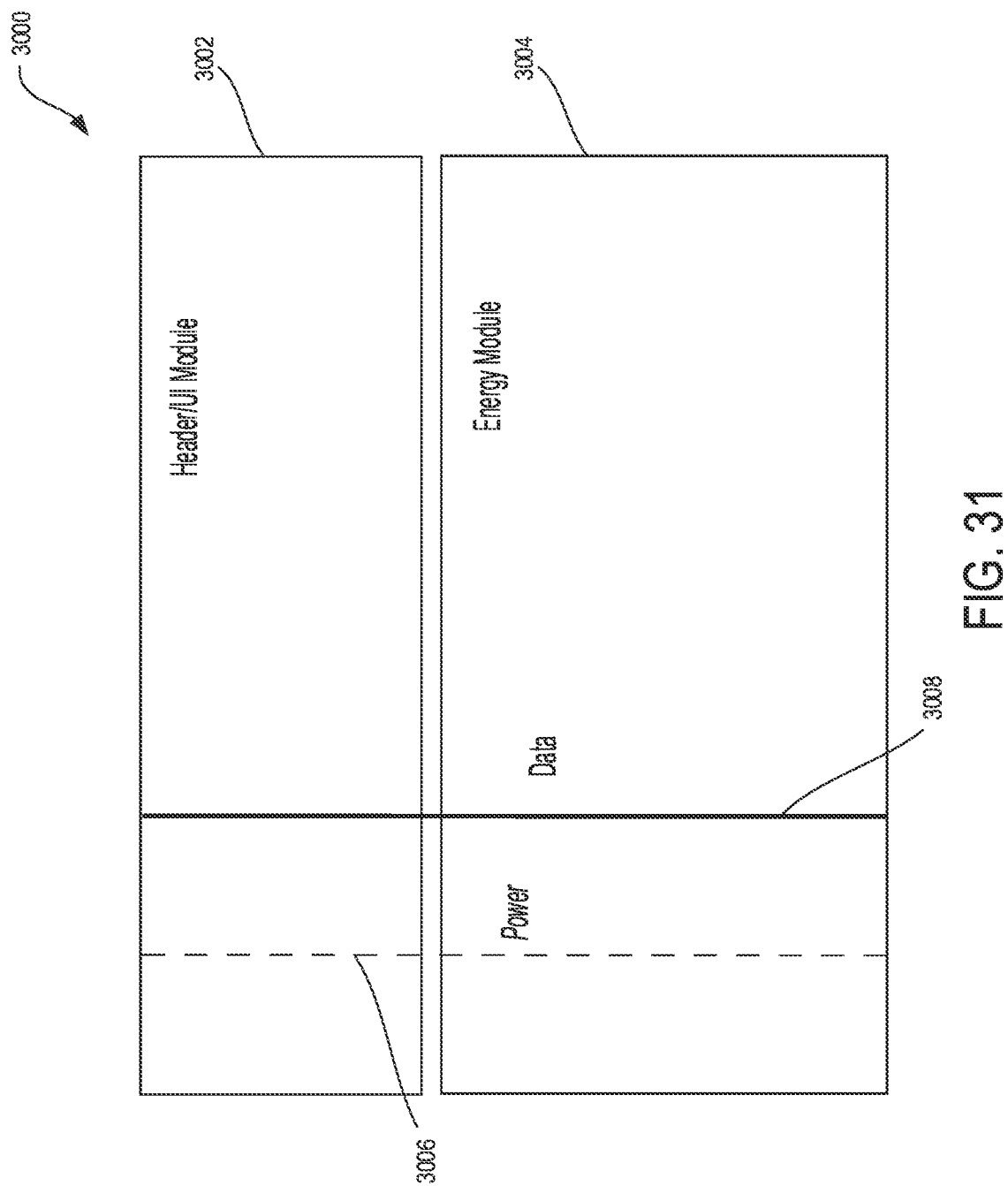
FIG. 31 is a block diagram of a stand-alone hub configuration of a modular energy system, in accordance with at least one aspect of the present disclosure.
Figure 32:
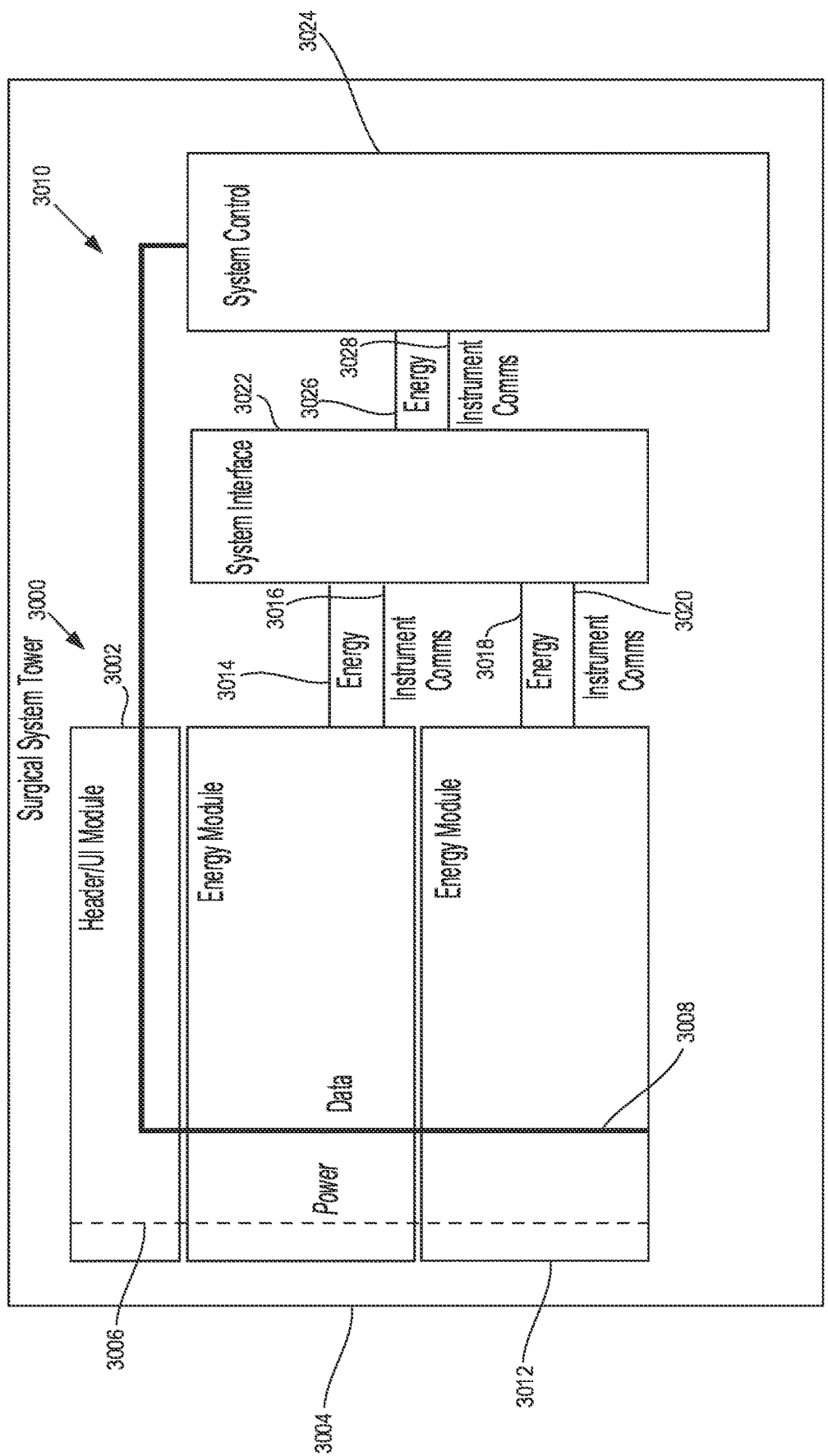
FIG. 32 is a block diagram of a hub configuration of a modular energy system integrated with a surgical control system, in accordance with at least one aspect of the present disclosure.

FIG. 31 is a block diagram of a stand-alone hub configuration of a modular energy system 3000, in accordance with at least one aspect of the present disclosure and FIG. 32 is a block diagram of a hub configuration of a modular energy system 3000 integrated with a surgical control system 3010, in accordance with at least one aspect of the present disclosure. As depicted in FIGS. 31 and 32, the modular energy system 3000 can be either utilized as stand-alone units or integrated with a surgical control system 3010 that controls and/or receives data from one or more surgical hub units. In the examples illustrated in FIGS. 31 and 32, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 31, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 32, a surgical hub configuration includes a modular energy system 3000 integrated with a control system 3010 and an interface system 3022 for managing, among other things, data and power transmission to and/or from the modular energy system 3000. The modular energy system depicted in FIG. 32 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

As described in more detail hereinbelow, the energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

Figure 33:
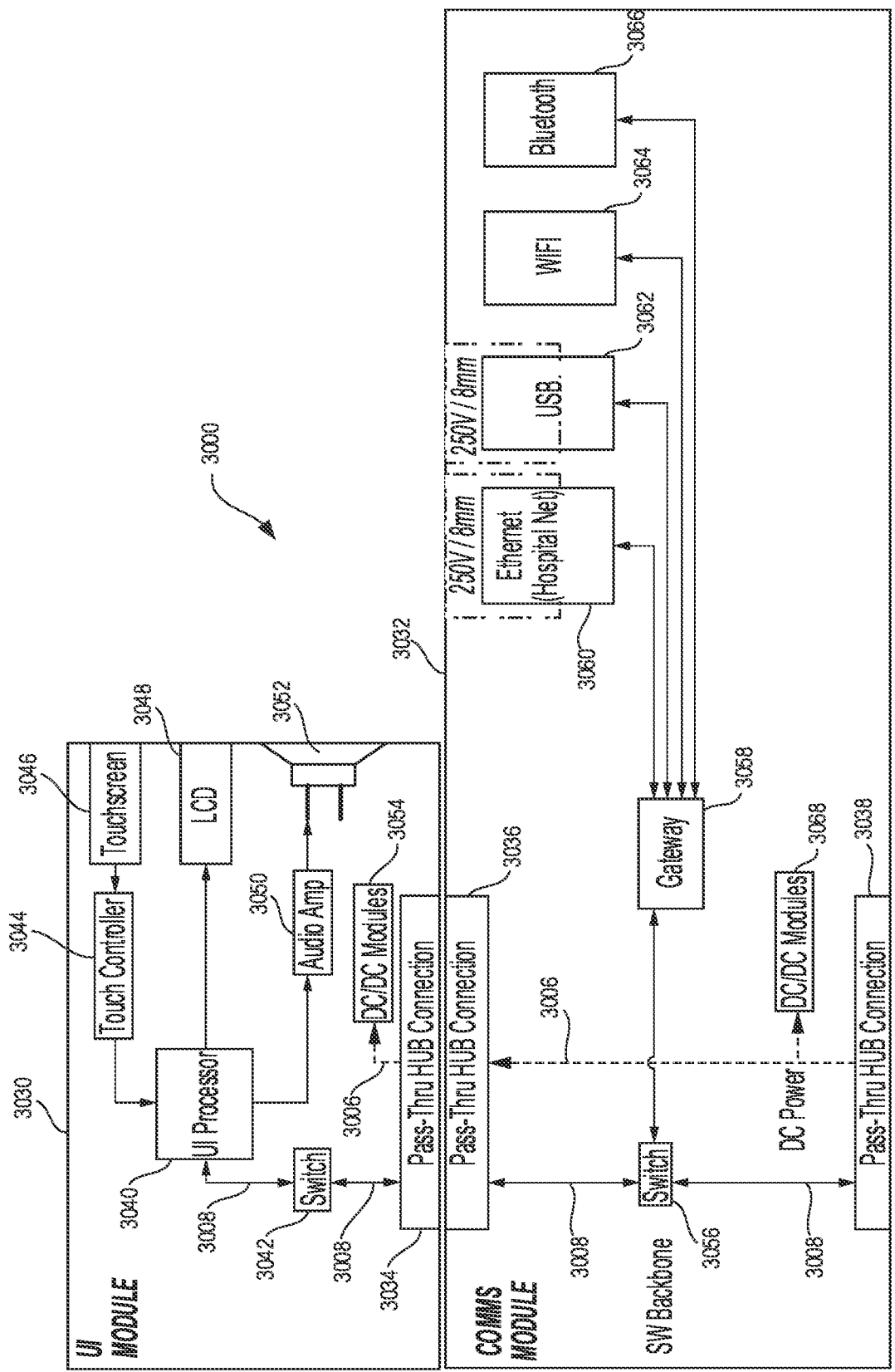
FIG. 33 is a block diagram of a user interface module coupled to a communications module of a modular energy system, in accordance with at least one aspect of the present disclosure.
Figure 34:
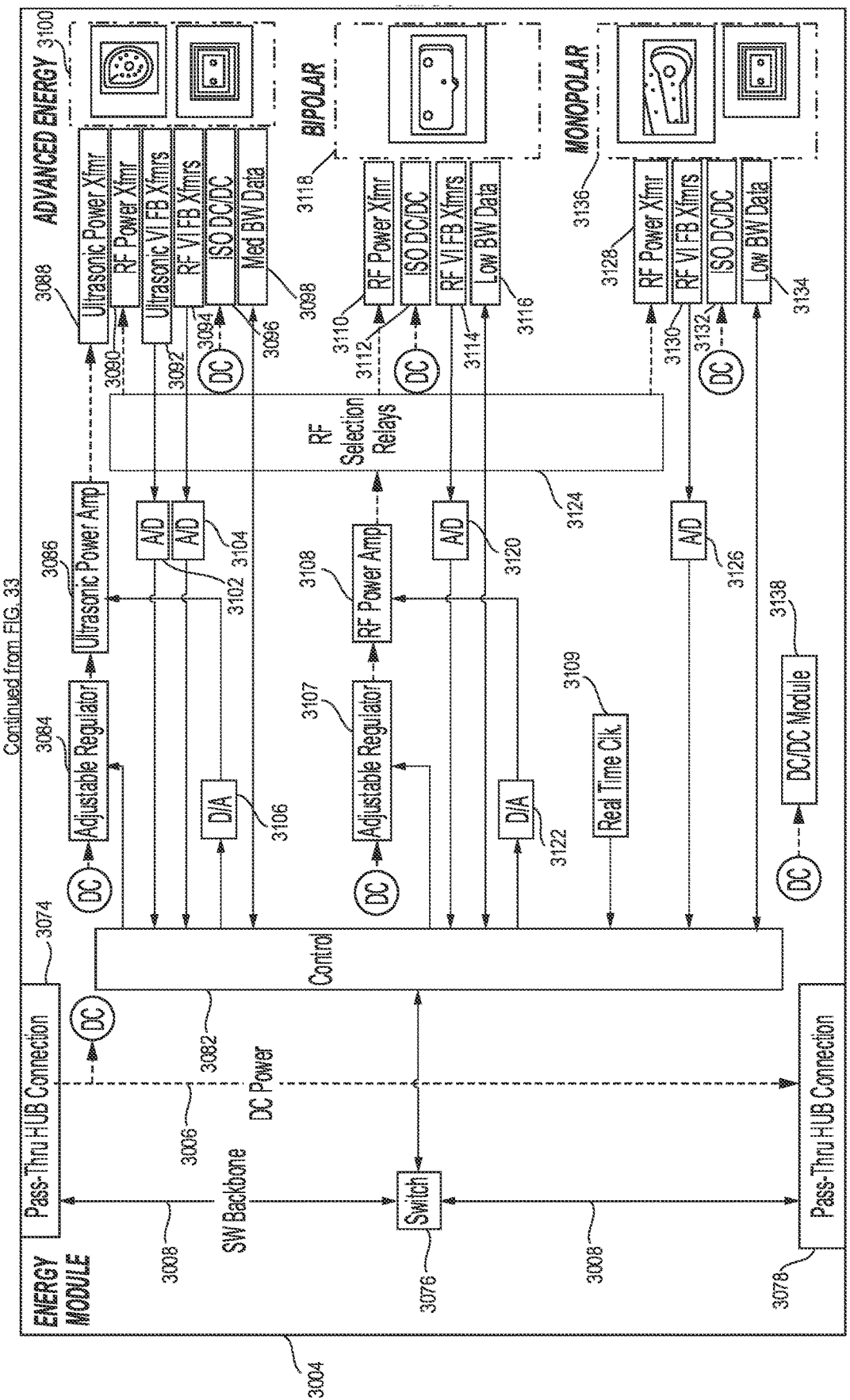
FIG. 34 is a block diagram of an energy module of a modular energy system, in accordance with at least one aspect of the present disclosure.
Figure 35A:
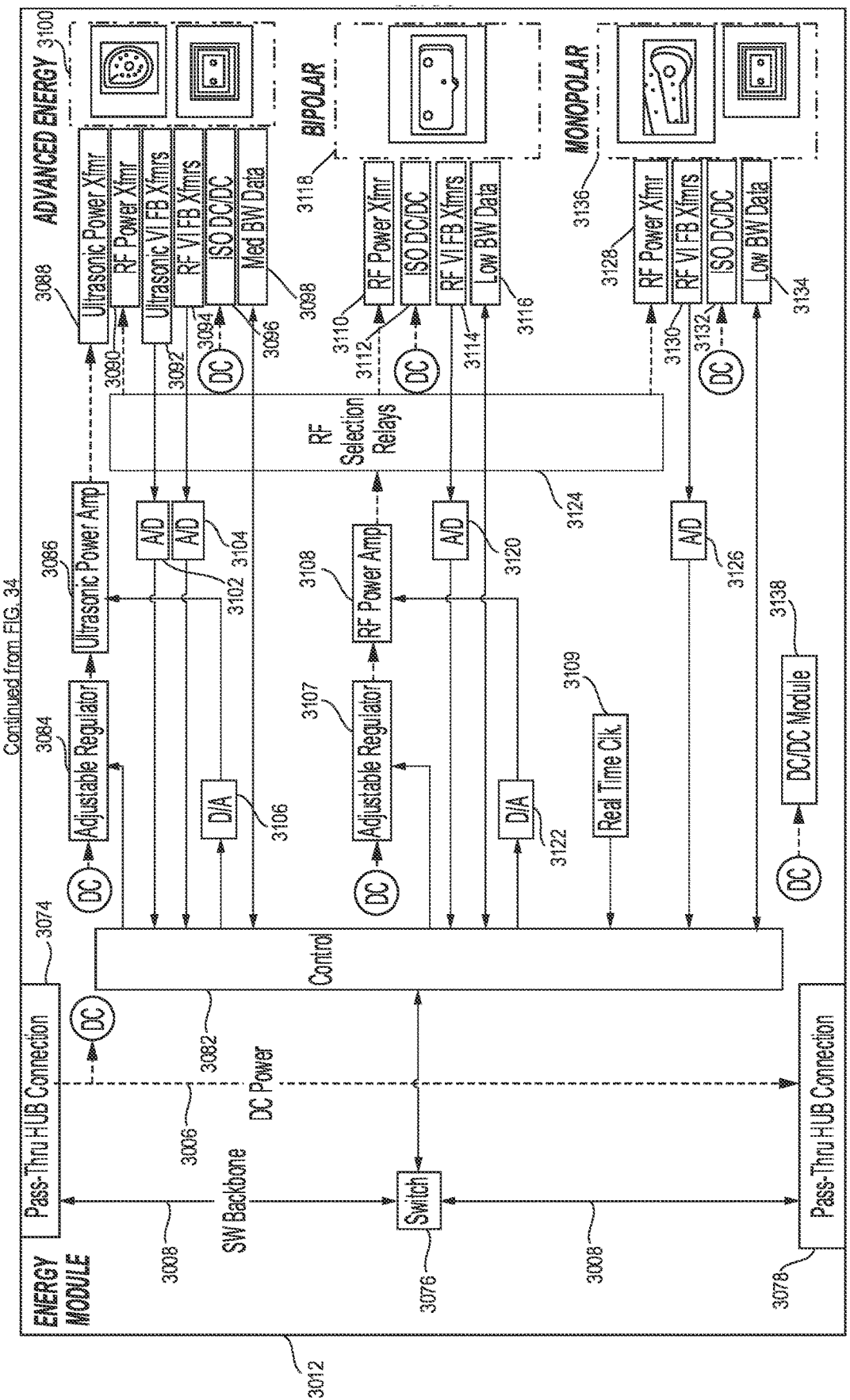
FIGS. 35A and 35B illustrate a block diagram of an energy module coupled to a header module of a modular energy system, in accordance with at least one aspect of the present disclosure.
Figure 35B:
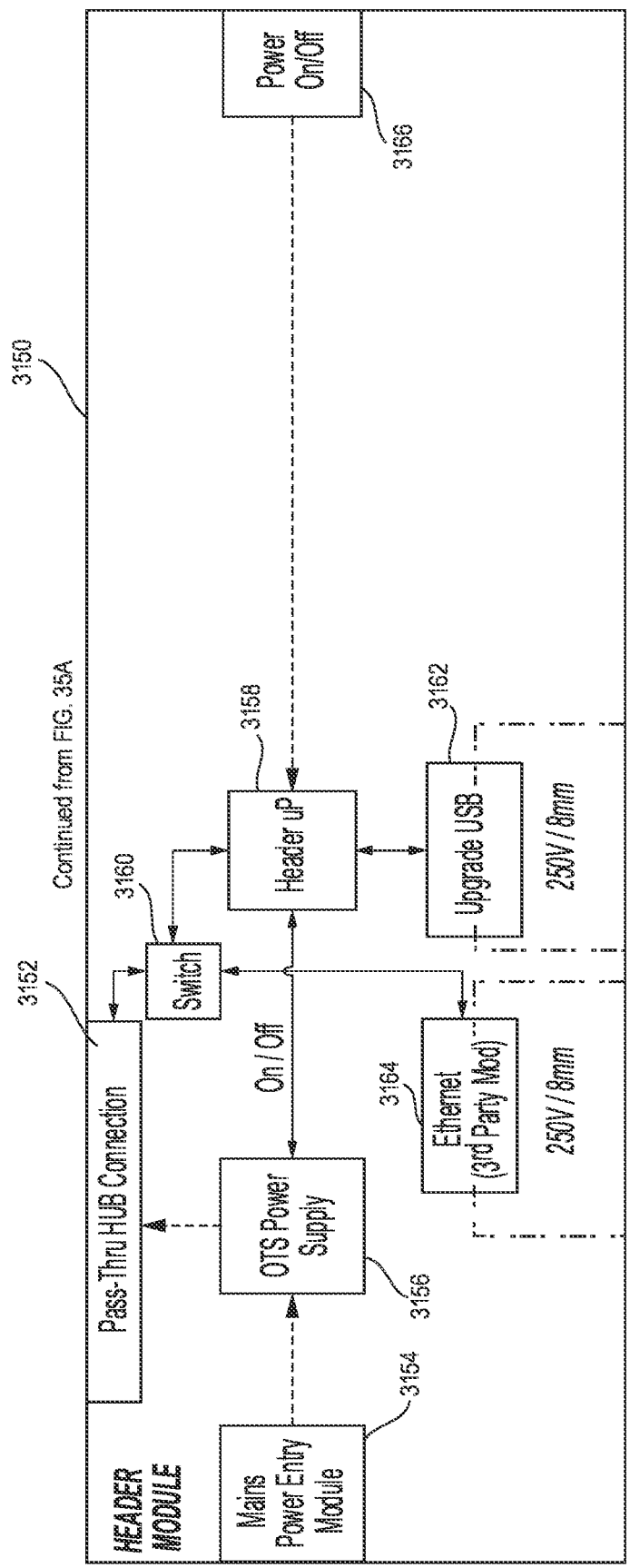

FIGS. 33-35 are block diagrams of various modular energy systems connected together to form a hub, in accordance with at least one aspect of the present disclosure. FIGS. 33-35 depict various diagrams (e.g., circuit or control diagrams) of hub modules. The modular energy system 3000 includes multiple energy modules 3004 (FIG. 34), 3012 (FIG. 35), a header module 3150 (FIG. 35), a UI module 3030 (FIG. 33), and a communications module 3032 (FIG. 33), in accordance with at least one aspect of the present disclosure. The UI module 3030 includes a touch screen 3046 displaying various relevant information and various user controls for controlling one or more parameters of the modular energy system 3000. The UI module 3030 is attached to the top header module 3150, but is separately housed so that it can be manipulated independently of the header module 3150. For example, the UI module 3030 can be picked up by a user and/or reattached to the header module 3150. Additionally, or alternatively, the UI module 3030 can be slightly moved relative to the header module 3150 to adjust its position and/or orientation. For example, the UI module 3030 can be tilted and/or rotated relative to the header module 3150.

In some aspects, the various hub modules can include light piping around the physical ports to communicate instrument status and also connect on-screen elements to corresponding instruments. Light piping is one example of an illumination technique that may be employed to alert a user to a status of a surgical instrument attached/connected to a physical port. In one aspect, illuminating a physical port with a particular light directs a user to connect a surgical instrument to the physical port. In another example, illuminating a physical port with a particular light alerts a user to an error related an existing connection with a surgical instrument.

Turning to FIG. 33, there is shown a block diagram of a user interface (UI) module 3030 coupled to a communications module 3032 via a pass-through hub connector 3034, in accordance with at least one aspect of the present disclosure. The UI module 3030 is provided as a separate component from a header module 3150 (shown in FIG. 35) and may be communicatively coupled to the header module 3150 via a communications module 3032, for example. In one aspect, the UI module 3030 can include a UI processor 3040 that is configured to represent declarative visualizations and behaviors received from other connected modules, as well as perform other centralized UI functionality, such as system configuration (e.g., language selection, module associations, etc.). The UI processor 3040 can be, for example, a processor or system on module (SOM) running a framework such as Qt, .NET WPF, Web server, or similar.

In the illustrated example, the UI module 3030 includes a touchscreen 3046, a liquid crystal display 3048 (LCD), and audio output 3052 (e.g., speaker, buzzer). The UI processor 3040 is configured to receive touchscreen inputs from a touch controller 3044 coupled between the touch screen 3046 and the UI processor 3040. The UI processor 3040 is configured to output visual information to the LCD display 3048 and to output audio information the audio output 3052 via an audio amplifier 3050. The UI processor 3040 is configured to interface to the communications module 3032 via a switch 3042 coupled to the pass-through hub connector 3034 to receive, process, and forward data from the source device to the destination device and control data communication therebetween. DC power is supplied to the UI module 3030 via DC/DC converter modules 3054. The DC power is passed through the pass-through hub connector 3034 to the communications module 3032 through the power bus 3006. Data is passed through the pass-through hub connector 3034 to the communications module 3032 through the data bus 3008. Switches 3042, 3056 receive, process, and forward data from the source device to the destination device.

Continuing with FIG. 33, the communications module 3032, as well as various surgical hubs and/or surgical systems can include a gateway 3058 that is configured to shuttle select traffic (i.e., data) between two disparate networks (e.g., an internal network and/or a hospital network) that are running different protocols. The communications module 3032 includes a first pass-through hub connector 3036 to couple the communications module 3032 to other modules. In the illustrated example, the communications module 3032 is coupled to the UI module 3030. The communications module 3032 is configured to couple to other modules (e.g., energy modules) via a second pass-through hub connector 3038 to couple the communications module 3032 to other modules via a switch 3056 disposed between the first and second pass-through hub connectors 3036, 3038 to receive, process, and forward data from the source device to the destination device and control data communication therebetween. The switch 3056 also is coupled to a gateway 3058 to communicate information between external communications ports and the UI module 3030 and other connected modules. The gateway 3058 may be coupled to various communications modules such as, for example, an Ethernet module 3060 to communicate to a hospital or other local network, a universal serial bus (USB) module 3062, a WiFi module 3064, and a Bluetooth module 3066, among others. The communications modules may be physical boards located within the communications module 3032 or may be a port to couple to remote communications boards.

Figure 36A:
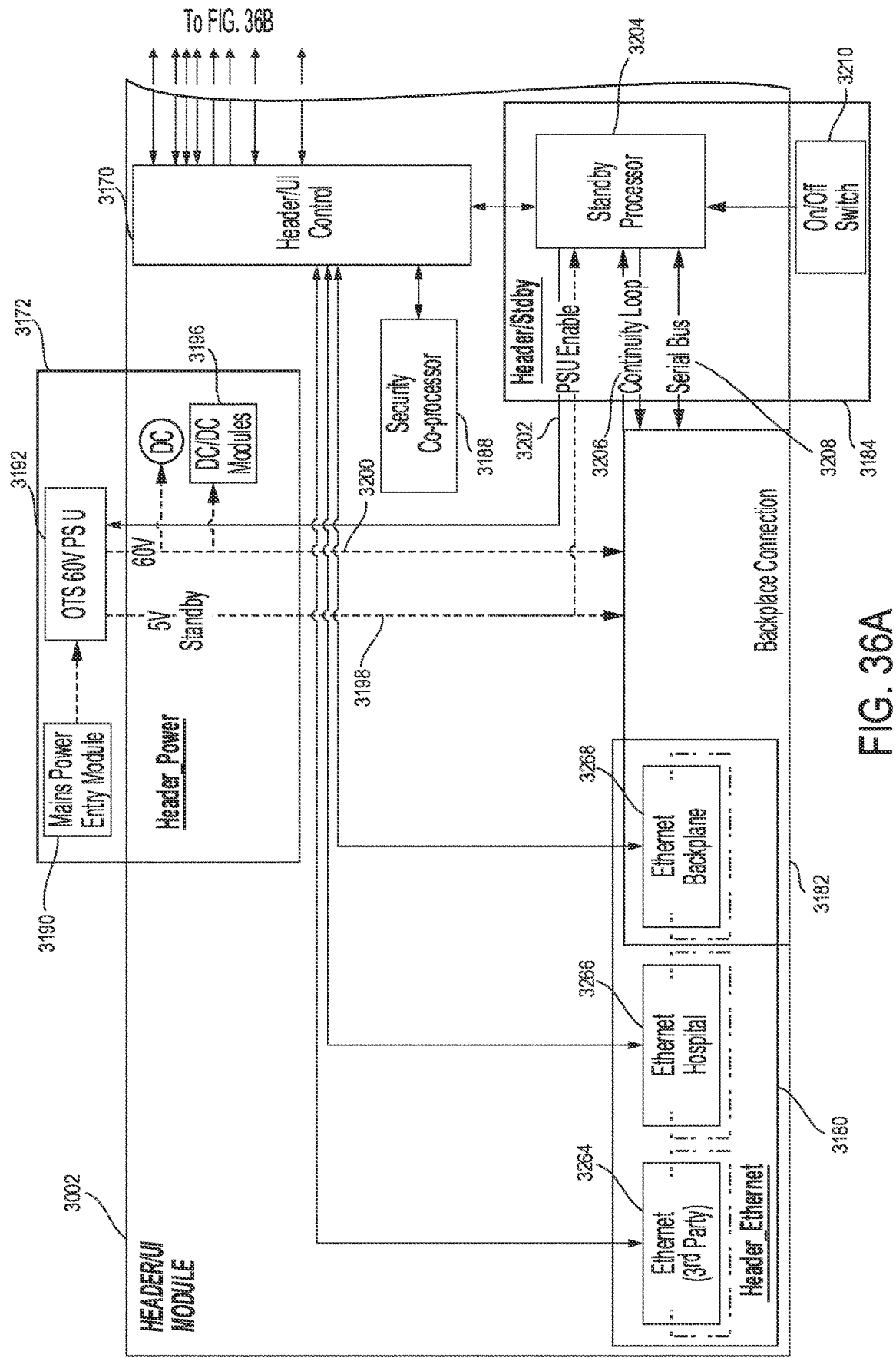
FIGS. 36A and 36B illustrate a block diagram of a header/user interface (UI) module of a modular energy system for a hub, such as the header module depicted in FIG. 33, in accordance with at least one aspect of the present disclosure.
Figure 36B:
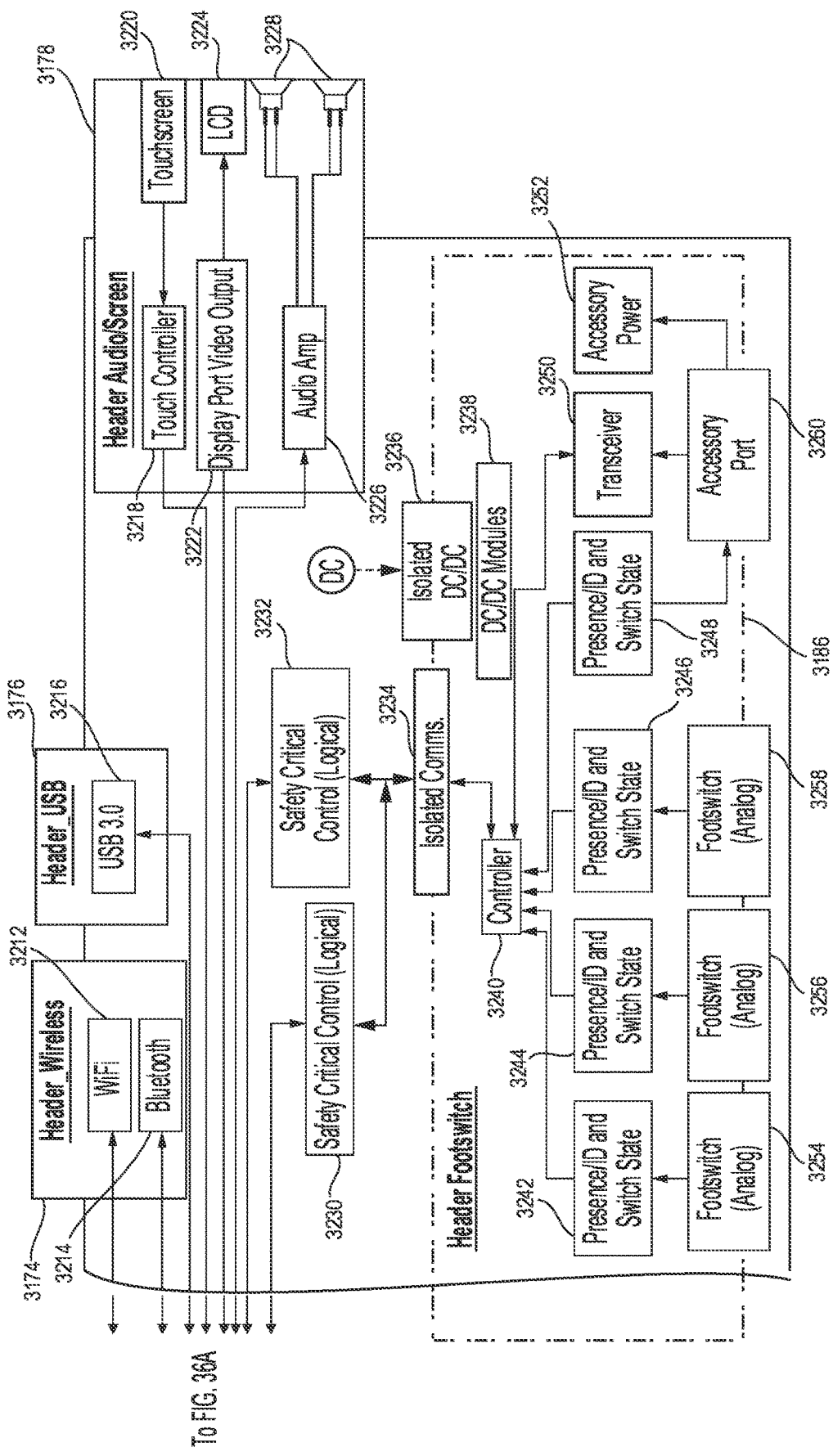

In some aspects, all of the modules (i.e., detachable hardware) are controlled by a single UI module 3030 that is disposed on or integral to a header module. FIG. 35 shows a stand alone header module 3150 to which the UI module 3030 can be attached. FIGS. 31, 32, and 36 show an integrated header/UI Module 3002. Returning now to FIG. 33, in various aspects, by consolidating all of the modules into a single, responsive UI module 3002, the system provides a simpler way to control and monitor multiple pieces of equipment at once. This approach drastically reduces footprint and complexity in an operating room (OR).

Turning to FIG. 34, there is shown a block diagram of an energy module 3004, in accordance with at least one aspect of the present disclosure. The communications module 3032 (FIG. 33) is coupled to the energy module 3004 via the second pass-through hub connector 3038 of the communications module 3032 and a first pass-through hub connector 3074 of the energy module 3004. The energy module 3004 may be coupled to other modules, such as a second energy module 3012 shown in FIG. 35, via a second pass-through hub connector 3078. Turning back to FIG. 34, a switch 3076 disposed between the first and second pass-through hub connectors 3074, 3078 receives, processes, and forwards data from the source device to the destination device and controls data communication therebetween. Data is received and transmitted through the data bus 3008. The energy module 3032 includes a controller 3082 to control various communications and processing functions of the energy module 3004.

DC power is received and transmitted by the energy module 3004 through the power bus 3006. The power bus 3006 is coupled to DC/DC converter modules 3138 to supply power to adjustable regulators 3084, 3107 and isolated DC/DC converter ports 3096, 3112, 3132.

In one aspect, the energy module 3004 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of an advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog-to-digital converter 3102 (A/D). Also coupled to the controller 3082 through the advanced energy receptacle 3100 is the isolated DC/DC converter port 3096, which receives DC power from the power bus 3006, and a medium bandwidth data port 3098.

In one aspect, the energy module 3004 can include a wideband RF power amplifier 3108, which in one aspect may be a linear class H amplifier that is capable of generating arbitrary waveforms and drive RF loads at a range of output frequencies. The wideband RF power amplifier 3108 is fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the wideband RF amplifier 3086 via a DAC 3122. The output of the wideband RF power amplifier 3108 can be fed through RF selection relays 3124. The RF selection relays 3124 are configured to receive and selectively transmit the output signal of the wideband RF power amplifier 3108 to various other components of the energy module 3004. In one aspect, the output signal of the wideband RF power amplifier 3108 can be fed through RF selection relays 3124 to an RF power transformer 3110, which is coupled to an RF output portion of a bipolar RF energy receptacle 3118. Bipolar RF voltage (V) and current (I) feedback (FB) signals, which may be employed to compute RF impedance, are fed back to the controller 3082 via an RF VI FB transformer 3114 through an input portion of the bipolar RF energy receptacle 3118. The RF voltage and current feedback signals are routed back to the controller 3082 through an ND 3120. Also coupled to the controller 3082 through the bipolar RF energy receptacle 3118 is the isolated DC/DC converter port 3112, which receives DC power from the power bus 3006, and a low bandwidth data port 3116.

As described above, in one aspect, the energy module 3004 can include RF selection relays 3124 driven by the controller 3082 (e.g., FPGA) at rated coil current for actuation and can also be set to a lower hold-current via pulse-width modulation (PWM) to limit steady-state power dissipation. Switching of the RF selection relays 3124 is achieved with force guided (safety) relays and the status of the contact state is sensed by the controller 3082 as a mitigation for any single fault conditions. In one aspect, the RF selection relays 3124 are configured to be in a first state, where an output RF signal received from an RF source, such as the wideband RF power amplifier 3108, is transmitted to a first component of the energy module 3004, such as the RF power transformer 3110 of the bipolar energy receptacle 3118. In a second aspect, the RF selection relays 3124 are configured to be in a second state, where an output RF signal received from an RF source, such as the wideband RF power amplifier 3108, is transmitted to a second component, such as an RF power transformer 3128 of a monopolar energy receptacle 3136, described in more detail below. In a general aspect, the RF selection relays 3124 are configured to be driven by the controller 3082 to switch between a plurality of states, such as the first state and the second state, to transmit the output RF signal received from the RF power amplifier 3108 between different energy receptacles of the energy module 3004.

As described above, the output of the wideband RF power amplifier 3108 can also fed through the RF selection relays 3124 to the wideband RF power transformer 3128 of the RF monopolar receptacle 3136. Monopolar RF voltage (V) and current (I) feedback (FB) signals, which may be employed to compute RF impedance, are fed back to the controller 3082 via an RF VI FB transformer 3130 through an input portion of the monopolar RF energy receptacle 3136. The RF voltage and current feedback signals are routed back to the controller 3082 through an ND 3126. Also coupled to the controller 3082 through the monopolar RF energy receptacle 3136 is the isolated DC/DC converter port 3132, which receives DC power from the power bus 3006, and a low bandwidth data port 3134.

The output of the wideband RF power amplifier 3108 can also fed through the RF selection relays 3124 to the wideband RF power transformer 3090 of the advanced energy receptacle 3100. RF voltage (V) and current (I) feedback (FB) signals, which may be employed to compute RF impedance, are fed back to the controller 3082 via an RF VI FB transformer 3094 through an input portion of the advanced energy receptacle 3100. The RF voltage and current feedback signals are routed back to the controller 3082 through an ND 3104.

FIG. 35 is a block diagram of a second energy module 3012 coupled to a header module 3150, in accordance with at least one aspect of the present disclosure. The first energy module 3004 shown in FIG. 34 is coupled to the second energy module 3012 shown in FIG. 35 by coupling the second pass-through hub connector 3078 of the first energy module 3004 to a first pass-through hub connector 3074 of the second energy module 3012. In one aspect, the second energy module 3012 can a similar energy module to the first energy module 3004, as is illustrated in FIG. 35. In another aspect, the second energy module 2012 can be a different energy module compared to the first energy module, such as an energy module illustrated in FIG. 37, described in more detail. The addition of the second energy module 3012 to the first energy module 3004 adds functionality to the modular energy system 3000.

The second energy module 3012 is coupled to the header module 3150 by connecting the pass-through hub connector 3078 to the pass-through hub connector 3152 of the header module 3150. In one aspect, the header module 3150 can include a header processor 3158 that is configured to manage a power button function 3166, software upgrades through the upgrade USB module 3162, system time management, and gateway to external networks (i.e., hospital or the cloud) via an Ethernet module 3164 that may be running different protocols. Data is received by the header module 3150 through the pass-through hub connector 3152. The header processor 3158 also is coupled to a switch 3160 to receive, process, and forward data from the source device to the destination device and control data communication therebetween. The header processor 3158 also is coupled to an OTS power supply 3156 coupled to a mains power entry module 3154.

FIG. 36 is a block diagram of a header/user interface (UI) module 3002 for a hub, such as the header module depicted in FIG. 33, in accordance with at least one aspect of the present disclosure. The header/UI module 3002 includes a header power module 3172, a header wireless module 3174, a header USB module 3176, a header audio/screen module 3178, a header network module 3180 (e.g., Ethernet), a backplane connector 3182, a header standby processor module 3184, and a header footswitch module 3186. These functional modules interact to provide the header/UI 3002 functionality. A header/UI controller 3170 controls each of the functional modules and the communication therebetween including safety critical control logic modules 3230, 3232 coupled between the header/UI controller 3170 and an isolated communications module 3234 coupled to the header footswitch module 3186. A security co-processor 3188 is coupled to the header/UI controller 3170.

The header power module 3172 includes a mains power entry module 3190 coupled to an OTS power supply unit 3192 (PSU). Low voltage direct current (e.g., 5V) standby power is supplied to the header/UI module 3002 and other modules through a low voltage power bus 3198 from the OTS PSU 3192. High voltage direct current (e.g., 60V) is supplied to the header/UI module 3002 through a high voltage bus 3200 from the OTS PSU 3192. The high voltage DC supplies DC/DC converter modules 3196 as well as isolated DC/DC converter modules 3236. A standby processor 3204 of the header/standby module 3184 provides a PSU/enable signal 3202 to the OTS PSU 3192.

The header wireless module 3174 includes a WiFi module 3212 and a Bluetooth module 3214. Both the WiFi module 3212 and the Bluetooth module 3214 are coupled to the header/UI controller 3170. The Bluetooth module 3214 is used to connect devices without using cables and the Wi-Fi module 3212 provides high-speed access to networks such as the Internet and can be employed to create a wireless network that can link multiple devices such as, for examples, multiple energy modules or other modules and surgical instruments, among other devices located in the operating room. Bluetooth is a wireless technology standard that is used to exchange data over short distances, such as, less than 30 feet.

The header USB module 3176 includes a USB port 3216 coupled to the header/UI controller 3170. The USB module 3176 provides a standard cable connection interface for modules and other electronics devices over short-distance digital data communications. The USB module 3176 allows modules comprising USB devices to be connected to each other with and transfer digital data over USB cables.

The header audio/screen module 3178 includes a touchscreen 3220 coupled to a touch controller 3218. The touch controller 3218 is coupled to the header/UI controller 3170 to read inputs from the touchscreen 3220. The header/UI controller 3170 drives an LCD display 3224 through a display/port video output signal 3222. The header/UI controller 3170 is coupled to an audio amplifier 3226 to drive one or more speakers 3228.

In one aspect, the header/UI module 3002 provides a touchscreen 3220 user interface configured to control modules connected to one control or header module 3002 in a modular energy system 3000. The touchscreen 3220 can be used to maintain a single point of access for the user to adjust all modules connected within the modular energy system 3000. Additional hardware modules (e.g., a smoke evacuation module) can appear at the bottom of the user interface LCD display 3224 when they become connected to the header/UI module 3002, and can disappear from the user interface LCD display 3224 when they are disconnected from the header/UI module 3002.

Further, the user touchscreen 3220 can provide access to the settings of modules attached to the modular energy system 3000. Further, the user interface LCD display 3224 arrangement can be configured to change according to the number and types of modules that are connected to the header/UI module 3002. For example, a first user interface can be displayed on the LCD display 3224 for a first application where one energy module and one smoke evacuation module are connected to the header/UI module 3002, and a second user interface can be displayed on the LCD display 3224 for a second application where two energy modules are connected to the header/UI module 3002. Further, the user interface can alter its display on the LCD display 3224 as modules are connected and disconnected from the modular energy system 3000.

In one aspect, the header/UI module 3002 provides a user interface LCD display 3224 configured to display on the LCD display coloring corresponds to the port lighting. In one aspect, the coloring of the instrument panel and the LED light around its corresponding port will be the same or otherwise correspond with each other. Each color can, for example, convey a unique meaning. This way, the user will be able to quickly assess which instrument the indication is referring to and the nature of the indication. Further, indications regarding an instrument can be represented by the changing of color of the LED light lined around its corresponding port and the coloring of its module. Still further, the message on screen and hardware/software port alignment can also serve to convey that an action must be taken on the hardware, not on the interface. In various aspects, all other instruments can be used while alerts are occurring on other instruments. This allows the user to be able to quickly assess which instrument the indication is referring to and the nature of the indication.

In one aspect, the header/UI module 3002 provides a user interface screen configured to display on the LCD display 3224 to present procedure options to a user. In one aspect, the user interface can be configured to present the user with a series of options (which can be arranged, e.g., from broad to specific). After each selection is made, the modular energy system 3000 presents the next level until all selections are complete. These settings could be managed locally and transferred via a secondary means (such as a USB thumb drive). Alternatively, the settings could be managed via a portal and automatically distributed to all connected systems in the hospital.

The procedure options can include, for example, a list of factory preset options categorized by specialty, procedure, and type of procedure. Upon completing a user selection, the header module can be configured to set any connected instruments to factory-preset settings for that specific procedure. The procedure options can also include, for example, a list of surgeons, then subsequently, the specialty, procedure, and type. Once a user completes a selection, the system may suggest the surgeon's preferred instruments and set those instrument's settings according to the surgeon's preference (i.e., a profile associated with each surgeon storing the surgeon's preferences).

In one aspect, the header/UI module 3002 provides a user interface screen configured to display on the LCD display 3224 critical instrument settings. In one aspect, each instrument panel displayed on the LCD display 3224 of the user interface corresponds, in placement and content, to the instruments plugged into the modular energy system 3000. When a user taps on a panel, it can expand to reveal additional settings and options for that specific instrument and the rest of the screen can, for example, darken or otherwise be de-emphasized.

In one aspect, the header/UI module 3002 provides an instrument settings panel of the user interface configured to comprise/display controls that are unique to an instrument and allow the user to increase or decrease the intensity of its output, toggle certain functions, pair it with system accessories like a footswitch connected to header footswitch module 3186, access advanced instrument settings, and find additional information about the instrument. In one aspect, the user can tap/select an "Advanced Settings" control to expand the advanced settings drawer displayed on the user interface LCD display 3224. In one aspect, the user can then tap/select an icon at the top right-hand corner of the instrument settings panel or tap anywhere outside of the panel and the panel will scale back down to its original state. In these aspects, the user interface is configured to display on the LCD display 3224 only the most critical instrument settings, such as power level and power mode, on the ready/home screen for each instrument panel. This is to maximize the size and readability of the system from a distance. In some aspects, the panels and the settings within can be scaled proportionally to the number of instruments connected to the system to further improve readability. As more instruments are connected, the panels scale to accommodate a greater amount of information.

The header network module 3180 includes a plurality of network interfaces 3264, 3266, 3268 (e.g., Ethernet) to network the header/UI module 3002 to other modules of the modular energy system 3000. In the illustrated example, one network interface 3264 may be a 3rd party network interface, another network interface 3266 may be a hospital network interface, and yet another network interface 3268 may be located on the backplane network interface connector 3182.

The header standby processor module 3184 includes a standby processor 3204 coupled to an On/Off switch 3210. The standby processor 3204 conducts an electrical continuity test by checking to see if electrical current flows in a continuity loop 3206. The continuity test is performed by placing a small voltage across the continuity loop 3206. A serial bus 3208 couples the standby processor 3204 to the backplane connector 3182.

The header footswitch module 3186 includes a controller 3240 coupled to a plurality of analog footswitch ports 3254, 3256, 3258 through a plurality of corresponding presence/ID and switch state modules 3242, 3244, 3246, respectively. The controller 3240 also is coupled to an accessory port 3260 via a presence/ID and switch state module 3248 and a transceiver module 3250. The accessory port 3260 is powered by an accessory power module 3252. The controller 3240 is coupled to header/UI controller 3170 via an isolated communication module 3234 and first and second safety critical control modules 3230, 3232. The header footswitch module 3186 also includes DC/DC converter modules 3238.

In one aspect, the header/UI module 3002 provides a user interface screen configured to display on the LCD display 3224 for controlling a footswitch connected to any one of the analog footswitch ports 3254, 3256, 3258. In some aspects, when the user plugs in a non hand-activated instrument into any one of the analog footswitch ports 3254, 3256, 3258, the instrument panel appears with a warning icon next to the footswitch icon. The instrument settings can be, for example, greyed out, as the instrument cannot be activated without a footswitch.

When the user plugs in a footswitch into any one of the analog footswitch ports 3254, 3256, 3258, a pop-up appears indicating that a footswitch has been assigned to that instrument. The footswitch icon indicates that a footswitch has been plugged in and assigned to the instrument. The user can then tap/select on that icon to assign, reassign, unassign, or otherwise change the settings associated with that footswitch. In these aspects, the system is configured to automatically assign footswitches to non hand-activated instruments using logic, which can further assign single or double-pedal footswitches to the appropriate instrument. If the user wants to assign/reassign footswitches manually there are two flows that can be utilized.

In one aspect, the header/UI module 3002 provides a global footswitch button. Once the user taps on the global footswitch icon (located in the upper right of the user interface LCD display 3224), the footswitch assignment overlay appears and the contents in the instrument modules dim. A (e.g., photo-realistic) representation of each attached footswitch (dual or single-pedal) appears on the bottom if unassigned to an instrument or on the corresponding instrument panel. Accordingly, the user can drag and drop these illustrations into, and out of, the boxed icons in the footswitch assignment overlay to assign, unassign, and reassign footswitches to their respective instruments.

In one aspect, the header/UI module 3002 provides a user interface screen displayed on the LCD display 3224 indicating footswitch auto-assignment, in accordance with at least one aspect of the present disclosure. As discussed above, the modular energy system 3000 can be configured to auto-assign a footswitch to an instrument that does not have hand activation. In some aspects, the header/UI module 3002 can be configured to correlate the colors displayed on the user interface LCD display 3224 to the lights on the modules themselves as means of tracking physical ports with user interface elements.

In one aspect, the header/UI module 3002 may be configured to depict various applications of the user interface with differing number of modules connected to the modular energy system 3000. In various aspects, the overall layout or proportion of the user interface elements displayed on the LCD display 3224 can be based on the number and type of instruments plugged into the header/UI module 3002. These scalable graphics can provide the means to utilize more of the screen for better visualization.

In one aspect, the header/UI module 3002 may be configured to depict a user interface screen on the LCD display 3224 to indicate which ports of the modules connected to the modular energy system 3000 are active. In some aspects, the header/UI module 3002 can be configured to illustrate active versus inactive ports by highlighting active ports and dimming inactive ports. In one aspect, ports can be represented with color when active (e.g., monopolar tissue cut with yellow, monopolar tissue coagulation with blue, bipolar tissue cut with blue, advanced energy tissue cut with warm white, and so on). Further, the displayed color will match the color of the light piping around the ports. The coloring can further indicate that the user cannot change settings of other instruments while an instrument is active. As another example, the header/UI module 3002 can be configured to depict the bipolar, monopolar, and ultrasonic ports of a first energy module as active and the monopolar ports of a second energy module as likewise active.

In one aspect, the header/UI module 3002 can be configured to depict a user interface screen on the LCD display 3224 to display a global settings menu. In one aspect, the header/UI module 3002 can be configured to display a menu on the LCD display 3224 to control global settings across any modules connected to the modular energy system 3000. The global settings menu can be, for example, always displayed in a consistent location (e.g., always available in upper right hand corner of main screen).

In one aspect, the header/UI module 3002 can be configured to depict a user interface screen on the LCD display 3224 configured to prevent changing of settings while a surgical instrument is in use. In one example, the header/UI module 3002 can be configured to prevent settings from being changed via a displayed menu when a connected instrument is active. The user interface screen can include, for example, an area (e.g., the upper left hand corner) that is reserved for indicating instrument activation while a settings menu is open. In one aspect, a user has opened the bipolar settings while monopolar coagulation is active. In one aspect, the settings menu could then be used once the activation is complete. In one aspect, the header/UI module 3002 can be is configured to never overlay any menus or other information over the dedicated area for indicating critical instrument information in order to maintain display of critical information.

In one aspect, the header/UI module 3002 can be configured to depict a user interface screen on the LCD display 3224 configured to display instrument errors. In one aspect, instrument error warnings may be displayed on the instrument panel itself, allowing user to continue to use other instruments while a nurse troubleshoots the error. This allows users to continue the surgery without the need to stop the surgery to debug the instrument.

In one aspect, the header/UI module 3002 can be configured to depict a user interface screen on the LCD display 3224 to display different modes or settings available for various instruments. In various aspects, the header/UI module 3002 can be configured to display settings menus that are appropriate for the type or application of surgical instrument (s) connected to the stack/hub. Each settings menu can provide options for different power levels, energy delivery profiles, and so on that are appropriate for the particular instrument type. In one aspect, the header/UI module 3002 can be configured to display different modes available for bipolar, monopolar cut, and monopolar coagulation applications.

In one aspect, the header/UI module 3002 can be configured to depict a user interface screen on the LCD display 3224 to display pre-selected settings. In one aspect, the header/UI module 3002 can be configured to receive selections for the instrument/device settings before plugging in instruments so that the modular energy system 3000 is ready before the patient enters the operating room. In one aspect, the user can simply click a port and then change the settings for that port. In the depicted aspect, the selected port appears as faded to indicate settings are set, but no instrument is plugged into that port.

Figure 37:
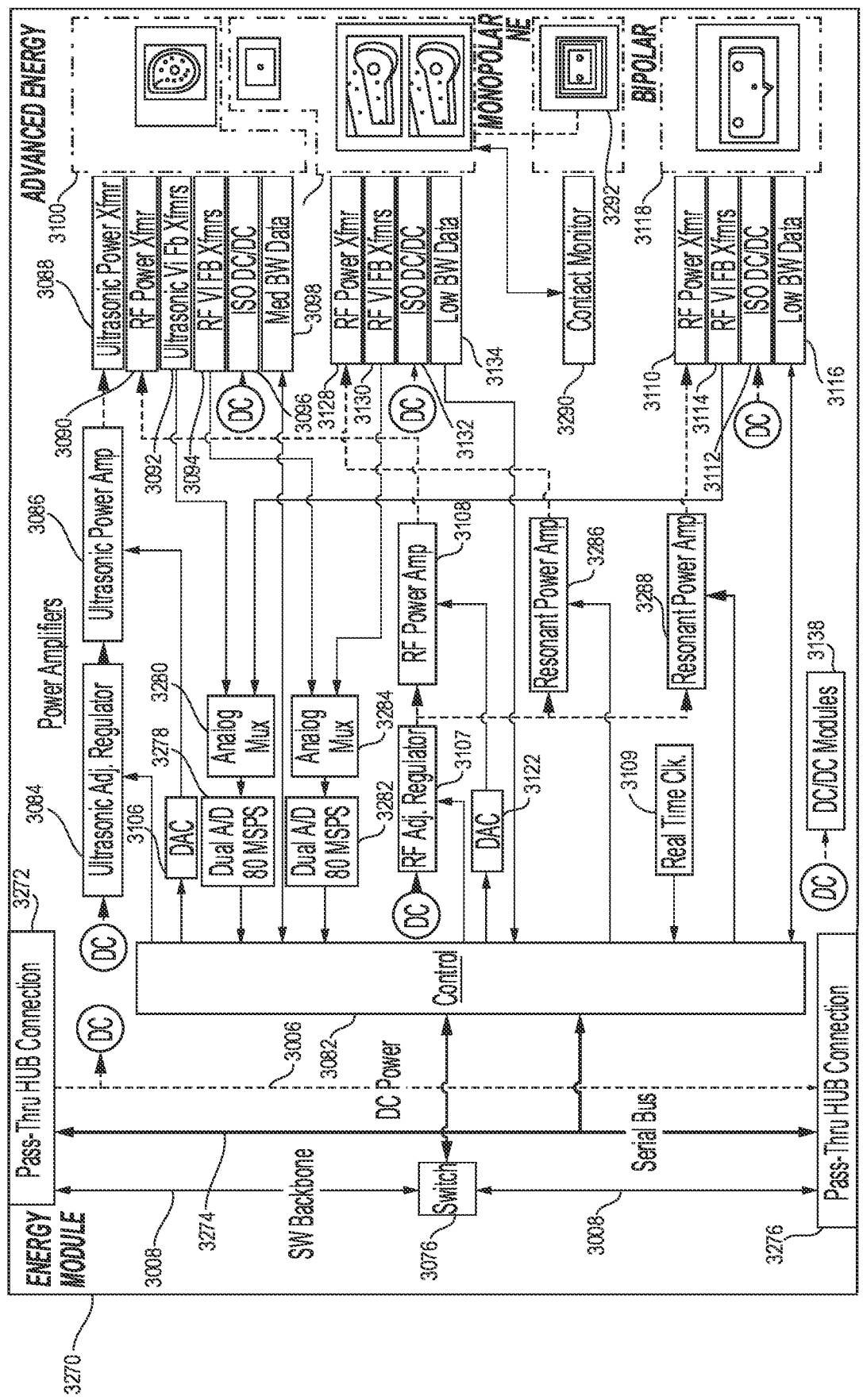
FIG. 37 is a block diagram of an energy module for a hub, such as the energy module depicted in FIGS. 31-36B, in accordance with at least one aspect of the present disclosure.

FIG. 37 is a block diagram of an energy module 3270 for a hub, such as the energy module depicted in FIGS. 31, 32, 34, and 35, in accordance with at least one aspect of the present disclosure. The energy module 3270 is configured to couple to a header module, header/UI module, and other energy modules via the first and second pass-through hub connectors 3272, 3276. A switch 3076 disposed between the first and second pass-through hub connectors 3272, 3276 receives, processes, and forwards data from the source device to the destination device and controls data communication therebetween. Data is received and transmitted through the data bus 3008. The energy module 3270 includes a controller 3082 to control various communications and processing functions of the energy module 3270.

DC power is received and transmitted by the energy module 3270 through the power bus 3006. The power bus 3006 is coupled to the DC/DC converter modules 3138 to supply power to adjustable regulators 3084, 3107 and isolated DC/DC converter ports 3096, 3112, 3132.

In one aspect, the energy module 3270 can include an ultrasonic wideband amplifier 3086, which in one aspect may be a linear class H amplifier that is capable of generating arbitrary waveforms and drive harmonic transducers at low total harmonic distortion (THD) levels. The ultrasonic wideband amplifier 3086 is fed by a buck adjustable regulator 3084 to maximize efficiency and controlled by the controller 3082, which may be implemented as a digital signal processor (DSP) via a direct digital synthesizer (DDS), for example. The DDS can either be embedded in the DSP or implemented in the field-programmable gate array (FPGA), for example. The controller 3082 controls the ultrasonic wideband amplifier 3086 via a digital-to-analog converter 3106 (DAC). The output of the ultrasonic wideband amplifier 3086 is fed to an ultrasonic power transformer 3088, which is coupled to an ultrasonic energy output portion of the advanced energy receptacle 3100. Ultrasonic voltage (V) and current (I) feedback (FB) signals, which may be employed to compute ultrasonic impedance, are fed back to the controller 3082 via an ultrasonic VI FB transformer 3092 through an input portion of the advanced energy receptacle 3100. The ultrasonic voltage and current feedback signals are routed back to the controller 3082 through an analog multiplexer 3280 and a dual analog-to-digital converter 3278 (ND). In one aspect, the dual A/D 3278 has a sampling rate of 80 MSPS. Also coupled to the controller 3082 through the advanced energy receptacle 3100 is the isolated DC/DC converter port 3096, which receives DC power from the power bus 3006, and a medium bandwidth data port 3098.

In one aspect, the energy module 3270 can include a plurality of wideband RF power amplifiers 3108, 3286, 3288, among others, which in one aspect, each of the wideband RF power amplifiers 3108, 3286, 3288 may be linear class H amplifiers capable of generating arbitrary waveforms and drive RF loads at a range of output frequencies. Each of the wideband RF power amplifiers 3108, 3286, 3288 are fed by an adjustable buck regulator 3107 to maximize efficiency and controlled by the controller 3082, which may be implemented as DSP via a DDS. The DDS can either be embedded in the DSP or implemented in the FPGA, for example. The controller 3082 controls the first wideband RF power amplifier 3108 via a DAC 3122.

Unlike the energy modules 3004, 3012 shown and described in FIGS. 34 and 35, the energy module 3270 does not include RF selection relays configured to receive an RF output signal from the adjustable buck regulator 3107. In addition, unlike the energy modules 3004, 3012 shown and described in FIGS. 34 and 35, the energy module 3270 includes a plurality of wideband RF power amplifiers 3108, 3286, 3288 instead of a single RF power amplifier. In one aspect, the adjustable buck regulator 3107 can switch between a plurality of states, in which the adjustable buck regulator 3107 outputs an output RF signal to one of the plurality of wideband RF power amplifiers 3108, 3286, 3288 connected thereto. The controller 3082 is configured to switch the adjustable buck regulator 3107 between the plurality of states. In a first state, the controller drives the adjustable buck regulator 3107 to output an RF energy signal to the first wideband RF power amplifier 3108. In a second state, the controller drives the adjustable buck regulator 3107 to output an RF energy signal to the second wideband RF power amplifier 3286. In a third state, the controller drives the adjustable buck regulator 3107 to output an RF energy signal to the third wideband RF power amplifier 3288.

The output of the first wideband RF power amplifier 3108 can be fed to an RF power transformer 3090, which is coupled to an RF output portion of an advanced energy receptacle 3100. RF voltage (V) and current (I) feedback (FB) signals, which may be employed to compute RF impedance, are fed back to the controller 3082 via RF VI FB transformers 3094 through an input portion of the advanced energy receptacle 3100. The RF voltage and current feedback signals are routed back to the controller 3082 through the RF VI FB transformers 3094, which are coupled to an analog multiplexer 3284 and a dual A/D 3282 coupled to the controller 3082. In one aspect, the dual A/D 3282 has a sampling rate of 80 MSPS.

The output of the second RF wideband power amplifier 3286 is fed through an RF power transformer 3128 of the RF monopolar receptacle 3136. Monopolar RF voltage (V) and current (I) feedback (FB) signals, which may be employed to compute RF impedance, are fed back to the controller 3082 via RF VI FB transformers 3130 through an input portion of the monopolar RF energy receptacle 3136. The RF voltage and current feedback signals are routed back to the controller 3082 through the analog multiplexer 3284 and the dual ND 3282. Also coupled to the controller 3082 through the monopolar RF energy receptacle 3136 is the isolated DC/DC converter port 3132, which receives DC power from the power bus 3006, and a low bandwidth data port 3134.

The output of the third RF wideband power amplifier 3288 is fed through an RF power transformer 3110 of a bipolar RF receptacle 3118. Bipolar RF voltage (V) and current (I) feedback (FB) signals, which may be employed to compute RF impedance, are fed back to the controller 3082 via RF VI FB transformers 3114 through an input portion of the bipolar RF energy receptacle 3118. The RF voltage and current feedback signals are routed back to the controller 3082 through the analog multiplexer 3280 and the dual ND 3278. Also coupled to the controller 3082 through the bipolar RF energy receptacle 3118 is the isolated DC/DC converter port 3112, which receives DC power from the power bus 3006, and a low bandwidth data port 3116.

A contact monitor 3290 is coupled to an NE receptacle 3292. Power is fed to the NE receptacle 3292 from the monopolar receptacle 3136.

In one aspect, with reference to FIGS. 31-37, the modular energy system 3000 can be configured to detect instrument presence in a receptacle 3100, 3118, 3136 via a photo-interrupter, magnetic sensor, or other non-contact sensor integrated into the receptacle 3100, 3118, 3136. This approach prevents the necessity of allocating a dedicated presence pin on the MTD connector to a single purpose and instead allows multi-purpose functionality for MTD signal pins 6-9 while continuously monitoring instrument presence.

In one aspect, with reference to FIGS. 31-37, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 31-37, the modules of the modular energy system 3000 can include a multi-function circuit block which can: (i) read presence resistor values via ND and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled and set to a high impedance state.

In one aspect, with reference to FIGS. 31-37, the modules of the modular energy system 3000 can include an amplifier pulse/stimulation/auxiliary DC amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

As described in greater detail herein, a modular surgical system comprises a header module and one or more functional or surgical modules. In various instances, the modular surgical system is a modular energy system. In various instances, the surgical modules include energy modules, communication modules, user interface modules; however, the surgical modules are envisioned to be any suitable type of functional or surgical module for use with the modular surgical system.

Modular surgical system offers many advantages in a surgical procedure, as described above in connection with the modular energy systems 2000 (FIG. 24-30), 3000 (FIG. 31, 32). However, cable management and setup/teardown time can be a significant deterrent. Various embodiments of the present disclosure provide a modular surgical system with a single power cable and a single power switch to control startup and shutdown of the entire modular surgical system, which obviated the need to individually activate and deactivate each individual module from which the modular surgical system is constructed. Also, various embodiments of the present disclosure provide a modular surgical system with power management schemes that facilitate a safe and, in some instances, concurrent delivery of power to the modules of a modular surgical system.

Figure 38:
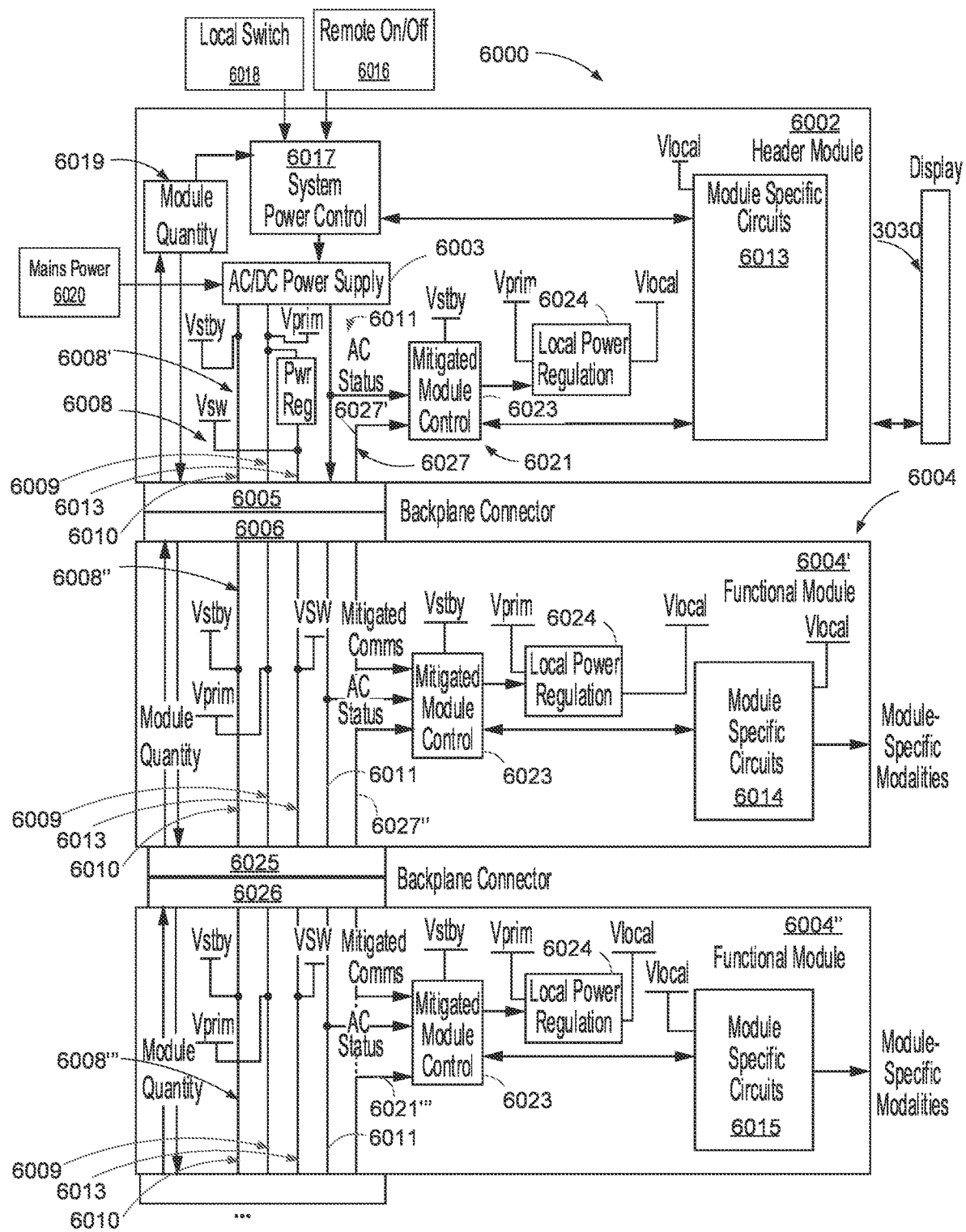
FIG. 38 is a schematic diagram of a modular surgical system stack illustrating a power backplane, in accordance with at least one aspect of the present disclosure.

In various aspects, as illustrated in FIG. 38, a modular surgical system 6000 that is similar in many respects to the modular surgical systems 2000 (FIG. 24-30), 3000 (FIG. 31, 32). For the sake of brevity, various details of the modular surgical system 6000, which are similar to the modular surgical system 2000 and/or the modular surgical system 3000, are not repeated herein.

The modular surgical system 6000 comprises a header module 6002 and an "N" number of surgical modules 6004, where "N" is an integer greater than or equal to one. In various examples, the modular surgical system 6000 includes a UI module such as, for example, the UI module 3030 and/or a communication module such as, for example, the communication module 3032. Furthermore, pass-through hub connectors couple individual modules to one another in a stack configuration. In the example of 38, the header module 6002 is coupled to a surgical module 6004 via pass-through hub connectors 6005, 6006.

The modular surgical system 6000 comprises an example power architecture that consists of a single AC/DC power supply 6003 that provides power to all the surgical modules in the stack. The AC/DC power supply 6003 is housed in the header module 6002, and utilizes a power backplane 6008 to distribute power to each module in the stack. The example of FIG. 38 demonstrates three separate power domains on the power backplane 6008: a primary power domain 6009, a standby power domain 6010, and an Ethernet switch power domain 6013.

In the example illustrated in FIG. 38, the power backplane 6008 extends from the header module 6002 through a number of intermediate modules 6004 to a most bottom, or farthest, module in the stack. In various aspects, the power backplane 6008 is configured to deliver power to a surgical module 6004 through one or more other surgical modules 6004 that are ahead of it in the stack. The surgical module 6004 receiving power from the header module 6002 can be coupled to a surgical instrument or tool configured to deliver therapeutic energy to a patient.

The primary power domain 6009 is the primary power source for the functional module-specific circuits 6013, 6014, 6015 of the modules 6002, 6004. It consists of a single voltage rail that is provided to every module. In at least one example, a nominal voltage of 60V can be selected to be higher than the local rails needed by any module, so that the modules can exclusively implement buck regulation, which is generally more efficient than boost regulation.

In various embodiments, the primary power domain 6009 is controlled by the header module 6002. In certain instances, as illustrated in FIG. 38, a local power switch 6018 is positioned on the header module 6002. In certain instances, a remote on/off interface 6016 can be configured to control a system power control 6017 on the header module 6002, for example. In at least one example, the remote on/off interface 6016 is configured to transmit pulsed discrete commands (separate commands for On and Off) and a power status telemetry signal. In various instances, the primary power domain 6009 is configured to distribute power to all the modules in the stack configuration following a user-initiated power-up.

Figure 39:
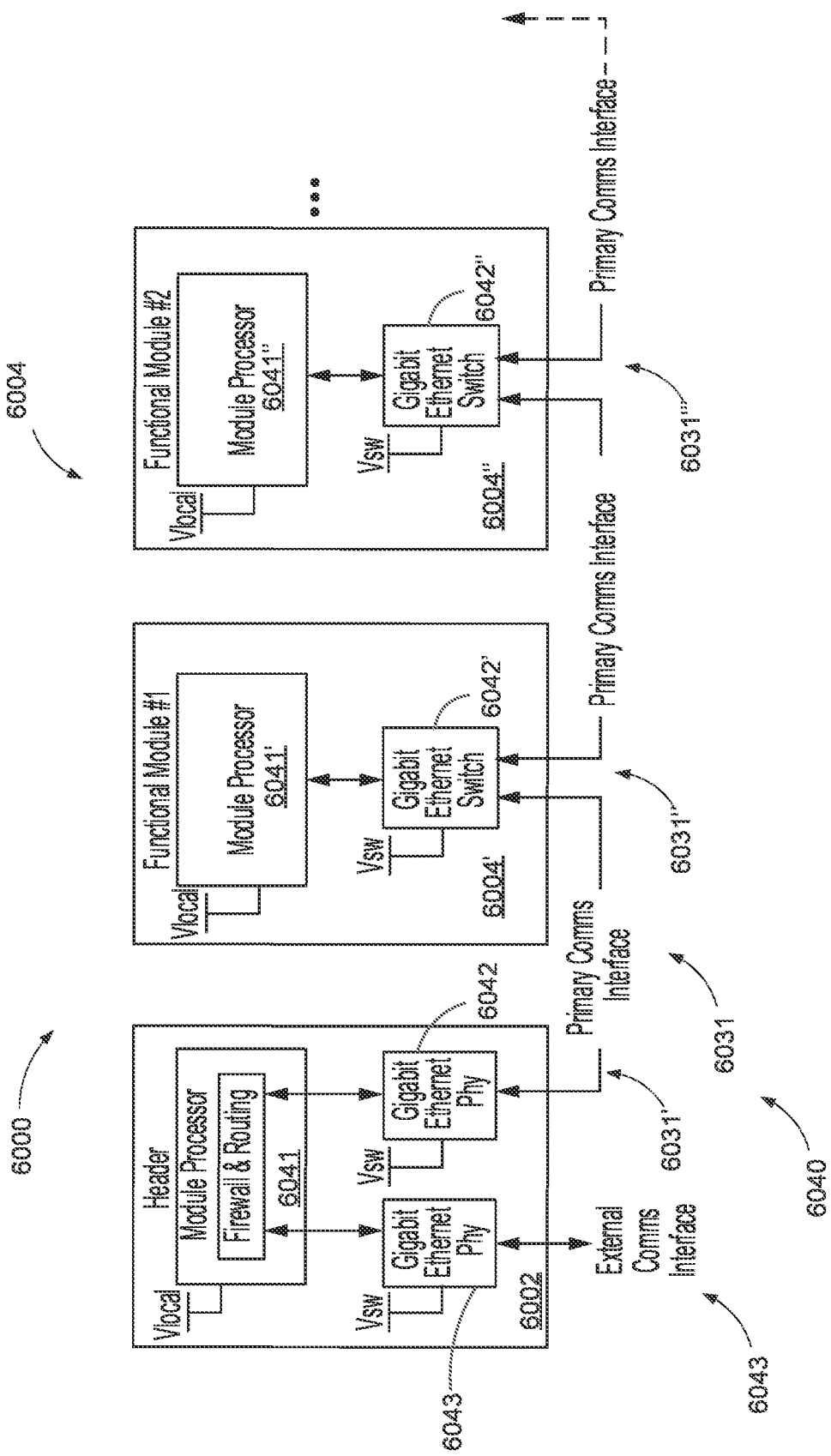
FIG. 39 is a schematic diagram of a modular surgical system, in accordance with at least one aspect of the present disclosure.

In various aspects, as illustrated in FIG. 39, the modules of the modular surgical system 6000 can be communicably coupled to the header module 6002 and/or to each other via a communication (Serial bus/Ethernet) interface 6040 such that data or other information is shared by and between the modules of which the modular surgical system is constructed. An Ethernet switch domain 6013 can be derived from the primary power domain 6009, for example. The Ethernet switch power domain 6013 is segregated into a separate power domain, so that the primary communications interface 6040 will remain alive when local power to a module is removed, which is configured to power Ethernet switches within each of the modules in the stack configuration. In at least one example, the primary communication interface 6040 comprises a 1000BASE-T Ethernet network, where each module represents a node on the network, and each module downstream from the header module 6002 contains a 3-port Ethernet switch for routing traffic to the local module or passing the data up or downstream as appropriate.

Furthermore, in certain examples, the modular surgical system 6000 includes secondary, low speed, communication interface between modules for critical, power related functions including module power sequencing and module power status. The secondary communications interface can, for example, be a multi-drop Local Interconnect Network (LIN), where the header module is the master and all downstream modules are slaves.

In various aspects, as illustrated in FIG. 38, a standby power domain 6010 is a separate output from the AC/DC power supply 6003 that is always live when the supply is connected to mains power 6020. The standby power domain 6010 is used by all the modules in the system to power circuitry for a mitigated communications interface, and to control the local power to each module. Further, the standby power domain 6010 is configured to provide power to circuitry that is critical in a standby mode such as, for example, on/off command detection, status LEDs, secondary communication bus, etc.

In various aspects, as illustrated in FIG. 38, the individual surgical modules 6004 lack independent power supplies and, as such, rely on the header module 6002 to supply power in the stack configuration. Only the header module 6002 is directly connected to the mains power 6020. The surgical modules 6004 lack direct connections to the mains power 6020, and can receive power only in the stack configuration. This arrangement improves the safety of the individual surgical modules 6004, and reduces the overall footprint of the modular surgical system 6000. This arrangement further reduces the number of cords required for proper operation of the modular surgical system 6000, which can reduce clutter and footprint in the operating room.

Accordingly, a surgical instrument connected to surgical modules 6004 of a modular surgical system 6000, in the stack configuration, receives therapeutic energy for tissue treatment that is generated by the surgical module 6004 from power delivered to the surgical module 6004 from the AC/DC power supply 6003 of the header module 6002.

In at least one example, while a header module 6002 is assembled in a stack configuration with a first surgical module 6004', energy can flow from the AC/DC power supply 6003 to the first surgical module 6004'. Further, while a header module 6002 is assembled in a stack configuration with a first surgical module 6004' (connected to the header module 6002) and a second surgical module 6004" (connected to the first surgical module 6004'), energy can flow from the AC/DC power supply 6003 to the second surgical module 6004" through the first surgical module 6004'.

The energy generated by the AC/DC power supply 6003 of the header module 6002 is transmitted through a segmented power backplane 6008 defined through the modular surgical system 6000. In the example of FIG. 38, the header module 6002 houses a power backplane segment 6008', the first surgical module 6004' houses a power backplane segment 6008", and the second surgical module 6004" houses a power backplane segment 6008'". The power backplane segment 6008' is detachably coupled to the power backplane segment 6008" in the stack configuration. Further, the power backplane 6008" is detachably coupled to the power backplane segment 6008'" in the stack configuration. Accordingly, energy flows from the AC/DC power supply 6003 to the power backplane segment 6008', then to the power backplane segment 6008", and then to the power backplane segment 6008'".

In the example of FIG. 38, the power backplane segment 6008' is detachably connected to the power backplane segment 6008" via pass-through hub connectors 6005, 6006 in the stack configuration. Further, the power backplane segment 6008" is detachably connected to the power backplane segment 6008'" via pass-through hub connectors 6025, 6056 in the stack configuration. In certain instances, removing a surgical module from the stack configuration severs its connection to the power supply 6003. For example, separating the second surgical module 6004" from the first surgical module 6004' disconnects the power backplane segment 6008' from the power backplane segment 6008". However, the connection between the power backplane segment 6008" and the power backplane segment 6008'" remains intact as long as the header module 6002 and the first surgical module 6004' remain in the stack configuration. Accordingly, energy can still flow to the first surgical module 6004' after disconnecting the second surgical module 6004" through the connection between the header module 6002 and the first surgical module 6004'. Separating connected modules can be achieved, in certain instances, by simply pulling the surgical modules 6004 apart.

In the example of FIG. 38, each of the modules 6002, 6004 includes a mitigated module control 6023 configured to determine an AC status based on an AC status of the AC/DC power supply 6003 based on an AC status signal 6011 transmitted to the mitigated module controls 6023 of the modules of the modular surgical system 6000. The mitigated module controls 6023 are coupled to corresponding local power regulation modules 6024 that are configured to regulate power based on input from the mitigated module controls 6023, which can be indicative of the AC status received by the mitigated module controls 6023, for each of the surgical modules.

The modular surgical system 6000 further includes a mitigated communications interface 6021 that includes a segmented communication backplane 6027 extending between the mitigated module controls 6023. The segmented communication backplane 6027 is similar in many respects to the segmented power backplane 6008. Mitigated Communication between the mitigated module controls 6023 of the header module 6002 and the surgical modules 6004 can be achieved through the segmented communication backplane 6027 defined through the modular surgical system 6000. In the example of FIG. 38, the header module 6002 houses a communication backplane segment 6027', the first surgical module 6004' houses a communication backplane segment 6027", and the second surgical module 6004" houses a communication backplane segment 6027'". The communication backplane segment 6027' is detachably coupled to the communication backplane segment 6027" in the stack configuration via the pass-through hub connectors 6005, 6006. Further, the communication backplane 6027" is detachably coupled to the communication backplane segment 6027" in the stack configuration via the pass-through hub connectors 6025, 6026.

Although the example of FIG. 38 depicts a modular surgical system 6000 includes a header module 6002 and two surgical modules 6004' 6004", this is not limiting. Modular surgical systems with more or less surgical modules are contemplated by the present disclosure. In some aspects, the modular surgical system 6000 includes other modules such as, for example, the communications module 3032 (FIG. 33). In some aspects, the header module 6502 supports a display screen such as, for example, the display 2006 (FIG. 25A) that renders a GUI such as, for example, the GUI 2008 for relaying information regarding the modules connected to the header module 6002. As described in greater detail in connection with the example of FIG. 33, in some aspects, the GUI 2008 of the display screen 2006 can provide a consolidated point of control all of the modules making up the particular configuration of a modular surgical system.

FIG. 39 depicts a simplified schematic diagram of the modular surgical system 6000, which illustrates a primary communications interface 6040 between the header module 6002 and the surgical modules 6004. The primary communications interface 6040 communicably connects module processors 6041, 6041", 6041" of the header module 6002 and the surgical modules 6004. Commands generated by the module processor 6041 of the header module are transmitted downstream to a desired functional surgical module via the primary communications interface 6040. In certain instances, the primary communications interface 6040 is configured to establish a two-way communication pathway between neighboring modules. In other instances, t the primary communications interface 6040 is configured to establish a one-way communication pathway between neighboring modules.

Furthermore, the primary communications interface 6040 includes a segmented communication backplane 6031, which is similar in many respects to the segmented power backplane 8006. Communication between the header module 6002 and the surgical modules 6004 can be achieved through the segmented communication backplane 6031 defined through the modular surgical system 6000. In the example of FIG. 39, the header module 6002 houses a communication backplane segment 6031', the first surgical module 6004' houses a communication backplane segment 6031", and the second surgical module 6004" houses a communication backplane segment 6031'". The communication backplane segment 6031' is detachably coupled to the communication backplane segment 6031" in the stack configuration via the pass-through hub connectors 6005, 6006. Further, the communication backplane 6031" is detachably coupled to the communication backplane segment 6031" in the stack configuration via the pass-through hub connectors 6025, 6026.

In at least one example, as illustrated in FIG. 39, the primary communications interface 6040 is implemented using the DDS framework running on a Gigabit Ethernet interface. The module processors 6041, 6041', 6041" are connected to Gigabit Ethernet Switches 6042, 6042', 6042". In the example of FIG. 39, the segmented communication backplane 6031 connects the Gigabit Ethernet Switches 6042 of the neighboring modules.

In various aspects, as illustrated in FIG. 39, the header module 6002 includes a separate Gigabit Ethernet Switch 6043 for an external communications interface 6043 with the processor module 6041 of the header module 6002. In at least one example, the processor module 6041 of the header module 6002 handles firewalls and information routing.

Figure 41:
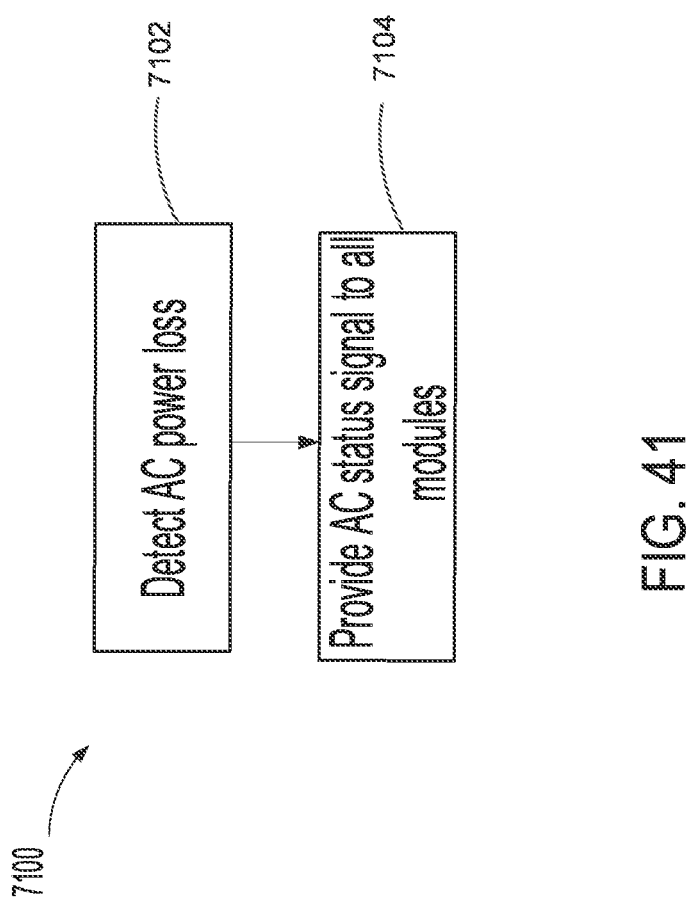
FIG. 41 is a logic flow diagram of a process depicting a control program or a logic configuration for managing a power failure among surgical modules of a modular surgical system, in accordance with at least one aspect of the present disclosure.

Referring to FIGS. 38 and 41, the AC/DC power supply 6003 may provide 7104 an AC Status signal 6011 that indicates a loss of AC power supplied by the AC/DC power supply 6003. The AC status signal 6011 can be provided 7104 to all the modules of the modular surgical system 6000 via the segmented power backplane 6008 to allow each module as much time as possible for a graceful shutdown, before primary output power is lost. The AC status signal 6011 can be received by a mitigated module control 6023 at each of the modules of the modular surgical system 6000, which is in communication with the module specific circuits 6013, 6014, 6015, for example. In various examples, the system power control 6017 can be configured to detect 7102 AC power loss. In at least one example, the AC power loss is detected via one or more suitable sensors.

Referring to FIGS. 38 and 39, to ensure that a local power failure in one of the modules of the modular surgical system 6000 does not disable the entire power bus, the primary power input to all modules can be fused. Further, Ethernet switch power is segregated into a separate power domain 6013 so that the primary communications interface 6040 remains alive when local power to a module is removed. In other words, primary power can be removes and/or diverted from a surgical module without losing its ability to communicate with other surgical modules 6004 and/or the header module 6002.

Figure 40:
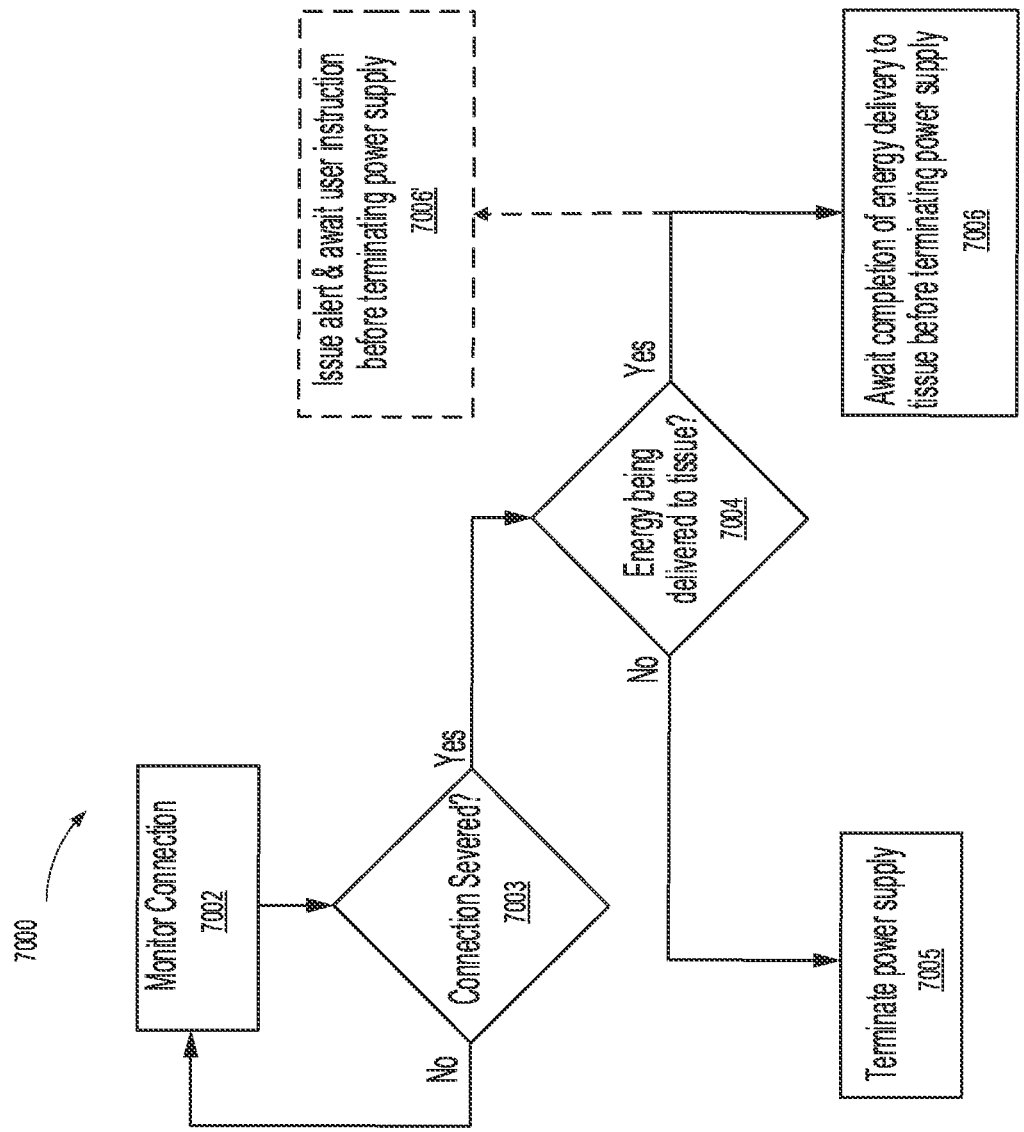
FIG. 40 is a logic flow diagram of a process depicting a control program or a logic configuration for managing power distribution among surgical modules of a modular surgical system, in accordance with at least one aspect of the present disclosure.

FIG. 40 is a logic flow diagram of a process 7000 depicting a control program or a logic configuration for managing power distribution among surgical modules of a modular surgical system such as, for example, the modular surgical system 6000. In at least one example, the process 7000 of FIG. 40 is executed by a module detection circuit 6019 (FIG. 38), which is in communication with the system power control 6017 of the header module 6017. In various examples, the system power control 6017 includes a processor 502 and a memory 504 storing a set of computer-executable instructions that, when executed by the processor 502, cause the processor 502 to perform the process 7000. Although the process 7000, and various other processes of the present disclosure, are described as being executed by a processor, this is merely for brevity, and it should be understood that the processes of the present disclosure can be executed by other suitable circuitry and various suitable systems described by the present disclosure such as, for example, the combinational logic circuit 510 (FIG. 14) or the sequential logic circuit 520 (FIG. 15).

The process 7000 monitors 7002 connections or contact points between modules of the modular surgical system 6000. In at least on example, any suitable sensors such as, for example, suitable pressure, contact, and/or or proximity sensors can be employed by the module detection circuit 6019, for example, to detect addition and/or removal of surgical modules to the modular surgical system 6000 and/or monitor surgical module-to-surgical module and/or surgical module-to-header/footer module connections or contact points. In at least one example, the system power control 6017 is configured to receive input from a module detection circuit 6019 indicative of whether one or more of the surgical module-to-surgical module and/or surgical module-to-header module connections are severed 7003. The module detection circuit 6019 extends through the header module 6002 and surgical modules 6004 of the modular surgical system 6000 in the stack configuration, as illustrated in FIG. 38, and can include, for example, one or more sensors for detecting addition and/or removal of surgical modules to the modular surgical system 6000 and/or monitoring the surgical module-to-surgical module and/or surgical module-to-header module connections.

In at least one example, one or more pressure sensors can be positioned on a bottom and/or top surface of the modules. Each of the pressure sensors is operable to sense pressure, such as by converting a physical deflection into an electrical signal, and thereby provide pressure data. A circuit such as, for example, the module detection circuit 6019 can detect whether modules of a modular surgical system are properly stacked based on pressure data generated by the pressure sensors. To distinguish pressure data caused by abutting against a working surface from pressure data caused by abutting against another module, the pressure sensor(s) can be placed on depressed portions, or ridges, in bottom surfaces of the modules. Corresponding raised portions, or protrusions, on top surfaces of the module are configured to engage the pressure sensors of the depressed portions when the modules are properly stacked in a stack configuration yielding unique pressure data that can signify a proper connection between two surgical modules or a surgical module and header/footer module. In at least one alternative example, the pressure sensor(s) can be placed on the raised portions instead of the depressed portions. The pressure sensors comprise any suitable type(s) of pressure sensors, including but not limited to piezoresistive, capacitive, strain gauges, or any other suitable sensor type, including combinations thereof.

In at least one example, a Hall-effect sensor or any suitable transducer that varies its output voltage in response to a magnetic field, can be employed by the module detection circuit 6019 to detect addition and/or removal of surgical modules to the modular surgical system 6000 and/or monitor surgical module-to-surgical module and/or surgical module-to-header/footer module connections. Hall-effect sensors and corresponding magnets can be installed onto the housings of modules of a modular surgical system 6000 to trigger hall-effect sensors in a connected configuration.

The module detection circuit 6019 can be implemented as described in greater detail in U.S. patent application Ser. No. 16/562,212, titled MODULAR SURGICAL ENERGY SYSTEM WITH MODULE POSITIONAL AWARENESS SENSING WITH VOLTAGE DETECTION, U.S. patent application Ser. No. 16/562,234, titled MODULAR SURGICAL ENERGY SYSTEM WITH MODULE POSITIONAL AWARENESS SENSING WITH TIME COUNTER, and U.S. patent application Ser. No. 16/562,243, titled MODULAR SURGICAL ENERGY SYSTEM WITH MODULE POSITIONAL AWARENESS WITH DIGITAL LOGIC, which are incorporated by reference herein in their entireties.

In various aspects, if the header module 6002 determines 7003 that one or more of the connections is severed 7003, the header module 6002 may further determine 7004 whether therapeutic energy is being delivered to the tissue prior to taking actions to mitigate the severed connection(s). If the header module 6002 determines 7004 that no therapeutic energy is being delivered to tissue, the header module 6002 can cause the system power control 6017 to terminate 7005 power supply to the surgical modules of the modular surgical system 6000. In one example, the header module 6002 may terminate all power supply to the surgical modules. In another example, the header module 6002 may terminate the primary power supply while maintaining the communication and/or standby power supplies.

If, however, the header module 6002 determines 7004 that therapeutic energy is being delivered to tissue by a surgical instrument or tool, the header module 6002 may maintain 7006 the primary power supply until the therapeutic energy delivery to tissue is completed. Alternatively, the header module 6002 may issue an alert 7006' and await user instructions before terminating the primary power supply In at least one example, the alert can be issued through the UI module 3030 (FIG. 33). In various examples, the header module 6002 may select to override or inhibit a power off command, resulting from a detected severed connection, if a surgical module in the stack is performing a therapeutic function at the time of a power off command.

In at least one example, the header module 6002 may query local control circuits (e.g. local control circuits 6013, 6014, 6015) of the surgical modules of the modular surgical system 6000 to determine 7004 whether therapeutic energy is being delivered to the tissue. In at least one example, the header module 6002 may query a surgical module status database stored in any suitable storage medium to determine 7004 whether therapeutic energy is being delivered to the tissue. The queried information may include status, type, energy modality, and/or number of surgical instruments delivering therapeutic energy to the tissue.

Further, the Header module 6002 may query local control circuits (e.g. local control circuits 6013, 6014, 6015) of the surgical modules of the modular surgical system 6000 through the communication backplane 6031 (FIG. 39), for example, to determine the number of surgical modules in the stack configuration. In at least one example, the header module 6002 may query a surgical module status database stored in any suitable storage medium to determine the number of surgical modules in the stack configuration. The header module 6002 may further compare the queried information to the number of surgical modules detected by the module detection circuit 6019 to update the database.

In at least one example, a modular surgical system 6000, which includes a header module 6002 and two surgical modules 6004', 6004", can implement the process 7000 to address a severed connection between the first surgical module 6004' and the second surgical module 6004" while therapeutic energy generated by the first surgical module 6004' is being delivered to tissue via a surgical instrument coupled to one of the ports of the first surgical module 6004'. Since the first surgical module 6004' is stacked between the header module 6002 and the second surgical module 6004", the severed connection occurred downstream from where therapeutic energy is being delivered to tissue by the surgical instrument through the first surgical module 6004'. Accordingly, the process 7000 maintains primary power supply to the first surgical module 6004' until therapeutic energy application to tissue is completed. In at least one alternative example, as illustrated in FIG. 40, the process 7000 may issue an alert 7006' and await user instructions before terminating the primary power supply.

In at least one example, the header module 6003 determines that therapeutic energy is being delivered to tissue through a feedback input from the first surgical module 6004'. The header module 6003 may query local control circuit 6014 of the surgical modules of the modular surgical system 6000 to determine 7004 whether therapeutic energy is being delivered to the tissue.

The modular surgical system 6000 permits a user to add or remove modules to adapt the modular surgical system 6000 to a surgical procedure, for example. The power budget of a modular surgical system 6000 varies based on the number of surgical modules 6004 present in the stack. Consequently, the power budget of the modular surgical systems disclosed herein is actively and adaptively managed to ensure that the stack as a whole does not consume more than the rated power.

In various examples, the header module 6002 can be configured to determine the number of surgical modules 6004 present in the stack configuration of the modular surgical system 6000, and allocate power to each of the surgical modules 6004 based on the determined number of surgical modules 6004 present in the stack configuration. In at least one example, a suitable circuit, which employs digital logic or a time counter for example, can be employed by the header module 6002 to determine the number and/or position of surgical modules 6004 present in the stack configuration. In another example, user input is solicited to determine or to confirm the number of surgical modules 6004 present in the stack configuration. This arrangement allows the modular surgical system 6000 to handle situations where surgical modules 6004 are added or removed by a user. In at least one example, the header module 6002 can infer the number of surgical modules 6004 present in the stack configuration based on the type of surgical procedure being performed, which can be ascertained from user-input, for example. In various aspects, a look-up table or a database of surgical procedure types and their surgical module requirements can be stored in a local memory or a remote server 113 on a cloud, and can be queried by the header module 6002 to determine the number of surgical modules 6004 present in the stack configuration based on the type of surgical procedure being performed.

As described above in greater detail in connection with FIGS. 24-30, a surgical module such as, for example, the surgical module 2004 can include a port assembly 2012 including a number of different ports configured to deliver different energy modalities to corresponding surgical instruments that are connectable thereto. Accordingly, the power requirements of a surgical module varies, at least in part, based on the types, energy modalities, and/or number of surgical instruments connected thereto. In various aspects, connecting or disconnecting a surgical instrument to one of the ports of the port assembly 2012 of a surgical module in a stack configuration causes the header module 6002 to reassess energy allocations to the surgical modules in the stack configuration, and can trigger an adjustment of the power allocations to the surgical modules.

In at least one example, referring primarily to FIG. 38, connecting a surgical instrument to the port assembly of the first surgical module 6004' causes the header module 6002 to increase a previously determined power allocation to the first surgical module 6004' and, consequently, decrease a previously determined power allocation to the second surgical module 6004' to free power for the additional power allocation to the first surgical module 6004'.

In various examples, as described above, a power allocation adjustment event can be triggered by connecting or disconnecting a surgical instrument to a port of the port assembly 2012. In at least on example, any suitable sensors such as, for example, suitable pressure, contact, and/or or proximity sensors can be employed by the header module 6003 to monitor the ports of the port assembly 2012 for a power-allocation adjustment triggering event. In other examples, the power-allocation adjustment triggering event can be the activation of a connected surgical instrument and/or a user-input through the UI module 3030 such as, for example, a selection of a surgical instrument setting such as, for example, an energy setting.

In various aspects, the modular surgical system 6000 actively and adaptively manages the power budget through an ongoing negotiation between the functional surgical modules 6004 and the header module 6002 to determine how much power is allocated to each of the surgical modules 6004. Various processes are disclosed herein for active power management of the modular surgical system. In at least one example, such processes can be executed by a control circuit of the modular surgical system such as, for example, the control circuit 500 (FIG. 13).

In various examples, a power-allocation adjustment triggering event can cause the header module 6002 to apply restricted power level settings to one or more of functional modalities of one or more of the surgical modules. In various examples, a power-allocation adjustment triggering event can cause the header module 6002 to prevent simultaneous activation of certain functional modalities of one or more of the surgical modules at certain power settings. In various examples, the header module 6002 can disable or deactivate a module if it is not needed for a particular surgical procedure.

When conflict arises in the power budget negotiations between the modules of a modular surgical system 6000, the header module 6002 can attempt to resolve the conflict or, alternatively, prompt a user to resolve the conflict through the UI 3030, for example. In various aspects, the power budget negotiation will be made transparent to the user. In certain aspects, the user can be notified of a limitation imposed by the header module 6002. Following the power budget negotiation, each module is responsible for monitoring its own input power and ensuring that it stays under predetermined limits. Further, each module implements its own mitigations to address a situation where the input power budgeted for the module is exceeded.

Figure 42A:
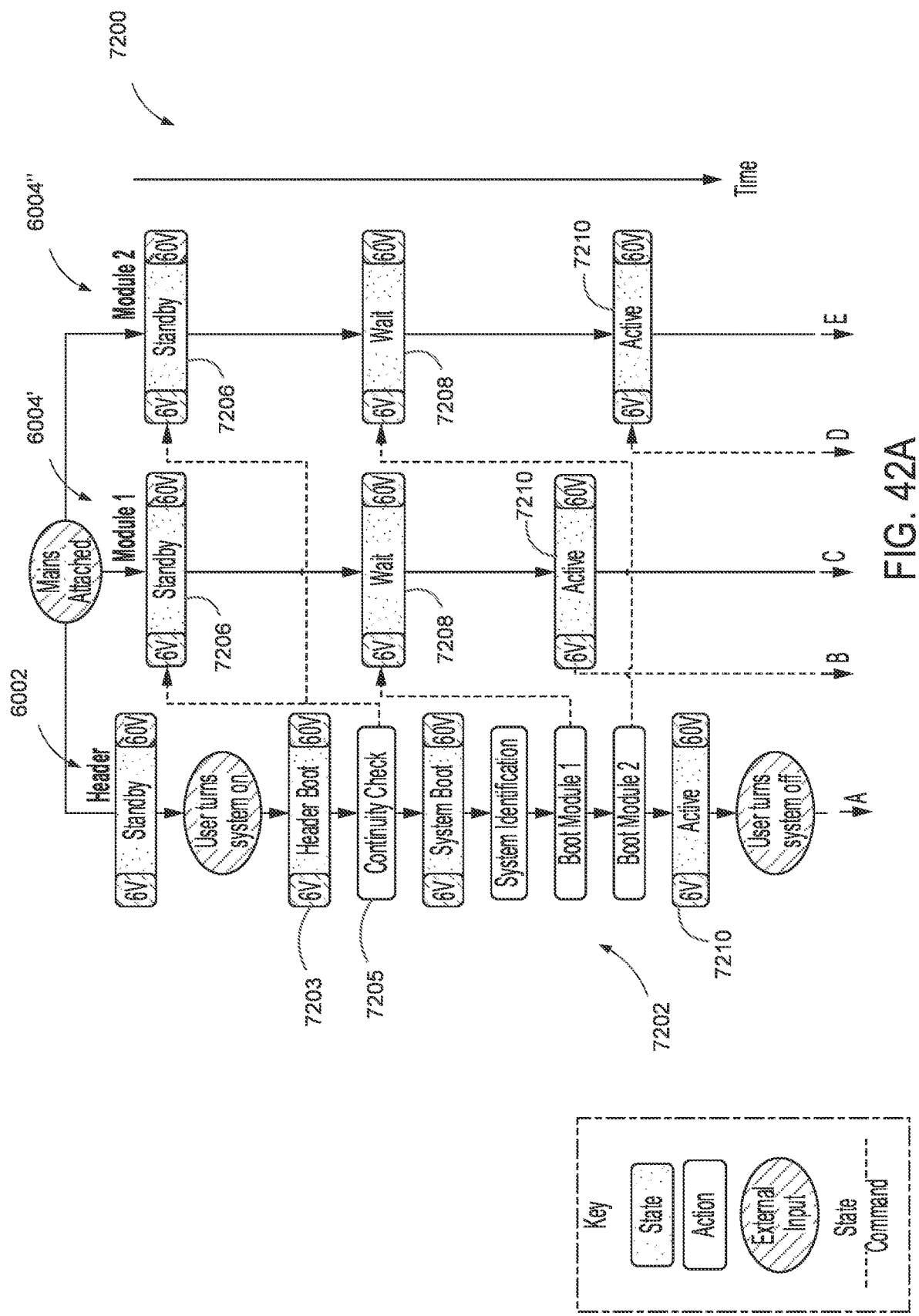
FIGS. 42A and 42B illustrate power up and power down sequences for a modular surgical system, in accordance with at least one aspect of the present disclosure.
Figure 42B:
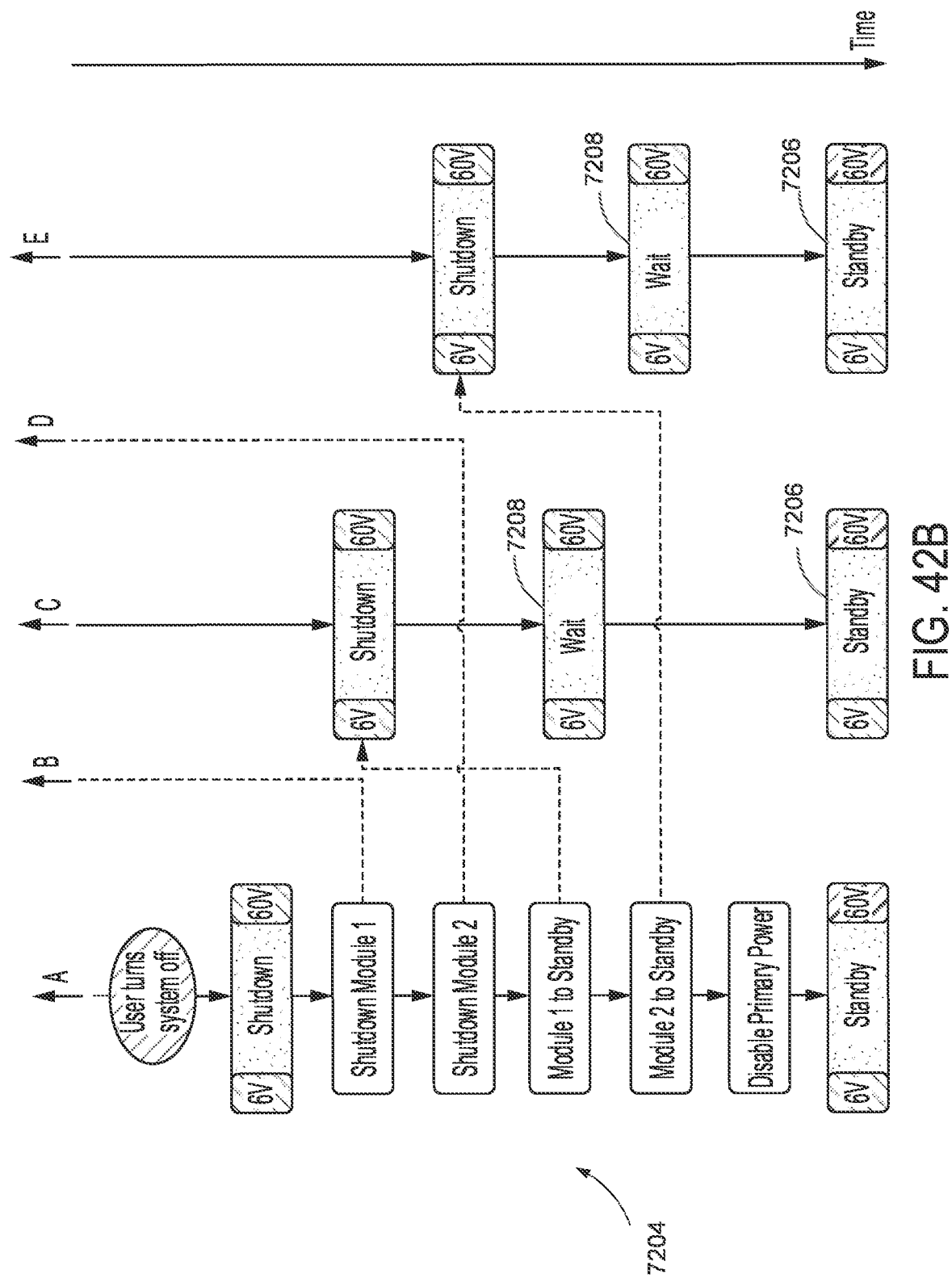

Referring primarily to FIGS. 42A and 42B, an example power up and power down sequence 7200 of a modular surgical system 6000 is depicted. The modular surgical system 6000 of FIGS. 42A and 42B includes a header module 6002 arranged in a stack configuration with a first surgical module 6004' and a second surgical module 6004". FIGS. 42A and 42B detail four unique power states or modes that modular surgical system 6000 may transition through during the power up sequence 7202 and/or power down sequence 7204.

Initially, the header module 6002 is shown in a standby mode 7206. The primary power and Communications are disabled in the standby mode 7260. The surgical modules 6004 await for commands from the Header module 6002 to transition from a standby mode 7206 to a wait mode 7208. Primary power and communications are enabled in the wait mode 7208, but the modules consume minimal power as only limited tasks are available in the wait mode 7208 such as, for example, system initialization, authentication, and/or module discovery. In contrast, the primary module functions, for example energy delivery on a surgical module, are disabled in the wait mode 7208. Accordingly, the surgical modules 6004 in the stack configuration is incapable of delivering therapeutic energy in the wait mode 7208.

Further to the above, the header module 6002, while in the standby mode 7206, is capable of receiving local 6018 (FIG. 38) and/or remote on/off 6016 (FIG. 38) detection commands. Upon receiving a booting command, the primary power is enabled and a main processor 6041 of the header module 6002 begins a boot sequence 7203. Then a module detection check 7205 is performed using the module detection circuit 6019, for example.

Due to the modular nature of the modular surgical system 6000, a module detection check 7205 is performed to ensure proper connections are achieved between the modules in the stack. If the module detection check is passed, the segmented power backplane 6008 of the stack is enabled at 60 volts, for example. If, however, the stack fails the module detection check 7205, an error message indicative of the failure can be provided through the user interface 3030 of the header module 6002, for example. Instructions as to the reason for the failure, and how to address it, can also be provided.

In various aspects, once the header module 6002 and the user interface 3030 are in active mode 7210, the remaining modules are then brought to an active mode 7210. The header module 6002 may query module types, versions, locations over Data Distribution Services (hereinafter "DDS") framework that may run on a Gigabit Ethernet interface. Once an active mode of the modular surgical system 6000 is achieved, a user may be prompted through the user interface 3030 that the modular surgical system 6000 is ready for use in a surgical procedure.

Like the power up sequence, the power down sequence 7204 can be triggered by a local 6018 and/or remote on/off 6016 command. In the power down sequence 7204, the modules primary functions are disabled, primary power consumption is reduced, and/or priority tasks (write logs, complete data transfers, etc.) are completed, ultimately causing the power level to be sufficiently reduced to match the wait mode 7208.

The modular surgical systems of the present disclosure such as, for example, the modular surgical system 6000 are assembled or modified by an end user either prior to or during a surgical procedure. Accordingly, various assembly and disassembly steps are performed on the modular surgical systems by someone other than the manufacturer. Many advantages are gained by such modularity, which also introduces potential failures. To protect against the potential failures, the modular surgical systems of the present disclosure are equipped with various mechanisms for fault isolation and minimization of single point failures. In addition, the modular surgical systems include various mechanisms for awareness of the quantity, type, and/or position of modules in the stack prior to and/or during application of power.

In at least one example, as illustrated in FIG. 38, the modular surgical system 6000 includes a mitigated communications interface 6021 between the modules in the stack. To enable fault isolation and minimization of single point failures, the mitigated communications interface 6021 is powered from the standby output of the AC/DC power supply 6003, allowing the mitigated communications interface 6021 to be alive when primary power is removed, or in the event of a local power failure in a module in the stack. Furthermore, the mitigated communications interface 6021 is implemented in a separate controller 6023 from the primary communications interface 6040 to ensure that a failure in the primary controller 6041, 6041', 6041" for a module 6002, 6004" 6004"', respectively, does not impact the mitigated communications interface 6021.

In various aspects, the Header module 6002 is configured to detect a failure in the modular surgical system 6000 by measuring the total current draw on the primary power domain 6009, and comparing the measured total current draw to the total system input current. If the total system input current is exceeded, the header module 6002 determines that a failure in the modular surgical system 6000 is detected, and can take steps to mitigate the failure, as described elsewhere herein in greater detail.

Further to the above, the mitigated communications interface 6021 could be implemented in either hardware or software. In at least one example, the mitigated communications interface 6021 is implemented as a serial bus or as a command/status shift register, with data/clock/latch signals. The serial bus interface could be either point-to-point or multi-drop. In various examples, as illustrated in FIG. 38, the mitigated communications interface 6021 is implemented in a segmented backplane 6027 connecting the mitigated module controls 6023 of the individual modules of the modular surgical system 6000.

In various aspects, the mitigated communications interface 6021 can facilitate communication between modules in the event of a failure of the primary communications interface 6040. The mitigated communications interface 6021 can also determine the quantity and type(s) of modules in the stack prior to application of power, enabling a stable, predictable power on sequence. Furthermore, module resets, module local power control, and/or module local power sequencing, if necessary, can be facilitated by the mitigated communications interface 6021. In certain examples, the mitigated Communications interface 6021 can be used to put a module into a reset and/or local power down state to isolate failures in a particular module from the rest of the stack.

In various aspects, the header module 6002 is configured to control the local power to each of the surgical modules in a stack via commands on the mitigated communications interface 6021. The Modules can be in one of a number of example power modes. In an off mode, a standby power is available, while the primary backplane power (e.g. 60V) is disabled. In the off mode, the header module 6002 is capable of identifying the presence and/or type of modules connected in the stack, for example.

Further to the above, the standby power is also available in the standby mode. In addition, the primary backplane power (e.g. 60V) is enabled in the standby mode. In contrast, a module secondary power is disabled in the standby mode. The header module 6002 may identify the presence and type of modules in the stack in the standby mode. In addition to the off and standby modes, a sleep mode can also be available, as discussed in connection with FIGS. 42A and 42B. In the sleep mode, the standby power and the backplane power (e.g. 60V) are enabled and module detection check through the module detection circuit 6019 is active. In contrast, all functionality not critical to module detection check, wake detection, module identification, and/or communication between modules is disabled. Further, a wake or active mode is also available. In the active mode, the standby power and the backplane (e.g. 60V) power are enabled and module detection check is active. Further, a module in the active mode participates in all backplane communications.

As discussed above, the one or more modules can be connected together in a variety of different stacked configurations to form various modular surgical system configurations. The stacked configuration of the modules effectively reduces the footprint needed for the modules in the operating room.

Figure 43A:
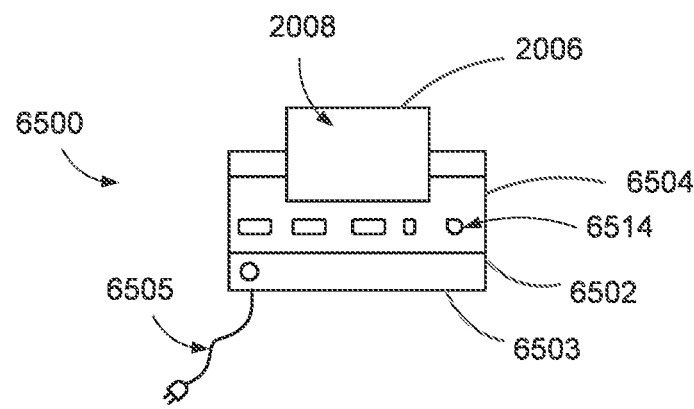
FIG. 43A illustrates a modular surgical system including a header module, a surgical module, and a footer module, in accordance with at least one aspect of the present disclosure.

Referring to FIG. 43A, an alternative modular surgical system 6500 is shown. The modular surgical system 6500 is similar in many respects to other modular surgical systems described elsewhere such as, for example, the modular surgical systems 2000, 6000. However, unlike the modular surgical system 6000, the modular surgical system 6500 includes a header module with a power supply that provides power to surgical modules stacked on top of the header module. Accordingly, the header module of the modular surgical system 6500 is referred to herein as a footer module 6502. Further, one or more surgical modules 6504 are configured to be stacked on top of the footer module 6502.

In some aspects, the modular surgical system 6500 further includes a display screen 6506 that renders a GUI 6508, as described in greater detail below. The positioning of the footer module 6502 beneath the other modules of the modular surgical system 6500 in the stack configuration improves weight distribution of the stack and increases its resistance to external forces when placed upon a work surface, thereby reducing the susceptibility of the stack to being tipped over during use.

As discussed above, it is desirable to reduce the number of cords for a modular surgical system by using a single AC/DC power for the entire system. The footer module 6502 of the modular surgical system 6500 comprises an enclosure or housing 6503 that is configured to be placed upon a work surface, such as a table or cart. The footer module 6502 of the modular surgical system 6500 provides the main AC/DC power supply for the entire system. The footer module 6502 includes a power cord 6505 that is configured to connect to an AC source. The footer module 6502 also includes an AC to DC converter, which is configured to convert the AC current from the AC source to DC voltage for the modules in the modular surgical system.

Like the header module 6002 of the modular surgical system 600, the footer module 6502 of the modular surgical system 6500 provides the main AC/DC power supply for the entire system. The footer module 6502 includes a power cord 6505 that is configured to connect to an AC source. The footer module 6502 also includes an AC to DC converter, which is configured to convert the AC current from the AC source to DC voltage for the modules in the modular surgical system 6500. Further, the footer module can include a power button, which can be used to turn the system on and off, without the need for unplugging and re-plugging the power cord 6505 with each use. The modular surgical system 6500 further includes a surgical module 6504 stacked above the footer module 6502. The surgical module 6504 is configured to support the delivery of energy to instruments that are attached thereto. The surgical module is able to deliver the energy in a multitude of modalities, such as ultrasonic, ABP, monopolar, and bipolar, for example.

Also, like the modular surgical system 6000, the modular surgical system 6500 includes a segmented power backplane similar in many respects to the segmented power backplane 6008 and, in some aspects, a segmented communication back plane similar in many respects to the segmented communication backplane 6021. The segmented power and/or communication backplanes couple the footer module 6502 to other modules of the modular surgical system 6500 in the stack configuration such as, for example, the surgical module 6504. This arrangement allows the footer module 6502 to distribute the DC voltage to the other modules in the system, thereby providing the system with a single energy source for the entire stack.

In some aspects, the modular surgical system 6500 includes a display screen 2006 that renders a GUI 2008 for relaying information regarding the modules 2001 connected to the footer module 6502. In some aspects, the GUI 2008 of the display screen 2006 can provide a consolidated point of control all of the modules making up the particular configuration of the modular surgical system 6500. Various aspects of the GUI 2008 are discussed in fuller detail below in connection with FIG. 30. In alternative aspects, the modular surgical system 6500 can lack the display screen 2006 or the display screen 2006 can be detachably connected to the housing of one of the modules of the modular surgical system 6500.

Figure 43B:
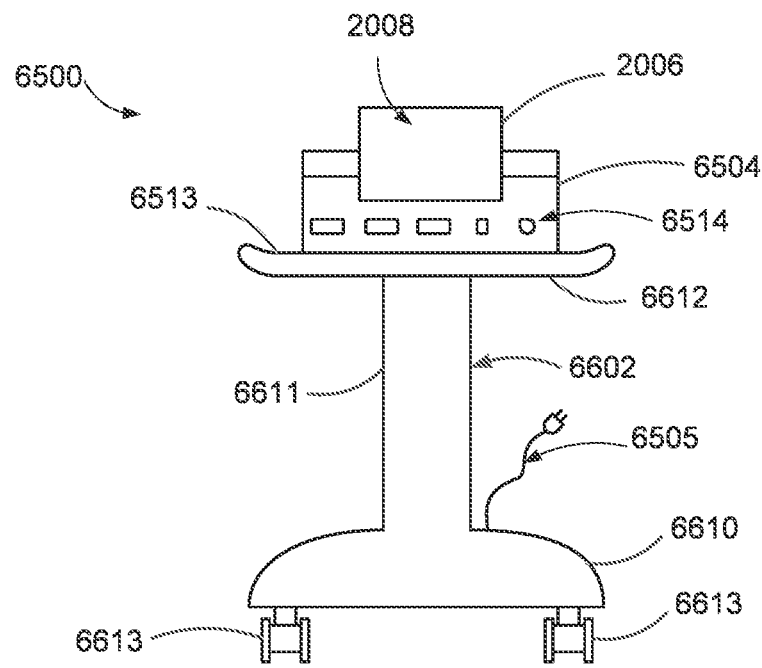
FIG. 43B illustrates a modular surgical system including a header module and a surgical module, the modular surgical system being seated on a footer module cart, in accordance with at least one aspect of the present disclosure.

Referring now to FIG. 43B, an alternative modular surgical system 6600 is depicted in a stack configuration. The modular surgical system 6600 is similar in many respects to the modular surgical system 6500; however, the modular surgical system 6600 includes a footer module 6602 that is integrated into a cart or any other suitable mobile configuration. This design allows the user to reposition the modular surgical system 6600 by rolling the footer module 6602 into its desired location without needing to pick up the modules from the stack. Like the footer module 6502, the footer module 6602 includes a power cord, which can be plugged into an AC source to receive power, which can then be converted to DC power for the modular surgical system 6600 by way of an AC to DC converter, for example.

The footer module 6600 includes a base 6610, a column 6611 extending from the base 6610, and a tray 6612 configured to support, and detachably connect the footer module 6602 to one or more surgical modules 6504 in a stack configuration. In at least one example, the height of the column 6611 can be adjusted by any suitable mechanism to raise or lower the tray 6612. In at least one example, various components of the footer module 6602 can be housed in the base 6610 to improve weight distribution of the stack and increase its resistance to external forces, and reduce the susceptibility of the stack to being tipped over during use.

In various aspects, the modular surgical system 6600 includes one or more of the surgical modules 6504 and/or the display screen 2006. The description of such components is not repeated herein for brevity.

In various aspects, the tray 6612 is detachably coupled to a surgical module 6504 via pass-through hub connectors. Further, like the modular surgical systems 6000, 6500, the modular surgical system 6600 includes a segmented power backplane similar in many respects to the segmented power backplane 6008 and, in some aspects, a segmented communication back plane similar in many respects to the segmented communication backplane 6021. The segmented power and/or communication backplanes couple the footer module 6602 to other modules of the modular surgical system 6600 in the stack configuration such as, for example, the surgical module 6504. This arrangement allows the footer module 6502 to distribute the DC voltage to the other modules in the system, thereby providing the system with a single energy source for the entire stack.

In various aspects, an address such as, for example, 3-bit address which is unique to each module in the stack configuration, is automatically generated in hardware at power-up. The address provides each module with its physical location within the stack configuration as described in greater detail in U.S. patent application Ser. No. 16/562,212, titled MODULAR SURGICAL ENERGY SYSTEM WITH MODULE POSITIONAL AWARENESS SENSING WITH VOLTAGE DETECTION, U.S. patent application Ser. No. 16/562,234, titled MODULAR SURGICAL ENERGY SYSTEM WITH MODULE POSITIONAL AWARENESS SENSING WITH TIME COUNTER, and U.S. patent application Ser. No. 16/562,243, titled MODULAR SURGICAL ENERGY SYSTEM WITH MODULE POSITIONAL AWARENESS WITH DIGITAL LOGIC, which are incorporated by reference herein in their entireties.

As described in greater detail herein, a modular surgical system comprises a header module and one or more functional or surgical modules. In various instances, the modular surgical system is a modular energy system. In various instances, the surgical modules include energy modules, communication modules, and/or user interface modules; however, the surgical modules are envisioned to be any suitable type of functional or surgical module for use with the modular surgical system.

The header module is configured to control the system-wide settings of each module/component connected thereto. In order to effectively control the modules, it is important for the header module to know and/or be aware of the physical location of each module in the system. In various instances, the physical location of each connected module is recognized and/or determined by the header module so that user interface content for each module can be arranged with a 1:1 association to the physical location of each module. In various instances, the physical location of each connected module is recognized by the header module so that a unique address can be assigned to each module. Assignment of a unique address allows the module to be used with a mitigated communication bus.

Figure 44:
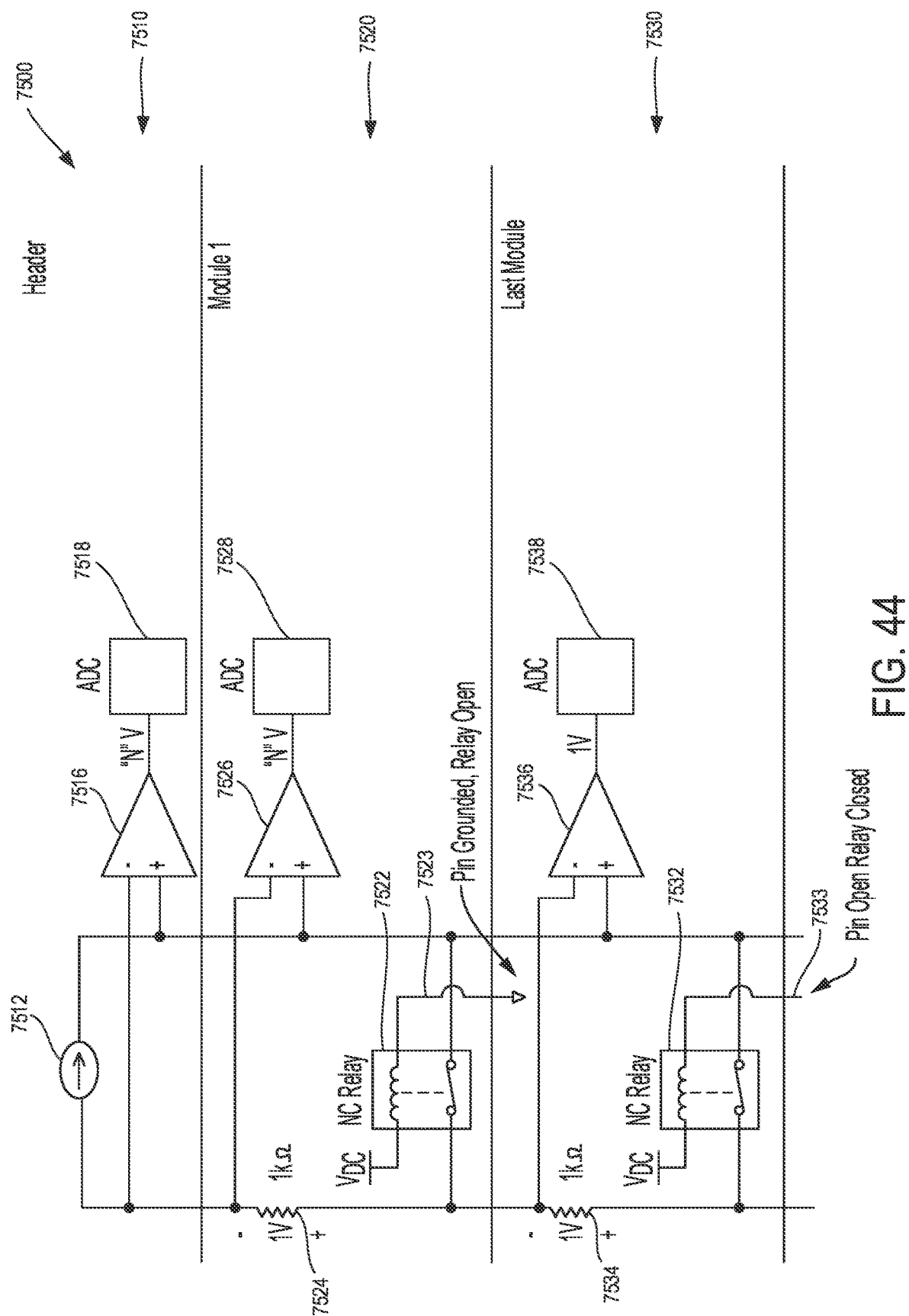
FIG. 44 is a module identification circuit of a modular surgical system, in accordance with at least one aspect of the present disclosure.

FIG. 44 illustrates a modular identification circuit 7500 of a modular surgical system, or a modular energy system. Among other things, the modular identification circuit 7500 is utilized to identify the physical location of one or more modules within a stack configuration of the modular surgical system. In various instances, the modular identification circuit 7500 is configured to detect the total number of modules present within the stack configuration. As shown in FIG. 44, the modular surgical system comprises a header module 7510, a first module 7520, and a second, or last, module 7530. The header module 7510 comprises a current source 7512. A current loop extends from the header module 7510 through each module of the modular surgical system, ultimately returning to the header module 7510. In order for the current to travel through each module of the modular surgical system, each module must be appropriately connected to the modular surgical system and/or each module must be functional.

The header module 7510 is stacked at a top position of the modular surgical system as shown in FIG. 44. A first module 7520 is shown stacked below the header module 7510 in an adjacent position. A second, or last, module 7530 is shown stacked below the first module 7520. In other words, the modular surgical system depicted in FIG. 44 comprises a stack configuration (from top to bottom) of: the header module 7510; the first module 7520; and the last module 7530.

The first module 7520 comprises a first pin 7523 and a normally-closed (NC) relay 7522. The NC relay 7522 is configurable in an open state and a closed state. When the first module 7520 is the only modular component connected to the header module 7510 and/or the first module 7520 is located at bottom-most position within the stack configuration, the first pin 7523 is open and the relay 7522 is closed. In such instances, the current runs from the header module 7510 though the first module 7520 and back to the header module 7510. In various instances, the first pin 7523 is open and the relay 7522 is closed when the first module 7520 is located at bottom-most position within the stack configuration. For example, the first module 7520 could be the only modular component connected to the header module 7510 and/or one or more modules can be positioned between the first module 7520 and the header module 7510.

The second, or last, module 7530 comprises a second pin 7233 and a normally-closed (NC) relay 7532. The NC relay 7532 is configurable in an open state and a closed state. When the second module 7530 is the only modular component connected to the header module 7510, the second pin 7533 is open and the relay 7532 is closed. In such instances, the current runs from the header module 7510 though the second module 7530 and back to the header module 7510. In various instances, such as shown in FIG. 44, the modular surgical system comprises a modular component, such as the first module 7520, positioned in between the second module 7530 and the header module 7510. The connection between the first module 7520 and the second module 7530 causes the first pin 7523 of the first module 7520 to be grounded and causes the NC relay 7522 to be in an open state. As the second module 7530 does not comprise any additional modular components connected and/or positioned underneath the second module 7530 in the stack configuration, the second pin 7233 is in the closed state. In such instances, the current runs from the header module 7510 through the first module 7520, from the first module 7520 through the second module 7520, from the second module 7520 back through the first module 7520, and from the first module 7520 back to the header module 7510.

The relay of the bottom functional modules is closed because its pin is open. In contrast, the relay of an intermediate functional module is open because its pin is grounded in a lower module chassis.

Each module adds series resistance to the current loop, creating a voltage divider. The first module 7520 comprises a first resistor 7524, and the second module 7530 comprises a second resistor 7534. The first resistor 7524 and the second resistor 7534 are placed in series with the current source 7512 of the header module 7510. By placing the resistors 7524, 7534 in series with the current source 7512, a voltage divider is created. The header module 7510 is configured to measure the total resistance in the loop to determine the total number of modules in the stack configuration and/or the modular surgical system.

By measuring the total voltage drop between the input and the output of the current source 7512, the header module 7510 is configured to detect the total number of modules present within the stack configuration. For example, the resistors 7524, 7534 have a resistance of 1 ohm. If the header module 7510 detects a total voltage drop of 1V, only 1 module is present and/or appropriately connected within the stack configuration. If the header module 7510 detects a total voltage drop of 2V, 2 modules are present and/or appropriately connected within the stack configuration. Such an ability of the header module 7510 provides a mitigation strategy, by providing the header module 7510 with a secondary means for detecting module quantity outside of a primary communication bus, such as, for example, an Ethernet cable.

Each module within the stack configuration is configured to measure the voltage from the current source 7512 of the header module 7510 to the low side of the module's resistor in the loop. By measuring the voltage drop between the current source 7512 of the header module 7510 and the low side of the module resistor, a module may detect its own physical position within the stack configuration. The header module comprises a differential amplifier 7516 and an analog to digital converter (ADC) 7518. The first module 7520 further comprises a differential amplifier 7526 and an ADC 7528. The second module 7530 further comprises a differential amplifier 7536 and an ADC 7538. It is envisioned that each module within the modular surgical system comprises a differential amplifier and an ADC for determining the voltage value at each of the modules. In the first module 7520, the differential amplifier 7526 is connected to a high side of the module 7520, which is a position in the module 7520 before the current passes through the resistor 7524. The differential amplifier 7526 is also connected to a low side of the module 7520, which is a position after the current has passed through the resistor 7524. The voltage drop between the header current source 7512 and the low side of the resistor 7524 is measured by the differential amplifier 7526 and is then passed to the ADC 7528. The ADC 7528 then uses this voltage drop to determine a physical location of the module 7520 within the stack configuration.

In a similar manner, the differential amplifier 7536 is connected to a high side of the second module 7530, which is a position in the module 7530 before the current passes through the resistor 7534. The differential amplifier 7536 is also connected to a low side of the module 7530, which is a position after the current has passed through the resistor 7534. The voltage drop between the header current source 7512 and the low side of the resistor 7534 is measured by the differential amplifier 7536 and is then passed to the ADC

7538. The ADC 7538 then uses this voltage drop to determine a physical location of the module 7530 within the stack configuration.

In the modular identification circuit 7500 illustrated in FIG. 44, the header module 7510 comprises a 1 mA current source 7512. The header module is stacked on top of a first module 7520 and a second module 7530. As described above the first module 7520 comprises a 1 kΩ resistor 7524, a differential amplifier 7526, and an ADC 7528. The second module 7530 comprises a 1 kΩ resistor 7534, a differential amplifier 7536, and an ADC 7538. While a 1 mA current source 7512 and 1 kΩ resistors 7524, 7534 are shown, it is envisioned that any suitable combination of current sources and resistors can be used.

The 1 mA current flows from the header module 7510 through the modules stacked therebelow. As discussed above, the high side of the differential amplifiers of the modules measure the voltage before the current passes through the resistor. The current from the header module 7510 flows through the high side of all of the differential amplifiers 7526, 7536 of the modules stack therebelow. Once the current reaches the last module of the stack configuration, the current begins to flow back toward the header module. For example, in FIG. 44, once the 1 mA current reaches the second module 7530, the 1 mA current begins flowing back toward the header module 7510.

As the current flows back toward the header module 7510, the 1 mA current passes across the 1 kΩ resistor 7534 of the second module 7530, which results in a 1V voltage drop between the header current source 7512 and the resistor 7534. The differential amplifier 7536 of the second module 7530 is configured to measure this 1V voltage drop and determine a 1V voltage differential between the header current source 7512 and the low side of the resistor 7534 of the second module 7530. The differential amplifier 7536 can then transmit a signal corresponding to this voltage differential to the ADC 7538, which can interpret this signal and assign a corresponding address to the second module 7530. In the illustrated example, the 1V voltage differential signal is converted to a digital reading by the ADC 7538. The digital reading is interpreted by a controller that assigns a corresponding and/or unique address to the second module 7530. The assigned address corresponds to a physical location of the second module 7530 within the stack configuration with respect to the header module 7510.

After the current passes through the resistor 7534 of the second module 7530 of the module stack, the current continues to flow back toward the header module 7510. As the current flows from the second module 7530 toward the header module 7510, the 1 mA current passes across the 1 kΩ resistor 7524 of the first module 7520. The differential amplifier 7526 of the first module 7520 is configured to measure this voltage drop and determine a 2V voltage differential between the header current source 7512 and the low side of the resistor 7524 of the first module 7520. The differential amplifier 7526 can then transmit a signal corresponding to this voltage differential to the ADC 7528, which can interpret this signal and assign a corresponding address to the first module 7520. In the illustrated example, the 2V voltage differential signal is converted to a digital reading by the ADC 7528. The digital reading is interpreted by a controller that assigns a corresponding and/or unique address to the first module 7520. The assigned address corresponds to a physical location of the first module 7520 within the stack configuration with respect to the header module 7510.

In instances where additional modular components are positioned between the second module 7530 and the header module 7510, each differential amplifier and ADC of the remaining modules are configured to measure the voltage drop across its respective module resistors and assign corresponding "N" addresses until the current returns to the header module. An address is not assigned to the header module.

The circuit illustrates a header module stack at the top position of the modular energy system configuration. In the example circuit, "N" modules are shown stack below the header module, where "N" represents any positive integer. While the example circuit illustrates two modules stack below the header module, more or fewer modules can be used.

In various instances, the module positioned at the bottom of the stack configuration is assigned an address "1" based on the detected voltage drop between the header current source and the low side of the module resistor. The next module measures a voltage drop of 2V and is assigned address "2", for example. The "Nth" module measures "N" V, and is assigned address N. In various aspects, the header module comprises a memory storing information indicating that the address "1" corresponds to a module at the bottom of the stack, and the module with the address "N" is on the top of the stack, wherein the bottom of the stack is furthest away from the header module, and wherein the top of the stack is closest to the header module.

As discussed in greater detail herein, in various instances, the modular surgical system further comprises a display screen, such as, for example, the display screen 2006. The display screen renders a graphical user interface for relaying information regarding the modules connected to the header module. In various instances, the display is configured to visually represent and/or communicate the determined physical location of each modular component within the stack configuration of the modular surgical system.

As described in greater detail herein, a modular surgical system comprises a header module, to control the system-wide settings of each module/component connected thereto. The header module can facilitate power transmission between the modules in the system. However, it is desirable for the header module to be able to verify the integrity of the connections between the one or more modules prior to applying power to the system.

Figure 45:
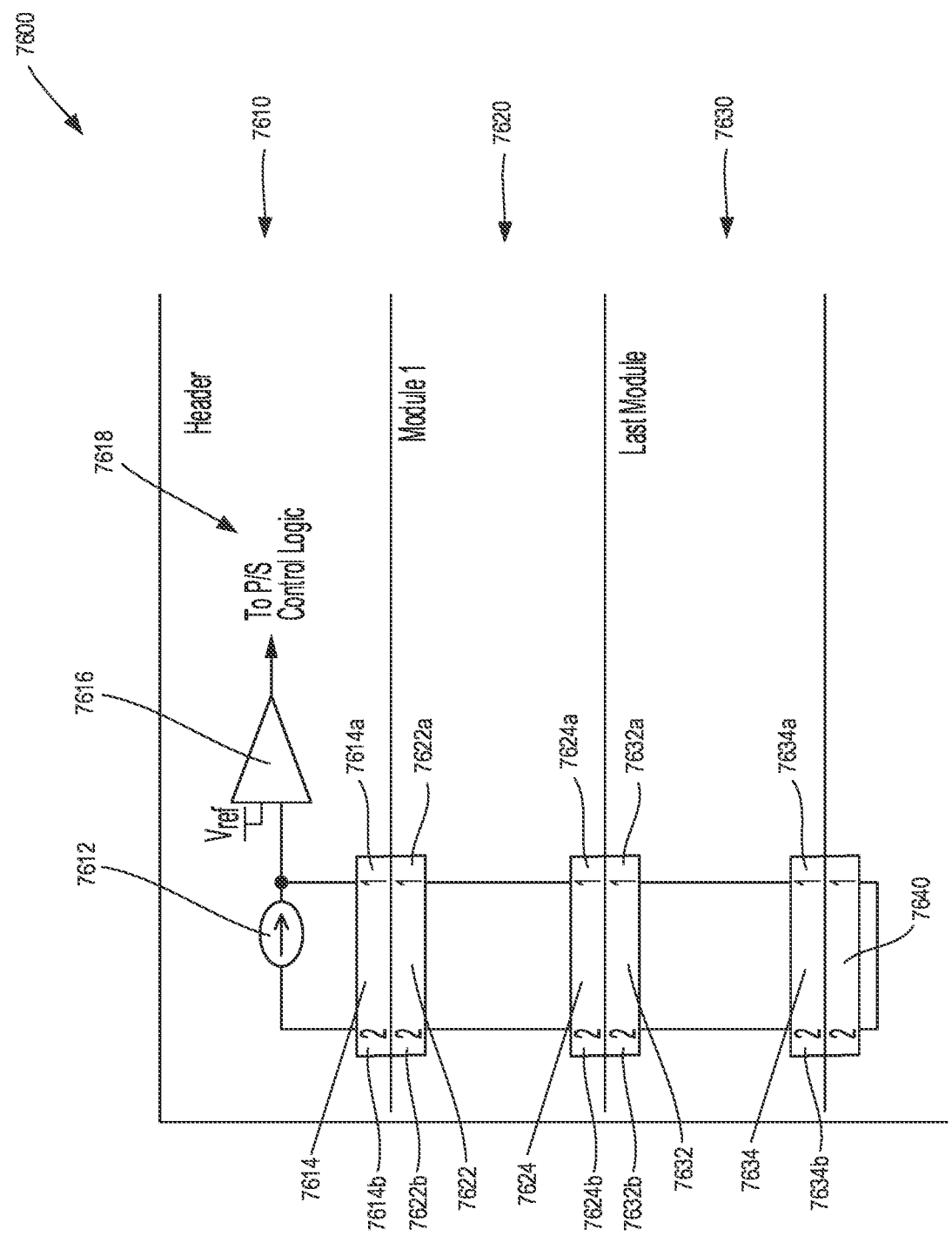
FIG. 45 is a connection integrity circuit of a modular surgical system, in accordance with at least one aspect of the present disclosure.

Referring now to FIG. 45, a connection integrity circuit 7600 a modular surgical system, or a modular energy system, is shown. The connection integrity circuit 7600 causes a header module 7610 to detect an open circuit (no voltage difference across a current source) when: (1) there are no modules connected to the header module 7610; (2) there is a broken pin and/or a broken connection on one of the modules connected downstream; and/or (3) there is a faulty relay in the last module. The modular surgical system comprises a header module 7610 and two modules stack therebelow. The two modules comprise a first module 7620 and a second module 7630. While the illustrated circuit 7600 depicts two modules connected with the header module 7610, any suitable number of modules can be used and/or connected.

The header module 7610 is connected to a first module 7620 by way of a bridge connector. The input bridge connector 7622 of the first module 7620 comprises a first pin 7622a and a second pin 7622b. The first pin 7622a and the second pin 7622b of the input bridge connector 7622 are configured to connect to a corresponding first pin 7614a and second pin 7614b in an output bridge connector 7614 of the header module 7610. In addition, the first module 7610 comprises an output bridge connector 7624 comprising a first pin 7624a and a second pin 7624b. The first and second pins 7624a, 7624b of the output bridge connector 7624 of the first module 7620 are configured to respectively connect to a first pin 7632a and a second pin 7632b of an input bridge connector 7632 of the next module in the stack, i.e., the second module 7630. The second module 7630, similar to the first module 7620, comprises an output bridge connector 7634 that comprises first and second pins 7634a, 7634b. As the second module 7630 is the last module in the depicted stack, a shorting plug 7640 connects the first and second pins 7634a, 7634b of the output bridge connector 7634, thereby completing the circuit.

In order to verify the integrity of the connections of the modules with the header module 7610, a continuity loop is utilized. The header module 7610 comprises a current source 7612, which is configured to pass a current through the first pins 7614a, 7624a, 7634a of the modules in the stack and return the current to the header module 7610 through the second pins 7634b, 7624b, 7614b of the modules in the stack. The continuity loop allows the header module 7610 to detect a high resistance and/or an open connection in one of the module-to-module bridge connectors 7614, 7622, 7624, 7632, 7634.

In various instances, the connection integrity circuit 7600 comprises an operational amplifier 7616. The voltage output of the operational amplifier 7616 can be indicative of the integrity of the connection to all modules in its stack. In at least one example, an analogue to digital converter ("ADC") 7618 can convert the voltage output of the operational amplifier 7616 into digital readings indicative of the integrity of the connection(s). The digital readings can be communicated to a controller that may issue an alert and/or disable power supply, for example, if the controller determines that the integrity of the connection is compromised. The alert can be issued through a user interface of the header module 7610 and can include instructions of how to properly connect the assembly of the stack, for example.

In various instances, the connection integrity circuit 7600 is configured to generate a first output indicative an uncompromised electrical connection to the modules in the stack. The connection integrity circuit 7600 is further configured to generate a second output, different than the first output, indicative of a compromised electrical connection between one or more modules in the stack.

Figure 46:
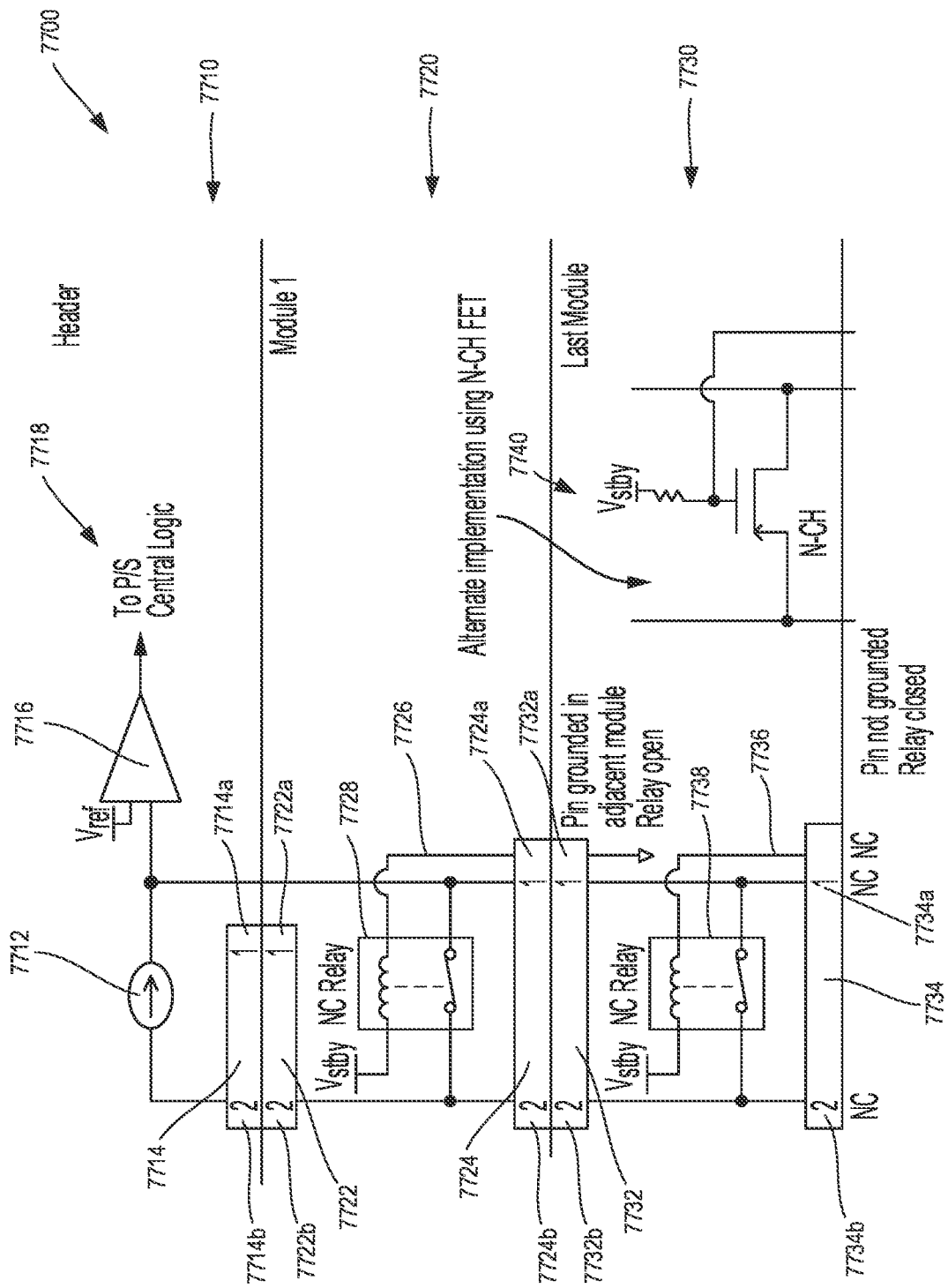
FIG. 46 is a connection integrity circuit of a modular surgical system, in accordance with at least one aspect of the present disclosure.

As discussed above, the connection integrity circuit 7600 of FIG. 45 comprises a shorting plug 7640 attached to the first and second pins 7634a, 7634b of the second module 7630 to complete the circuit. Referring now to FIG. 46, a connection integrity circuit 7700 is shown that does not require a shorting plug. The circuit 7700 is similar to the circuit 7600 shown and described in FIG. 45 in that there is, among other things, a header module 7710 comprising a current source 7712, a first module 7720, and a second module 7730. As discussed above, while two modules are depicted in connection with the header module, any suitable number of modules can be used and/or connected.

The header module 7710 is connected to the first module 7720 by way of a bridge connector. An input bridge connector 7722 of the first module 7720 comprises a first pin 7722a and a second pin 7722b. The first pin 7722a and the second pin 7722b of the input bridge connector 7722 are configured to connect to a corresponding first pin 7714a and second pin 7714b in an output bridge connector 7714 of the header module 7710. In addition, the first module 7710 comprises an output bridge connector 7724 comprising a first pin 7724a and a second pin 7724b. The first and second pins 7724a, 7724b of the output bridge connector 7724 of the first module 7720 are configured to respectively connect to a first pin 7732a and a second pin 7732b of an input bridge connector 7732 of the next module in the stack, i.e., the second module 7730. The second module 7730, similar to the first module 7720, comprises an output bridge connector 7734 that comprises first and second pins 7734a, 7734b.

In order to verify the integrity of the connections of the modules with the header module 7710, a continuity loop is utilized. The header module 7710 comprises a current source 7712, which is configured to pass a current through the first pins 7714a, 7724a, 7734a of the modules in the stack and return the current to the header module 7710 through the second pins 7734b, 7724b, 7714b of the modules in the stack. The continuity loop allows the header module 7610 to detect a high resistance and/or an open connection in one of the module-to-module bridge connectors 7714, 7722, 7724, 7732, 7734.

As illustrated in FIG. 46, instead of connecting a shorting plug to the first and second pins 7734a, 7734b of the second module 7730, an NC relay can be incorporated into each module. More specifically, the first module 7720 comprises a NC relay 7728 and the second module 7730 comprises a NC relay 7738. The NC relays are normally closed; however, the NC relays are driven open when a pin in the adjacent module is pulled down to ground. Thus, in the depicted circuit, an NC relay is driven open in all modules except the last module, as the control pin is not pulled to ground. In various instances, the NC relays 7728, 7738 can be replaced by an N-Channel MOSFET 7740.

One of the limitations of the NC relay/FET solution is that the control of the relay relies on a connection being made in the same connector interface that is being checked for continuity on other pins. Accordingly, various alternative connection integrity circuits are presented, which control the relay using different mechanisms of detecting whether a module is the last/bottom module in the stack.

In various instances, the bottom module can be detected by a Hall Effect sensor. A magnet is placed on or near a top surface of the functional modules, and a Hall Effect sensor is placed on or near the bottom surface of the functional modules. The Hall Effect sensor of an upper module will detect the magnet of a lower adjacent module in the stack configuration. Since the bottom module in a stack is not followed by a lower module, its Hall Effect sensor will not detect a magnet. The absence of a magnet indicates the absence of a lower module. Signals from a Hall Effect sensor of a functional module can be analyzed by a control circuit to determine whether the module is the bottom module in the stack.

In various instances, the bottom module can be detected by any suitable type of near field communication. A tag is placed on or near a top surface of the functional modules, and a tag reader is placed on or near the bottom surface of the functional modules. The tag reader of an upper module will detect the tag of a lower adjacent module in the stack configuration. Since the bottom module in a stack is not followed by a lower module, its tag reader will not detect a tag. The absence of a tag indicates the absence of a lower module. Signals from a tag reader of a functional module can be analyzed by a control circuit to determine whether the module is the bottom module in the stack.

In various instances, a mechanical switch in the upper module can be tripped by a feature in the lower module. Accordingly, an un-tripped switch is indicative of the last/bottom module in the stack.

In various instances, an optical sensor in the upper module can be tripped by a feature in a lower module. Accordingly, an un-tripped optical sensor is indicative of the last/bottom module in the stack.

Figure 47:
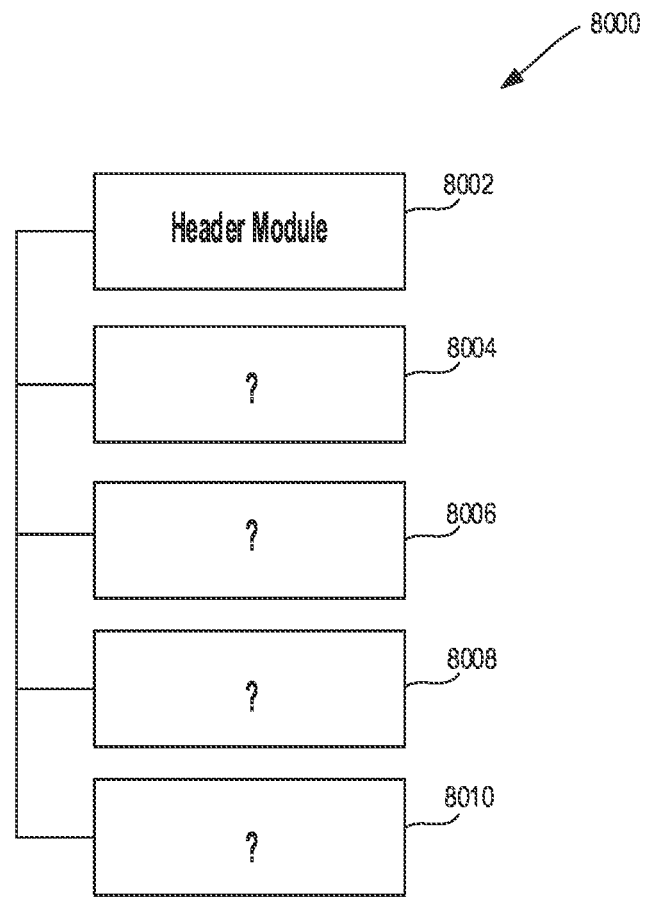
FIG. 47 is a schematic diagram of a modular energy system, in accordance with at least one aspect of the present disclosure.

As discussed above, the one or more modules can be connected to a header module, such as header module 2002, in a variety of different stacked configurations to form various modular energy system configurations, such as modular energy system 2000. For example, as illustrated in FIG. 47, a modular energy system 8000 can include a header module 8002 connected to a top module 8004, a bottom module 8010, and two intermediate modules 8006, 8006. In certain instances, the header module 8002 requires the physical location of the modules in its stack so that user interface content from a GUI, such as GUI 2008, for each module can be arranged with a 1:1 association to the physical location of each module. In certain instances, the header module requires the physical location of each module in the stack so that an address can be assigned, and so that the module can be used with a mitigated communications bus, such as data bus 3008. In various examples, the header modular identifies the physical location of each module and assigns an address by way of an analog signal, such as in application Ser. No. 16/562,212, now U.S. Patent Application Publication No. 2020/0078119, or a digital signal, such as in application Ser. No. 16/562,243, now U.S. Patent Application Serial No. 2020/0078120, both of which are incorporated by reference in their entireties. In other examples, as described below, the header module identifies the physical location of each module and assigns an address with a clock pulse signal. Positional awareness of the modules 8004, 8006, 8008, 8010 with respect to the header module 8002 and/or with respect to each other facilitates a proper interaction between the modules 8004, 8006, 8008, 8010 and the header module 8002.

In various aspects, to avoid a faulty start of a modular energy system, it is desirable to perform at least an initial determination of the physical positions of the modules in a stack at low power and without aid or support from the processors of the modules in the stack. The present disclosure provides a reliable mechanism for identification of the physical positions of the modules in a stack, which does not require primary or intensive backplane (serial bus/Ethernet) communication to identify the modules.

Figure 48:
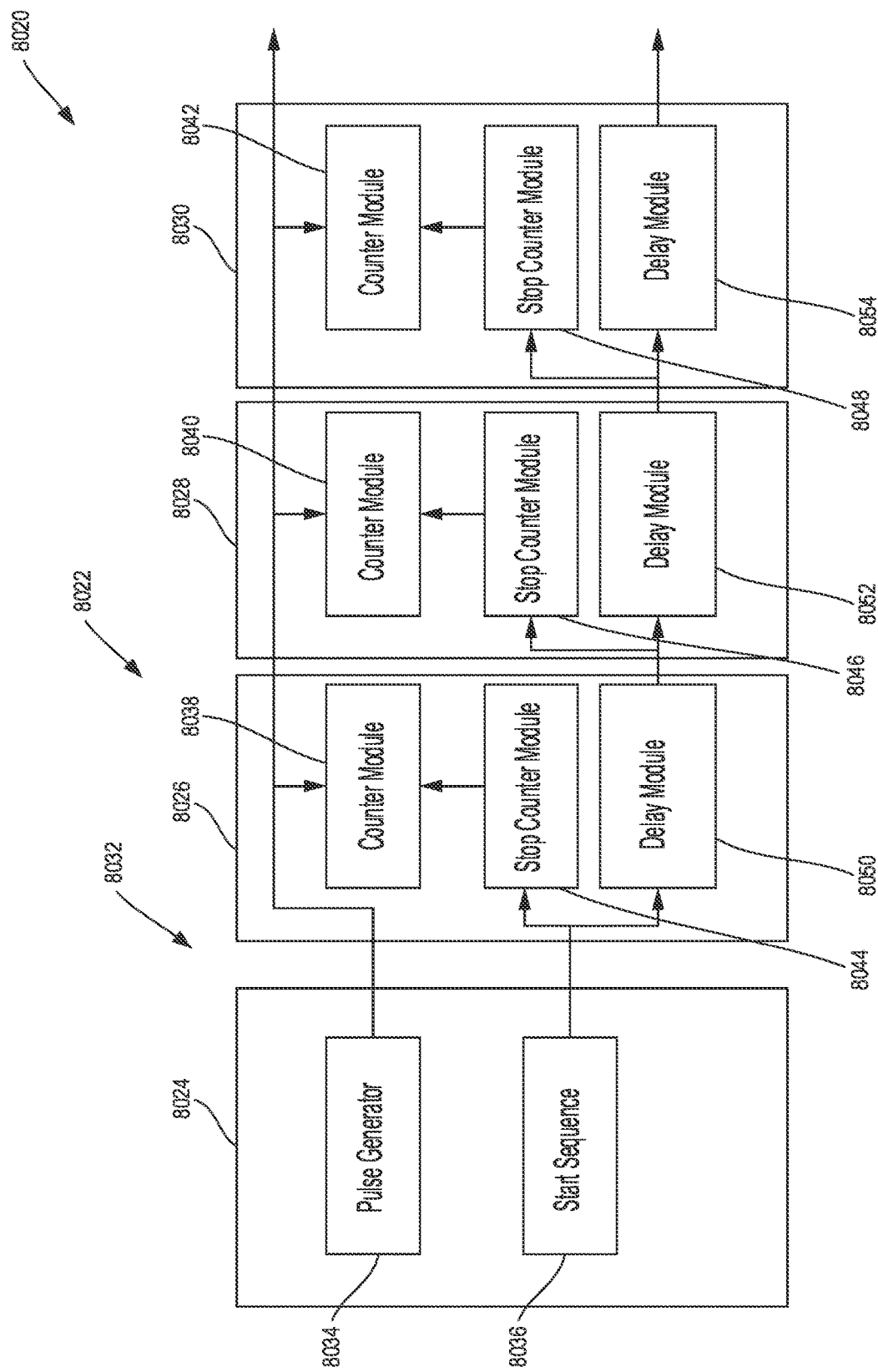
FIG. 48 is a schematic diagram of an identification circuit for determining physical locations of modules in a modular energy system utilizing a timing signal or clock pulses, in accordance with at least one aspect of the present disclosure.

Referring to FIG. 48, a modular energy system 8020 can include an identification circuit 8022, which is employed by a header module 8024 to determine the physical position of modules, such as modules 8026, 8028, 8030, within the modular energy system 8020. While three modules 8026, 8028, 8030 are shown and described, any more or less modules can be used. The identification circuit 8022 defines a communication interface 8032 configured to electrically couple the modules 8026, 8028, 8030 to the header module 8024 and/or to one other. The communication interface 8032 can, for example, be implemented by a separate communication bus (e.g. Ethernet, serial bus, LIN, etc.), which can be defined by detachably couplable communication backplane segments of the individual modules. In at least one example, the communication interface 8032 is a two-wire interface.

The header module 8024 can use the communication interface 8032 to interact with the modules 8026, 8028, 8030 to identify and determine the physical position of the modules 8026, 8028, 8030 within the modular energy system 8020. Additionally, or alternatively, the modules 8026, 8028, 8030 can utilize the communication interface 8032 to interact with one another to exchange addresses and/or other relevant information, independently from the header module 8024. In one embodiment, the physical position of the modules 8026, 8028, 8030 can be a physical position relative to the header module 8024. In another embodiment, the physical position can be a physical position relative to a module other than the header module 8024. In at least one example, the identification circuit 8022 does not require software to perform the identification of the modules 8026, 8028, 8030.

In one embodiment, the header module 8024 can include a pulse generator module 8034 and a start sequence module 8036. The pulse generator module 8034 can be configured to generate a timing signal or clock pulses that can be synchronously transmitted to each of the modules 8026, 8028, 8030 in the modular energy system 8020 by way of the communication interface 8032. The start sequence module 8036 can configured to generate a sequence signal that can be transmitted to the first module in the modular energy system 8020, such as module 8026, by way of the communication interface 8032.

Each of the modules 8026, 8028, 8030 in the modular energy system 8020 can include a counter module 8038, 8040, 8042, a stop-counter module 8044, 8046, 8048, and a delay module 8050, 8052, 8054, respectively. When the header module 8024 is electrically coupled to the modules 8026, 8028, 8030 in the modular energy system 8020 by way of the communication interface 8032, the pulse generator module 8034 can be configured to electrically couple to each of the counter modules 8038, 8040, 8042. This configuration can allow a timing signal or clock pulses from the pulse generator module 8034 to be received by each of the counter modules 8038, 8040, 8042 at substantially the same time. When the header module 8024 is electrically coupled to the modules 8026, 8028, 8030 in the modular energy system 8020 by way of the communication interface 8032, the start sequence module 8036 can be configured to electrically couple to the stop-counter module 8044 and the delay module 8050 of the first module 8026. This configuration can allow a sequence signal from the start sequence module 8034 to be only be received by the stop-counter module 8044 and the delay module 8050 of the first module 8026.

Each of the delay modules can be configured to couple to the subsequent stop-counter module and delay module in the modular energy system 8020. In this configuration, a sequence signal for each stop-counter module and delay module, after the first module, can be received from the previous delay module. In one example, the delay module 8050 is configured to couple to the stop-counter module 8046 and delay module 8052 of the second module 8028 and provide a sequence signal thereto. In a second example, the delay module 8052 is configured to couple to the stop-counter module 8048 and delay module 8054 of the third module 8030 and provide a sequence signal thereto.

To perform the identification process, each of the counter modules 8038, 8040, 8042 can be configured to initiate at count 0. A timing signal comprising a first pulse train can be transmitted from the pulse generator module 8034 to each counter module 8038, 8040, 8042 through the communication interface 8032. Upon reception of a first pulse from the pulse generator module 8034, each counter module 8038, 8040, 8042 can be configured to increment. In one example, a first pulse can be configured to increment each counter module 8038, 8040, 8042 to 1. Subsequent pulses from the pulse generator module 8034 can cause the counter modules 8038, 8040, 8042 to further increment and count the number of pulses received from the pulse generator module 8034.

At substantially the same time as the first pulse from the pulse generator module 8034, a sequence signal can be transmitted from the start sequence module 8036 to the stop-counter module 8044 and the delay module 8050 through the communication interface 8032. In at least one other embodiment, the start sequence module 8036 can be configured to transmit the sequence signal at a time after the first pulse from the pulse generator 8034, but before a second pulse from the pulse generator 8034. Upon reception of the sequence signal from the start sequence module 8036, the stop-counter module 8044 can be configured to deliver a stop signal to the counter module 8038 to stop the counter module 8038 from further incrementing. The final increment at which the counter module 8038 is at upon reception of the stop signal from the stop-counter module 8044 can be locked in and stored in the counter module 8038, such as in a memory. A module ID number can be assigned to the first module 8026 based on the final increment count.

In one embodiment, the pulse generator module 8034 can transmit a first pulse to the counter module 8038 at substantially the same time that the start sequence module 8036 transmits a sequence signal to the stop-counter module 8044, which then sends a stop signal to the counter module 8038. The counter modules can be configured to process and interpret near simultaneous increment signals and a stop signal. In one example, the counter module 8038 can give priority to the stop signal, at a rising edge of a pulse from the pulse generator module 8034, stopping count at 0. In a second example, the counter module 8038 can give priority to the increment signal and increment to 1 at a rising edge of a pulse from the pulse generator module 8034. In one embodiment where the stop signal is given priority over the increment signal, the counter module 8038 can be finalized before receiving the first pulse from the pulse generator module 8034. In this embodiment, the counter module 8038 has not incremented beyond 0 when it has finalized. This 0 value can be used to provide a module ID number to the module. In one example, the final increment number can be the module ID number. In the example described above where counter module 8038 has finalized at 0, the first module 8026 can be assigned module ID number 0. The module ID number can be used to indicate the physical position of the module within the modular energy system 8020.

Continuing from above, upon reception of the sequence signal from the start sequence module 8036, the delay module 8050 can be configured to delay the sequence signal from the start sequence module 8036 by a predetermined time delay, which can be, for example, one pulse. In at least one example, the one pulse delay can be substantially the same as the period of the pulses generated by the pulse generator module 8034. In at least one example, the predetermined time delay is measured in number of timing-signal pulses.

After the one pulse delay, the delay module 8050 can be configured to transmit a sequence signal to the stop-counter module 8046 and the delay module 8052 of the second module 8040. Similar to above, the stop-counter module 8046 can be configured to transmit a stop signal to the counter module 8040 upon reception of the sequence signal from the delay module 8050. The stop signal from the stop-counter module 8046 can be configured to stop the counter module 8040 from further incrementing and lock in the final increment count. As the stop signal from the stop-counter module 8046 was delayed one pulse by the delay module 8050, the counter module 8040 can at least be allowed to increment in response to the first pulse from the pulse generator module 8034. In one embodiment, the counter module 8040 can increment to 1 before the stop-counter module 8046 transmits a stop signal to the counter module 8040. In one example where the stop signal is given priority over a pulse from the pulse generator module 8034, the final increment on counter module 8040 can be 1, which can be used to assign a module ID number 1 to the module 8028.

Accordingly, the identification circuit formed by the stack is capable of determining the position of each of the modules in the stack and assigning a unique identifier to each module using only two backplane signals in a low power setting without aid or support from the primary processors of the modules. The number of modules identifiable using the identification circuit is limited only by the pulse-counters count.

In some aspects, the header module 8024 can include or support a display, such as display 2006. After the identification process, the modules 8026, 8028, 8030 can be configured to determine their own module ID number without involvement from the header module 8024. This can allow the modules 8026, 8028, 8030 to act on information without header module 8024 involvement, such as setting up the modules' communication addresses for other communication buses. In another embodiment, the header module 8024 can be configured to receive the module ID numbers from the modules 8026, 8028, 8030. In one example, the header module 8024 can be configured to receive the module ID number through the communication interface 8032. The header module 8024 can be configured to interpret the module ID numbers and provide a visual representation of the modules 8026, 8028, 8030 on the display in relative position representing their physical position in the modular energy system 8020. The display can provide information about the modules 8026, 8028, 8030, such as the type of module, status of module, availability of the module, health of module, etc. A user can select one of the modules from the display, such as with a touchscreen, in order to provide instructions to the module by way of a user interface.

Figure 49:
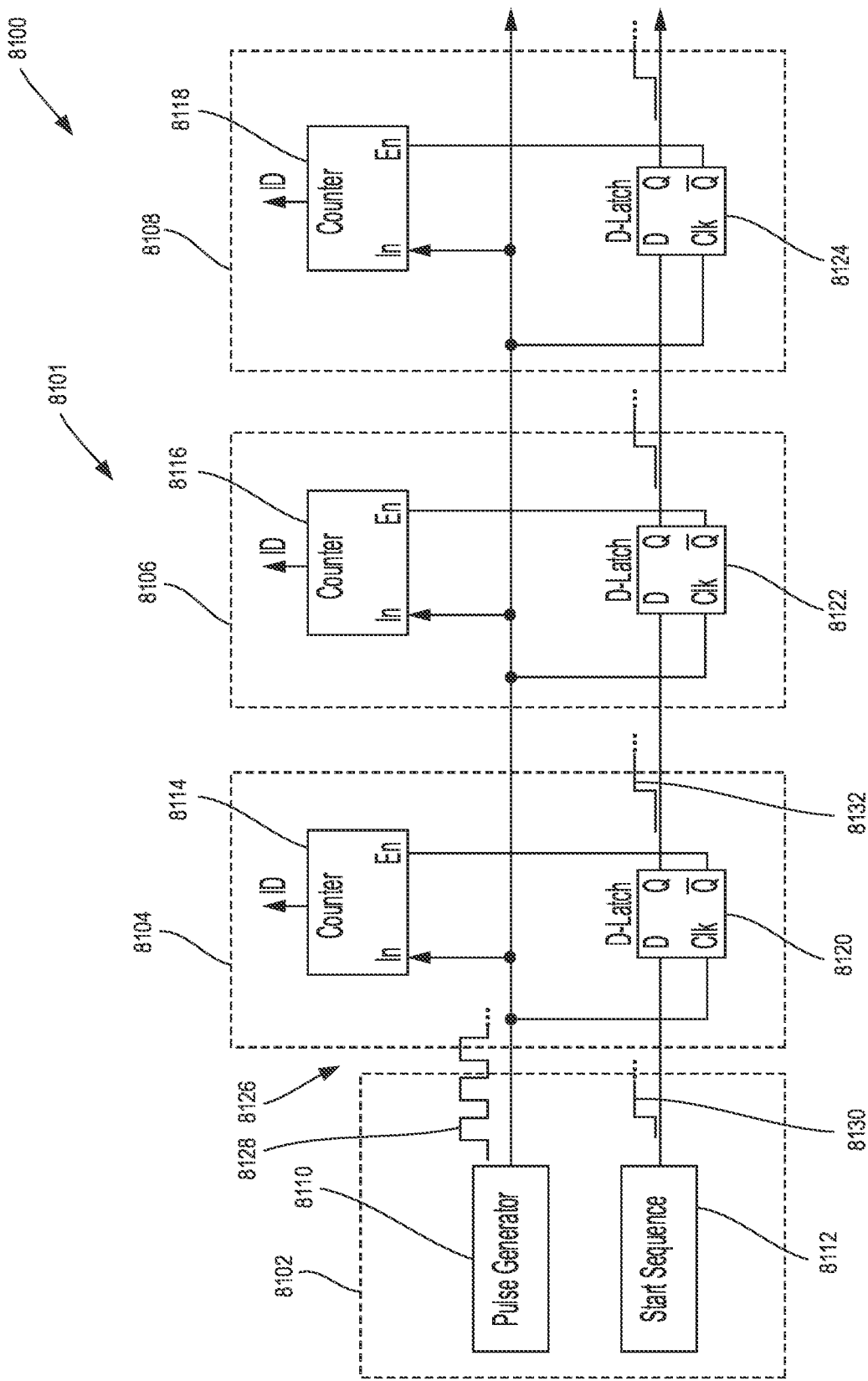
FIG. 49 is a schematic diagram of another identification circuit for determining physical locations of modules in a modular energy system utilizing a timing signal or clock pulses, in accordance with at least one aspect of the present disclosure.

Referring now to FIG. 49, another embodiment of a modular energy system 8100 is shown that can assign a unique identifier to each module in a modular energy system using only two backplane signals in a low power setting. The modular energy system 8100 can include an identification circuit 8101 that can be employed by a header module 8102 to determine the physical position of modules, such as modules 8104, 8106, 8108, within the modular energy system 8100. While three modules 8104, 8106, 8108 are shown and described, any more or less modules can be utilized. The identification circuit 8101 defines a communication interface 8126 configured to electrically couple the modules 8104, 8106, 8108 to the header module 8102 and/or to one another. The communication interface 8126 can, for example, be implemented by a separate communication bus (e.g. Ethernet, serial bus, LIN, etc.), which can be defined by detachably couplable communication backplane segments of the individual modules. In at least one example, the communication interface 8126 is a two-wire interface. The header module 8102 can be configured to use the two-wire interface 8126 to interact with the modules 8104, 8106, 8108 to identify and determine the physical position of the modules 8104, 8106, 8108 within the modular energy system 8100. Additionally, or alternatively, the modules 8104, 8106, 8108 can utilize the communication interface 8126 to interact with one another to exchange addresses and/or other relevant information, independently from the header module 8102. In a first embodiment, the physical position of the modules can be a physical position relative to the header module 8102. In a second embodiment, the physical position can be a physical position relative to a module other than the header module 8102. In at least one example, the identification circuit 8101 does not require software to perform the identification of the modules.

In one embodiment, the header module 8102 can include a pulse generator module 8110 and a start sequence module 8112. The pulse generator module 8034 can be configured to generate a timing signal or clock pulses 8128 to each of the modules 8104, 8106, 8108 in the modular energy system 8100 by way of the communication interface 8126. The start sequence module 8112 can be configured to generate a data signal 8130 to the first module in the modular energy system 8100, such as module 8104, by way of the communication interface 8126.

Each of the modules 8104, 8106, 8108 in the modular energy system 8100 can include a counter module 8114, 8116, 8118. Each of the counter modules 8114, 8116, 8118 can include a first input (In) and a second input (En). The counter modules 8114, 8116, 8118 can be configured to receive a timing signal or clock pulses, such as clock pulses 8128, at the first inputs. Upon reception of a first pulse from a clock pulse, the counter modules 8114, 8116, 8118 can be configured to initiate at 0. Upon reception of additional clock pulses, the counter modules 8114, 8116, 8118 can be configured to increment and count additional clock pulses received from the pulse generator module 8110 after the first clock pulse. In at least one other embodiment, the counter modules 8114, 8116, 8118 can be configured to initiate at 0 prior to receiving a first pulse from the pulse generator module 8110 such that a first pulse from the pulse generator module 8110 increments the counter modules 8114, 8116, 8118.

The counter modules 8114, 8116, 8118 can be configured to stop incrementing upon receiving a disabling signal at the second input. In one example, the disabling signal can be a falling edge of a signal received at the second input. In one example, the disabling signal can be a rising edge of a signal received at the second input. The final increment value of a counter module after reception of a disabling signal at the second input can be used to assign a module ID number to the respective module. The module ID number can be based on the final increment count and can correspond to a physical location of the module in the modular energy system 8100. In one example, the first module 8104 can receive a first clock pulse from the pulse generator 8110. The counter module 8114 can be configured to initiate at 0 upon reception of the first clock pulse. The counter module 8114 can then receive a disable signal at the second input of the counter module 8114 before reception of a second clock pulse from the pulse generator 8110, which can cause the counter module 8114 to finalize at the count 0. This 0 count can be used to assign the first module 8104 with a module ID number. In one example, the module ID number can be module Address 0 based on the 0 count, which can indicate that the first module 8104 is the first module in the modular system 8100 relative to the header module 8102.

Each of the modules 8104, 8106, 8108 in the modular energy system 8100 can further include a D-latch flip-flop 8120, 8122, 8124. Each of the flip-flops 8120, 8122, 8124 can be configured to receive a timing signal or clock pulses at the clock inputs (CLK) from a clock pulse source, such as the pulse generator module 8110. The flip-flops 8120, 8122, 8124 can be configured in a series configuration. In one example, the first flip-flop after the header module 8102, such as flip-flop 8120, can be configured to receive a data signal from a data source, such as a data signal 8130 from the start sequence module 8112, at the data input (D). The subsequent flip-flops after the first flip-flop can be configured to receive a data signal from the Q output of the proceeding flip-flop in the modular energy system 8100. In one example, flip-flop 8122 can be configured to receive a data signal 8132 from the Q output of flip-flop 8120. The flip-flops can further be configured to couple the $\overline{Q}$ outputs to the second inputs of the counter modules. In one example, the $\overline{Q}$ output of flip-flop 8120 can be configured to couple to the second input of the first counter module 8114.

In one example, flip-flop 8120 can be in the $\overline{Q}$ output state, where the data input signal 8130 from the start sequence module 8112 can be transmitted to the second input of the first counter module 8114. Upon reception of a clock signal from the pulse generator module 8110, the flip-flop 8120 can be configured to transition from the output state to the Q output state. The loss of the data input signal 8130 at the second input of the counter module 8114 (disabled low signal) can cause the counter module 8114 to stop incrementing. Further, the transition from the $\overline{Q}$ output state to the Q output state can cause flip-flop 8120 to transmit the data signal 8132 to the data input of flop-flop 8122.

To perform the identification process, a clock signal 8128 can be transmitted from the pulse generator module 8110 to each of the counter modules 8114, 8116, 8118 through the communication interface 8126. The first pulse from the clock signal 8128 can cause each of the counter modules 8114, 8116, 8118 to initiate at 0. Further, the clock signal can be transmitted to each of the clock inputs of the flip-flops 8120, 8122, 8124.

At a time after the rising edge of the first pulse from the clock signal 8128, the start sequence module 8112 can be configured to transmit a data signal 8130 to flip-flop 8120 by way of the communication interface 8126. In one example, the start sequence module 8112 can transmit the data signal 8130 during the falling edge of the first pulse from the clock signal 8128. Upon reception of the data signal 8130 from the start sequence module 8112, the flip-flop 8120 can be configured to transmit a signal from the $\overline{Q}$ output to the second input of the counter module 8114.

At the rising edge of a second pulse from the clock signal 8128, each of the counter modules 8114, 8116, 8118 can be configured to increment. At substantially the same time, the flip-flop 8120 can be configured to receive the second pulse at the clock input of flip-flop 8120 and transition from the $\overline{Q}$ output state to the Q output state. Transitioning from the $\overline{Q}$ output state to the Q output state removes the data signal from the second input of the counter module 8114, which can be a disabling signal for counter module 8114. The disabling signal can cause the counter module 8114 to stop incrementing and finalize. In one example, the counter modules can be configured to process and interpret near simultaneous increment signals and disabling signals. In one example, the counter module can give priority to the disabling signal, at a rising edge pulse from the clock signal 8128, at a rising edge of a pulse from the pulse generator module 8034, stopping count at 0. In a second example, the counter module can give priority to the increment signal and increment to 1 at a rising edge pulse from the clock signal 8128. In the above described example where the counter module 8114 gives priority to the stop incrementing signal, the counter module 8114 is disabled at 0 before incrementing to 1. In one aspect, the counter module 8114 can assign a module ID number to the first module 8104 based on the final increment value. In one example, the first module 8104 can be assigned module ID number 0.

Further to the above, after flip-flop 8120 receives the second pulse at the clock input and transitions from the $\overline{Q}$ output state to the Q output state, a data signal 8132 from the Q output of the flip-flop 8120 can be transmitted to the data input of flip-flop 8122. Flip-flop 8122 can be configured such that the data signal 8132 is transmitted from the $\overline{Q}$ output to the second input of the counter module 8116.

At the rising edge of a third pulse from the clock signal 8128, each of the non-disabled counter modules 8116, 8118 can be configured to further increment. At substantially the same time, flip-flop 8122 can be configured to receive the third pulse at the clock input and transition from the $\overline{Q}$ output state to the Q output state. Similar to above, transitioning from the $\overline{Q}$ output state to the Q output state can remove the data signal 8132 from the second input of the counter module 8116, which can cause the counter module 8116 to stop incrementing. In one example where the counter module 8116 gives priority to the stop incrementing signal, the counter module 8116 can be disabled at 1 before incrementing to 2. In one aspect, the counter module 8116 can assign a module ID number to the second module 8106 based on the final increment value. In one example, the second module 8106 can be assigned module ID number 1.

The above-described process can occur for each module in the modular energy system 8100 until each of the counter modules have been disabled and a final counter value has been determined. Each of the counter modules can output this value a control circuit, control logic, microprocessor, microcontroller, logic, or FPGA, or various combinations thereof, as an example, which can assign each module a module ID number based on the final counter value from its respective counter. In a separate embodiment, the counter modules can include a memory and the module ID number can be stored therein. This module ID number can correspond to a physical location of the module within the modular energy system 8100 relative to the header module.

Accordingly, the identification circuit formed by the stack is capable of determining the position of each of the modules in the stack and assigning a unique identifier to each module using only two backplane signals in a low power setting without aid or support from the processors of the modules. The number of modules identifiable using the identification circuit is limited only by the pulse-counters count.

In some aspects, the header module 8102 can include or support a display, such as display 2006. After the identification process, the header module 8102 can be configured to receive the module ID numbers from the modules 8104, 8106, 8108. In one example, the header module 8024 can be configured to receive the module ID number through the communication interface 8126. The header module 8102 can be configured to interpret the module ID numbers and provide a visual representation of the modules 8104, 8106, 8108 on the display in relative position representing their physical position in the modular energy system 8100. The display can provide information about the modules 8104, 8106, 8108, such as the type of module, status of module, availability of the module, health of module, etc. A user can select one of the modules from the display, such as with a touchscreen, in order to provide instructions to the module by way of a user interface.

In some aspects, the above-described embodiments represent ways to determine a physical position of modules in a modular energy system by implementing counter modules to incrementally count the number of pulses received before a stop signal disables the counter modules. The number of pulses can be utilized to assign a module ID number to the modules based on the incremental count. In other aspects, it can be possible to determine a physical position of modules in a modular energy system by utilizing a timer module and a single clock pulse. In one instance, the timer modules can be configured to measure an elapsed time between a first signal at a first input, in which the timer module can be configured to initiate a timer, and a second signal at a second input, in which the timer module can be configured to disable the timer. The timer modules can utilized the elapsed time to assign a module ID number to the modules based on the final timer count.

Figure 50:
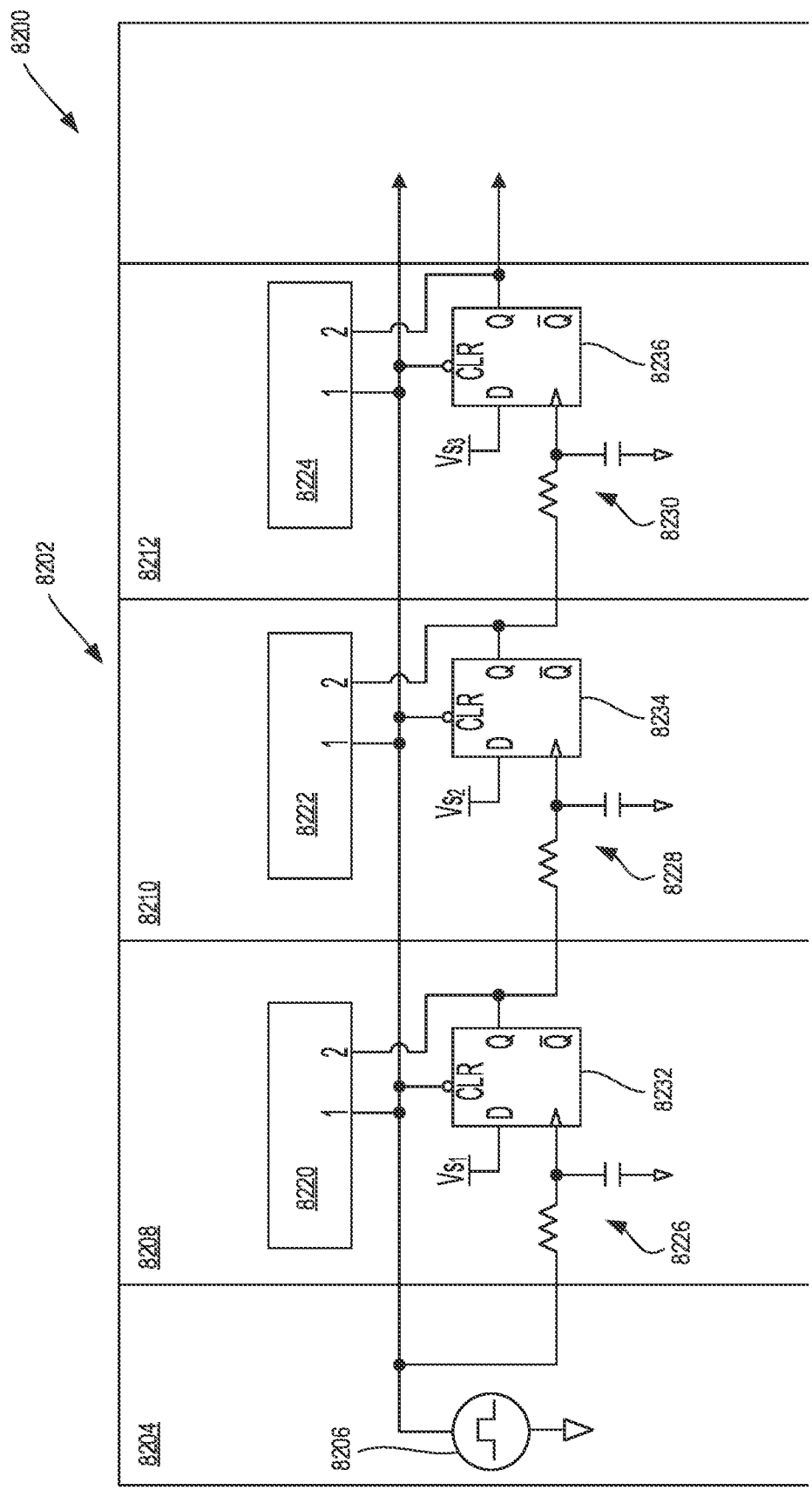
FIG. 50 is a schematic diagram of another identification circuit for determining physical locations of modules in a modular energy system utilizing a single clock pulse, in accordance with at least one aspect of the present disclosure.

Referring now to FIG. 50, an example module position-identification circuit 8202 for determining the position of modules in stacked modular energy system 8200 using a timer module is shown. The stacked modular energy system 8200 can include a header module 8204 that can include a clock pulse generator 8206 configured to produce a clock pulse signal. The stacked modular energy system 8200 can further include any number of modules coupled with the header module 8204. In one embodiment, as is illustrated in FIG. 50, the stacked modular energy system 8200 can include a first module 8208, a second module 8210, a third module 8212, coupled with the header module 8204. In one embodiment, each of the modules 8208, 8210, 8212 can include a timer module 8220, 8222, 8224, an RC delay circuit 8226, 8228, 8230, and a D-type flip-flop 8232, 8234, 8236. The timer module could be any one of a control circuit, control logic, microprocessor, microcontroller, logic, or FPGA, or various combinations thereof.

Each timer module 8220, 8222, 8224 of the stacked modular configuration 8200 can include two input pins, which are identified as "1" and "2" on each timer module, respectively. The first pin of each timer module 8220, 8222, 8224 can be electrically connected with the clock pulse generator 8206 of the header module 8204. The clock pulse generator 8206 can be configured to generate a clock pulse that can be synchronously received by each of the timer modules 8220, 8222, 8224 at the first pins. The first input pins of the timer modules 8220, 8222, 8224 can be configured to receive a rising edge of the clock pulse signal from the clock pulse generator 8206 and begin a timer. The timer modules 8220, 8222, 8224 can be configured to measure the amount of time it takes to receive a signal at their respective second input pins after receiving the rising edge of the clock pulse at the first input pins. In addition, the clock signal from the clock pulse generator can be transmitted to a clear state input (CLR) on each flip-flop 8232, 8234, 8236. In at least one example, the falling edge or low side of the clock signal transmitted to the clear state input can reset the flip-flops 8232, 8234, 8236 to a reset state, which will be described in more detail below.

The electrical output from the clock pulse generator 8206 of the header module 8204 can be branched such that a clock pulse signal can be transmitted to an RC delay circuit 8226 of the first module 8208. The RC delay circuit 8226 can be configured such that the clock pulse received by the RC delay circuit 8226 is delayed from being transmitted to the flip-flop 8232 of the first module 8208 by a predetermined amount of time. In one example, the delay can be 1 ms. In a second example, the delay can be more or less than 1 ms. The delay from the RC delay circuit 8226 can be configured to create a first delayed clock signal.

After the RC delay circuit 8226 of the first module 8208, the first delayed clock signal is configured to be transmitted to the flip-flop 8232 of the first module 8208. When the first delayed clock signal from the RC delay circuit 8226 is transmitted to the clock input of the flip-flop 8232, the flip-flop 8232 is configured to transition from a $\overline{Q}$ initial output state to a Q output state. The Q output of flip-flop 8232 can configured to transmit a supply voltage $V_{s1}$ at the data input D of the flip-flop 8232 through the Q output. The output of the Q output of flip-flop 8232 can be branched such that the Q output signal can be transmitted to the second input pin of the timer module 8220 and an RC delay circuit 8228 of the second module 8210.

When the flip-flop 8232 of the first module 8208 transitions from the $\overline{Q}$ initial output state to the Q output state, $V_{s1}$ can be transmitted to the second input pin of the timer module 8220. The $V_{s1}$ signal is configured to be received by the second input pin of the timer module 8220 at a time after the timer module 8220 receives the clock signal from the clock pulse generator 8206. The timer module 8220 can be configured to compute the time difference between the two signals, such as by a timer. The timer module 8220 can be configured to interpret this time difference and assign a corresponding module ID to the module 8208 based on this time difference. This module ID can correspond to a physical location of the module 8208 in the stacked modular energy system 8200.

In one example, the RC delay circuit 8226 can be set to delay the initial clock pulse by 1 ms. The first pin of the timer module 8220 can receive the initial clock pulse from the clock pulse generator 8206 at approximately 0 seconds and the second pin of the timer module 8220 can receive the $V_{s1}$ signal from the flip-flop 8232 at approximately 1 ms. As a result, the timer module 8220 can compute the time difference between the two pins as approximately 1 ms and assign a modular identifying address based on the timing difference between the two signals. The timer module 8220 can assign the first module 8208 Address 1, as an example, which can correspond to the first module after the header module 8204 in the modular energy system 8200.

Further to the above, the $V_{s1}$ signal from the flip-flop 8232 of the first module 8210 can be configured to be transmitted to the RC delay circuit 8228 of the second module 8210. Similar to above, the RC delay circuit 8228 of the second module 8210 can be configured to delay the $V_{s1}$ signal to the flip-flop 8234, creating a second delayed clock signal. In one example, the RC delay circuit 8228 can delay the $V_{s1}$ signal by the same time as the first RC delay circuit 8226. The second delayed clock signal can be transmitted to the clock input of the flip-flop 8234 of the second module 8210. The flip-flop 8234 of the second module 8210 can be configured to transition from a $\overline{Q}$ initial output state to a Q output state and output a $V_{s2}$ supply signal at the data input to the Q output. The flip-flop 8234 of the second module 8210 can be configured to transmit the $V_{s2}$ signal to the second input pin of the timer module 8222 and an RC delay circuit 8230 of the third module 8212. As the $V_{s2}$ signal at the second input pin of the timer module 8222 is delayed compared to the initial clock signal from the clock pulse generator 8206, the timer module 8222 can interpret this time difference value and use the value to assign a module ID to the second module 8210. This module ID can correspond to a physical location of the second module 8210 in the stacked modular energy system 8200. In one example, the clock signal at the second input pin the second timer module 8222 can be delayed by 2 ms as a result of a 1 ms delay at both the first RC delay circuit 8226 and the second RC delay circuit 8228. In this example, the 2 ms delay interpreted by the timer module 8222 can result in the second module 8210 being assigned Address 2, as an example.

The second delayed clock signal from the flip-flop 8234 of the second module 8210, as described above, can be transmitted to the third module 8212 in the modular energy system 8200. The above-described process can occur until each of the timer modules have assigned their respective modules a module ID number. The time delay due to the RC delay circuit allows the timer modules of each of the modules to determine their physical location relative to the header module. The timer modules can continue to assign addresses until the last module in the system is reached. After each module has been assigned a module ID, the falling edge of the clock pulse from the clock pulse generator 8206 can be configured to be received at the clear input states of each flip-flop to transition each flip-flop in the modular energy system 8200 back to a reset state. In at least one example, the falling edge of the initial clock signal can be configured to transition each flip-flop from the Q output state to the Q output state. In at least one example, the initial pulse signal from the clock pulse generator is made sufficiently large to exceed the sum of all the delays in the modular energy system to ensure that the flip-flops are not reset before all of the modules have been assigned a module ID number.

In some aspects, the header module 8204 can include or support a display, such as display 2006. After the identification process, the header module 8204 can be configured to receive the module ID numbers from the modules 8208, 8210, 8212. The header module 8204 can be configured to interpret the module ID numbers and provide a visual representation of the modules 8208, 8210, 8212 on the display in relative position representing their physical position in the modular energy system 8100. The display can provide information about the modules 8208, 8210, 8212, such as the type of module, status of module, availability of the module, health of module, etc. A user can select one of the modules from the display, such as with a touchscreen, in order to provide instructions to the module by way of a user interface.

Figure 51:
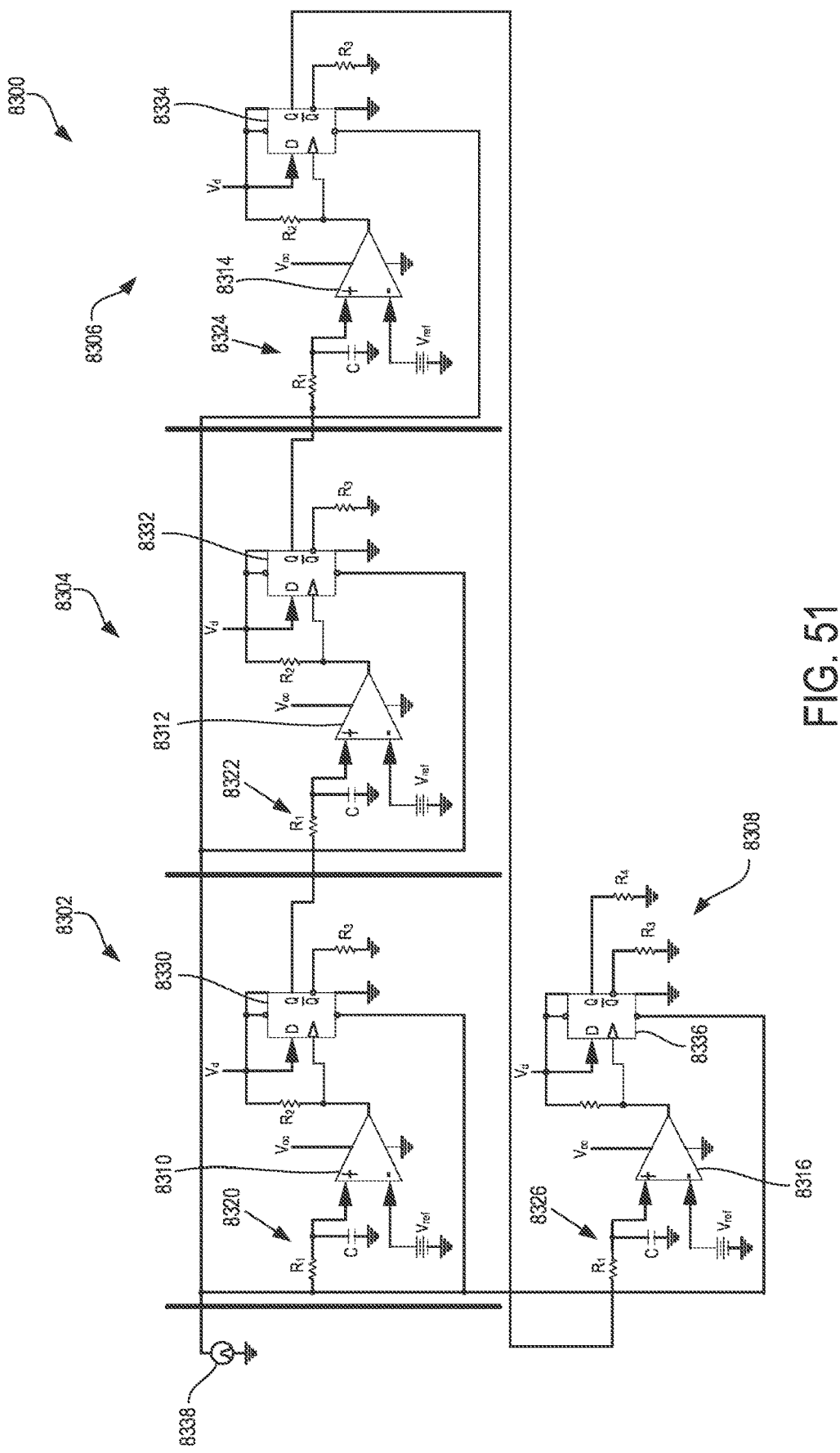
FIG. 51 is a wire diagram of an example circuit of the identification circuit of FIG. 50, in accordance with at least one aspect of the present disclosure.

Depending on the logic family selected for implementation of the circuit described above, it may be necessary to insert a comparator, Schmitt-Trigger style buffer, or other equivalent circuits in order to provide a fast-rising edge at the clock input of the flip-flops. As can be seen in FIG. 51, a schematic of a stacked modular configuration 8300 is illustrated that can include four modules 8302, 8304, 8306, 8308 and a clock pulse generator 8338. The clock pulse generator 8338 can be a part of a header module, for example. Each module can include a comparator 8310, 8312, 8314, 8316, an RC delay circuit 8320, 8322, 8324, 8326, and a flip-flop 8330, 8332, 8334, 8336. The comparators 8310, 8312, 8314, 8316 can be placed in between RC delay circuits 8320, 8322, 8324, 8326 and the clock signal inputs of the flip-flops 8330, 8332, 8334, 8336. The comparators can be provided with a supply voltage $V_{cc}$ and be configured to compare the output voltage of the RC delay circuits against a reference voltage $V_{ref}$. In one embodiment, when the output of the RC delay circuit exceeds the reference voltage $V_{ref}$, the comparators can transmit the supply voltage $V_{cc}$ to the clock input of the flip-flops.

Figure 52:
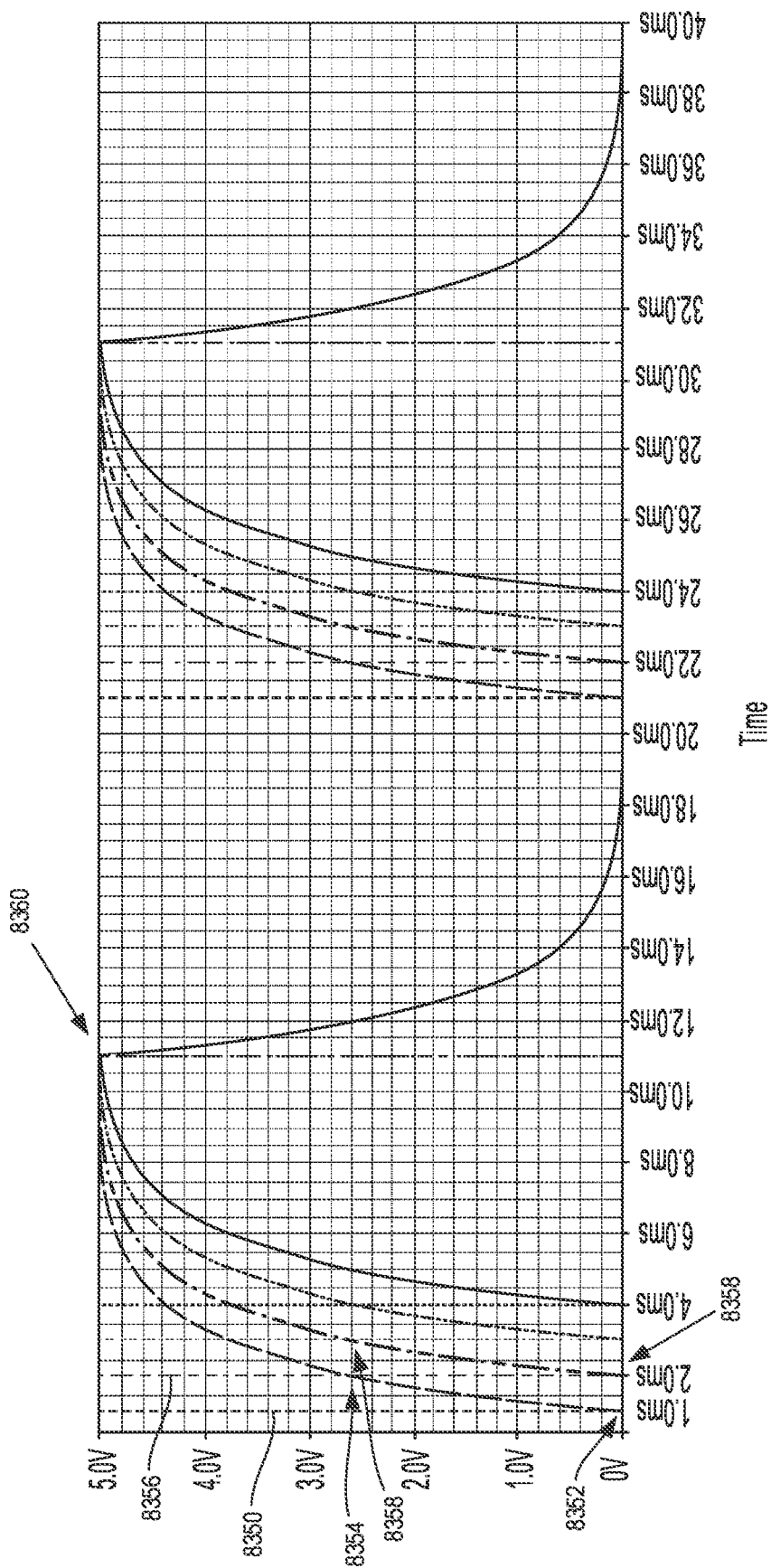
FIG. 52 illustrates simulation results of the example circuit of FIG. 51, in accordance with at least one aspect of the present disclosure.

Referring now to FIG. 52, simulation results for the above-described circuit can be seen. For the simulation, $V_{cc}$ and $V_d$ were selected to be 5V, $V_{ref}$ was selected to be 2.5V, C was selected to be 0.1 µF, R1 was selected to be 14.4 kΩ, R2 was selected to be 1 KΩ, and R3 and R4 were selected to be 10MΩ.

At 1 ms, the clock pulse generator 8338 provides an initial clock pulse signal 8350 to the RC delay circuit 8320 of the first module 8302. The RC delay circuit 8320 begins to charge 8352 and outputs a signal to the comparator 8310. Once the RC delay circuit 8320 has charged to provide an output voltage signal that exceeds the reference voltage $V_{ref}$ of the comparator 8310, the comparator 8310 outputs the supply voltage $V_{cc}$ to the flip-flop 8330. Based on the above provided values, the RC delay circuit 8320 exceeds the reference voltage $V_{ref}$ approximately 1 ms after receiving the rising edge of the initial clock signal from the clock pulse generator 8338, which can be seen at 8354.

After the comparator 8310 of the first module 8302 outputs the supply voltage $V_{cc}$ to the flip-flop 8330, the flip-flop 8330 transitions from the $\overline{Q}$ output state to the Q output state and transmits a data signal $V_d$ 8356 to the RC delay circuit 8322 of the second module 8304, which begins to charge 8358 the RC delay circuit 8322. Similar to what was described above, the RC delay circuit 8322 begins to charge 8358 and outputs a signal to the comparator 8312. Once the RC delay circuit 8322 has charged to provide an output voltage signal that exceeds the reference voltage $V_{ref}$ of the comparator 8312, the comparator outputs the supply voltage $V_{cc}$ to the flip-flop 8332. Based on the above provided values, the RC delay circuit 8322 exceeds the reference voltage approximately 2 ms after the initial clock pulse signal, which can be seen at 8358.

The above-described process occurs for each module in the modular stack 8300 until the falling edge of the initial clock pulse signal from the clock pulse generator 8338 occurs, which can be seen at 8360. At the falling edge of the initial clock pulse signal, each flip-flop 8330, 8332, 8334, 8336 can be transitioned back to a cleared state by way of the clear inputs of the flip-flops, as described above. In one example, the clock pulse signal can be sufficiently set so that each module in the modular stack will receive a delayed signal before the flip-flops are returned to a clear state. In one embodiment, the flip-flops can transition from the Q output state to the $\overline{Q}$ output state upon receiving the falling edge of the clock pulse. After the RC delay circuits have been sufficiently discharged, the identification process can be completed again.

As described in greater detail herein, a modular surgical system comprises a header module and one or more functional or surgical modules. In various instances, the modular surgical system is a modular energy system. In various instances, the surgical modules include energy modules, communication modules, user interface modules; however, the surgical modules are envisioned to be any suitable type of functional or surgical module for use with the modular surgical system.

One or more surgical modules of a modular surgical system can be connected to a header module in a variety of different stacked configurations. To function properly, a modular surgical system needs to determine the physical location of the modules in its stack. Positional awareness of the modules with respect to the header module and/or with respect to each other facilitates a proper interaction between the modules and the header module, and allows a UI module such as, for example, the UI module 3030 (FIG. 33) to provide a visual representation of the modules where each module is arranged with a 1:1 association to its physical location. In certain instances, the physical location of a module in the stack configuration is associated with, or corresponds to, a unique address (e.g. a unique bit pattern) that identifies the module, and facilitates proper communication with the header module and/or other modules in the stack configuration.

In various examples, the physical location of each module is identified and/or an address is assigned to it by way of an analog signal or a clock pulse signal, as described in greater detail in U.S. patent application Ser. No. 16/562,212, titled MODULAR SURGICAL ENERGY SYSTEM WITH MODULE POSITIONAL AWARENESS SENSING WITH VOLTAGE DETECTION and U.S. patent application Ser. No. 16/562,234, titled MODULAR SURGICAL ENERGY SYSTEM WITH MODULE POSITIONAL AWARENESS SENSING WITH TIME COUNTER, which are incorporated by reference herein in their entireties.

In various aspects, to avoid a faulty start of a modular surgical system, it is desirable to perform at least an initial determination of the physical positions of the modules in the stack. The present disclosure provides reliable mechanisms for identification of the physical positions of the modules in a stack.

In various aspects, the Header module of a modular surgical system is configured to interact with the modules in a stack configuration via unique addresses, associated with each of the modules, which are based on the physical location of the modules in the stack configuration. Accordingly, a user can stack identical modules in any desirable stack configuration, or change an existing stack configuration, without having to manually provide the physical positions of the modules to the header module. Instead, each module is able to identify its own position in the stack configuration, and a unique address associated with such position. The header module is then able to deduce the relative positions of the modules, and the number of modules, in the stack configuration according to whether the header module is able to successfully communicate with such addresses.

For example, if the header module is able to establish a successful communication with a surgical module using an address associated with a first position in the stack configuration, the header module deduces the presence of a surgical module in the first position, and that at least one surgical module is in the stack configuration. If the header module is able to establish a successful communication with a surgical module using an address associated with a second position in the stack configuration, the header module deduces the presence of a surgical module in the second position, and that at least two surgical modules are in the stack configuration. If the header module is able to establish a successful communication with a surgical module using an address associated with a third position in the stack configuration, the header module deduces the presence of a surgical module in the third position, and that at least three surgical modules are in the stack configuration. In various examples, such communication attempts are carried out by a communication interface that uses any suitable communication means (e.g., a LIN or Ethernet network).

Accordingly, a user can stack identical modules in any desirable stack configuration, and depending on their positons in the stack configuration, unique addresses are generated for each of the identical modules. In various aspects, the unique addresses and their corresponding physical positions are stored in any suitable storage medium, in the form of a look-up table or database, for example, and are accessible by a processor of the header module.

Figure 53:
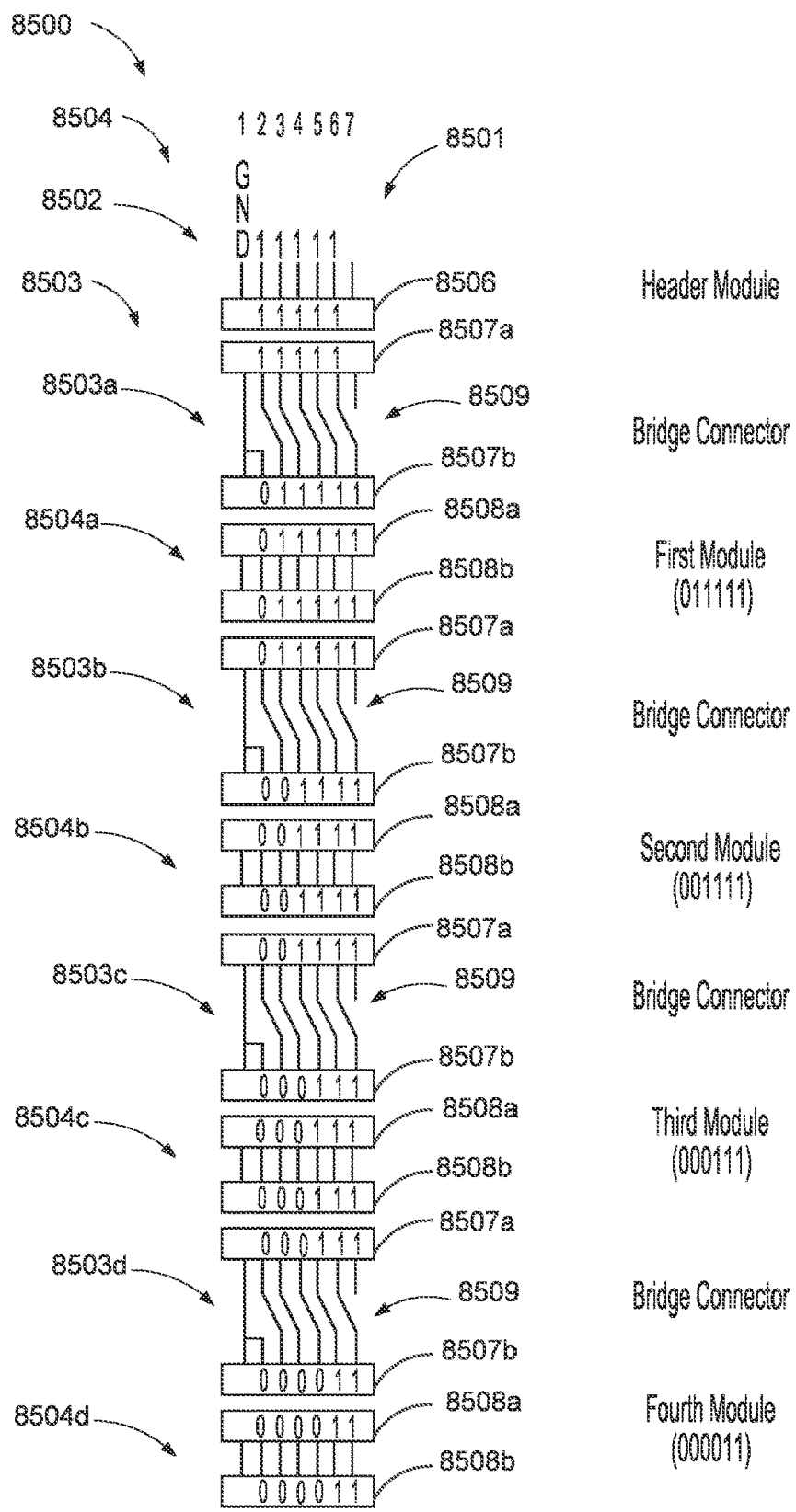
FIG. 53 illustrates a simplified schematic diagram of a positional awareness circuit of a modular energy system, in accordance with at least one embodiment of the present disclosure.

FIG. 53 illustrates a simplified schematic diagram of a positional awareness circuit 8501 of a modular surgical system 8500, which is configured to identify relative positions of surgical modules in a stack configuration of the modular surgical system 8500, and produce unique addresses for each of the surgical modules, as described above. Like other modular surgical systems described elsewhere herein, the modular surgical system 8500 includes a header module 8502 configured to be arranged in a stack configuration with one or more surgical modules 8504. In the example of FIG. 53, the modular surgical system 8500 includes four surgical modules 8504a, 8504b, 8504c, 8504d, which are collectively referred to herein as surgical modules 8504. However, this number of surgical modules is not limiting. In other examples, a modular surgical system 8500 can include more or less than four surgical modules in a stack configuration.

Further, the modular surgical system 8500 also includes a number of backplane connectors 8503 configured to connect consecutive modules in the stack configuration. For example, a backplane connector 8503a connects the header module 8502 and the surgical module 8504a, a backplane connector 8503b connects the surgical module 8504a and the surgical module 8504b, a backplane connector 8503c connects the surgical module 8504b and the surgical module 8504c, and a backplane connector 8503d connects the surgical module 8504c and the surgical module 8504d. The positional awareness circuit 8501 employs a shifting bit pattern, defined by the backplane connectors 8503, to identify the number of surgical modules 8504 and/or the position of each of the surgical modules 8504 in the stack configuration.

Each of the surgical modules 8504 in the stack configuration of the modular surgical system 8500 is identifiable by a unique bit pattern produced by preceding backplane connector(s) 8503 in the stack configuration. Each backplane connector connecting a directly-upstream surgical module and a directly-downstream surgical module in the stack configuration yields a bit pattern, shifted to the right by one position from the bit pattern of the directly-upstream surgical module, which is configured to identify the directly-downstream surgical module.

Each of the backplane connectors 8503 includes a top or first coupling portion 8507a and a bottom or second coupling portion 8507b. Conductor elements extend between the first coupling portion 8507a and the second coupling portion 8507b defining a conductor layout 8509 that yields the shifting bit pattern of the positional awareness circuit 8501. A left-most conductor element extends from a 1st position of the first coupling portion 8507a to a 1st position of the second coupling portion 8507b. The left-most conductor comprises a split that extends to the 2nd position of the second coupling portion 8507b. The left-most conductor is a common ground reference for transmitted logic signals, and may be utilized in performing other functions.

The shifting bit pattern of the positional awareness circuit 8501 is achieved using conductor elements, without active components. In various aspects, the conductor layout 8509 includes a plurality of shifting conductor elements. In the example illustrated in FIG. 53, the conductor layout 8509 further includes a conductor element that extends from a 2nd position of the first coupling portion 8507a to a 3rd position of the second coupling portion 8507b. Similarly, a conductor element extends from a 3rd position of the first coupling portion 8507a to a 4th position of the second coupling portion 8507b. Similarly, a conductor element extends from a 4th position of the first coupling portion 8507a to a 5th position of the second coupling portion 8507b. Similarly, a conductor element extends from a 5th position of the first coupling portion 8507a to a 6th position of the second coupling portion 8507b. Similarly, a conductor element extends from a 6th position of the first coupling portion 8507a to a 7th position of the second coupling portion 8507b.

As illustrated in FIG. 53, backplane connectors 8503 with the conductor layout 8509 yield different, unique, bit patterns depending on the position of such backplane connectors 8503 in the stack configuration. The first or top backplane connector 8503a, which extends between a coupling portion 8506 of the header module 8502 and the first coupling portion 8508a of the surgical module 8504a, yields a bit pattern "011111" that identifies the surgical module 8504a as the first surgical module in the stack configuration of the modular surgical system 8500. Notably, any surgical module positioned directly below the header module, and in connection with the backplane connector 8503a, will be assigned the bit pattern "011111". Accordingly, the header module 8502 is able to deduce that the surgical module 8504a is the first surgical module in the stack configuration of the modular surgical system 8500, and that it is situated directly below the header module 8502, from successful communication with the surgical module 8504a using the bit pattern "011111".

Further to the above, the backplane connector 8503b, which extends between the second coupling portion 8508b of the first surgical module 8504a and the first coupling portion 8508a of the surgical module 8504b, yields a bit pattern "001111" that identifies the surgical module 8504b as the second surgical module in the stack configuration of the modular surgical system 8500. Notably, any surgical module positioned directly below the first surgical module 8504a, and in connection with the backplane connector 8503b, will be assigned the bit pattern "001111". Accordingly, the header module 8502 is able to deduce that the surgical module 8504b is the second surgical module in the stack configuration of the modular surgical system 8500, and that it is situated directly below the surgical module 8504a, from successful communication with the surgical module 8504b using the bit pattern "001111". Similarly, the header module 8502 is able to deduce that the surgical modules 8504c, 8504d are the third and fourth surgical modules in the stack configuration of the modular surgical system 8500 from successful communication with the surgical modules 8504c 8504d using the bit patterns "000111" and "000011", respectively, which are produced by the backplane connectors 8503c, 8503d, respectively.

In various instances, the backplane connectors 8503 are integrated with their respective directly-upstream modules in the stack configuration, and are detachably couplable to their respective directly-downstream modules in the stack configuration. For example, the backplane connector 8503a can be integrated with the header module 8502, and can be detachably couplable to the surgical module 8504a. Likewise, the backplane connector 8503b can be integrated with the surgical module 8504a, and can be detachably couplable to the surgical module 8504b. Similarly, the backplane connector 8503c can be integrated with the surgical module 8504b, and can be detachably couplable to the surgical module 8504c. Also, the backplane connector 8503d can be integrated with the surgical module 8504c, and can be detachably couplable to the surgical module 8504d. Alternatively, in other instances, the backplane connectors 8503 can be integrated with their respective directly-downstream modules in the stack configuration, and can be detachably couplable to their respective directly-upstream modules in the stack configuration. Alternatively, in certain instances, the backplane connectors 8503 can be independent components that are detachably couplable to their respective directly-upstream and directly-downstream modules in the stack configuration.

In various aspects, the header module 8502 employs a look-up table or a database, which can be stored in any suitable storage medium to correlate the bit patterns "011111", "001111", "000111", and "000011", with a first position, second position, third position, and fourth position, respectively, below the header module 8502, respectively, in the stack configuration. Accordingly, the header module 8502 can deduce whether a surgical module occupies a position in the stack configuration of the modular surgical system 8500 by querying the look-up table or database for the address associated with the position, and attempting to communicate using the address. If a successful communication with a surgical module is achieved, the header module 8502 concludes that the surgical module is located at the position associated with the address that caused the successful communication. Further, the header module 8502 can deduce that the number of modules in the stack configuration is at least the number that corresponds to the ranking of the position. For example, the header module 8502 can deduce that the surgical module 8504c occupies the third position in the stack configuration of the modular surgical system 8500 by querying the look-up table or database for the address associated with the third position, which is the bit pattern "000111," and performing a successful communication using the address. If a successful communication with a surgical module is achieved, the header module 8502 concludes that the surgical module 8504c is located at the third position. Further, the header module 8502 can deduce that the number of modules in the stack configuration is at least the three. Similar conclusions can be made regarding the surgical modules in the first, second, and fourth positions.

In the example embodiment illustrated in FIG. 53, the header module 8502 is configured to deduce the number and relative position of the modules in a stack configuration of the modular surgical system 8500 using the shifting bit pattern produced by the backplane connectors 8503. It is, however, understood that various other suitable backplane connectors and shifting bit patterns can be equally employed by the header module 8502 to deduce the number and relative position of the modules in a stack configuration of the modular surgical system 8500. Further, the shifting bit pattern need not be produced by the backplane connectors. In various examples, as illustrated in FIG. 54, a shifting bit pattern for identification of the number and relative position of the modules in a stack configuration can be produced by the modules themselves.

Figure 54:
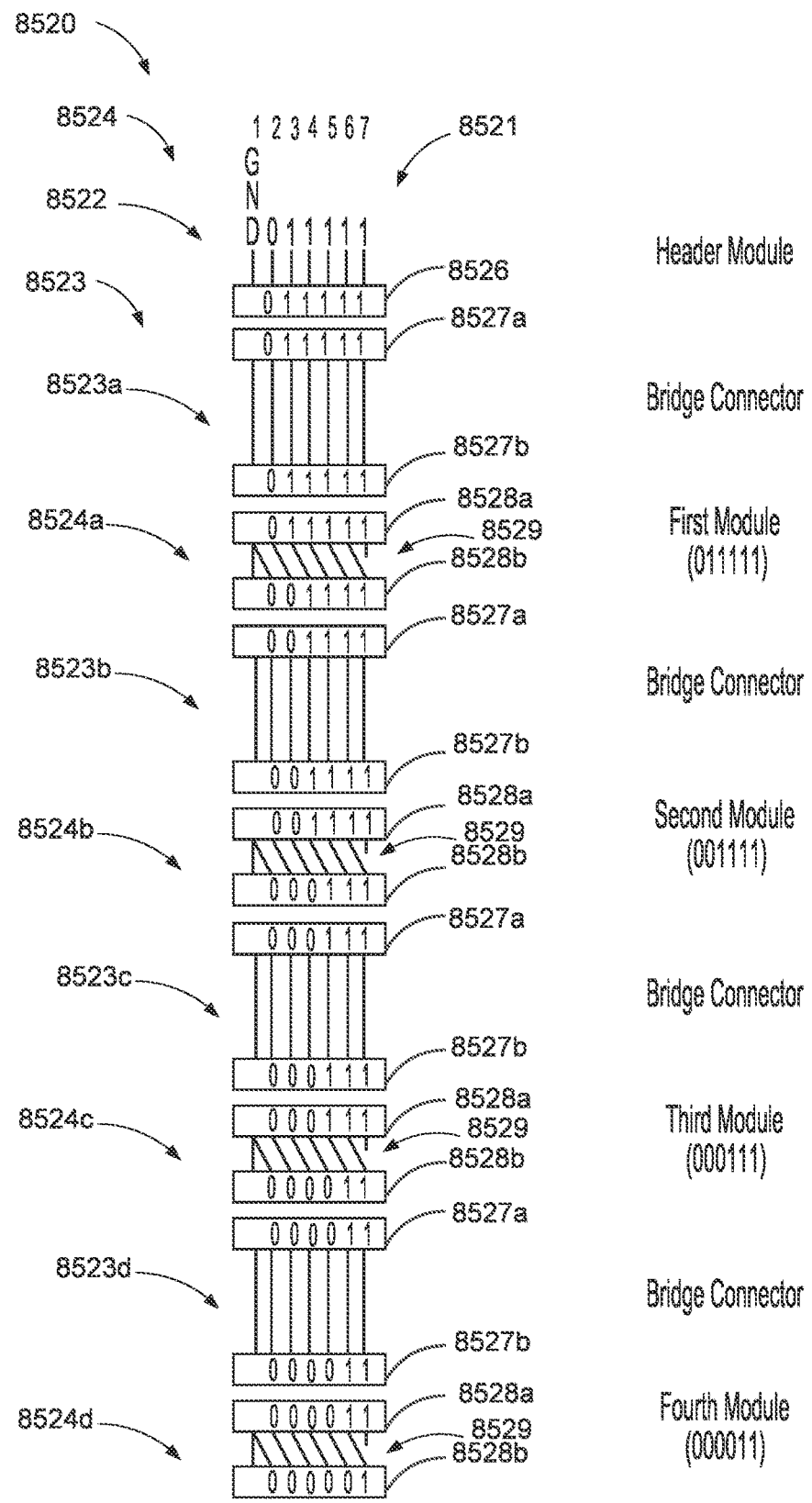
FIG. 54 illustrates a simplified schematic diagram of a positional awareness circuit of a modular energy system, in accordance with at least one embodiment of the present disclosure.

FIG. 54 illustrates a simplified schematic diagram of a positional awareness circuit 8521 of a modular surgical system 8520, which is configured to identify relative positions of surgical modules in a stack configuration of the modular surgical system 8520, and produce unique addresses for each of the surgical modules, as described above. The modular surgical system 8520 is similar in many respects to other modular surgical systems disclosed elsewhere herein such as, for example, the modular surgical system 8500. Like the modular surgical system 8500, the modular surgical system 8520 includes a header module 8522 configured to be arranged in a stack configuration with one or more surgical modules 8524. In the example of FIG. 54, the modular surgical system 8520 includes four surgical modules 8524a, 8524b, 8524c, 8524d, which are collectively referred to herein as surgical modules 8524. However, this number of surgical modules is not limiting. In other examples, a modular surgical system 8520 can include more or less than four surgical modules in a stack configuration.

Further, the modular surgical system 8520 also includes a number of backplane connectors 8523 configured to connect consecutive modules in the stack configuration. For example, a backplane connector 8523a connects the header module 8522 and the surgical module 8524a, a backplane connector 8523b connects the surgical module 8524a and the surgical module 8524b, a backplane connector 8523c connects the surgical module 8524b and the surgical module 8524c, and a backplane connector 8523d connects the surgical module 8524c and the surgical module 8524d. The positional awareness circuit 8521 employs a shifting bit pattern, defined by the surgical modules 8524, to identify the number of surgical modules 8524 and/or the position of each of the surgical modules 8524 in the stack configuration.

Each of the surgical modules 8524 in the stack configuration of the modular surgical system 8520 is identifiable by a unique bit pattern produced by preceding surgical module (s) in the stack configuration. Each new surgical module added to the bottom of a preceding surgical module in the stack configuration is configured to receive a new bit pattern, shifted to the right by one position from the bit pattern of the preceding surgical module. The new bit pattern is configured to identify the newly added surgical module, and is produced by the preceding surgical module(s) in the stack configuration.

Each of the surgical modules 8524 includes a top or first coupling portion 8528a and a bottom or second coupling portion 8528b. Conductor elements extend between the first coupling portion 8528a and the second coupling portion 8528b defining a conductor layout 8529 that yields the shifting bit pattern of the positional awareness circuit 8521. A left-most conductor element extends from a 1st position of the first coupling portion 8528a to a 1st position of the second coupling portion 8528b. The left-most conductor comprises a split that extends to the 2nd position of the second coupling portion 8528b. The left-most conductor is a common ground reference for transmitted logic signals, and may be utilized in performing other functions.

Like the shifting bit pattern of the positional awareness circuit 8501, the shifting bit pattern of the positional awareness circuit 8521 is achieved using conductor elements, without active components. In various aspects, the conductor layout 8529 includes a plurality of shifting conductor elements. In the example illustrated in FIG. 54, the conductor layout 8529 further includes a conductor element that extends from a 2nd position of the first coupling portion 8528a to a 3rd position of the second coupling portion 8528b. Similarly, a conductor element extends from a 3rd position of the first coupling portion 8528a to a 4th position of the second coupling portion 8528b. Similarly, a conductor element extends from a 4th position of the first coupling portion 8528a to a 5th position of the second coupling portion 8528b. Similarly, a conductor element extends from a 5th position of the first coupling portion 8528a to a 6th position of the second coupling portion 8528b. Similarly, a conductor element extends from a 6th position of the first coupling portion 8528a to a 7th position of the second coupling portion 8528b.

As illustrated in FIG. 54, the surgical modules 8524 with the conductor layout 8529 yield different, unique, bit patterns depending on the position of such surgical modules 8524 in the stack configuration, which are configured to identify their respective following surgical modules in the stack configuration. The first surgical module 8524a received its identifying bit pattern "011111" from the header module 8522. Notably, any surgical module positioned directly below the header module, and in connection with the backplane connector 8523a, will be assigned the bit pattern "011111". Accordingly, the header module 8522 is able to deduce that the surgical module 8524a is the first surgical module in the stack configuration of the modular surgical system 8520, situated directly below the header module 8522, from successful communication with the surgical module 8524*a* using the bit pattern "011111".

Further, the conductor layout of the surgical module 8524*a*, yields a bit pattern "001111" that identifies the surgical module 8524*b* as the second surgical module in the stack configuration of the modular surgical system 8520. Notably, any surgical module in a second position below a header module 8522 will be assigned the bit pattern "001111".

Accordingly, the header module 8522 is able to deduce that the surgical module 8524*b* is the second surgical module in the stack configuration of the modular surgical system 8520, and that it is situated directly below the surgical module 8524*a*, from successful communication with the surgical module 8524*b* using the bit pattern "001111". Similarly, the header module 8522 is able to deduce that the surgical modules 8524*c*, 8524*d* are the third and fourth surgical modules in the stack configuration of the modular surgical system 8520 from successful communication with the surgical modules 8524*c* 8524*d* using the bit patterns "000111" and "000011", respectively, which are produced by the surgical modules 8524*b*, 8524*c*, respectively.

In various aspects, the header module 8522 employs a look-up table or a database, which can be stored in any suitable storage medium to correlate the bit patterns "011111", "001111", "000111", and "000011", with a first position, second position, third position, and fourth position, respectively, below the header module 8522, respectively, in the stack configuration. Accordingly, the header module 8522 can deduce whether a surgical module occupies a position in the stack configuration of the modular surgical system 8520 by querying the look-up table or database for the address associated with the position, and attempting to communicate using the address. If a successful communication with a surgical module is achieved, the header module 8522 concludes that the surgical module is located at the position associated with the address that caused the successful communication. Further, the header module 8522 can deduce that the number of modules in the stack configuration is at least the number that corresponds to the ranking of the position. For example, the header module 8522 can deduce that the surgical module 8524*c* occupies the third position in the stack configuration of the modular surgical system 8520 by querying the look-up table or database for the address associated with the third position, which is the bit pattern "000111," and performing a successful communication using the address. If a successful communication with a surgical module is achieved, the header module 8522 concludes that the surgical module 8524*c* is located at the third position. Further, the header module 8522 can deduce that the number of modules in the stack configuration is at least the three. Similar conclusions can be made regarding the surgical modules in the first, second, and fourth positions.

In the example embodiments illustrated in FIGS. 53 and 54, the header module 8522 is configured to deduce the number and relative position of the modules in a stack configuration of the modular surgical system using a shifting bit pattern. This, however, is not limiting. In other examples, as illustrated in FIGS. 55 and 56, a rotating bit pattern can be employed to identify the number and relative position of the modules in a stack configuration of a modular surgical system.

Figure 55:
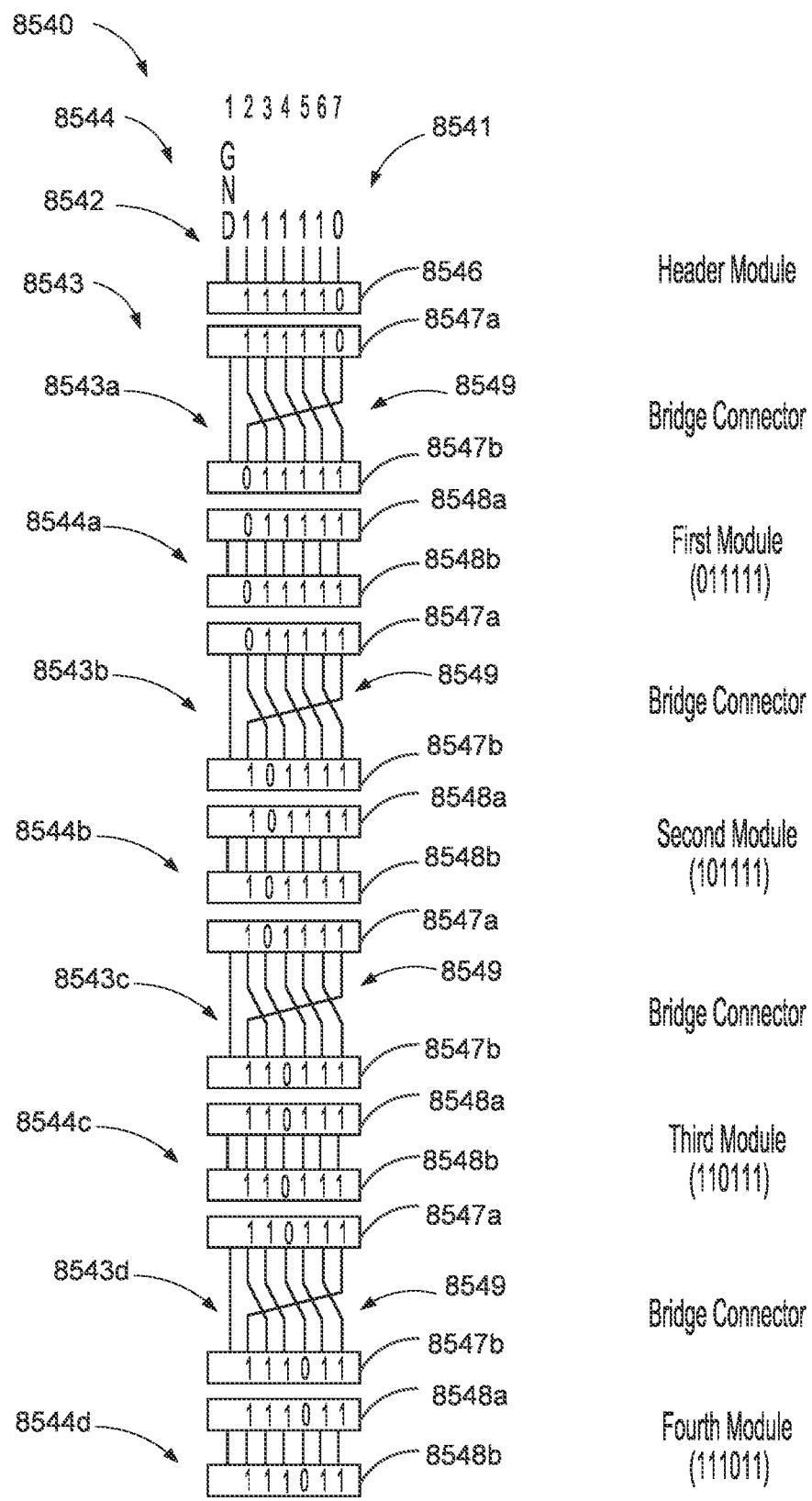
FIG. 55 illustrates a simplified schematic diagram of a positional awareness circuit of a modular energy system, in accordance with at least one embodiment of the present disclosure.
Figure 56:
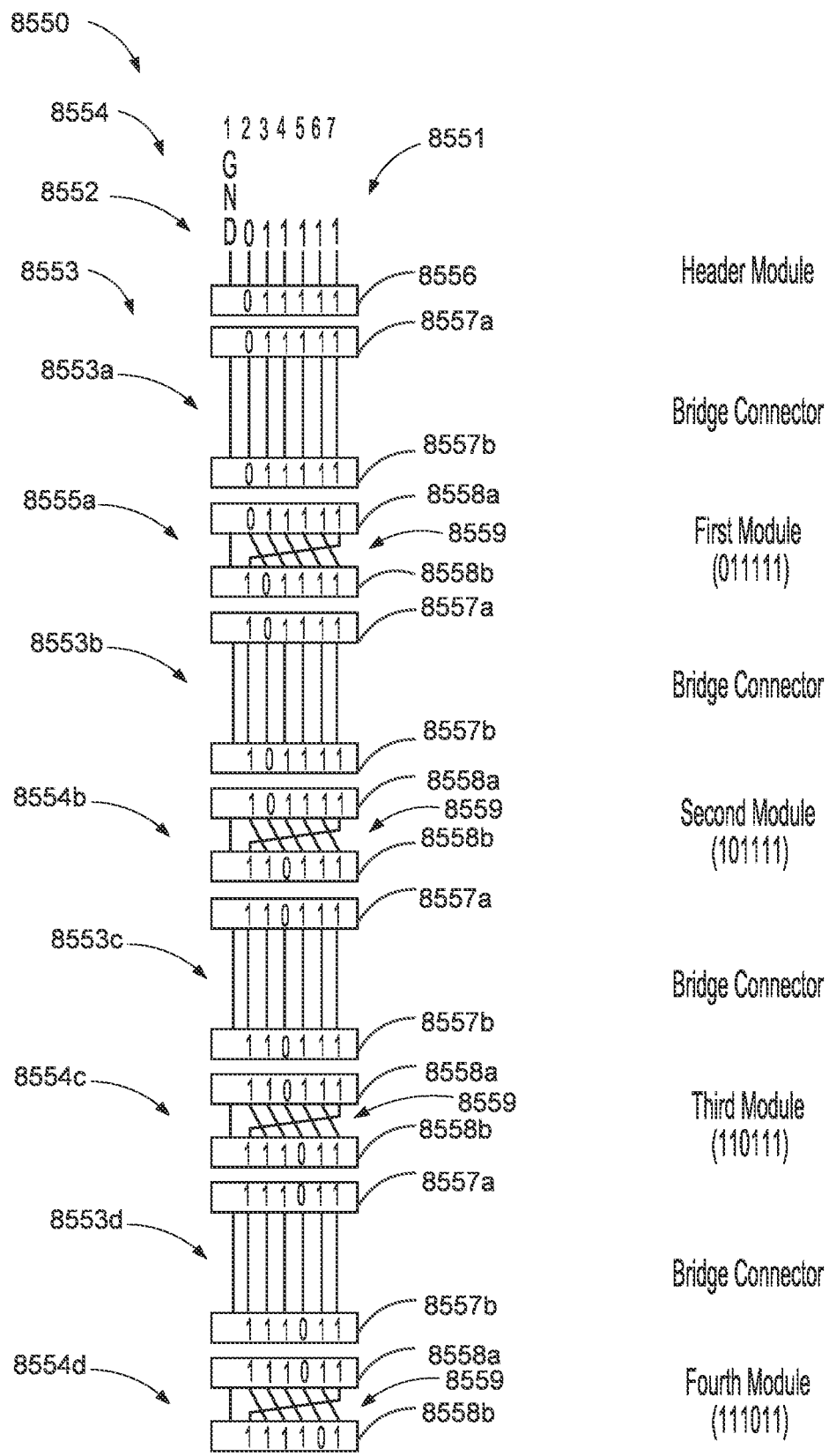
FIG. 56 illustrates a simplified schematic diagram of a positional awareness circuit of a modular energy system, in accordance with at least one embodiment of the present disclosure.

FIG. 55 illustrates a simplified schematic diagram of a positional awareness circuit 8541 of a modular surgical system 8540, which is configured to identify relative positions of surgical modules in a stack configuration of the modular surgical system 8500, and produce unique addresses for each of the surgical modules, as described above. Like other modular surgical systems described elsewhere herein, the modular surgical system 8540 includes a header module 8542 configured to be arranged in a stack configuration with one or more surgical modules 8544. In the example of FIG. 55, the modular surgical system 8540 includes four surgical modules 8544*a*, 8544*b*, 8544*c*, 8544*d*, which are collectively referred to herein as surgical modules 8544. However, this number of surgical modules is not limiting. In other examples, a modular surgical system 8540 can include more or less than four surgical modules in a stack configuration.

Further, the modular surgical system 8540 also includes a number of backplane connectors 8543 configured to connect consecutive modules in the stack configuration. For example, a backplane connector 8543*a* connects the header module 8542 and the surgical module 8544*a*, a backplane connector 8543*b* connects the surgical module 8544*a* and the surgical module 8544*b*, a backplane connector 8543*c* connects the surgical module 8544*b* and the surgical module 8544*c*, and a backplane connector 8543*d* connects the surgical module 8544*c* and the surgical module 8544*d*. The positional awareness circuit 8541 employs a rotating bit pattern, defined by the backplane connectors 8543, to identify the number of surgical modules 8544 and/or the position of each of the surgical modules 8544 in the stack configuration.

Each of the surgical modules 8544 in the stack configuration of the modular surgical system 8540 is identifiable by a unique bit pattern produced by preceding backplane connector(s) 8543 in the stack configuration. Each backplane connector connecting a directly-upstream surgical module and a directly-downstream surgical module in the stack configuration yields a bit pattern that is different than the bit pattern identifying the directly-upstream surgical module, and is configured to identify the directly-downstream surgical module.

Each of the backplane connectors 8543 includes a top or first coupling portion 8547*a* and a bottom or second coupling portion 8547*b*. Conductor elements extend between the first coupling portion 8547*a* and the second coupling portion 8547*b* defining a conductor layout 8549 that yields the rotating bit pattern of the positional awareness circuit 8541. A left-most conductor element extends from a 1st position of the first coupling portion 8547*a* to a 1st position of the second coupling portion 8547*b*. The left-most conductor is a common ground reference for transmitted logic signals, and may be utilized in performing other functions.

The rotating bit pattern of the positional awareness circuit 8541 is achieved using conductor elements, without active components. In various aspects, the conductor layout 8529 includes a plurality of shifting conductor elements, and a rotating conductor element. In the example illustrated in FIG. 55, the conductor layout 8549 further includes a conductor element that extends from a 2nd position of the first coupling portion 8547*a* to a 3rd position of the second coupling portion 8547*b*. Similarly, a conductor element extends from a 3rd position of the first coupling portion 8547*a* to a 4th position of the second coupling portion 8547*b*. Similarly, a conductor element extends from a 4th position of the first coupling portion 8547*a* to a 5th position of the second coupling portion 8547*b*. Similarly, a conductor element extends from a 5th position of the first coupling portion 8547*a* to a 6th position of the second coupling portion 8547*b*. Similarly, a conductor element extends from a 6th position of the first coupling portion 8547*a* to a 7th position of the second coupling portion 8547b. Finally, a conductor element extends, in a rotating fashion, from a 7th position of the first coupling portion 8547a to a 2nd position of the second coupling portion 8547b, facilitating the rotation of the rotating bit pattern.

As illustrated in FIG. 55, backplane connectors 8543 with the conductor layout 8549 yield different, unique, bit patterns depending on the position of such backplane connectors 8543 in the stack configuration. The first or top backplane connector 8543a, which extends between a coupling portion 8546 of the header module 8542 and the first coupling portion 8548a of the surgical module 8544a, yields a bit pattern "011111" that identifies the surgical module 8544a as the first surgical module in the stack configuration of the modular surgical system 8540. Notably, any surgical module positioned directly below the header module 8542, and in connection with the backplane connector 8543a, will be assigned the bit pattern "011111". Accordingly, the header module 8542 is able to deduce that the surgical module 8544a is the first surgical module in the stack configuration of the modular surgical system 8540, situated directly below the header module 8542, from successful communication with the surgical module 8544a using the bit pattern "011111".

Further to the above, the backplane connector 8543b, which extends between the second coupling portion 8548b of the first surgical module 8544a and the first coupling portion 8548a of the surgical module 8544b, yields a bit pattern "101111" that identifies the surgical module 8544b as the second surgical module in the stack configuration of the modular surgical system 8540. Notably, any surgical module positioned directly below the first surgical module 8544a, and in connection with the backplane connector 8543b, will be assigned the bit pattern "101111".

Accordingly, the header module 8542 is able to deduce that the surgical module 8544b is the second surgical module in the stack configuration of the modular surgical system 8540, and that it is situated directly below the surgical module 8544a, from successful communication with the surgical module 8544b using the bit pattern "101111". Similarly, the header module 8542 is able to deduce that the surgical modules 8544c, 8544d are the third and fourth surgical modules in the stack configuration of the modular surgical system 8540 from successful communication with the surgical modules 8544c 8544d using the bit patterns "110111" and "111011", respectively, which are produced by the backplane connectors 8543c, 8543d, respectively In various aspects, the header module 8542 employs a look-up table or a database, which can be stored in any suitable storage medium to correlate the bit patterns "011111", "101111", "110111", and "111011", with a first position, second position, third position, and fourth position, respectively, below the header module 8542, respectively, in the stack configuration. Accordingly, the header module 8542 can deduce whether a surgical module occupies a position in the stack configuration of the modular surgical system 8540 by querying the look-up table or database for the address associated with the position, and attempting to communicate using the address. If a successful communication with a surgical module is achieved, the header module 8542 concludes that the surgical module is located at the position associated with the address that caused the successful communication. Further, the header module 8542 can deduce that the number of modules in the stack configuration is at least the number that corresponds to the ranking of the position. For example, the header module 8542 can deduce that the surgical module 8544c occupies the third position in the stack configuration of the modular surgical system 8540 by querying the look-up table or database for the address associated with the third position, which is the bit pattern "110111," and performing a successful communication using the address. If a successful communication with a surgical module is achieved, the header module 8542 concludes that the surgical module 8544c is located at the third position. Further, the header module 8542 can deduce that the number of modules in the stack configuration is at least the three. Similar conclusions can be made regarding the surgical modules in the first, second, and fourth positions.

In various instances, the backplane connectors 8543 are integrated with their respective directly-upstream modules in the stack configuration, and are detachably couplable to their respective directly-downstream modules in the stack configuration. For example, the backplane connector 8543a can be integrated with the header module 8542, and can be detachably couplable to the surgical module 8544a. Likewise, the backplane connector 8543b can be integrated with the surgical module 8544a, and can be detachably couplable to the surgical module 8544b. Similarly, the backplane connector 8543c can be integrated with the surgical module 8544b, and can be detachably couplable to the surgical module 8544c. Also, the backplane connector 8543d can be integrated with the surgical module 8544c, and can be detachably couplable to the surgical module 8544d. Alternatively, in other instances, the backplane connectors 8543 can be integrated with their respective directly-downstream modules in the stack configuration, and can be detachably couplable to their respective directly-upstream modules in the stack configuration. Alternatively, in certain instances, the backplane connectors 8543 can be independent components that are detachably couplable to their respective directly-upstream and directly-downstream modules in the stack configuration.

In the example embodiment illustrated in FIG. 55, the header module 8542 is configured to identify the number and relative position of the modules in a stack configuration of the modular surgical system 8540 using the rotating bit pattern produced by the backplane connectors 8543. It is, however, understood that various other suitable backplane connectors and rotating bit patterns can be equally employed by the header module 8502 to identify the number and relative position of the modules in a stack configuration of the modular surgical system 8540. Further, the rotating bit pattern need not be produced by the backplane connectors. In various examples, as illustrated in FIG. 56, a rotating bit pattern for identification of the number and relative position of the modules in a stack configuration can be produced by the modules themselves.

FIG. 56 illustrates a simplified schematic diagram of a positional awareness circuit 8551 of a modular surgical system 8550, which is configured to identify relative positions of surgical modules in a stack configuration of the modular surgical system 8500, and produce unique addresses for each of the surgical modules, as described above. The modular surgical system 8550 is similar in many respects to other modular surgical systems disclosed elsewhere herein such as, for example, the modular surgical system 8500. Like the modular surgical system 8500, the modular surgical system 8550 includes a header module 8552 configured to be arranged in a stack configuration with one or more surgical modules 8554. In the example of FIG. 56, the modular surgical system 8550 includes four surgical modules 8554a, 8554b, 8554c, 8554d, which are collectively referred to herein as surgical modules 8554. However, this number of surgical modules is not limiting. In other examples, a modular surgical system 8550 can include more or less than four surgical modules in a stack configuration.

Further, the modular surgical system 8550 also includes a number of backplane connectors 8553 configured to connect consecutive modules in the stack configuration. For example, a backplane connector 8553a connects the header module 8552 and the surgical module 8554a, a backplane connector 8553b connects the surgical module 8554a and the surgical module 8554b, a backplane connector 8553c connects the surgical module 8554b and the surgical module 8554c, and a backplane connector 8553d connects the surgical module 8554c and the surgical module 8554d. The positional awareness circuit 8551 employs a rotating bit pattern, defined by the surgical modules 8554, to identify the number of surgical modules 8554 and/or the position of each of the surgical modules 8554 in the stack configuration.

Each of the surgical modules 8554 in the stack configuration of the modular surgical system 8550 is identifiable by a unique bit pattern produced by a directly preceding surgical module in the stack configuration. Each new surgical module added to the bottom of a preceding surgical module in the stack configuration is configured to receive a new bit pattern configured to identify the newly added energy, and is produced by the directly surgical module in the stack configuration.

Each of the surgical modules 8554 includes a top or first coupling portion 8558a and a bottom or second coupling portion 8558b. Conductor elements extend between the first coupling portion 8558a and the second coupling portion 8558b defining a conductor layout 8559 that yields the rotating bit pattern of the positional awareness circuit 8551. A left-most conductor element extends from a 1st position of the first coupling portion 8558a to a 1st position of the second coupling portion 8558b. The left-most conductor comprises a split that extends to the 2nd position of the second coupling portion 8558b. The left-most conductor is a common ground reference for transmitted logic signals, and may be utilized in performing other functions.

Like the shifting bit pattern of the positional awareness circuit 8541, the rotating bit pattern of the positional awareness circuit 8551 is achieved using conductor elements, without active components. In various aspects, the conductor layout 8529 includes a plurality of shifting conductor elements, and a rotating conductor element. In the example illustrated in FIG. 56, the conductor layout 8559 further includes a conductor element that extends from a 2nd position of the first coupling portion 8558a to a 3rd position of the second coupling portion 8558b. Similarly, a conductor element extends from a 3rd position of the first coupling portion 8558a to a 4th position of the second coupling portion 8558b. Similarly, a conductor element extends from a 4th position of the first coupling portion 8558a to a 5th position of the second coupling portion 8558b. Similarly, a conductor element extends from a 5th position of the first coupling portion 8558a to a 6th position of the second coupling portion 8558b. Similarly, a conductor element extends from a 6th position of the first coupling portion 8558a to a 7th position of the second coupling portion 8558b. Finally, a conductor element extends, in a rotating fashion, from a 7th position of the first coupling portion 8558a to a 2nd position of the second coupling portion 8558b, facilitating the rotation of the rotating bit pattern.

As illustrated in FIG. 56, the surgical modules 8554 with the conductor layout 8559 yield different, unique, bit patterns depending on the position of such surgical modules 8554 in the stack configuration, which are configured to identify their respective following surgical modules in the stack configuration. The first surgical module 8554a received its identifying bit pattern "011111" from the header module 8552. Notably, any surgical module positioned directly below the header module, and in connection with the backplane connector 8553a, will be assigned the bit pattern "011111". Accordingly, the header module 8552 is able to deduce that the surgical module 8554a is the first surgical module in the stack configuration of the modular surgical system 8550, situated directly below the header module 8552, from successful communication with the surgical module 8554a using the bit pattern "011111".

Further, the conductor layout of the surgical module 8554a, yields a bit pattern "101111" that identifies the surgical module 8554b as the second surgical module in the stack configuration of the modular surgical system 8550. Notably, any surgical module in a second position below a header module 8552 will be assigned the bit pattern "101111". Accordingly, the header module 8552 is able to deduce that the surgical module 8554b is the second surgical module in the stack configuration of the modular surgical system 8550, and that it is situated directly below the surgical module 8554a, from successful communication with the surgical module 8554b using the bit pattern "101111". Similarly, the header module 8552 is able to deduce that the surgical modules 8554c, 8554d are the third and fourth surgical modules in the stack configuration of the modular surgical system 8550 from successful communication with the surgical modules 8554c 8554d using the bit patterns "110111" and "111011", respectively, which are produced by the surgical modules 8554b, 8554c, respectively.

In various aspects, the header module 8552 employs a look-up table or a database, which can be stored in any suitable storage medium to correlate the bit patterns "011111", "101111", "110111", and "111011", with a first position, second position, third position, and fourth position, respectively, below the header module 8552, respectively, in the stack configuration. Accordingly, the header module 8552 can deduce whether a surgical module occupies a position in the stack configuration of the modular surgical system 8550 by querying the look-up table or database for the address associated with the position, and attempting to communicate using the address. If a successful communication with a surgical module is achieved, the header module 8552 concludes that the surgical module is located at the position associated with the address that caused the successful communication. Further, the header module 8552 can deduce that the number of modules in the stack configuration is at least the number that corresponds to the ranking of the position. For example, the header module 8552 can deduce that the surgical module 8554c occupies the third position in the stack configuration of the modular surgical system 8550 by querying the look-up table or database for the address associated with the third position, which is the bit pattern "110111," and performing a successful communication using the address. If a successful communication with a surgical module is achieved, the header module 8552 concludes that the surgical module 8554c is located at the third position. Further, the header module 8552 can deduce that the number of modules in the stack configuration is at least the three. Similar conclusions can be made regarding the surgical modules in the first, second, and fourth positions.

Referring to FIGS. 53-56, the modular surgical systems 8500, 8520, 8540, 8550 comprise positional awareness circuits 8501, 8521, 8541, 8551 that can be configured to support identification of a maximum number of surgical modules permissible in their the stack configurations. By choosing the number of shifted (or rotated) lines of the conductor layout to be one more than the maximum number of surgical modules allowed in the stack, the surgical module added to the stack that exceeds the maximum permissible number of shifted (or rotated) lines will see a zero on the right-most conductor (the sixth data conductor in the example embodiments shown in FIGS. 53-56, which are sized for a maximum of five modules in the stack). In other examples, however, it is foreseeable that a modular surgical system can include a positional awareness circuit configured to support a maximum of more or less than five surgical modules. In at least one example, by providing an additional sense line or conductor element 8511, as illustrated in FIG. 57 with respect to a positional awareness circuit 8501' of a modular surgical system 8500', to each of the positional awareness circuits 8501, 8521, 8541, 8551, all modules, including the header module, of the modular surgical systems 8500, 8520, 8540, 8550 are able to detect a module limit-exceeded status.

Figure 57:
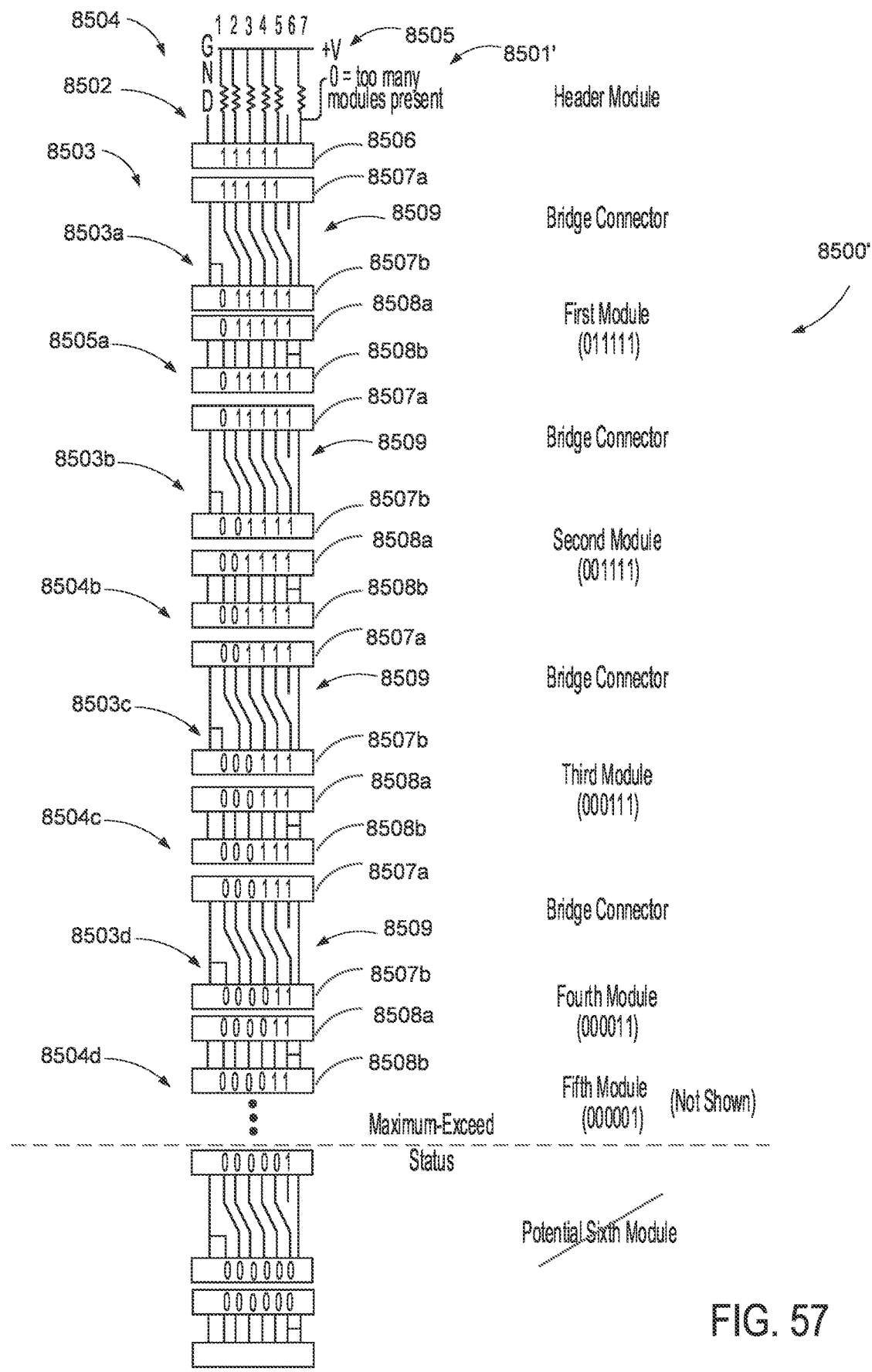
FIG. 57 illustrates a simplified schematic diagram of a positional awareness circuit of a modular energy system, in accordance with at least one embodiment of the present disclosure.

FIG. 57 illustrates a simplified schematic diagram of a positional awareness circuit 8501' of a modular surgical system 8500', which is configured to identify relative positions of surgical modules in a stack configuration of the modular surgical system 8500, and produce unique addresses for each of the surgical modules, as described above. The modular surgical system 8500' is similar in many respects to other modular surgical systems disclosed elsewhere herein such as, for example, the modular surgical system 8500. Like the modular surgical system 8500, the modular surgical system 8500' includes a header module 8502 configured to be arranged in a stack configuration with one or more surgical modules 8504'. In the example of FIG. 57, the modular surgical system 8500' includes four surgical modules 8504a, 8504b, 8504c, 8504d, which are collectively referred to herein as surgical modules 8504'. However, this number of surgical modules is not limiting. In other examples, a modular surgical system 8500 can include more or less than four surgical modules in a stack configuration.

Further to the above, the positional awareness circuit 8501' of the modular surgical system 8500' includes a segmented conductor that defines an additional sense line 8511 that can be extended through all the modules and backplane connectors of the modular surgical system 8500' in the stack configuration, as illustrated in FIG. 57. The sense line 8511 is employed to detect a module limit-exceeded status. As illustrated in FIG. 57, all lines of the modular surgical system 8500' are pulled high through resistors 8505. During operation all the lines are shorted low if module limit-exceeded status is triggered. The voltage across the resistors 8505 can be monitored by the header module 8602 to detect the module limit-exceeded status. In the example of FIG. 57, attaching a sixth module to the stack configuration of the modular surgical system 8500' is impermissible because it exceeds the maximum limit of permissible modules. The header module 8502 is able to detect a maximum-exceeded status when a user attempts to attach a sixth module by monitoring the resistors 8505 for a transition from high to low.

Figure 58:
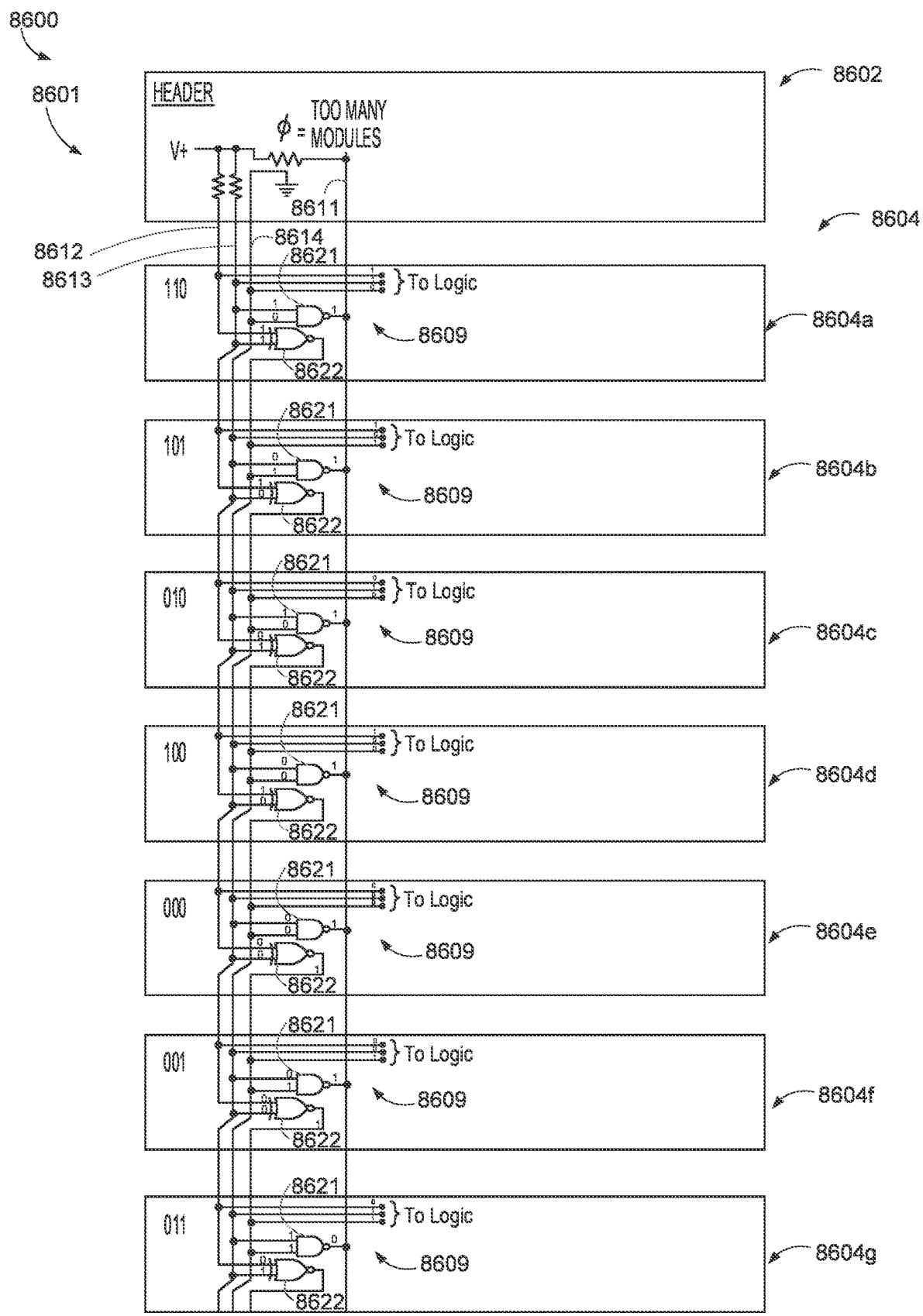
FIG. 58 illustrates a simplified schematic diagram of a positional awareness circuit of a modular energy system, in accordance with at least one embodiment of the present disclosure.

The conductor layouts of the surgical modules 8504' of the modular surgical system 8500' are slightly modified from their counterparts in the modular surgical system 8500 to include an H-bridge between the sense line conductors and the sixth line conductors positioned next to the sense line conductors, as illustrated in FIG. 58. The H-bridge shorts the sense line when a surgical module is added to the stack configuration beyond the maximum number of permissible surgical modules, thereby triggering the maximum-exceeded status. In the example of FIG. 57, adding a sixth surgical module to the stack configuration exceeds the maximum number of permissible surgical modules, which triggers the maximum-exceeded status by shorting all the data lines. In response, in certain instances, the header module 8602, may cause an alert to be issued through the UI module 3030 (FIG. 33), for example.

In various aspects, other modular surgical systems of the present disclosure such as, for example, the modular surgical systems 8500, 8510, 8520, 8540, 8550 can be modified to include a sense line, as discussed above.

The modular surgical systems of FIGS. 53-57 are configured to identify the position and number of surgical modules in their respective stack configuration using inactive-state components. In alternative embodiments, however, active-state components can be employed instead of the inactive-state components to identify the position and number of surgical modules in a stack configuration. For example, FIG. 58 illustrates a modular surgical system 8600 that relies on a logic gate configuration 8609 to identify the position and number of surgical modules in its stack configuration.

FIG. 58 illustrates a simplified schematic diagram of a positional awareness circuit 8601 of the modular surgical system 8600, which is configured to identify relative positions of surgical modules in a stack configuration of the modular surgical system 8500, and produce unique addresses for each of the surgical modules, as described above. The modular surgical system 8600 is similar in many respects to other modular surgical systems disclosed elsewhere herein such as, for example, the modular surgical system 8500. Like the modular surgical system 8500, the modular surgical system 8600 includes a header module 8602 configured to be arranged in a stack configuration with one or more surgical modules 8604. In the example of FIG. 58, the modular surgical system 8600 includes seven surgical modules 8604a, 8604b, 8604c, 8604d, 8604e, 8604f, 8604g which are collectively referred to herein as surgical modules 8604. However, this number of surgical modules is not limiting. In other examples, a modular surgical system 8600 can include more or less than seven surgical modules in a stack configuration.

Each of the surgical modules 8604 includes a logic gate configuration 8609 that yields a different bit pattern depending on the position of its surgical module below the header module 8602 in the stack configuration. In the example of FIG. 58, the first position below the header module 8602 corresponds to a bit pattern "110", the second position below the header module 8602 corresponds to a bit pattern "101", the third position below the header module 8602 corresponds to a bit pattern "010", the fourth position below the header module 8602 corresponds to a bit pattern "100", the fifth position below the header module 8602 corresponds to a bit pattern "000", the sixth position below the header module 8602 corresponds to a bit pattern "001", and the seventh position below the header module 8602 corresponds to a bit pattern "011". Although the logic gate configuration of the surgical modules 8604 is a three-bit sequence, this is not limiting. Modular surgical systems with logic gate configurations comprising more or less than three bits are contemplated by the present disclosure.

In the example illustrated in FIG. 58, one logic gate configuration is repeated in all the surgical modules 8604 in the stack configuration. Each logic gate configuration 8609, however, yields a unique bit pattern depending on the position of its surgical module in the stack configuration, as discussed above.

Further, the logic gate configurations 8609 include NAND gates 8621 and EXNOR gates 8622. The NAND gates 8621 comprise outputs that are coupled to the sense line 8611. In the example of FIG. 58, the positional awareness circuit 8601 is designed to yield a high output for all NAND gates 8621 of all the surgical modules 8604 in the stack configuration that are at or below a maximum number (e.g. six) of permissible surgical modules. The NAND gates 8621 of the surgical modules 8604*a*, 8604*b*, 8604*c*, 8604*d*, 8604*e*, 8604*f*, which are at or below the maximum permissible number of surgical modules for 8600, yield high outputs before attachment of the surgical module 8604*g*. Upon attachment of the surgical module 8604*g* in a seventh position in the stack configuration, the NAND gate 8621 of the surgical module 8604*g* yields a low output because the surgical module 8604*g* causes the number of surgical modules 8604 in the stack configuration to be greater than the maximum permissible number (e.g. six) of surgical modules for 8600. The low output is detectable by the header module 8602 as being indicative of a module maximum-exceeded status. In at least one example, the header module 8602 monitors the sense line 8611 to determine if a module-exceeded status is triggered.

In addition to the NAND gates 8621, the logic gate configurations 8609 include EXNOR gates 8622 that are arranged with the NAND gates 8621 to set the maximum permissible number of surgical modules in the stack configuration of the module surgical system 8600. In the example of FIG. 58, the positional awareness circuit 8601 of the modular surgical system 8600 is designed to limit the maximum permissible number of surgical modules in the stack configuration to six. Accordingly, the addition of a seventh surgical module 8604*g* to the stack configuration already comprising the surgical modules 8604*a*, 8604*b*, 8604*c*, 8604*d*, 8604*e*, 8604*f* yields a maximum-exceeded signal or status that alerts the header module 8602 to the attachment of a surgical module that exceeds the maximum permissible number of surgical modules in the stack configuration. In response, the header module 8602 may alert a user through the UI module 3030 (FIG. 33), for example, that the surgical module 8604*g* exceeds the maximum permissible number of surgical modules in the stack configuration and/or instruct the user to remove the surgical module 8604*g* from the stack configuration.

In some aspects, the header modules described herein can include or support a display, such as display 3046 of the UI module 3030. The header modules can be configured to provide a visual representation of the modules in their stack configuration on the display in relative position representing their physical position in their respective modular surgical systems. The display can provide information about the modules, such as the type of module, status of module, availability of the module, health of module, etc. A user can select one of the modules from the display, such as with a touchscreen, in order to provide instructions to the module by way of a user interface.

EXAMPLES

Various aspects of the subject matter described herein are set out in the following numbered examples:

Example 1—A method of operating a modular surgical system including a control module, a first surgical module, and a second surgical module, the method comprising detachably connecting the first surgical module to the control module by stacking the first surgical module with the control module in a stack configuration, detachably connecting the second surgical module to the first surgical module by stacking the second surgical module with the control module and the first surgical module in the stack configuration, powering up the modular surgical system, and monitoring distribution of power from a power supply of the control module to the first surgical module and the second surgical module.

Example 2—The method of Example 1, further comprising the step of supplying power to the second surgical module through the first surgical module.

Example 3—The method of Examples 1 or 2, further comprising the step of identifying a physical position of the first surgical module in the stack configuration.

Example 4—The method of any one of Examples 1-3, further comprising the step of identifying a physical position of the second surgical module in the stack configuration.

Example 5—The method of any one of Examples 1-4, further comprising the step of preventing simultaneous activation of surgical instruments attached to the first surgical module and the second surgical module.

Example 6—The method of any one of Examples 1-5, further comprising the steps of attaching a first surgical instrument to an energy port of the first surgical module and attaching a second surgical instrument to an energy port of the second surgical module.

Example 7—The method of Example 6, wherein the first surgical instrument comprises an energy modality that is different from an energy modality of the second surgical instrument.

Example 8—A method of operating a modular surgical system including a control module, a first surgical module, and a second surgical module, the method comprising detachably connecting the first surgical module to the control module by stacking the first surgical module with the control module in a stack configuration, detachably connecting the second surgical module to the first surgical module by stacking the second surgical module with the control module and the first surgical module in the stack configuration, attaching a first surgical instrument to an energy port of the first surgical module, attaching a second surgical instrument to an energy port of the second surgical module, activating the first surgical instrument, activating the second surgical instrument, and allocating power from a power supply of the control module to the first surgical module and the second surgical module.

Example 9—The method of Example 8, further comprising the step of adjusting power allocations to the first surgical module and the second surgical module based on energy requirements of the first surgical instrument and the second surgical instrument.

Example 10—The method of Examples 8 or 9, further comprising the step of supplying power to the second surgical module through the first surgical module.

Example 11—The method of any one of Examples 8-10, further comprising the step of identifying a physical position of the first surgical module in the stack configuration.

Example 12—The method of Example 11, further comprising the step of identifying a physical position of the second surgical module in the stack configuration.

Example 13—The method of any one of Examples 8-12, wherein the first surgical instrument comprises an energy modality that is different from an energy modality of the second surgical instrument.

Example 14—A method of operating a modular surgical system including a control module, a first surgical module, and a second surgical module, the method comprising detachably connecting the first surgical module to the control module by stacking the first surgical module with the control module in a stack configuration, detachably connecting the second surgical module to the first surgical module by stacking the second surgical module with the control module and the first surgical module in the stack configuration, and simultaneously supplying power from a power supply in the control module to the first surgical module to generate a first therapeutic energy and to the second surgical module through the first surgical module to generate a second therapeutic energy.

Example 15—The method of Example 14, further comprising the step of monitoring distribution of the power to the first surgical module and the second surgical module.

Example 16—The method of Examples 14 or 15, further comprising the step of identifying a physical position of the first surgical module in the stack configuration.

Example 17—The method of any one of Examples 14-16, further comprising the step of identifying a physical position of the second surgical module in the stack configuration.

Example 18—The method of any one of Examples 14-17, wherein the first therapeutic energy is different from the second therapeutic energy.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A modular surgical system, comprising:
   a header module comprising:
      a power supply comprising:
         a standby power; and
         a primary power; and
      a control circuit;
   a first surgical module arrangeable in a stack configuration with the header module; and
   a second surgical module arrangeable in the stack configuration, wherein the first surgical module and the second surgical module are in a standby mode, and wherein the control circuit is configured to:
      cause the power supply to provide standby power to the first surgical module and the second surgical module;
      receive a power on command from a user;
      responsive to the power on command, perform a module detection check for the first surgical module and the second surgical module;
      cause the first surgical module and the second surgical module to transition to an active mode based on the module detection check; and
      cause the power supply to provide primary power to the first surgical module and the second surgical module in the active mode.

2. The modular surgical system of claim 1, wherein the control circuit is further configured to:
   determine that the first module is not properly connected based on the module detection check; and
   transmit an error message indicative of the improper connection to a user interface.

3. The modular surgical system of claim 1, wherein in the standby mode, therapeutic energy delivery is disabled for the first surgical module and the second surgical module.

4. The modular surgical system of claim 1, wherein in the active mode, therapeutic energy delivery is enabled for the first surgical module and the second surgical module.

5. The modular surgical system of claim 1, further comprising a power backplane configured to deliver power from the power supply to the first module and the second module.

6. The modular surgical system of claim 5, wherein the first surgical module is stacked between the header module and the second module, and wherein the standby power is provided to the second module through the first module.

7. The modular surgical system of claim 5, wherein the power backplane comprises:
   a first power backplane housed in the header module;
   a second power backplane housed in the first module; and
   a third power backplane housed in the second module.

8. The modular surgical system of claim 1, wherein in the active mode the first surgical module is configured to supply power to a first surgical instrument, and wherein in the active mode the second surgical module is configured to supply power to a second surgical instrument.

9. A modular surgical system, comprising:
   a header module comprising:
      a power supply comprising:
         a standby power; and
         a primary power; and
      a control circuit;
   a first surgical module arrangeable in a stack configuration with the header module; and
   a second surgical module arrangeable in the stack configuration, wherein the first surgical module and the second surgical module are in an active mode, and wherein the control circuit is configured to:
      cause the power supply to provide primary power and standby power to the first surgical module and the second surgical module;
      receive a power off command;
      responsive to the power off command, analyze the first surgical module and the second surgical module to determine if either module is supplying therapeutic energy to a surgical instrument;
      cause the first surgical module and the second surgical module to transition to a standby mode based on the analysis; and
      cause the power supply to disable primary power to the first surgical module and the second surgical module in the standby mode.

10. The modular surgical system of claim 9, wherein the control circuit is further configured to:
   detect that the first surgical module is supplying therapeutic energy to a first surgical instrument based on the analysis; and
   cause the first surgical module to remain in the active mode during the delivery of therapeutic energy.

11. The modular surgical system of claim 9, wherein in the standby mode, therapeutic energy delivery is disabled for the first surgical module and the second surgical module.

12. The modular surgical system of claim 9, wherein in the active mode, therapeutic energy delivery is enabled for the first surgical module and the second surgical module.

13. The modular surgical system of claim 9, further comprising a power backplane configured to deliver power from the power supply to the first module and the second module.

14. The modular surgical system of claim 13, wherein the first surgical module is stacked between the header module and the second module, and wherein the standby power is provided to the second module through the first module.

15. The modular surgical system of claim 13, wherein the power backplane comprises:
   a first power backplane housed in the header module;
   a second power backplane housed in the first module; and
   a third power backplane housed in the second module.

16. The modular surgical system of claim 9, wherein in the active mode the first surgical module is configured to supply power to a first surgical instrument, and wherein in the active mode the second surgical module is configured to supply power to a second surgical instrument.

17. A modular surgical system, comprising:
   a control module comprising:
      a power supply comprising:
         a standby power; and
         a primary power; and
      a control circuit;
   a first surgical module detachably coupled to the control module, wherein the first surgical module is placed in a stack configuration with the control module; and
   a second surgical module detachably coupled to the first surgical module, wherein the second surgical module is stacked in the stack configuration with the first surgical module and the control module, wherein the first surgical module and the second surgical module are in a standby mode, and wherein the control circuit is configured to:
      cause the power supply to provide standby power to the first surgical module and the second surgical module;
      receive a power on command;
      responsive to the power on command, perform a module detection check for the first surgical module and the second surgical module;
      cause the first surgical module and the second surgical module to transition to an active mode based on the module detection check; and
      cause the power supply to provide primary power to the first surgical module and the second surgical module in the active mode.

18. The modular surgical system of claim 17, wherein the first surgical module is stacked between the control module and the second module, and wherein the standby power is provided to the second module through the first module.

19. The modular surgical system of claim 17, wherein the first surgical module comprises a first energy port configured to supply power to a first surgical instrument that is attached to the first energy port, and wherein the second surgical module comprises a second energy port configured to supply power to a second surgical instrument that is attached to the second energy port.

20. The modular surgical system of claim 17, further comprising a power backplane configured to deliver power from the power supply to the first module and the second module.

* * * * *